US007169932B2

(12) United States Patent
Kucera et al.

(10) Patent No.: US 7,169,932 B2
(45) Date of Patent: Jan. 30, 2007

(54) HIV PROTEASE INHIBITORS, COMPOSITIONS CONTAINING THE SAME, THEIR PHARMACEUTICAL USES, MATERIAL FOR THEIR SYNTHESIS

(75) Inventors: David John Kucera, Del Mar, CA (US); Robert William Scott, San Diego, CA (US)

(73) Assignee: Pfizer Inc., San Diego, CA (US)

( * ) Notice: Subject to any disclaimer, the term of this patent is extended or adjusted under 35 U.S.C. 154(b) by 511 days.

(21) Appl. No.: 10/728,602

(22) Filed: Dec. 4, 2003

(65) Prior Publication Data
US 2004/0171842 A1 Sep. 2, 2004

Related U.S. Application Data

(63) Continuation-in-part of application No. 10/166,957, filed on Jun. 11, 2002, now Pat. No. 6,953,858.

(60) Provisional application No. 60/297,729, filed on Jun. 11, 2001, provisional application No. 60/297,460, filed on Jun. 11, 2001.

(51) Int. Cl.
C07D 277/06 (2006.01)
(52) U.S. Cl. .................................... 548/200
(58) Field of Classification Search ................ 548/200
See application file for complete search history.

(56) References Cited

U.S. PATENT DOCUMENTS

| 5,629,406 | A | 5/1997 | Higashida et al. |
| 5,644,028 | A | 7/1997 | Mimoto et al. |
| 5,932,550 | A | 8/1999 | Kato et al. |
| 5,962,640 | A | 10/1999 | Kato et al. |
| 6,222,043 | B1 | 4/2001 | Kato et al. |
| 6,313,094 | B1 | 11/2001 | Mimoto et al. |
| 6,329,502 | B1 | 12/2001 | Mimoto et al. |
| 2002/0049165 | A1 | 4/2002 | Mimonto et al. |

FOREIGN PATENT DOCUMENTS

| AU | 705193 | 2/1997 |
| CA | 2179935 | 12/1996 |
| EP | 0490667 | 6/1992 |
| EP | 0498680 | 8/1992 |
| EP | 0574135 A | 12/1993 |
| EP | 0706794 | 4/1996 |
| EP | 0751145 A2 | 6/1996 |
| JP | 8259532 | 10/1996 |
| JP | 10-867489 | 4/1998 |
| JP | 10101654 | 4/1998 |
| JP | 2003119137 | 4/2003 |
| WO | WO 93/13066 | 7/1993 |
| WO | WO 2002 100845 | 12/2002 |
| WO | WO 2002100844 | 12/2002 |
| WO | WO 03/035076 | 5/2003 |
| WO | WO 03/035650 A1 | 5/2003 |
| WO | WO 03/049690 | 6/2003 |
| WO | WO 03/062204 | 7/2003 |
| WO | WO 03/062238 | 7/2003 |
| WO | WO 03/047564 | 12/2003 |

OTHER PUBLICATIONS

Andres, "Stereoselective Cyanation Of Chiral α-Amino Aldehydes By Reaction With Nagata's Reagent: A Route To Enantiopure β-Amino-α-Hydroxy Acids," *Tetrahedron Asymm.*, 2001, pp. 347-353, vol. 12.
Blanco, M. et al., "Enantiospecific And Stereoselective Synthesis Of Polyhydroxylated Pyrrolidines And Indolizidines From *Trans*-4-Hydroxy-L-Proline," *J. Org. Chem.*, 1996, pp. 4748-4755, vol. 61.
Humphrey, J. et al., "Chemical Synthesis Of Natural Product Peptides: Coupling Methods For The Incorporation Of Noncoded Amino Acids Into Peptides," *Chemical Reviews*, 1997, 2243-2266 vol. 97.
Ikunaka, et al., "A Concise Synthesis of (2S,3S)-BocAHPBA and ®-BocDMTA, Chiral Building Blocks for Peptide-Mimetic HIV Protease Inhibitors," *Tetrahedron Asymmetry*, 2002, vol. 13, 1201, Index Only, pp. 435-447.
Jacques, et al., *Enantiomers, Racemates, and Resolutions*, 1981, John Wiley & Sons, New York, Contens Only, pp. Xiii-XXViii.
Larock, et al., *Comprehensive Organic Transformations*, 1989, Chapter 9, New York.
Sasai, H., et al., "Diatereoselective Cataytic Asymmetric Nitroaldol Reaction Utilizing Rare Earth-Li-(R)-BINOL Complex. A Highly Efficient Synthesis Of Norstatine," *Tetrahedron Letters*, 1994, pp. 6123-6126, vol. 35, No. 33.
Sharma, R. et al., "Regioselective Enolization And Alkylation Of 4-Oxo-N-(9-Phenylfluoren-9-yl)Proline: Synthesis Of Enantipure Proline-Valine And Hydroxyproline-Valine Chimeras," *J. Org Chem.*, 1996, pp. 202-209, vol. 61.

(Continued)

*Primary Examiner*—Laura L. Stockton
(74) *Attorney, Agent, or Firm*—Jeffrey H. Tidwell; Bryan C. Zielinski

(57) ABSTRACT

Compounds of the formula:

where the formula variables are as defined herein, are disclosed that advantageously inhibit or block the biological activity of the HIV protease. These compounds, as well as pharmaceutical compositions containing these compounds, are useful for treating patients or hosts infected with the HIV virus. Intermediates and synthetic methods for preparing such compounds are also described.

1 Claim, No Drawings

OTHER PUBLICATIONS

Sustmann, et al., *Comprehensive Organic Synthesis*, 1991, vol. 6, 301-434, Trost.

Bell, et al., "Development of Orally Active Oxytocin Antagonists: on 1-(1-{4-[1-2- Methyl-1-oxidophyridin-3-ylmethyl)piperidin-4-yloxy]-2-methoxybenzoyl}peperidin-5-yl)-1-4-dihydrobenz[d][1,3]oxazin-2-one (L-372,662) and Related Pyridines," *Journal of Medicinal Chemistry*, 1998, 2146-2163, vol. 41.

Yoshiaki, Patent Abstracts of Japan, Publication No. 10182601, 1998, No. 12.

Sheha, et al., *Euro J. Med. Chem.*, 2000, 887-894, vol. 35, No. 10.

Kitzaki, et al., *Chem & Pharm. Bulletin*, Pharm. Soc. Of Japan, 1994, 2636-2640, vol. 42, No. 12.

Slee, et al., *J.A.C.S.*, 1995, 11867-11878, vol. 117, No. 48.

Komai, et al., *Biorg. Med. Chem.*, 1996, 1365-1377, Volo. 4, No. 8.

Kiso., et al., *Arch. Pharm.*, Pharm. Med. Chem., 1998, 87-89, vol. 331.

Matsumoto, et al., *Biorg. Med. Chem.*, 2001, 417-430, vol. 9, No. 2.

Tam, et al., *J. Med. Chem.*, 1992, 1318-1320, vol. 35, No. 7.

Van-Duc Le, et al., "Structure-Activity of FIV and HIV Protease Inhibitors Containing Allophenylnorstatine," *Biorg. Med. Chem.*, 2001, 1185-1195, vol. 9.

Mimoto, et al., "Structure-Activity Relationship of Orally Potent Tripeptide-Based HIV Protease Inhibitors containing HydroxymethylCarbonyl Isotease," *Chem & Pharm. Bulletin*, Pharm Soc. Of Japan, 2000, 1310-1326, vol. 48, No. 9.

Sodergren, et al., "Allylic Alcohols Via Catalytic Asymmetric Expoxide Rearrangement," *J. Am. Chem. Soc.*, 2000, 6610-6018, vol. 122, No. 28.

Falorni, et. al., "Optically Active 4-Oxaproline Deriviatives: New Useful Chiral Lsynthons Derived from Serine and Threonine," *Tetrahedron: Asymmetry*, 1995, vol. 6, No. 1, p. 287-294.

Bobbitt, et al., "Synthesis of Isoquinoline Alkaloids. II. The synthesis and Reasctions of 4-Methyl-3-pyridinecarboxaldehyde and Other 4-methyl-3-substituted Pyridines," J. Org. Chem., 1959, 560, vol. 25.

Bundgaard, Design of Prodrugs, 1985, Subject Index Only, p. 355-360.

Carlsen, et al., "Thermolysis of *N*-Allylic 1,2,4-Triazoles," *Institute of Organic Chemistry*, 1997, 797-805, vol. 34.

Charlesworth, et. al., "Phthalide Formation," *Can. J. Chem.*, 1963, 1071-1077, vol. 41.

Demange, et al., "Practical Synthesis of Boc and Fmoc Protected 4-Fluoro and 4-Difluoroprolines from *Trans*-4-Hydrozyproline," *Tetrahedron Letters*, 1998, 1169-1172, vol. 39.

Dondoni., et al., "Total Synthesis of (+)-Galactostatin. An Illustration of the Utility of the Thizole-Aldehyde Synthesis," *J. Org. Chem..*, 1995, 4749-4754, vol. 60.

*Enantiomers, Racemates, and Racemates, and Resoloutions*, 1991, Jacques et al., Index Only pp. 435-447.

Fujiwara, et. al., "Orientation in Nitration and Sulfonation of 2,5-Dimethylbenzoic Acid," *Can. J. Chem.*, 1970, 1346-1349, vol. 48.

Harada, et. al., "Synthesis and Resolution of -*N*-[1-methyl-4(3-methylbenzyl)hexahydro-1*H*-1,4-*diazepin*-6-yl]-1*H*-indazole-3-Carboxamide By Preferential Crystallization," *Tetrahedron Asymmetry*, 1997, 2367-2374, vol. 8, No. 14.

Holzgrabe, U., "Cer(IV)sulfat-Oxidationen: Intramolekulare Cyclisierung von N-benzyl-β-Aminoketonen zu 4-Benzoyl-1,2,3,4-tetrahydro-isochinolinen," *Arch. Pharm.*, 1987, 647-654, vol. 320.

Huang, et al., "The Improved Preparation of 7,8-Dihydro-Quinoline-596*H*)-One And 6,7-Dihydro-5*H*-1-Pyrindin-5-One," *Synthetic Communications*, 1998, 1197-1200, vol. 28, No. 7.

Hursthouse, et al., "Reactions of Ethyl 2-acetyl-2-azabicyclo[2.2.1]Hept-5-ene-3-Carboxylate and 4-acetylamino-2-oxabicyclo[3.3.o]oct-7-en-3-one With Some Electrophiles," *J. Chem. Soc.*, 1995, 2419-2425, vol. 1.

Karanewsky, et. al., "Phosphinyloxy)acyl Amino Acid Inhibitors of Angiotensin Converting Enzyme," *J. Med. Chem.*, 1990, 1459-1469, vol. 33.

Ludeman, et al., "Synthesis and Antitumor Activity of Cyclophosphamide Analogs. 1. Benzo Annulated Cyclophosphamide and Related Systesm," Journal of Medicinal Chemistry, 1975, 1251, vol. 18, No. 12.

Matayoshi, et. al., "Novel Fluorogenic Substrates For Assaying Retroviral Proteses by Resonance Engergy Transfer," *Science*, 1990, 954-958, vol. 247.

Miller, et al., "Preparation of Crystalline Diphenyldiazomethane," *J. Org. Chem.*, 1958, 560-561, vol. 24.

Mimoto, et. al., "Structure-Activity Relationship of Small-Sized HIV Protease Inhibitors Containing Allophenylnorstatine," *J. Med. Chem.*, 1999, 1789-1802, vol. 42.

Nagasawa, et. al., "β-Substituted Cysteines as Sequestering Agents for Ethanol-Derived Acetaldehyde in Vivo," *J. Med. Chem.*, 1987, 1373, vol. 30.

Nussbaumer, et. al., "Synthesis and Structure-Activity Relationships of Benzo[*b*]thienylallylamine Antimycotics," *Med. Chem.*, 1991, 65-73, vol. 34.

O'Brien, et. al., "Inhibotors of Acyl-CoA:Cholesterol )-Acyl Transferase (ACAT) as Hypocholesterolemic Agents. Incorporation of Amide or Amine Funtionalities into a Series of Disubstituted Ureas and Carbamates. Effects on ACAT Inhibition in Vitro and Efficacy In Vivo," *J. Med. Chem.*, 1994, 1810-1822, vol. 37.

Onda, et al., "Structure of Carzinophilin. II. A New Amino Acid and Its Derivative Form Carzinophillin," *Chem. Pharm. Bull.*, 1971, 2013-2019, vol. 19, No. 10.

Pauwels, et. al., "rapid and Automated Tetrazolium-Based colorimetric Assay for the Detetion of Anti-HIV Compounds," *Journal of virological Methods*, 1988, 309-321, vol. 20.

Petropoulos, et. al., "a novel Phenotypic Drug Susceptibility Assay for Human Immunodeficiency Virus type 1," *Antimicrob Agents Chemother*, 2000, 920-928, vol. 44, No. 4.

*Protective Groups in Organic Synthesis*, 3rd Edition, 1999., Green et al., Index Only pp. 749-778.

Weislow, et. al., "New Soluble-Formazan Assay for HIV-1 Cytopathic Effects: Application to High-Flux for AIDS-Antiviral Activity," *Journal of the National Cancer Institute*, 1989, 577-586, vol. 18, No. 8.

WIPF, et. al., "SN2'-Reactions of Peptide Aziridines. A Cuprate-Based Approach to (*E*)-Alkene Isosteres," *J. Org. Chem.*, 1994, 4875-4886, vol. 59.

Yoshimura, et al., "JE-2147: A Dipeptide Protease Inhibitor (PI) that Potently Inhibits Multi-PH-Resistant HIV-1," Proc. Natl. Acad. Sci. USA, Jul. 1999, 8675-8680, vol. 96.

HIV PROTEASE INHIBITORS, COMPOSITIONS CONTAINING THE SAME, THEIR PHARMACEUTICAL USES, MATERIAL FOR THEIR SYNTHESIS

This application is a continuation-in-part of U.S. application Ser. No. 10/166,957, filed Jun. 11, 2002, now U.S. Pat. No. 6,953,858, which claims the benefit of U.S. Provisional Application No. 60/297,460, filed on Jun. 11, 2001, and U.S. Provisional Application No. 60/297,729, filed on Jun. 11, 2001, all of which are hereby incorporated by reference.

BACKGROUND OF THE INVENTION

1. Field of the Invention

This invention relates to novel compounds as useful as HIV protease inhibitors and to the use of such compounds as antiviral agents for treatment of HIV infected individuals. This invention also relates to methods of preparation of these compounds and to intermediates that are useful in the preparation thereof.

2. Related Background Art

Acquired Immune Deficiency Syndrome (AIDS) causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus III (HTLV-III), now more commonly referred to as the human immunodeficiency virus or HIV.

HIV is a member of the class of viruses known as retroviruses. The retroviral genome is composed of RNA, which is converted to DNA by reverse transcription. This retroviral DNA is then stably integrated into a host cell's chromosome and, employing the replicative processes of the host cells, produces new retroviral particles and advances the infection to other cells. HIV appears to have a particular affinity for the human T-4 lymphocyte cell, which plays a vital role in the body's immune system. HIV infection of these white blood cells depletes this white cell population. Eventually, the immune system is rendered inoperative and ineffective against various opportunistic diseases such as, among others, pneumocystic carini pneumonia, Kaposi's sarcoma, and cancer of the lymph system.

Although the exact mechanism of the formation and working of the HIV virus is not understood, identification of the virus has led to some progress in controlling the disease. For example, the drug azidothymidine (AZT) has been found effective for inhibiting the reverse transcription of the retroviral genome of the HIV virus, thus giving a measure of control, though not a cure, for patients afflicted with AIDS. The search continues for drugs that can cure or at least provide an improved measure of control of the deadly HIV virus.

Retroviral replication routinely features post-translational processing of polyproteins. This processing is accomplished by virally encoded HIV protease enzyme. This yields mature polypeptides that will subsequently aid in the formation and function of infectious virus. If this molecular processing is stifled, then the normal production of HIV is terminated. Therefore, inhibitors of HIV protease may function as anti-HIV viral agents.

HIV protease is one of the translated products from the HIV structural protein pol gene. This retroviral protease specifically cleaves other structural polypeptides at discrete sites to release these newly activated structural proteins and enzymes, thereby rendering the virion replication-competent. As such, inhibition of the HIV protease by potent compounds may prevent proviral integration of infected T-lymphocytes during the early phase of the HIV-1 life cycle, as well as inhibit viral proteolytic processing during its late stage. Additionally, the protease inhibitors may have the advantages of being more readily available, longer lived in virus, and less toxic than currently available drugs, possibly due to their specificity for the retroviral protease.

Related inhibitors of HIV proteases have been described in, e.g., U.S. Pat. No. 5,962,640, U.S. Pat. No. 5,932,550, Australian Patent No. 705193, Canadian Patent Application No. 2,179,935, European Patent Application No. 0 751 145, and Japanese Patent Application No.100867489. Other related HIV protease inhibitors have been described in K. Yoshimura, et al., *Proct. Natl. Acad. Sci.* USA, 96, 8675–8680 (1999) and T. Mimoto, et al., *J. Med. Chem.*, 42, 1789–1802 (1999).

On-going treatment of HIV-infected individuals with compounds that inhibit HIV protease has led to the development of mutant viruses that possess proteases that are resistant to the inhibitory effect of these compounds. Thus, to be effective, new HIV protease inhibitors must be effective not only against wild-type strains of HIV, but must also demonstrate efficacy against the newly emerging mutant strains that are resistant to the commercially available protease inhibitors. Accordingly, there continues to be a need for new inhibitors targeting the HIV protease in both wild type and mutant strains of HIV.

SUMMARY OF THE INVENTION

This invention relates to compounds useful for inhibiting the activity of HIV-protease of Formula I:

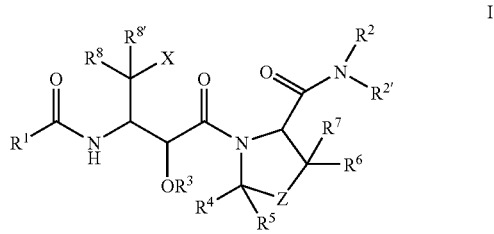

wherein:

$R^1$ is a 5- or 6-membered mono-cyclic carbocyclic or heterocyclic group, wherein said carbocyclic or heterocyclic group is saturated, partially unsaturated or fully unsaturated and is unsubstituted or substituted by one or more suitable substituents;

$R^2$ is a substituted alkyl group, a substituted or unsubstituted alkenyl group, a substituted or unsubstituted alkynyl group, a substituted phenyl group, a substituted phenylalkyl group, a substituted or unsubstituted phenylalkenyl group or a substituted or unsubstituted phenylalkynyl group, $R^{2'}$ is H or a substituted or unsubstituted $C_1$–$C_4$ alkyl group;

X is

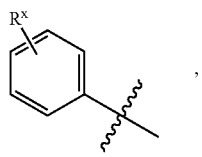, wherein $R^x$ is H or one or more suitable substituents;

Z is S, O, SO, $SO_2$, $CH_2$ or CFH;

$R^3$ is H or an optionally substituted or unsubstituted $C_1$–$C_4$ alkyl group;

$R^4$, $R^5$, $R^6$ and $R^7$ are independently selected from H or a $C_1$–$C_6$ alkyl group; and $R^8$ and $R^{8'}$ are independently selected from H, halo, a $C_1$–$C_4$ aliphatic group or a $C_1$–$C_4$ halo-substituted aliphatic group;

where any of said substituted alkyl, alkenyl or alkynyl groups are substituted by one or more suitable substituents provided that said 5- or 6-membered mono-cyclic heterocycloalkyl, heterocycloalkenyl or heteroaryl group contains at least two heteroatoms when $R^2$ is a substituted phenyl group, a substituted phenylalkyl group, a substituted or unsubstituted phenylalkenyl group or a substituted or unsubstituted phenylalkynyl group; or provided that said alkyl, alkenyl or alkynyl moiety of said substituted phenylalkyl, phenylalkenyl or phenylalkynyl group is substituted by one or more substituents selected from halo or keto; or provided that said substituted phenyl group or phenyl moiety of said substituted phenylalkyl, phenylalkenyl or phenylalkynyl group is substituted by one or more suitable substituents other than halo or methyl.

The present invention relates to compounds of Formula I below, and prodrugs, pharmaceutically active metabolites, and pharmaceutically acceptable salts and solvates thereof that inhibit the protease encoded by human immunodeficiency virus (HIV) type 1 (HIV-1) or type 2 (HIV-2), as well as mutant strains thereof. These compounds are useful in the treatment of infection by HIV and the treatment of the acquired immune deficiency syndrome (AIDS). The compounds, their pharmaceutically acceptable salts, and the pharmaceutical compositions of the present invention can be used alone or in combination with other antivirals, immunomodulators, antibiotics or vaccines. Compounds of the present invention can also be converted to prodrugs, by derivatization, according to conventional techniques. Methods of treating AIDS, methods of treating HIV infection and methods of inhibiting HIV protease are disclosed.

The present invention also relates to methods and processes useful for the preparation of compounds of formula I.

Furthermore, the present invention relates to chemical intermediates that are useful in the preparation of compounds of formula I.

DETAILED DESCRIPTION OF INVENTION AND PREFERRED EMBODIMENTS

The term "reacting," as used herein, refers to a chemical process or processes in which two or more reactants are allowed to come into contact with each other to effect a chemical change or transformation. For example, when reactant A and reactant B are allowed to come into contact with each other to afford a new chemical compound(s) C, A is said to have "reacted" with B to produce C.

The term "protecting," as used herein, refers to a process in which a functional group in a chemical compound is selectively masked by a non-reactive functional group in order to allow a selective reaction(s) to occur elsewhere on said chemical compound. Such non-reactive functional groups are herein termed "protecting groups." For example, the term "hydroxyl protecting group," as used herein refers to those groups that are capable of selectively masking the reactivity of a hydroxyl (—OH) group. The term "suitable protecting group," as used herein refers to those protecting groups that are useful in the preparation of the compounds of the present invention. Such groups are generally able to be selectively introduced and removed using mild reaction conditions that do not interfere with other portions of the subject compounds. Protecting groups that are suitable for use in the processes and methods of the present invention are known to those of ordinary skill in the art. The chemical properties of such protecting groups, methods for their introduction and their removal can be found, for example, in T. Greene and P. Wuts, *Protective Groups in Organic Synthesis* (3$^{rd}$ ed.), John Wiley & Sons, NY (1999). The terms "deprotecting," "deprotected," or "deprotect," as used herein, are meant to refer to the process of removing a protecting group from a compound.

The term "leaving group," as used herein refers to a chemical functional group that generally allows a nucleophilic substitution reaction to take place at the atom to which it is attached. For example, in acid chlorides of the formula Cl—C(O)R, wherein R is alkyl, aryl, or heterocyclic, the —Cl group is generally referred to as a leaving group because it allows nucleophilic substitution reactions to take place at the carbonyl carbon. Suitable leaving groups are known to those of ordinary skill in the art and can include halides, aromatic heterocycles, cyano, amino groups (generally under acidic conditions), ammonium groups, alkoxide groups, carbonate groups, formates, and hydroxy groups that have been activated by reaction with compounds such as carbodiimides. For example, suitable leaving groups can include, but are not limited to, chloride, bromide, iodide, cyano, imidazole, and hydroxy groups that have been allowed to react with a carbodiimide such as dicyclohexylcarbodiimide (optionally in the presence of an additive such as hydroxybenzotriazole) or a carbodiimide derivative.

The term "$C_{1-6}$ alkylcarbonyloxy," as used herein, refers to groups of the formula —OC(O)R, wherein R is an alkyl group comprising from 1 to 6 carbon atoms.

The term "$C_{6-10}$ arylcarbonyloxy," as used herein, refers to a group of the formula —OC(O)R, wherein R is an aryl group comprising from 6 to 10 carbons.

The term "heteroarylcarbonyloxy," as used herein, refers to a group of the formula —OC(O)R, wherein R is a heteroaromatic group as defined above.

In accordance with a convention used in the art,

is used in structural formulas herein to depict the bond that is the point of attachment of the moiety or substituent to the core or backbone structure. When the phrase, "substituted with at least one substituent" is used herein, it is meant to indicate that the group in question may be substituted by at least one of the substituents chosen. The number of substituents a group in the compounds of the invention may have depends on the number of positions available for substitution. For example, an aryl ring in the compounds of the invention may contain from 1 to 5 additional substituents, depending on the degree of substitution present on the ring. The maximum number of substituents that a group in the compounds of the invention may have can be determined by those of ordinary skill in the art.

As used herein, the term "aliphatic" represents a saturated or unsaturated, straight- or branched-chain hydrocarbon, containing 1 to 10 carbon atoms which may be unsubstituted or substituted by one or more of the substituents described below. The term "aliphatic" is intended to encompass alkyl, alkenyl and alkynyl groups.

As used herein, the term "alkyl" represents a straight- or branched-chain saturated or unsaturated hydrocarbon, containing 1 to 10 carbon atoms which may be unsubstituted or substituted by one or more of the substituents described below. Exemplary alkyl substituents include, but are not limited to methyl (Me), ethyl (Et), propyl, isopropyl, butyl, isobutyl, t-butyl, and the like. The term "lower alkyl" refers to an alkyl group containing from 1 to 6 carbon atoms The term "alkenyl" represents a straight- or branched-chain hydrocarbon, containing one or more carbon-carbon double bonds and having 2 to 10 carbon atoms which may be unsubstituted or substituted by one or more of the substituents described below. Exemplary alkenyl substituents include, but are not limited to ethenyl, propenyl, butenyl, allyl, pentenyl and the like.

The term "alkynyl" represents a straight- or branched-chain hydrocarbon, containing one or more carbon-carbon triple bonds and having 2 to 10 carbon atoms which may be unsubstituted or substituted by one or more of the substituents described below. An alkynyl moiety may also contain one or more carbon-carbon double bonds. Exemplary alkynyl substituents include, but are not limited to ethynyl, butynyl, propynyl (propargyl) isopropynyl, pentynyl, hexynyl and the like.

The term "carbocyclic" represents a saturated, partially saturated, or fully unsaturated (aromatic) cyclic hydrocarbon group containing from 3 to 14 carbon atoms which may be unsubstituted or substituted by one or more of the substituents described herein below. The term "carbocyclic" is intended to encompass mono-, bi- and tri-cyclic saturated, partially saturated, or fully unsaturated hydrocarbon groups; for example, cycloalkyl, cycloalkenyl and aryl groups. The term "carbocyclic" is also intended to encompass bi- and tri-cyclic hydrocarbon groups which contain any combination of ring moieties that are saturated, partially saturated, or fully unsaturated (aromatic). Partially saturated carbocycles include, for example, dihydroarenes (e.g., indanyl) or tetrahydro-arenes (e.g. tetrahydronaphthalene), wherein any one or more points of saturation may occur in any ring moiety of the carbocycle. In addition, it is understood that bonding between any bi- or tri-cyclic carbocyclic group and any other substituent or variable group may be made at any suitable position of the carbocycle. The term "carbocyclic-aliphatic" group is intended to encompass aliphatic groups having a carbocyclic substituent (e.g., phenylmethyl- (benzyl), phenylethyl-, cyclopropylmethyl-, etc.), wherein the carbocyclic moiety and the aliphatic moiety thereof may be independently substituted by one or more suitable substituents.

The term "cycloalkyl" represents a group comprising a non-aromatic monocyclic, bicyclic, or tricyclic hydrocarbon containing from 3 to 14 carbon atoms which may be unsubstituted or substituted by one or more of the substituents described below. Exemplary cycloalkyls include mono-cyclic rings having from 3–8 carbon atoms, such as cyclopropyl, cyclobutyl, cyclopentyl, cyclohexyl, cycloheptyl and the like. Illustrative examples of cycloalkyl groups include the following:

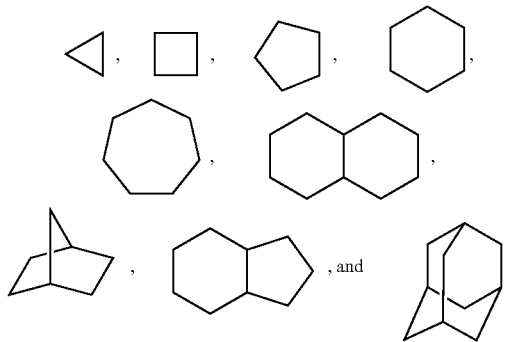

The term "cycloalkenyl" represents a group comprising a non-aromatic monocyclic, bicyclic, or tricyclic hydrocarbon containing from 4 to 14 carbon atoms which may be unsubstituted or substituted by one or more of the substituents described below and contains at least one carbon-carbon double bond. Exemplary monocyclic cycloalkenyls include groups having from 4–8, preferably 5–6, carbon atoms, such as cyclopentenyl, cyclopentadienyl, cyclohexenyl, cycloheptenyl and the like. Illustrative examples of cycloalkenyl groups include the following:

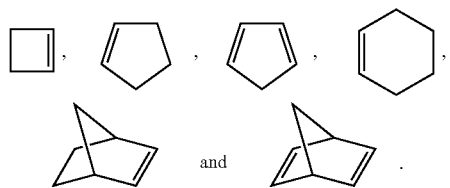

The term "aryl" represents a group comprising an aromatic, monovalent monocyclic, bicyclic, or tricyclic radical containing from 6 to 18 carbon ring atoms, which may be unsubstituted or substituted by one or more of the substituents described below.

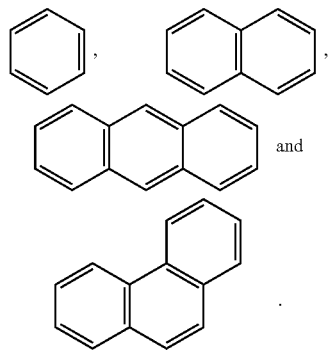

The term "carbocyclic" also to encompasses mixed bi- and tri-cyclic cycloalkyl/cycloalkenyl/aryl groups, which may be unsubstituted or substituted by one or more of the substituents described below. Illustrative examples of such mixed bi- and tri-cyclic groups include the following:

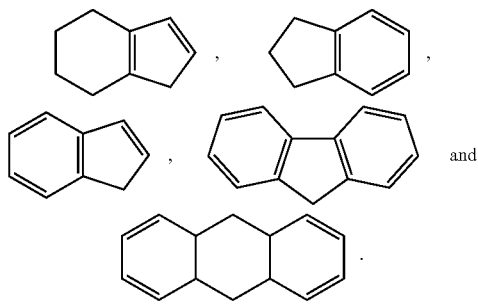

It is understood that bonding or substitution of any bi-cyclic or tri-cyclic carbocyclic or heterocyclic group described herein may be at any suitable position on any ring.

Illustrative examples of such bonding in mixed bi-and tri-cyclic carbocyclic groups include the following:

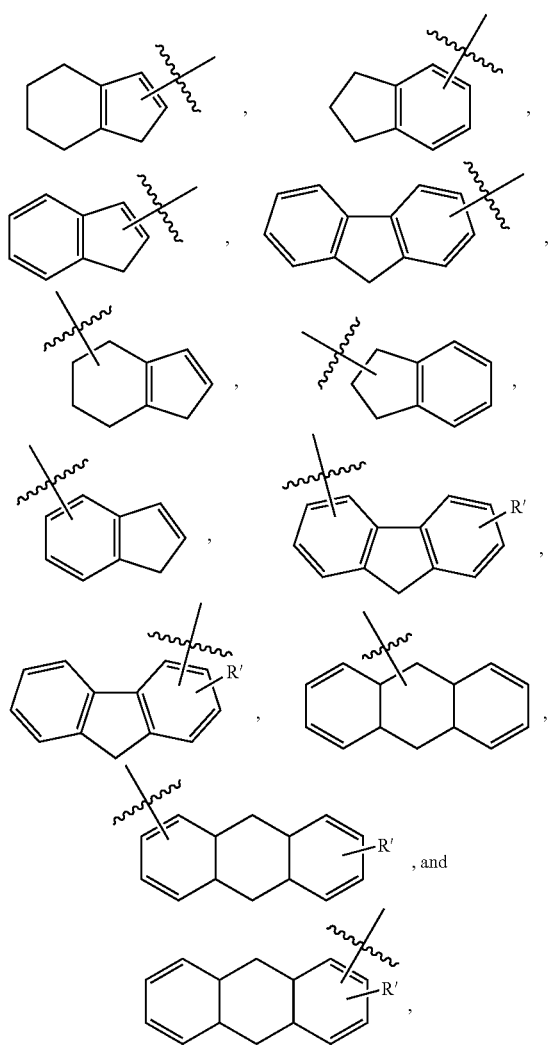

wherein R' is any suitable substituent.

The term "heterocyclic" represents a saturated, partially saturated, or fully unsaturated (aromatic) cyclic group containing from 3 to 18 ring atoms, which includes 1 to 5 heteroatoms selected from nitrogen, oxygen and sulfur, and which may be unsubstituted or substituted by one or more of the substituents described herein below. The term "heterocyclic" is intended to encompass mono-, bi- and tri-cyclic saturated, partially saturated, or fully unsaturated heteroatom-containing cyclic groups; for example, heterocycloalkyl, heterocycloalkenyl and heteroaryl groups. The term "heterocyclic" is also intended to encompass bi- and tri-cyclic groups which contain any combination of ring moieties that are saturated, partially saturated, or fully unsaturated (aromatic). Partially saturated heterocycles include, for example, dihydroheteroarenes (e.g., dihydroindole) or tetrahydro-heteroarenes (e.g. tetrahydroquinoline), wherein any one or more points of saturation may occur in any ring moiety of the heterocycle. In addition, it is understood that bonding between any bi- or tri-cyclic heterocyclic group and any other substituent or variable group may be made at any suitable position of the heterocycle (i.e., there is no restriction that a substituent or variable group must be bonded to the heteroatom-containing moiety of a bi- or tri-cyclic heterocyclic group). The term "heterocyclic-aliphatic" group is intended to encompass aliphatic groups having a heterocyclic substituent (e.g., pyridylmethyl-, thiazolylmethyl-, tetrahydrofuranylmethyl-, etc.) wherein the heterocyclic moiety and the aliphatic moiety thereof may be independently substituted by one or more suitable substituents.

"Heterocycloalkyl" represents a group comprising a saturated monovalent monocyclic, bicyclic, or tricyclic radical, containing 3 to 18 ring atoms, which includes 1 to 5 heteroatoms selected from nitrogen, oxygen and sulfur, and which may be unsubstituted or substituted by one or more of the substituents described below. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, tetrahydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1] octyl, azabicylo[3.3.1]nonyl, azabicylo[4.3.0]nonyl, oxabicylo[2.2.1]heptyl, 1,5,9-triazacyclododecyl, and the like. Illustrative examples of heterocycloalkyl groups include the following:

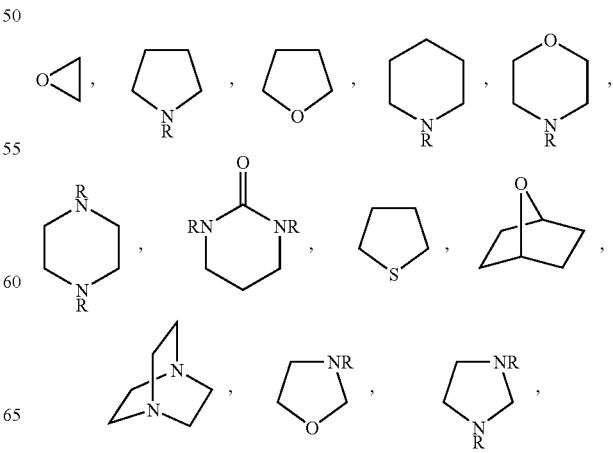

-continued

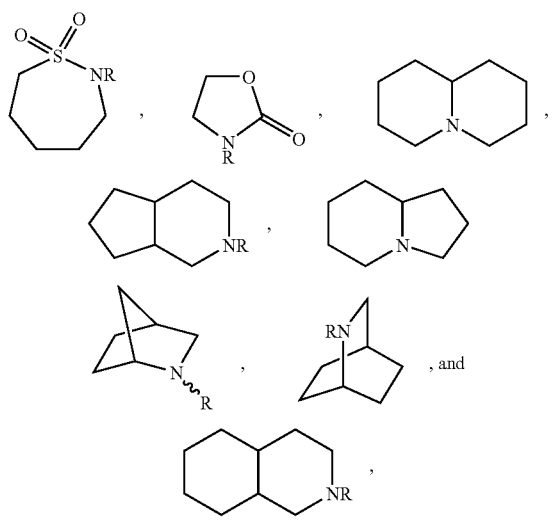

wherein R is H, alkyl, hydroxyl or represents a compound according to Formula I, and the bond depicted as " ~~ ",represents bonding to either face of the bi-cyclic moiety (i.e., endo or exo).

The term "heterocycloalkenyl" is used herein to represent a non-aromatic, monovalent monocyclic, bicyclic, or tricyclic radical, containing 4 to 18 ring atoms, which may include from 1 to 5 heteroatoms selected from nitrogen, oxygen and sulfur, and which may be unsubstituted or substituted by one or more of the substituents described below and which contains at least one carbon-carbon or carbon-heteroatom double bond. Exemplary monocyclic heterocycloalkenyls include groups having from 4–8, preferably 5–6, ring atoms. Illustrative examples of heterocycloalkenyl groups include, but are not limited to, dihydrofuryl, dihydropyranyl, isoxazolinyl, dihydropyridyl, tetrahydropyridyl, and the like. Illustrative examples of heterocycloalkenyl groups include the following:

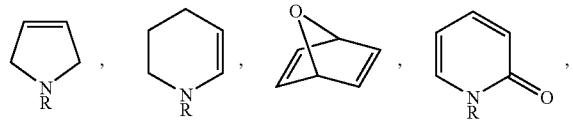

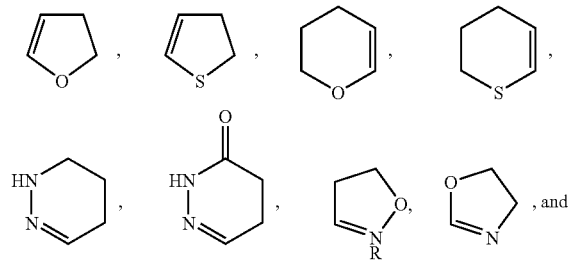

-continued wherein R is H, alkyl, hydroxyl or represents a compound according to Formula I.

The term "Heteroaryl" represents a group comprising an aromatic monovalent monocyclic, bicyclic, or tricyclic radical, containing 5 to 18 ring atoms, including 1 to 5 heteroatoms selected from nitrogen, oxygen and sulfur, which may be unsubstituted or substituted by one or more of the substituents described below. As used herein, the term "heteroaryl" is also intended to encompass the N-oxide derivative (or N-oxide derivatives, if the heteroaryl group contains more than one nitrogen such that more than one N-oxide derivative may be formed) of the nitrogen-containing heteroaryl groups described herein. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl. Illustrative examples of N-oxide derivatives of heteroaryl groups include, but are not limited to, pyridyl N-oxide, pyrazinyl N-oxide, pyrimidinyl N-oxide, pyridazinyl N-oxide, triazinyl N-oxide, isoquinolyl N-oxide, and quinolyl N-oxide. Further examples of heteroaryl groups include the following moieties:

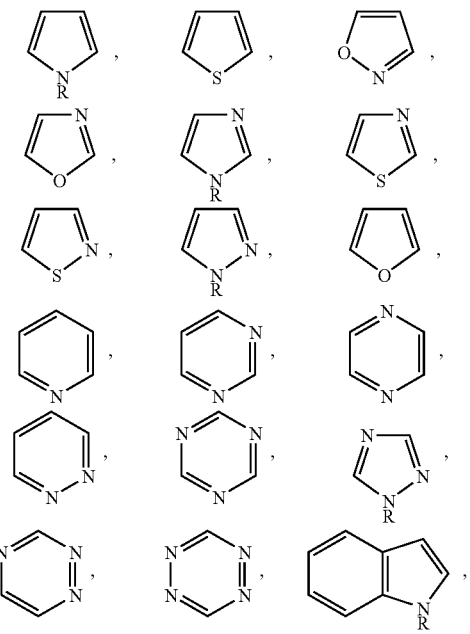

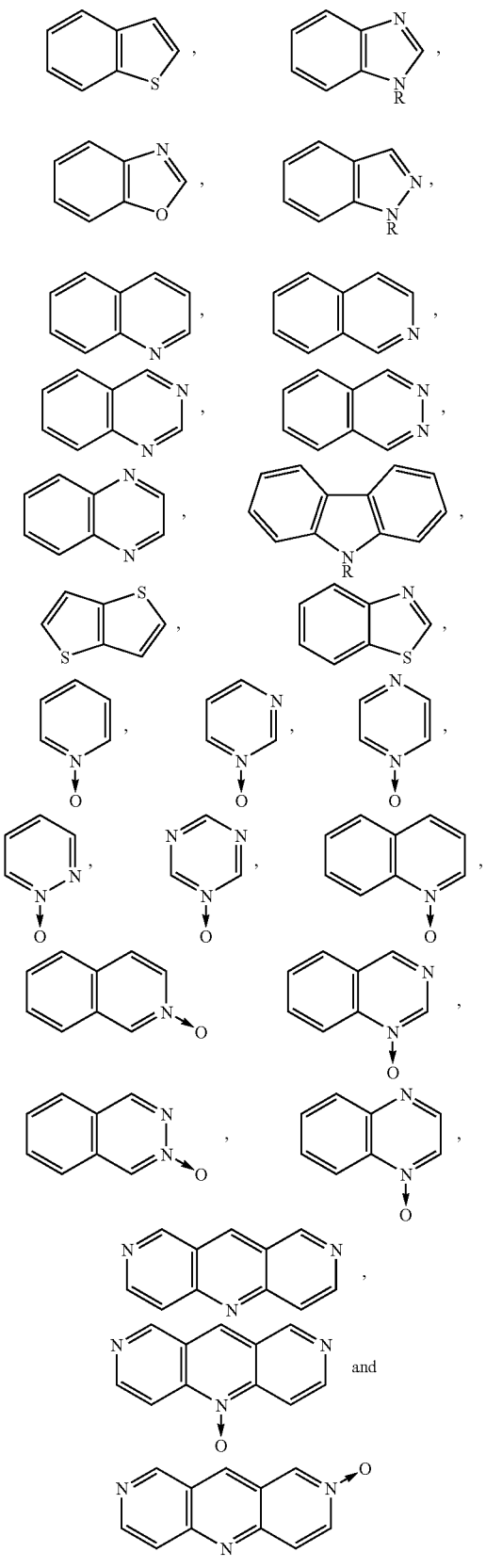

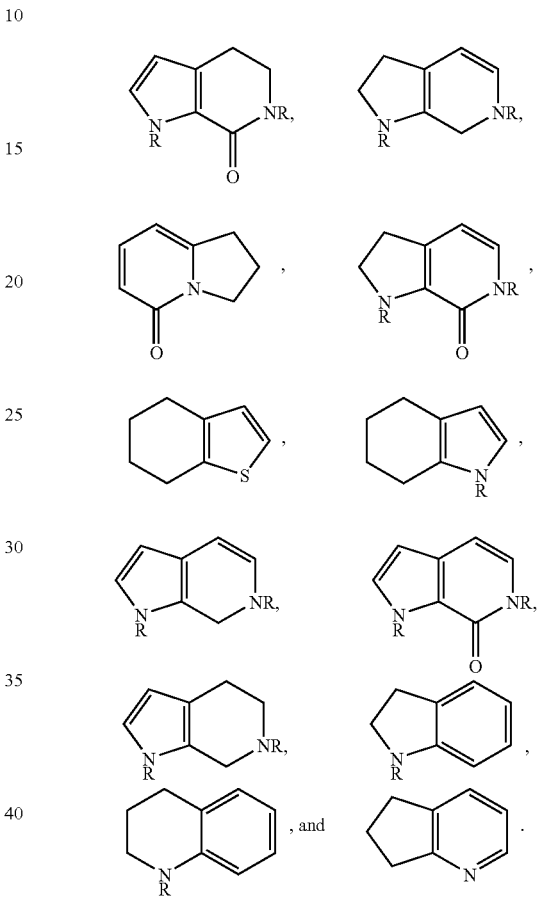

wherein R is H, alkyl, hydroxyl or represents a compound according to Formula I.

The term "heterocyclic" also to encompasses mixed bi- and tri-cyclic heterocycloalkyl/heterocycloalkenyl/heteroaryl groups, which may be unsubstituted or substituted by one or more of the substituents described below. Illustrative examples of such mixed bi- and tri-cyclic heterocyclic groups include the following:

Illustrative examples of such bonding in mixed bi- and tri-cyclic heterocyclic groups include the following:

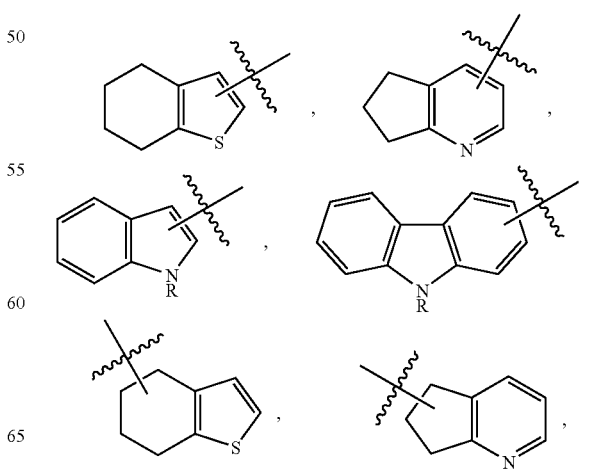

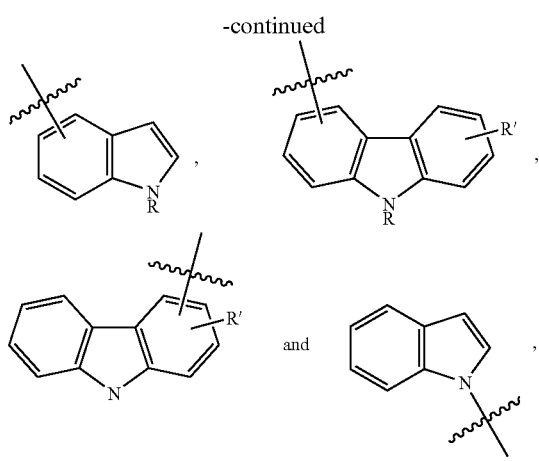

wherein R' is any suitable substituent.

In the compounds of this invention, the alkyl, alkenyl and alkynyl groups may be optionally substituted by one or more suitable substituents independently selected from phenyl, nitro, amino, cyano, halogen, hydroxyl, alkoxy, haloalkoxy, aryloxy, cycloalkyloxy, cycloalkylalkyloxy, cycloalkenyloxy, cycloalkenylalkyloxy, heterocycloalkoxy, heterocycloalkylalkyloxy, heterocycloalkenyloxy, heterocycloalkenylalkyloxy, heteroaryloxy, alkylcarbonyl, alkenylcarbonyl, alkynylcarbonyl, alkyloxycarbonyl, alkenyloxycarbonyl, alkynyloxycarbonyl, alkylcarbonyloxy, alkenylcarbonyloxy, alkynylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, alkenylamino, alkynylamino, cycloalkylamino, cycloalkenylamino, arylamino, heterocycloalkylamino, heterocycloalkenylamino, heteroarylamino, dialkylamino, alkylaminocarbonyl, alkenylaminocarbonyl, alkynylaminocarbonyl, cycloalkylaminocarbonyl, cycloalkenylamino, arylaminocarbonyl, heterocycloalkylaminocarbonyl, heterocycloalkenylcarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, haloalkylthio, arylthio and heteroarylthio groups, wherein any of the alkyl, alkenyl, alkynyl, aryl, cycloalkyl, cycloalkenyl, heterocycloalkyl, heterocycloalkenyl, heteroaryl moieties present in the above substituents may be further substituted. The alkyl, alkenyl, alkynyl, cycloalkyl, cycloalkenyl, heterocycloalkyl, heterocycloalkenyl, aryl, and heteroaryl moieties of any of the above substituents may be optionally substituted by one or more groups independently selected from alkyl (except for alkyl), haloalkyl, aryl, nitro, amino, alkylamino, dialkylamino, halogen, hydroxyl, alkoxy, haloalkoxy, aryloxy, mercapto, alkylthio, haloalkylthio or arylthio groups.

In the compounds of this invention the substituted carbocyclic or heterocyclic groups may be optionally substituted by one or more suitable substituents independently selected from alkyl, haloalkyl, alkenyl, alkynyl, aryl, cycloalkyl, cycloalkenyl, heterocycloalkyl, heterocycloalkenyl, heteroaryl, nitro, amino, cyano, halogen, hydroxyl, alkoxy, haloalkoxy, alkenyloxy, alkynyloxy, alkylenedioxy, aryloxy, cycloalkyloxy, cycloalkylalkyloxy, cycloalkenyloxy, cycloalkenylalkyloxy, heterocycloalkoxy, heterocycloalkylalkyloxy, heterocycloalkenyloxy, heterocycloalkenylalkyloxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, haloalkylthio, arylthio and heteroarylthio groups, wherein any of the alkyl, alkylene, aryl, cycloalkyl, heterocycloalkyl, heteroaryl moieties present in the above substituents may be further substituted. Preferred "suitable substituents" include alkyl, alkenyl, alkynyl, aryl, cycloalkyl, heterocycloalkyl, heteroaryl, halogen, hydroxyl, alkoxy, alkylenedioxy, aryloxy, cycloalkoxy, heteroaryloxy, alkylthio, haloalkylthio and carboxyl. The alkyl, alkylene, cycloalkyl, heterocycloalkyl, aryl, and heteroaryl moieties of any of the above substituents may be optionally substituted by one or more groups independently selected from: alkyl, haloalkyl, nitro, amino, alkylamino, dialkylamino, halogen, hydroxyl, alkoxy, haloalkoxy, mercapto, alkylthio, haloalkylthio or arylthio groups.

For example, in the compounds of this invention, the substituted phenyl or phenyl moiety of $R^2$ may comprise at least one substituent (other than halo or methyl) selected from haloalkyl, hydroxyalkyl, alkoxyalkyl, cycloalkoxyalkyl, alkylcarbonylalkyl, haloalkoxyalkyl, aryloxyalkyl, alkylthioalkyl, haloalkylthioalkyl, arylthioalkyl, cyanoalkyl, aminoalkyl, alkylaminoalkyl, alkenyl, alkynyl, aryl, cycloalkyl, cycloalkenyl, heterocycloalkyl, heterocycloalkenyl, heteroaryl, nitro, amino, cyano, hydroxyl, alkoxy, haloalkoxy, alkenyloxy, alkynyloxy, alkylenedioxy, aryloxy, cycloalkyloxy, cycloalkylalkyloxy, cycloalkenyloxy, cycloalkenylalkyloxy, heterocycloalkoxy, heterocycloalkylalkyloxy, heterocycloalkenyloxy, heterocycloalkenylalkyloxy, heteroaryloxy, alkylcarbonyl, alkyloxycarbonyl, alkylcarbonyloxy, arylcarbonyl, aryloxycarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyloxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, haloalkylthio, arylthio and heteroarylthio groups, wherein any of the alkyl, alkylene, aryl, cycloalkyl, heterocycloalkyl, heteroaryl moieties present in the above substituents may be further substituted. Preferred "suitable substituents" include alkyl, alkenyl, alkynyl, aryl, cycloalkyl, heterocycloalkyl, heteroaryl, halogen, hydroxyl, alkoxy, alkylenedioxy, aryloxy, cycloalkoxy, heteroaryloxy, alkylthio, haloalkylthio and carboxyl. The alkyl, alkylene, cycloalkyl, heterocycloalkyl, aryl, and heteroaryl moieties of any of the above substituents may be optionally substituted by one or more groups independently selected from: alkyl, haloalkyl, nitro, amino, alkylamino, dialkylamino, halogen, hydroxyl, alkoxy, haloalkoxy, mercapto, alkylthio, haloalkylthio or arylthio groups.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protective Groups in Organic Synthesis* (3$^{rd}$ ed.), John Wiley & Sons, New York (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

In the compounds of this invention, $R^2$ and $R^{2'}$, independently or taken together, may be a suitable nitrogen protecting group. As indicated above, nitrogen protecting groups are well known in the art and any nitrogen protecting group that is useful in the methods of preparing the compounds of this invention or may be useful in the HIV protease inhibitory compounds of this invention may be used. Exemplary nitrogen protecting groups include alkyl, substituted alkyl, carbamate, urea, amide, imide, enamine, sulfenyl, sulfonyl, nitro, nitroso, oxide, phosphinyl, phosphoryl, silyl, organometallic, borinic acid and boronic acid groups. Examples of each of these groups, methods for protecting nitrogen moieties using these groups and methods for removing these groups from nitrogen moieties are disclosed in T. Greene and P. Wuts, supra. Preferably, when $R^2$ and/or $R^{2'}$ are independently suitable nitrogen protecting groups, suitable $R^2$ and $R^{2'}$ substituents include, but are not limited to, carbamate protecting groups such as alkyloxycarbonyl (e.g., Boc: t-butyloxycarbonyl) and aryloxycarbonyl (e.g., Cbz: benzyloxycarbonyl, or FMOC: fluorene-9-methyloxycarbonyl), alkyloxycarbonyls (e.g., methyloxycarbonyl), alkyl or arylcarbonyl, substituted alkyl, especially arylalkyl (e.g., trityl (triphenylmethyl), benzyl and substituted benzyl), and the like. When $R^2$ and $R^{2'}$ taken together are a suitable nitrogen protecting group, suitable $R^2/R^{2'}$ substituents include phthalimido and a stabase (1,2-bis (dialkylsilyl)) ethylene).

The terms "halogen" and "halo" represent chloro, fluoro, bromo or iodo substituents. "Heterocycle" is intended to mean a heteroaryl or heterocycloalkyl group. "Acyl@ is intended to mean a —C(O)—R radical, where R is a substituted or unsubstituted alkyl, cycloalkyl, aryl, heterocycloalkyl or heteroaryl group. "Acyloxy" is intended to mean an —OC(O)—R radical, where R is a substituted or unsubstituted alkyl, cycloalkyl, aryl, heterocycloalkyl or heteroaryl group. "thioacyl" is intended to mean a —C(S)—R radical, where R is a substituted or unsubstituted alkyl, cycloalkyl, aryl, heterocycloalkyl or heteroaryl group. "Sulfonyl" is intended to mean an —S$_2$— biradical. "Sulfenyl" is intended to mean an —SO— biradical. "Sulfo" is intended to mean an —SO$_2$H radical. "Hydroxy" is intended to mean the radical —OH. "Amine" or "amino" is intended to mean the radical —NH$_2$. "Alkylamino" is intended to mean the radical —NHR$_a$, where R$_a$ is an alkyl group. "Dialkylamino" is intended to mean the radical —NR$_a$R$_b$, where R$_a$ and R$_b$ are each independently an alkyl group, and is intended to include heterocycloalkyl groups, wherein R$_a$ and R$_b$, taken together, form a heterocyclic ring that includes the amine nitrogen. "Alkoxy" is intended to mean the radical —OR$_a$, where R$_a$ is an alkyl group. Exemplary alkoxy groups include methoxy, ethoxy, propoxy, and the like. "Lower alkoxy" groups have alkyl moieties having from 1 to 4 carbons. "Alkoxycarbonyl" is intended to mean the radical —C(O)OR$_a$, where R$_a$ is an alkyl group. "Alkylsulfonyl" is intended to mean the radical —SO$_2$R$_a$, where R$_a$ is an alkyl group. "Alkylenedioxy" is intended to mean the divalent radical —OR$_a$O— which is bonded to adjacent atoms (e.g., adjacent atoms on a phenyl or naphthyl ring), wherein R$_a$ is a lower alkyl group. "Alkylaminocarbonyl" is intended to mean the radical —C(O)NHR$_a$, where R$_a$ is an alkyl group. "Dialkylaminocarbonyl" is intended to mean the radical —C(O)NR$_a$R$_b$, where R$_a$ and R$_b$ are each independently an alkyl group. "Mercapto" is intended to mean the radical —SH. "Alkylthio" is intended to mean the radical —SR$_a$, where R$_a$ is an alkyl group. "Carboxy" is intended to mean the radical —C(O)OH. "Keto" or "oxo" is intended to mean the diradical =O.

"Thioketo" is intended to mean the diradical =S. "Carbamoyl" is intended to mean the radical —C(O)NH$_2$. "Cycloalkylalkyl" is intended to mean the radical Balkylcycloalkyl, wherein alkyl and cycloalkyl are defined as above, and is represented by the bonding arrangement present in the groups —CH$_2$-cyclohexane or —CH$_2$-cyclohexene. "Arylalkyl" is intended to mean the radical Balkylaryl, wherein alkyl and aryl are defined as above, and is represented by the bonding arrangement present in a benzyl group. "Aminocarbonylalkyl" is intended to mean the radical BalkylC(O)NH$_2$ and is represented by the bonding arrangement present in the group —CH$_2$CH$_2$C(O)NH$_2$. "Alkylaminocarbonylalkyl" is intended to mean the radical BalkylC(O)NHR$_a$, where R$_a$ is an alkyl group and is represented by the bonding arrangement present in the group —CH$_2$CH$_2$C(O)NHCH$_3$. "Alkylcarbonylaminoalkyl" is intended to mean the radical BalkylNHC(O)-alkyl and is represented by the bonding arrangement present in the group —CH$_2$NHC(O)CH$_3$. "Dialkylaminocarbonylalkyl" is intended to mean the radical BalkylC(O)NR$_a$R$_b$, where R$_a$ and R$_b$ are each independently an alkyl group. "Aryloxy" is intended to mean the radical —OR$_c$, where R$_c$ is an aryl group. "Heteroaryloxy" is intended to mean the radical —OR$_d$, where R$_d$ is a heteroaryl group. "Arylthio" is intended to mean the radical —SR$_c$, where R$_c$ is an aryl group. If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

Specific embodiments of the compounds of this invention comprising the compounds depicted by Formula I may also be described. For example, this invention relates to compounds useful for inhibiting the activity of HIV-protease of Formula I, above, wherein:

R$^1$ is a 5- or 6-membered monocyclic cycloalkyl, cycloalkenyl, aryl, heterocycloalkyl, heterocycloalkenyl or heteroaryl group, where said cycloalkyl, cycloalkenyl, aryl, heterocycloalkyl, heterocycloalkenyl or heteroaryl group is unsubstituted or substituted with one or more substituents independently selected from alkyl, haloalkyl, amino, cyano, halogen, hydroxyl, alkoxy, haloalkoxy, alkylenedioxy, di-haloalkylenedioxy, aryloxy, cycloalkoxy, cycloalkylalkoxy, cycloalkenyloxy, cycloalkenylalkoxy, heterocycloalkoxy, heterocycloalkylalkoxy, heterocycloalkenyloxy, heterocycloalkenylalkoxy, heteroaryloxy, alkylcarbonyloxy, arylcarbonyloxy, heteroarylcarbonyloxy, alkylamino, dialkylamino, keto, alkylsulfonyl, arylsulfonyl, alkylcarbonylamino, alkylthio, haloalkylthio and arylthio, wherein any of the alkyl, alkylene, aryl, cycloalkyl, heterocycloalkyl, heteroaryl moieties present in the above substituents may be further substituted by one or more groups independently selected from alkyl, haloalkyl, aryl, nitro, amino, alkylamino, dialkylamino, halogen, hydroxyl, alkoxy, haloalkoxy, aryloxy, mercapto, alkylthio, haloalkylthio and arylthio groups;

R$^2$ is a substituted alkyl group, a substituted or unsubstituted alkenyl group, or a substituted or unsubstituted alkynyl group, wherein said alkyl, alkenyl or alkynyl group is a straight or branched chained group, and where said substituted alkyl, alkenyl or alkynyl group is substituted by one or more substituents independently selected from amino, cyano, halogen, hydroxyl, alkoxy, haloalkoxy, aryloxy, cycloalkoxy, cycloalkylalkoxy, cycloalkenyloxy, cycloalkenylalkoxy, heterocycloalkoxy, heterocycloalkylalkoxy, heterocycloalkenyloxy, heterocycloalkenlalkoxy, heteroaryloxy, alkylamino, dialkylamino, alkylsulfonyl, arylsulfonyl, alkylsulfenyl, arylsulfenyl, alkylthio, haloalkylthio, arylthio and heteroarylthio groups, wherein any of the alkyl, alkenyl, alkynyl, aryl, cycloalkyl, cycloalkenyl, heterocycloalkyl, heterocycloalkenyl, heteroaryl moieties present in the above substituents may be further substituted by one or more groups independently selected from alkyl, haloalkyl, halogen, hydroxyl, alkoxy, haloalkoxy, alkylthio and haloalkylthio groups;

R$^{2'}$ is H, methyl, ethyl or propyl, where said methyl, ethyl or propyl is unsubstituted or substituted by halo or hydroxyl;

X is

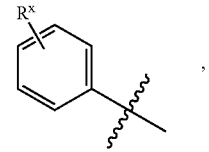

wherein R$^x$ is H or one or more substituents independently selected from halogen, alkyl, haloalkyl, alkoxy, haloalkoxy, hydroxyl, alkylenedioxy, di-haloalkylenedioxy, alkylamino, dialkylamino, alkylthio and haloalkylthio;

Z is S, O, SO, SO$_2$, CH$_2$ or CFH;

R$^3$ is H;

R$^4$, R$^5$, R$^6$ and R$^7$ are independently selected from H or methyl; and

R$^8$ and R$^{8'}$ are independently selected from H, halogen, methyl, monohalo-methyl, dihalo-methyl and tri-halomethyl;

or a prodrug, pharmaceutically active metabolite or pharmaceutically active salt or solvate thereof.

In more specific embodiments, this invention relates to compounds of Formula I, above, wherein:

R$^1$ is phenyl, pyrrolyl, pyrrolidinyl, isoxazolyl, pyrazolyl, thiazolyl, tetrahydrofuranyl, furanyl, thienyl or tetrahydropyridazinyl, where said phenyl, pyrrolyl, pyrrolidinyl, isoxazolyl, pyrazolyl, thiazolyl, tetrahydrofuranyl, furanyl, thienyl or tetrahydropyridazinyl is unsubstituted or substituted with one or more substituents independently selected from alkyl, haloalkyl, halogen, and hydroxyl;

R$^2$ is a substituted alkyl group, a substituted or unsubstituted C$_1$–C$_6$ alkenyl group, or a substituted or unsubstituted C$_1$–C$_6$ alkynyl group, wherein said alkyl, alkenyl or alkynyl group is a straight or branched chained group, and where said substituted alkyl, alkenyl or alkynyl group is substituted by one or more substituents independently selected from cyano, halogen and alkylamino;

R$^{2'}$ is H, methyl or ethyl;

X is

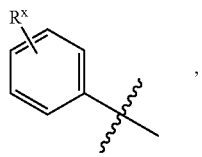

wherein $R^x$ is H, halogen, or alkoxy;
Z is S, O, $CH_2$ or CFH;
$R^3$, $R^4$, $R^5$, $R^8$ and $R^{8'}$ are each H; and
$R^6$ and $R^7$ are independently selected from H or methyl;
or a prodrug, pharmaceutically active metabolite or pharmaceutically active salt or solvate thereof.

In preferred specific embodiments, this invention relates to compounds of Formula I, above, wherein:
$R^1$ is phenyl, where said phenyl is substituted with one or more substituents independently selected from alkyl, halogen or hydroxyl;
$R^2$ is a $C_1$–$C_6$ alkenyl group or a $C_1$–$C_6$ alkynyl group, wherein said alkenyl or alkynyl group is a straight or branched chained group, and
where said alkenyl or alkynyl group is unsubstituted or is substituted by one or more halogen substituents;
$R^{2'}$ is H;
X is

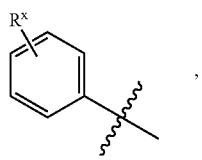

wherein $R^x$ is H;
Z is S;
$R^3$, $R^4$, $R^5$, $R^8$ and $R^{8'}$ are each H; and
$R^6$ and $R^7$ are each methyl;
or a prodrug, pharmaceutically active metabolite or pharmaceutically active salt or solvate thereof.

More specifically, this invention relates to compounds useful for inhibiting the activity of HIV-protease of Formula I, above, wherein:
$R^1$ is a 5- or 6-membered mono-cyclic cycloalkyl, cycloalkenyl, aryl, heterocycloalkyl, heterocycloalkenyl or heteroaryl group, where said cycloalkyl, cycloalkenyl, aryl, heterocycloalkyl, heterocycloalkenyl or heteroaryl group is unsubstituted or substituted with one or more substituents independently selected from alkyl, haloalkyl, amino, cyano, halogen, hydroxyl, alkoxy, haloalkoxy, alkylenedioxy, dihaloalkylenedioxy, aryloxy, cycloalkoxy, cycloalkylalkoxy, cycloalkenyloxy, cycloalkenylalkoxy, heterocycloalkoxy, heterocycloalkylalkoxy, heterocycloalkenyloxy, heterocycloalkenylalkoxy, heteroaryloxy, alkylcarbonyloxy, arylcarbonyloxy, heteroarylcarbonyloxy, alkylamino, dialkylamino, alkylsulfonyl, arylsulfonyl, alkylcarbonylamino, alkylthio, haloalkylthio and arylthio, wherein any of the alkyl, alkylene, aryl, cycloalkyl, heterocycloalkyl, heteroaryl moieties present in the above substituents are substituted by one or more groups independently selected from alkyl, haloalkyl, aryl, nitro, amino, alkylamino, dialkylamino, halogen, hydroxyl, alkoxy, haloalkoxy, aryloxy, mercapto, alkylthio, haloalkylthio and arylthio groups;
$R^2$ is a substituted phenyl group, a substituted phenylalkyl group, a substituted or unsubstituted phenylalkenyl group or a substituted or unsubstituted phenylalkynyl group;
where said alkyl, alkenyl or alkynyl moiety of said phenylalkyl, phenylalkenyl or phenylalkynyl group is a straight or branched chain moiety;
$R^{2'}$ is H, methyl, ethyl or propyl, where said methyl, ethyl or propyl is unsubstituted or substituted with halo or hydroxyl;
X is

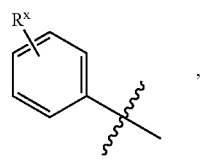

wherein $R_x$ is H or one or more substituents independently selected from halogen, alkyl, haloalkyl, alkoxy, haloalkoxy, hydroxyl, alkylenedioxy, di-haloalkylenedioxy, alkylamino, dialkylamino, alkylthio and haloalkylthio;
Z is S, O, SO, $SO_2$, $CH_2$ or CFH;
$R^3$ is H;
$R^4$, $R^5$, $R^6$ and $R^7$ are independently selected from H or methyl; and
$R^8$ and $R^{8'}$ are independently selected from H, halogen, methyl, monohalo-methyl, dihalo-methyl and tri-halomethyl;
provided that said 5- or 6-membered mono-cyclic heterocycloalkyl, heterocycloalkenyl or heteroaryl group contains at least two heteroatoms; or
provided that said alkyl, alkenyl or alkynyl moiety of said substituted phenylalkyl, phenylalkenyl or phenylalkynyl group is substituted by one or more substituents selected from halo or keto; or
provided that said substituted phenyl group or phenyl moiety of said substituted phenylalkyl, phenylalkenyl or phenylalkynyl group is substituted by one or more substituents other than halo or methyl, where said one or more substituents is independently selected from haloalkyl, hydroxyalkyl, alkoxyalkyl, cycloalkoxyalkyl, alkylcarbonylalkyl, haloalkoxyalkyl, aryloxyalkyl, alkylthioalkyl, haloalkylthioalkyl, arylthioalkyl, cyanoalkyl, aminoalkyl, alkylaminoalkyl, alkenyi, alkynyl, aryl, cycloalkyl, cycloalkenyl, heterocycloalkyl, heterocycloalkenyl, heteroaryl, nitro, amino, cyano, hydroxyl, alkoxy, haloalkoxy, alkenyloxy, alkynyloxy, alkylenedioxy, aryloxy, cycloalkoxy, cycloalkylalkoxy, cycloalkenyloxy, cycloalkenylalkoxy, heterocycloalkoxy, heterocycloalkylalkoxy, heterocycloalkenoxy, heterocycloalkenylalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto, thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, haloalkylthio, arylthio and heteroarylthio groups, wherein any of the alkyl, alkylene, aryl, cycloalkyl, heterocycloalkyl, or heteroaryl moieties present in the above substituents are unsubstituted or substituted by one or more groups independently selected from alkyl, haloalkyl, halogen, hydroxyl, alkoxy, haloalkoxy, alkylthio and haloalkylthio groups;

or a prodrug, pharmaceutically active metabolite or pharmaceutically active salt or solvate thereof. If the phenyl group or phenyl moiety of $R^2$ contains more than one substituent, the substituents may be the same or different, and may be independently selected from the above-described substituents.

More specifically, this invention relates to compounds useful for inhibiting the activity of HIV-protease of Formula I, above, wherein:

$R^1$ is phenyl, pyrrolyl, pyrrolidinyl, isoxazolyl, pyrazolyl, thiazolyl, tetrahydrofuranyl, furanyl, thienyl or tetrahydropyridazinyl, where said phenyl, pyrrolyl, pyrrolidinyl, isoxazolyl, pyrazolyl, thiazolyl, tetrahydrofuranyl, furanyl, thienyl or tetrahydropyridazinyl is unsubstituted or substituted with one or more substituents independently selected from alkyl, haloalkyl, halogen, and hydroxyl;

$R^2$ is a substituted phenylalkyl group, where said alkyl moiety of said substituted phenylalkyl group is a straight or branched chain alkyl moiety;

$R^{2'}$ is H, methyl, ethyl or propyl, where said methyl, ethyl or propyl is unsubstituted or substituted with hydroxyl;

X is

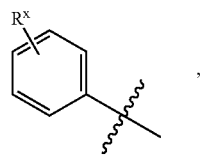

wherein $R^x$ is H, halogen, or alkoxy;

Z is S, O, $CH_2$ or CFH;

$R^3$, $R^4$, $R^5$, $R^8$ and $R^{8'}$ are each H; and $R^6$ and $R^7$ are independently selected from H or methyl;

provided that $R^1$ is selected from isoxazolyl, pyrazolyl, thiazolyl or tetrahydropyridazinyl, where said is isoxazolyl, pyrazolyl, thiazolyl or tetrahydropyridazinyl is unsubstituted or substituted with one or more substituents independently selected from alkyl, haloalkyl, halogen, and hydroxyl when $R^2$ is a substituted or unsubstituted phenylalkyl group or provided that $R^1$ is selected from phenyl, pyrrolyl, pyrrolidinyl, isoxazolyl, pyrazolyl, thiazolyl, tetrahydrofuranyl, furanyl, thienyl or tetrahydropyridazinyt when $R^2$ is a substituted phenylalkyl group and said phenyl moiety of said substituted phenylalkyl group comprises one or more substituents other than halo or methyl, where said one or more substituents is independently selected from haloalkyl, amino, hydroxyl, alkoxy, haloalkoxy, alkylenedioxy, dihaloalkylenedioxy, cycloalkylalkyloxy, dialkylamino, alkylsulfonyl and alkylthio;

or a prodrug, pharmaceutically active metabolite or pharmaceutically active salt or solvate thereof.

In preferred embodiments, this invention relates to compounds of Formula I, above, wherein:

$R^1$ is phenyl, where said phenyl is substituted with one or more substituents independently selected from methyl, halogen or hydroxyl;

$R^2$ is a substituted phenylalkyl group, where said alkyl moiety of said substituted phenylalkyl group is a straight or branched chain alky moiety;

where said phenyl moiety of said substituted phenylalkyl group comprises one or more substituents other than halo or methyl, where said one or more substituents is independently selected from trifluoromethyl, amino, hydroxyl, $C_1$–$C_4$alkoxy, alkylenedioxy, di-fluoro-alkylenedioxy, cyclopropylmethoxy, di-methyl-amino, methanesulfonyl and methylthio;

$R^{2'}$ is H, methyl or ethyl;

X is

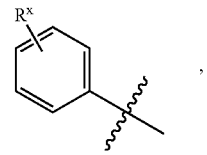

wherein $R^x$ is H;

Z is S or O; and $R^3$, $R^4$, $R^5$, $R^6$, $R^7$, $R^8$ and $R^{8'}$ are each H;

or a prodrug, pharmaceutically active metabolite or pharmaceutically active salt or solvate thereof.

All compounds of this invention contain at least one chiral center and may exist as single stereoisomers (e.g., single enantiomers or single diastereomers), any mixture of stereoisomers (e.g., any mixture of enantiomers or diastereomers) or racemic mixtures thereof. All such single stereoisomers, mixtures and racemates are intended to be encompassed within the broad scope of the present invention. Compounds identified herein as single stereoisomers are meant to describe compounds that are present in a form that contains at least 90% of a single stereoisomer of each chiral center present in the compounds. Where the stereochemistry of the chiral carbons present in the chemical structures illustrated herein is not specified, the chemical structure is intended to encompass compounds containing either stereoisomer of each chiral center present in the compound. Preferably, however, the inventive compounds are used in optically pure, that is, stereoisomerically pure, form or substantially optically pure (substantially stereoisomerically pure) form. As used herein, the term "stereoisomeric" purity (or "optical" purity) refers to the "enantiomeric" purity and/or "diastereomeric" purity of a compound. Compounds that are substantially enantiomerically pure contain at least 90% of a single isomer and preferably contain at least 95% of a single isomer of each chiral center present in the enantiomer. Compounds that are substantially diastereomerically pure contain at least 90% of a single isomer of each chiral center present in the diastereomer, and preferably contain at least 95% of a single isomer of each chiral center. More preferably, the substantially enantiomerically and diastereomerically pure compounds in this invention contain at least 97.5% of a single isomer and most preferably contain at least 99% of a single isomer of each chiral center in the compound. The term Aracemic@ or A"racemic mixture@ refers to a mixture of equal amounts of enantiomeric compounds, which encompasses mixtures of enantiomers and mixtures of enantiomeric diastereomers. The compounds of this invention may be obtained in stereoisomerically pure (i.e., enantiomerically and/or diastereomerically pure) or substantially stereoisomerically pure (i.e., substantially enantiomerically and/or diastereomerically pure) form. Such compounds may be obtained synthetically, according to the procedures described herein using optically pure or substantially optically pure materials. Alternatively, these compounds may be obtained by resolution/separation of a mixture of stereoisomers, including racemic mixtures, using conventional procedures. Exemplary methods that may be useful for the resolution/separation of stereoisomeric mixtures include chromatography and crystallization/recrystallization. Other useful methods may be found in "*Enantiomers, Racemates, and Resolutions,*" J. Jacques et al., 1981, John Wiley and Sons, New York, N.Y., the disclosure of which is incorporated herein by reference. Preferred stereoisomers of the compounds of this invention are described herein.

Especially preferred embodiments of this invention comprise compounds, wherein the stereogenic centers (chiral carbons) have the following designated stereochemistry:

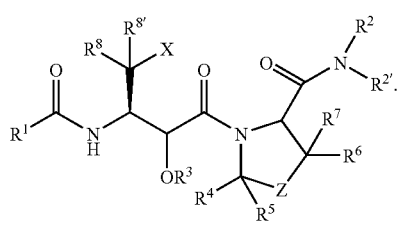

More preferably, at least two of the stereogenic centers have the following designated stereochemistry:

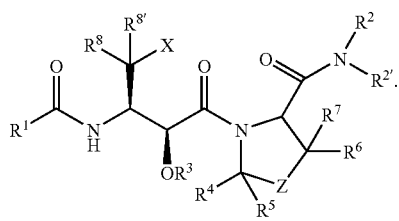

Even more preferably, at least three of the stereogenic centers have the following designated stereochemistry:

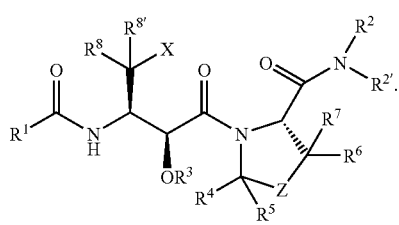

Exemplary compounds of this invention include:

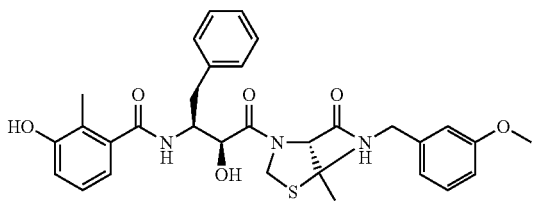
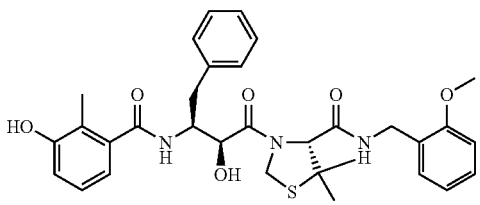

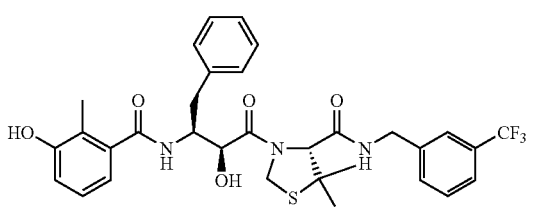
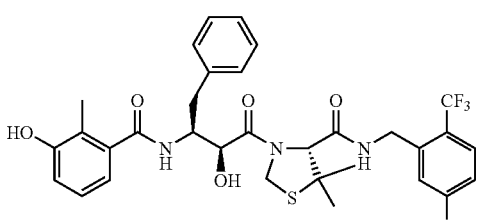

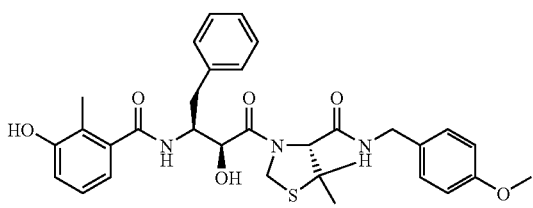
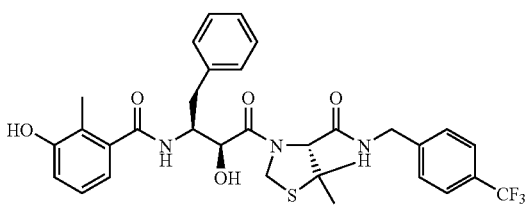

-continued
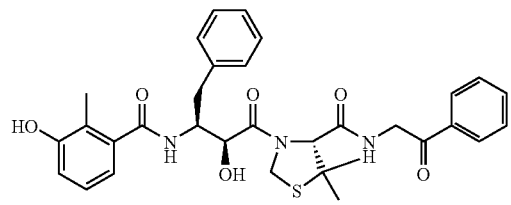
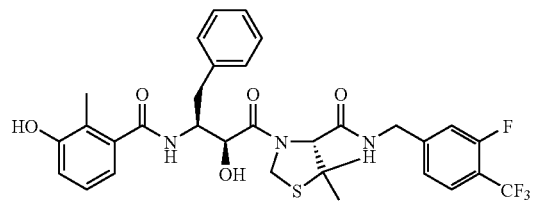
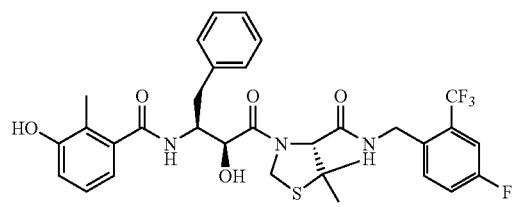
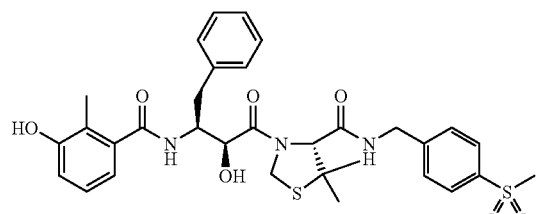
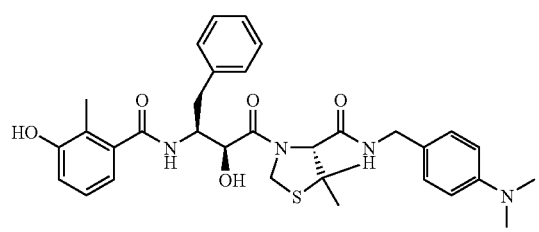
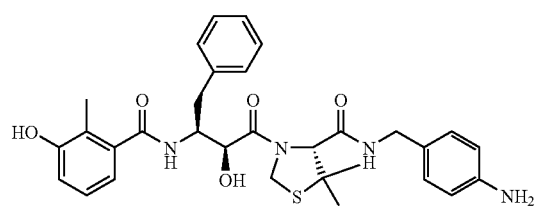
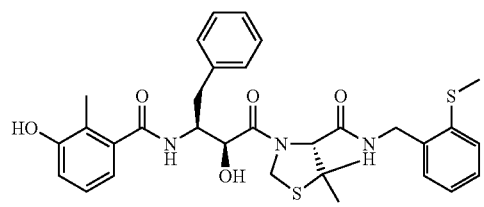
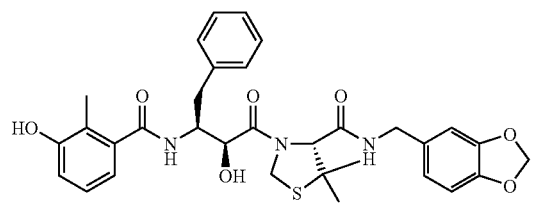
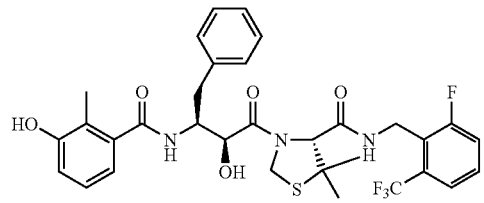
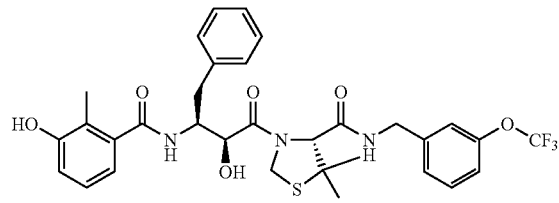
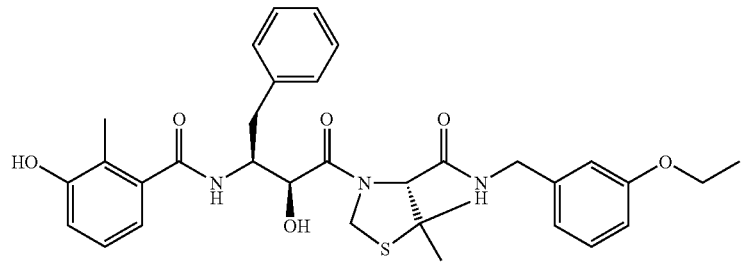
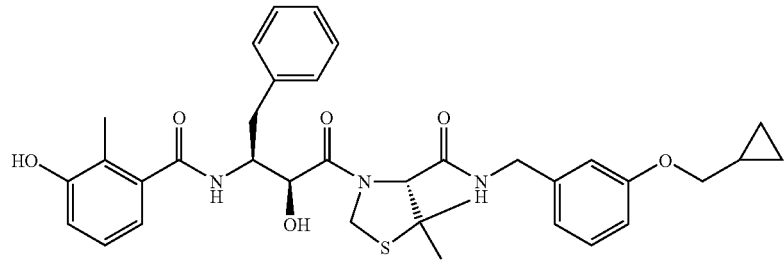

-continued
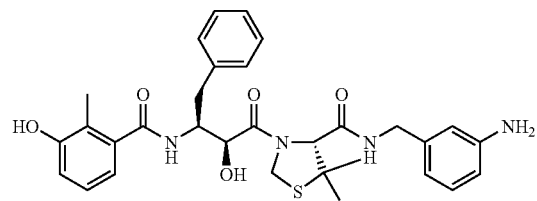
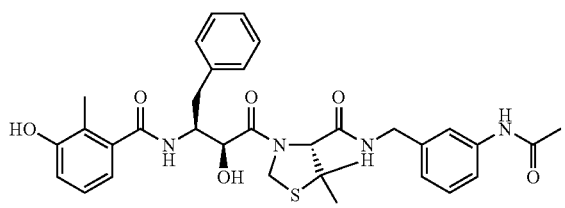
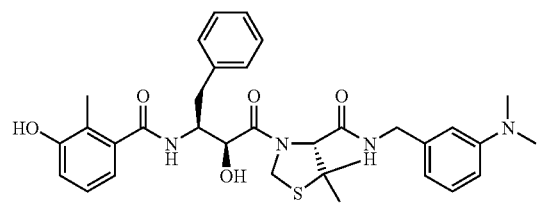
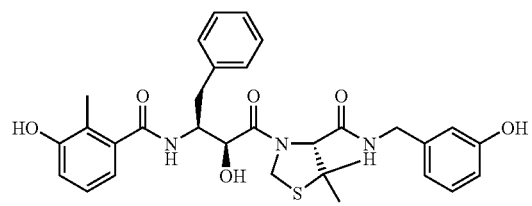
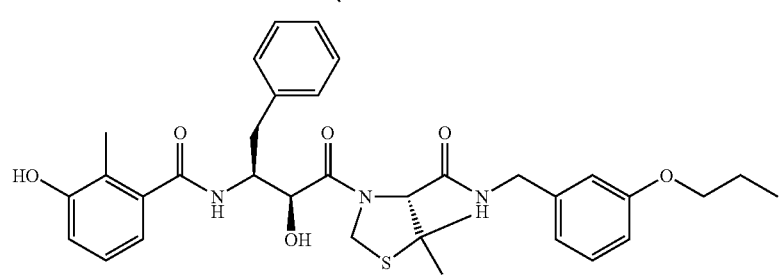
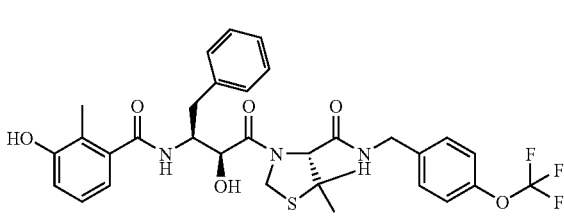
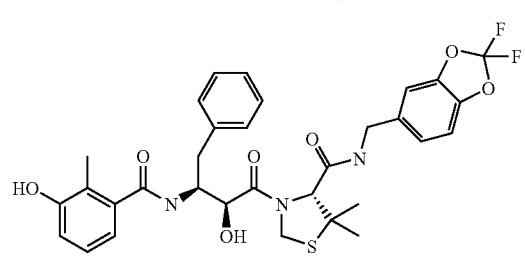
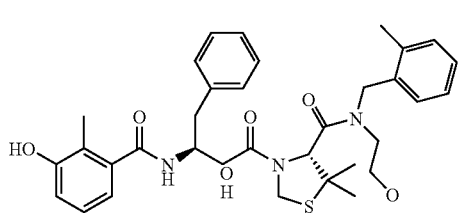
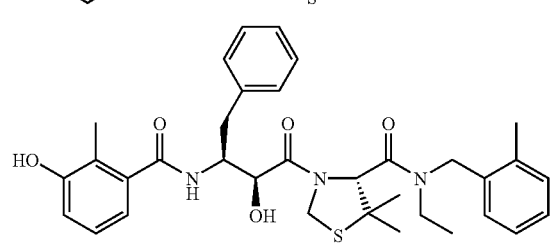
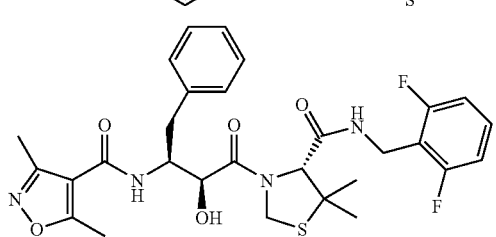
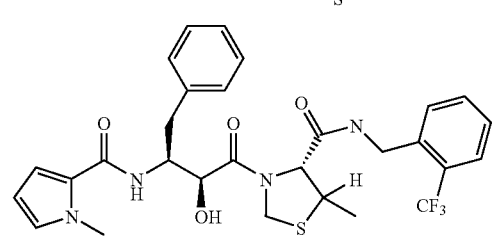
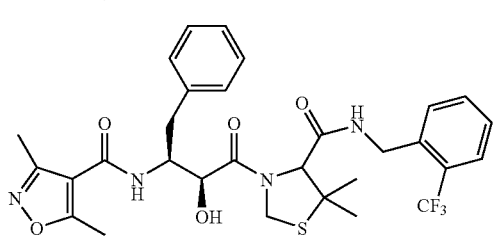

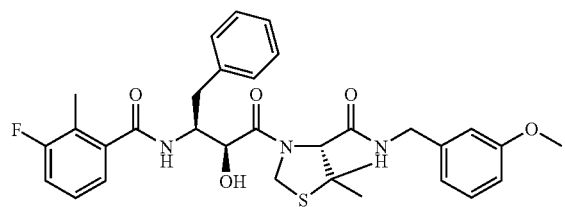
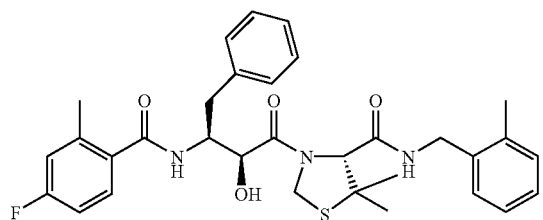
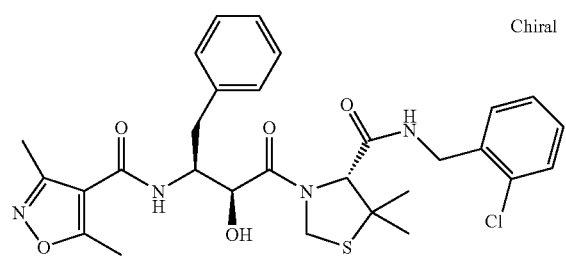
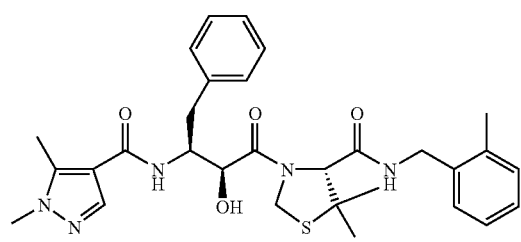
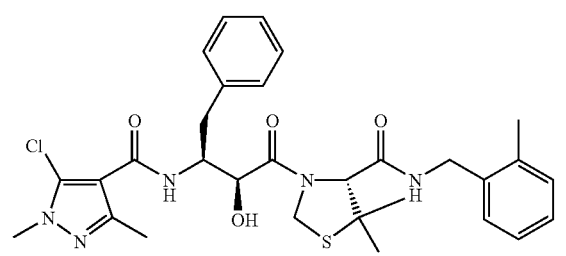
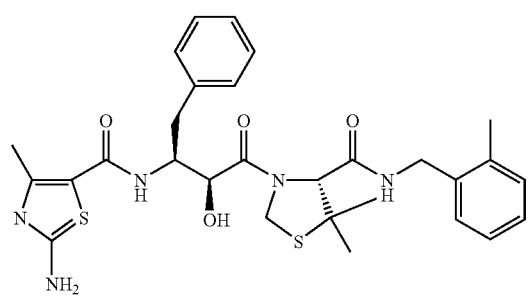
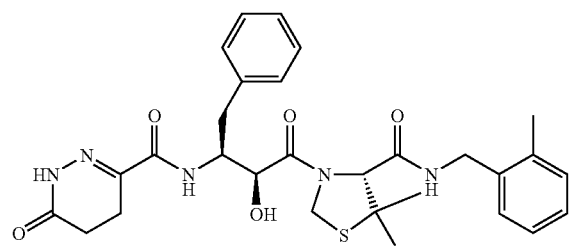
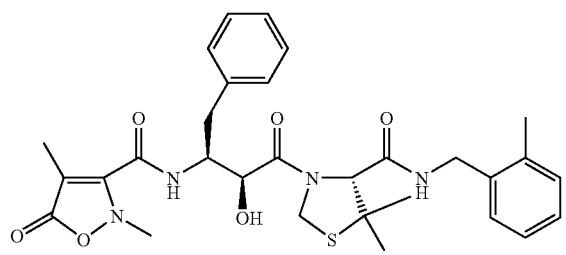
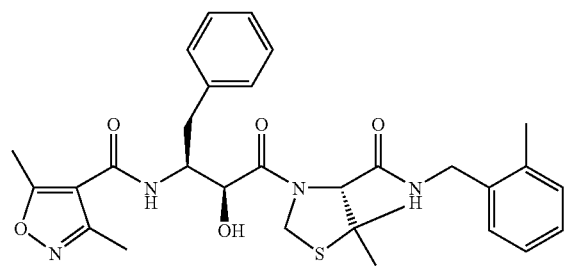
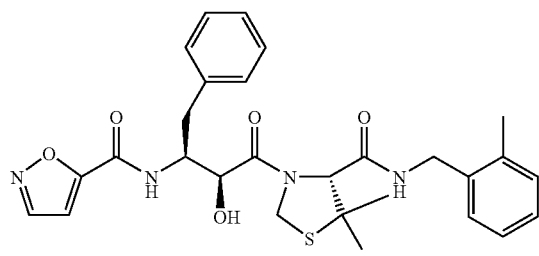
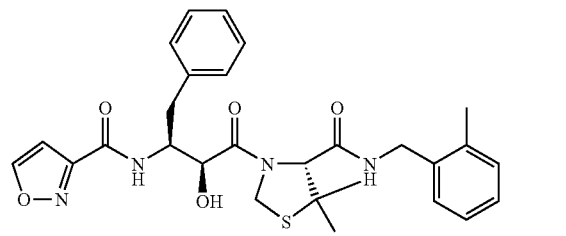
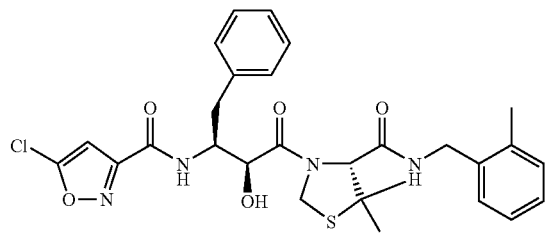

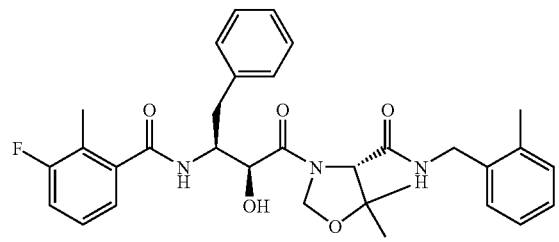
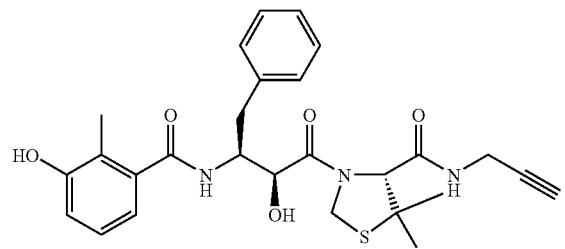
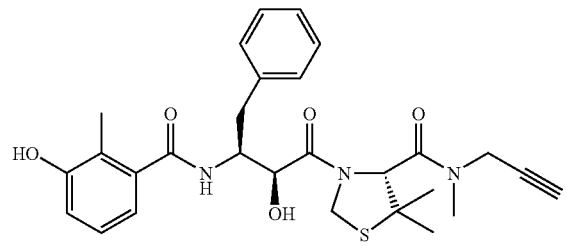
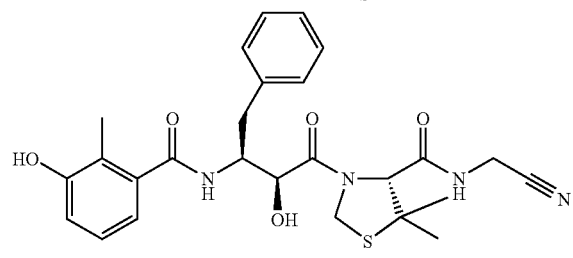
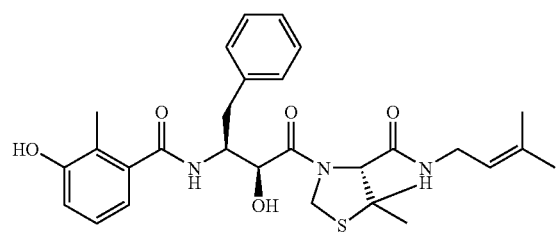
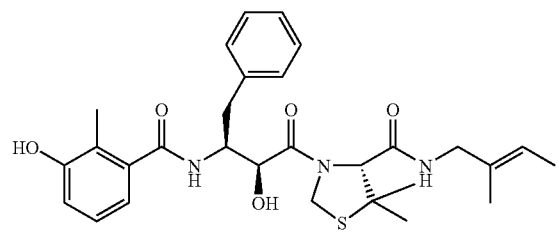
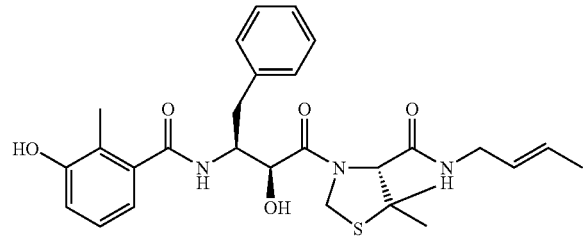
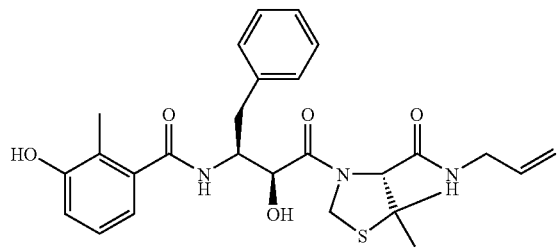
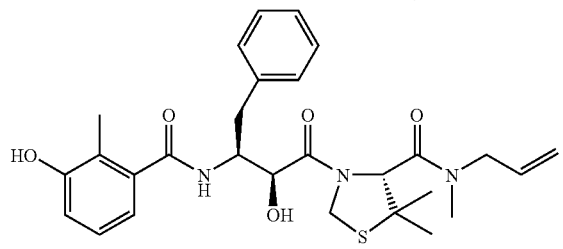
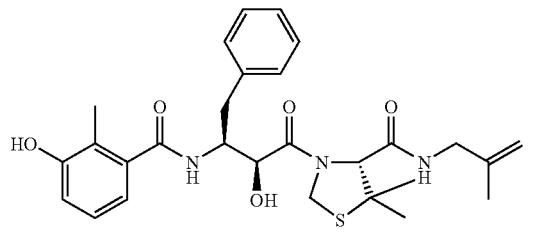
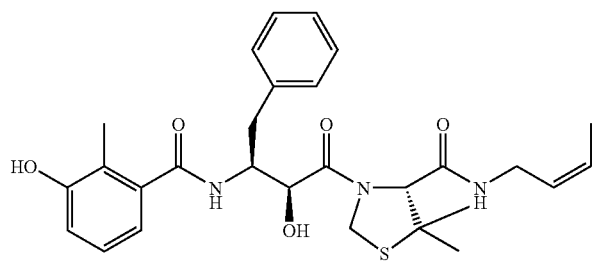
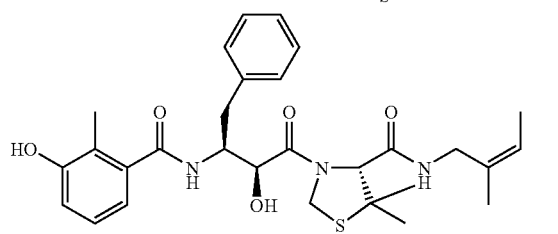
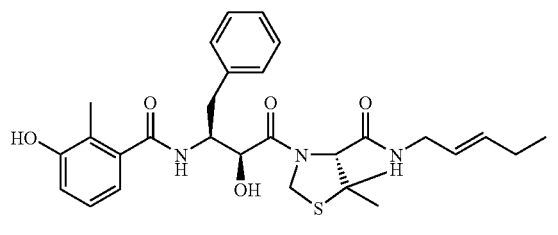
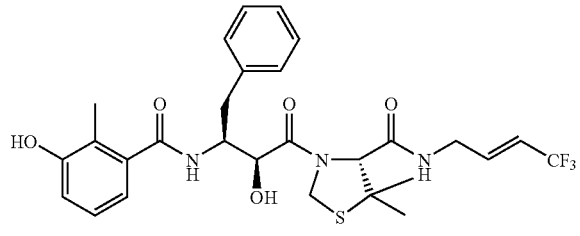

-continued
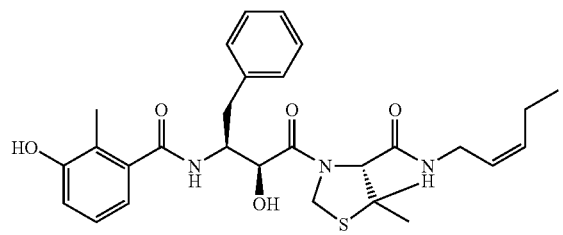
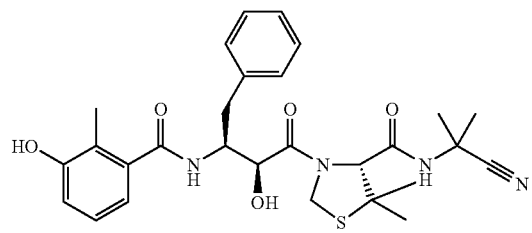
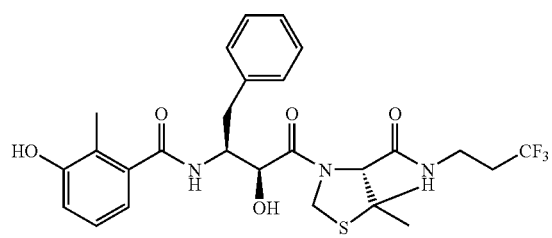
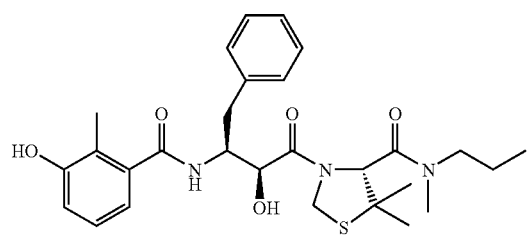
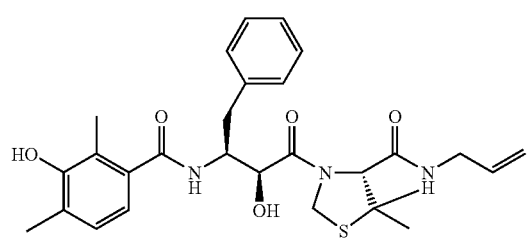
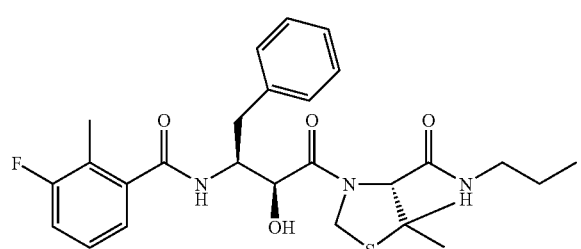
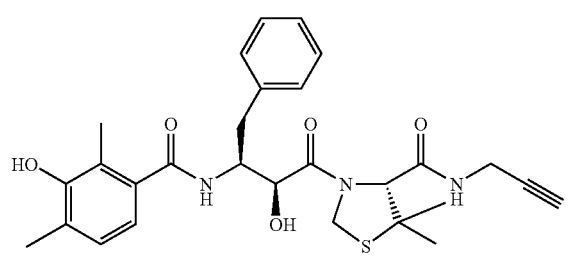
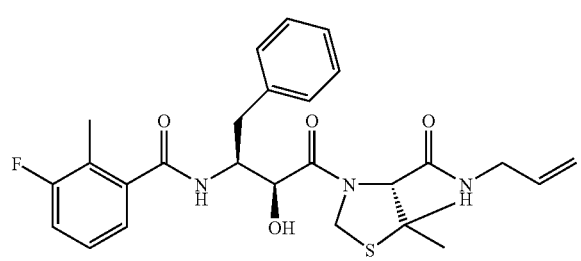
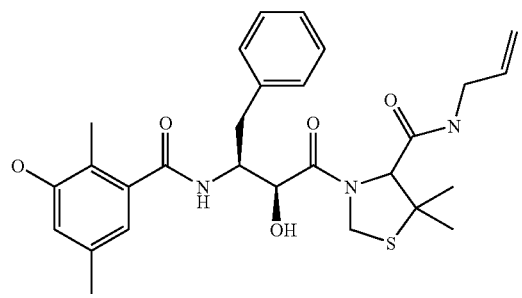
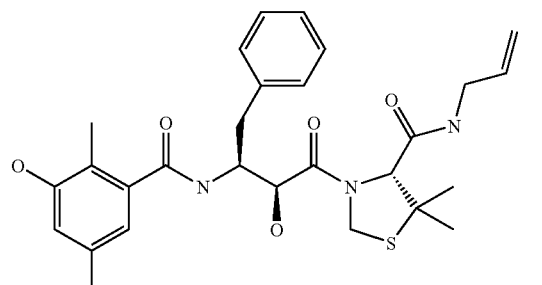
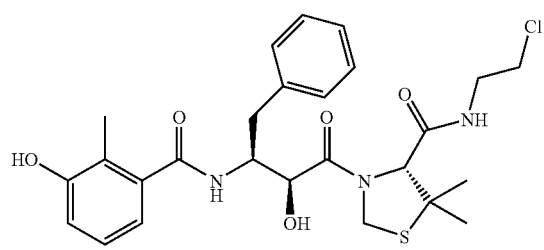
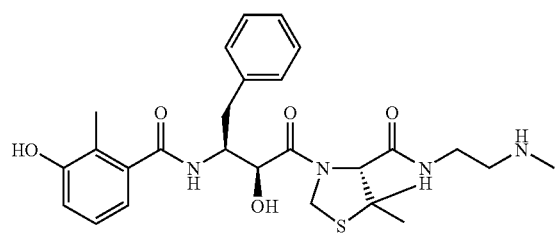

-continued

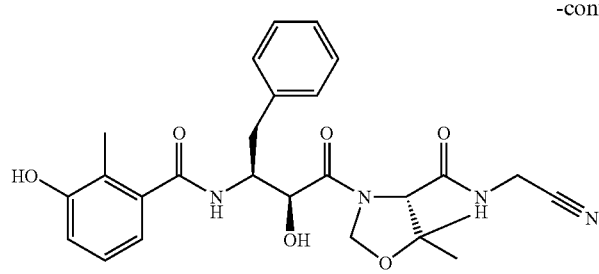

and the prodrugs, pharmaceutically active metabolites, and pharmaceutically acceptable salts and solvates thereof.

The invention is also directed to the intermediates of Formula II, which are useful in the synthesis of certain compounds of Formula I:

20a
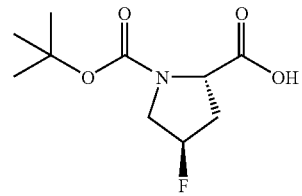

20b
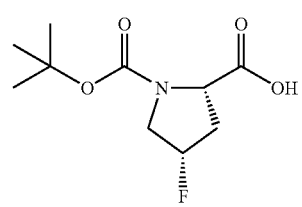

20c
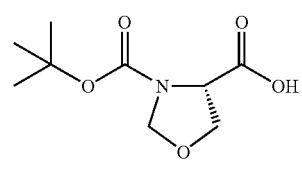

20d
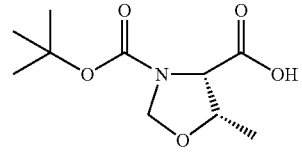

20e
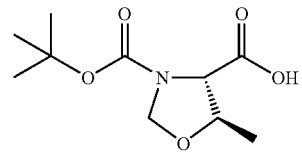

20f
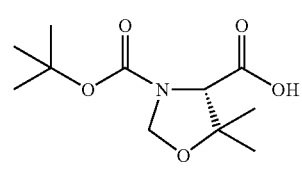

The present invention also provides processes for the preparation of compounds of formula (I-A), or a prodrug, pharmaceutically active metabolite, or pharmaceutically active salt or solvate thereof,

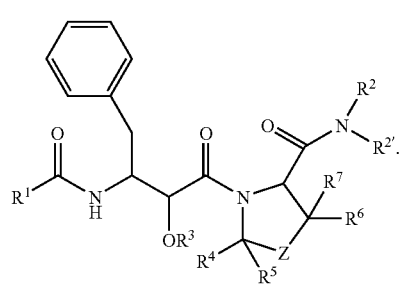
(I-A)

wherein:

R$^1$ is a 5- or 6-membered mono-cyclic carbocyclic or heterocyclic group, wherein said carbocyclic or heterocyclic group is saturated, partially unsaturated or fully unsaturated and is optionally substituted by at least one substituent chosen from C$_{1-6}$ alkyl, hydroxyl, C$_{1-6}$ alkylcarbonyloxy, C$_{6-10}$ arylcarbonyloxy, and heteroarylcarbonyloxy;

R$^2$ is C$_{2-6}$ alkenyl or C$_{1-6}$ alkyl optionally substituted with at least one halogen;

R$^{2'}$ is H or C$_{1-4}$ alkyl;

Z is S, O, SO, SO$_2$, CH$_2$ or CFH;

R$^3$ is H or C$_1$–C$_4$ alkyl; and

R$^4$, R$^5$, R$^6$ and R$^7$ are independently chosen from H and C$_1$–C$_6$ alkyl; comprising:

reacting a compound of formula (II), wherein Y$^1$ is hydroxyl or a leaving group, with a compound of formula (III), or a salt or solvate thereof.

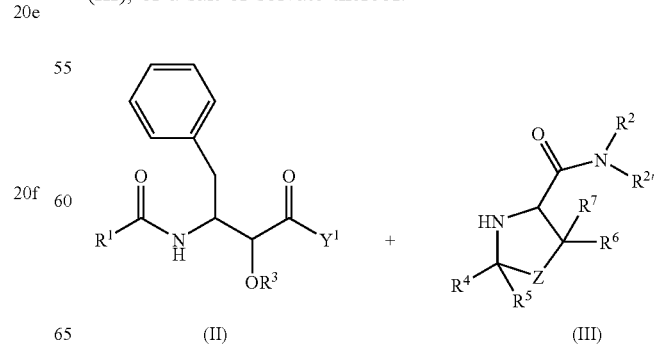
(II)     (III)

In another aspect of the present invention are provided processes for the preparation of compounds of fomula (I-A), wherein in the compounds of formula (II), $Y^1$ is hydroxyl.

In still another aspect of the present invention are provided processes for the preparation of compounds of formula (I), wherein:

$R^1$ is phenyl optionally substituted by at least one substituent independently chosen from $C_{1-6}$ alkyl, hydroxyl, $C_{1-6}$ alkylcarbonyloxy, $C_{6-10}$ arylcarbonyloxy, and heteroarylcarbonytoxy;

$R^2$ is $C_{2-6}$ alkenyl or $C_{1-6}$ alkyl optionally substituted with at least one halogen;

$R^{2'}$ is H or $C_{1-4}$ alkyl;

Z is S, O, SO, $SO_2$, $CH_2$ or CFH;

$R^3$ is H or $C_1$–$C_4$ alkyl; and $R^4$, $R^5$, $R^6$ and $R^7$ are independently chosen from H and methyl.

The present invention also provides processes for the preparation of compounds of formula (I), wherein:

$R^1$ is phenyl optionally substituted by at least one substituent independently chosen from $C_{1-6}$ alkyl, hydroxyl, $C_{1-6}$ alkylcarbonyloxy, $C_{6-10}$ arylcarbonyloxy, and heteroarylcarbonyloxy;

$R^2$ is $C_{2-6}$ alkenyl or $C_{1-6}$ alkyl optionally substituted with at least one halogen;

$R^{2'}$ is H or $C_{1-4}$ alkyl;

Z is S, O, SO, $SO_2$, $CH_2$ or CFH;

$R^3$ is H or $C_1$–$C_4$ alkyl; and $R^4$, $R^5$, $R^6$ and $R^7$ are independently chosen from H and methyl.

In yet another aspect of the present invention are provides processes for the preparation of compounds of formula (I-A), wherein:

$R^1$ is phenyl optionally substituted by at least one substituent independently chosen from $C_{1-6}$ alkyl, hydroxyl, $C_{1-6}$ alkylcarbonyloxy, $C_{6-10}$ arylcarbonyloxy, and heteroarylcarbonyloxy;

$R^2$ is $C_{2-6}$ alkenyl or $C_{1-6}$ alkyl optionally substituted with at least one halogen;

$R^{2'}$ is H;

Z is S, O, SO, or $SO_2$;

$R^3$ is H or $C_1$–$C_4$ alkyl; and $R^4$, $R^5$, $R^6$ and $R^7$ are independently chosen from H and methyl.

Still another aspect of the present invention provides processes for the preparation of compounds of formula (I-A), wherein:

$R^1$ is phenyl optionally substituted by at least one substituent independently chosen from $C_{1-6}$ alkyl, hydroxyl, $C_{1-6}$ alkylcarbonyloxy, $C_{6-10}$ arylcarbonyloxy, and heteroarylcarbonyloxy;

$R^2$ is $C_{2-6}$ alkenyl;

$R^{2'}$ is H;

Z is S, O, SO, or $SO_2$;

$R^3$ is H or $C_1$–$C_4$ alkyl; and $R^4$, $R^5$, $R^6$ and $R^7$ are independently chosen from H and methyl.

The present invention also provides provides processes for the preparation of compounds of formula (I-A), wherein:

$R^1$ is phenyl optionally substituted by at least one substituent independently chosen from $C_{1-6}$ alkyl, hydroxyl, $C_{1-6}$ alkylcarbonyloxy, $C_{6-10}$ arylcarbonyloxy, and heteroarylcarbonyloxy;

$R^2$ is $C_{2-6}$ alkenyl;

$R^{2'}$ is H;

Z is S or O;

$R^3$ is H; and $R^4$, $R^5$, $R^6$ and $R^7$ are independently chosen from H and methyl.

In still a further aspect of the present invention are provided processes for the preparation of compounds of formula (I-A), wherein:

$R^1$ is phenyl optionally substituted by at least one substituent independently chosen from $C_{1-6}$ alkyl, hydroxyl, $C_{1-6}$ alkylcarbonyloxy, $C_{6-10}$ arylcarbonyloxy, and heteroarylcarbonyloxy;

$R^2$ is $C_{2-6}$ alkenyl;

$R^{2'}$ is H;

Z is S;

R3 is H;

$R^4$ and $R^5$ are H; and $R^6$ and $R^7$ are methyl.

In still a further aspect of the present invention are provided processes for the preparation of compounds of formula (I-A), wherein:

$R^1$ is phenyl substituted by at least one substituent independently chosen from $C_{1-6}$ alkyl, hydroxyl, $C_{1-6}$ alkylcarbonyloxy, $C_{6-10}$ arylcarbonyloxy, and heteroarylcarbonyloxy;

$R^2$ is $C_{2-6}$ alkenyl;

$R^{2'}$ is H;

Z is S;

$R^3$ is H;

$R^4$ and $R^5$ are H; and $R^6$ and $R^7$ are methyl.

The present invention also provides processes for the preparation of compounds of formula (I-A), wherein:

$R^1$ is phenyl substituted by $C_{1-6}$ alkyl and hydroxyl;

$R^2$ is allyl;

$R^{2'}$ is H;

Z is S;

$R^3$ is H;

$R^4$ and $R^5$ are H; and $R^6$ and $R^7$ are methyl.

Furthermore, the present invention provides processes for the preparation of compounds of formula (I-A), wherein:

$R^1$ is phenyl substituted by methyl and hydroxyl;

$R^2$ is allyl;

$R^{2'}$ is H;

Z is S;

$R^3$ is H;

$R^4$ and $R^5$ are H; and $R^6$ and $R^7$ are methyl.

Another aspect of the present invention provides processes for the preparation of compounds of formula (I-A), wherein the compound of formula (I-A) is:

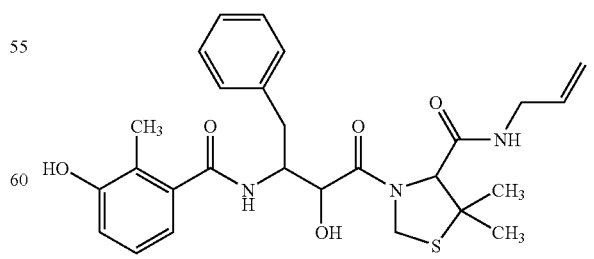

In yet another aspect of the present invention are provided processes for the preparation of compounds of formula (I-A), wherein:

$R^1$ is phenyl substituted by at least one substituent independently chosen from $C_{1-6}$ alkyl and $C_{1-6}$ alkylcarbonyloxy;

$R^2$ is $C_{2-6}$ alkenyl;

$R^{2'}$ is H;

Z is S;

$R^3$ is H;

$R^4$ and $R^5$ are H; and $R^6$ and $R^7$ are methyl.

The present invention further provides processes for the preparation of compounds of formula (I-A), wherein:

$R^1$ is phenyl substituted by methyl and methylcarbonyloxy;

$R^2$ is allyl;

$R^{2'}$ is H;

Z is S;

$R^3$ is H;

$R^4$ and $R^5$ are H; and $R^6$ and $R^7$ are methyl.

Furthermore, the present invention provides processes for the preparation of compounds of formula (I-A), wherein the compound of formula (I-A) is:

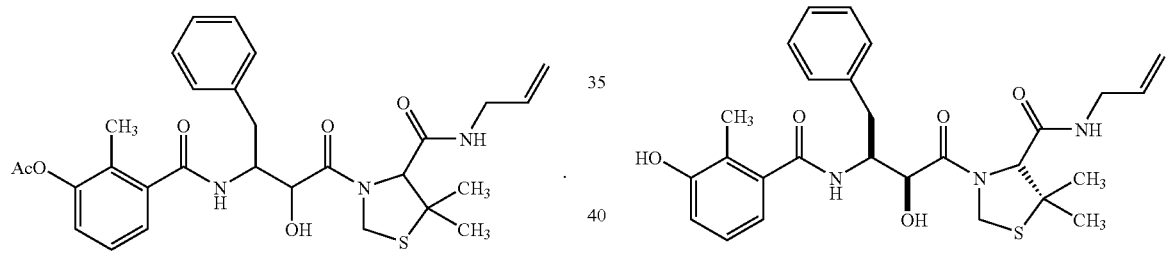

The present invention further provides processes for the preparation of compounds of formula (I-B), (I-B)

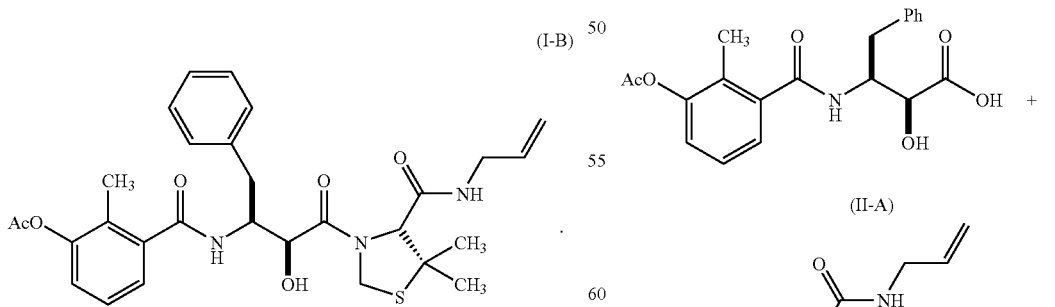

comprising:

reacting a compound of formula (II-A) with a compound of formula (III-A), or a salt or solvate thereof.

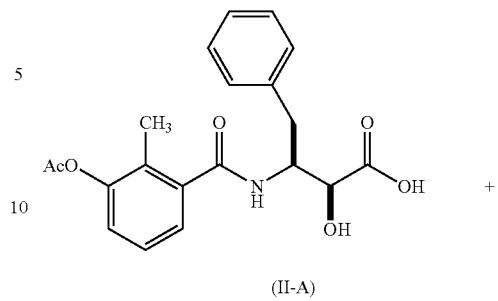

(II-A)

(III-A)

The present invention further provides process for preparing a compound of formula (I-C), (I-C)

comprising:

(i) reacting a compound of formula (II-A) with a compound of formula (III-A), or a salt or solvate thereof,

(II-A)

(III-A)

-continued

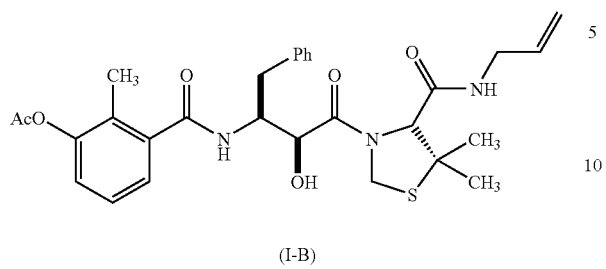

(I-B)

to afford a compound of formula (I-B); and
(ii) deprotecting the compound of formula (I-B).

In yet another aspect of the present invention are provided processes for preparing a compound of formula (I-C),

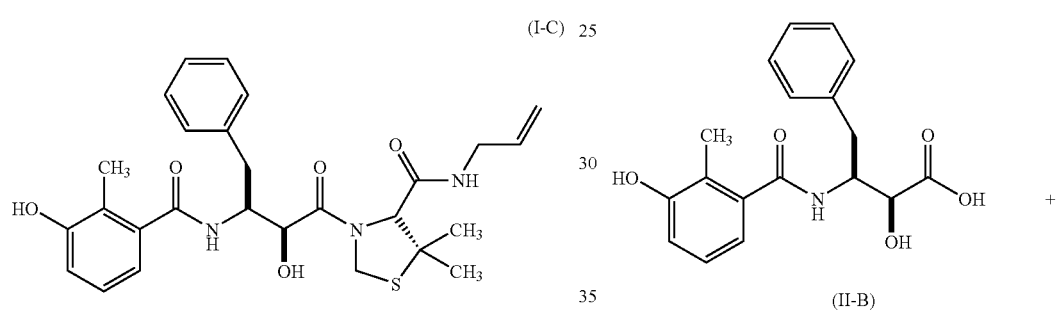

comprising:
reacting a compound of formula (II-B) with a compound of formula (III-A), or a salt or solvate thereof.

The present invention also provides processes for the preparation of a compound of formula (I-C),

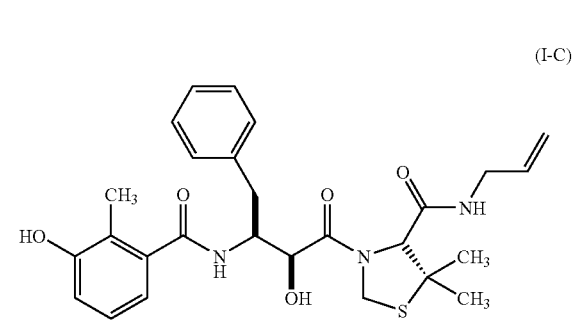

comprising:
reacting a compound of formula (II-B) with a compound of formula (III-A), or a salt or solvate thereof.

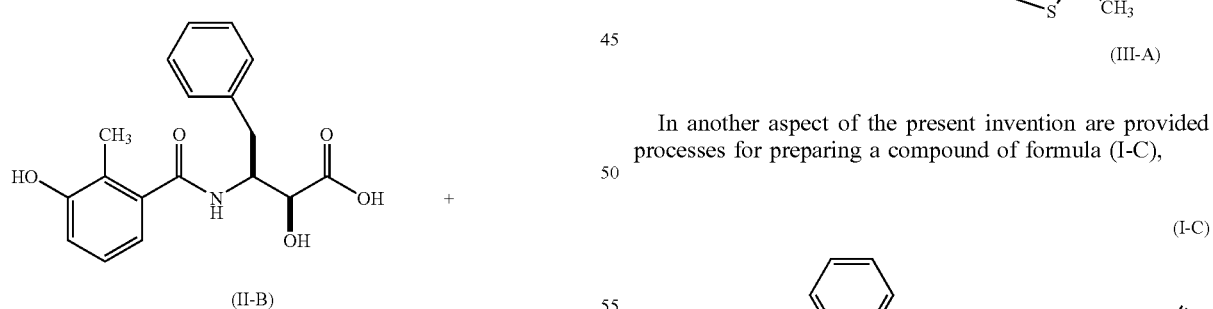

In another aspect of the present invention are provided processes for preparing a compound of formula (I-C),

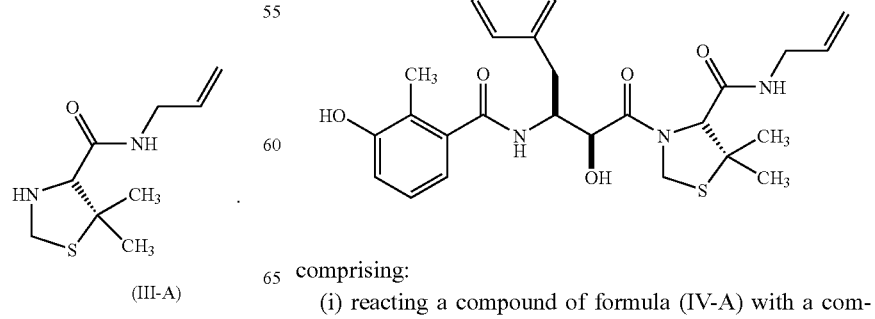

comprising:
(i) reacting a compound of formula (IV-A) with a compound of formula (V-A),

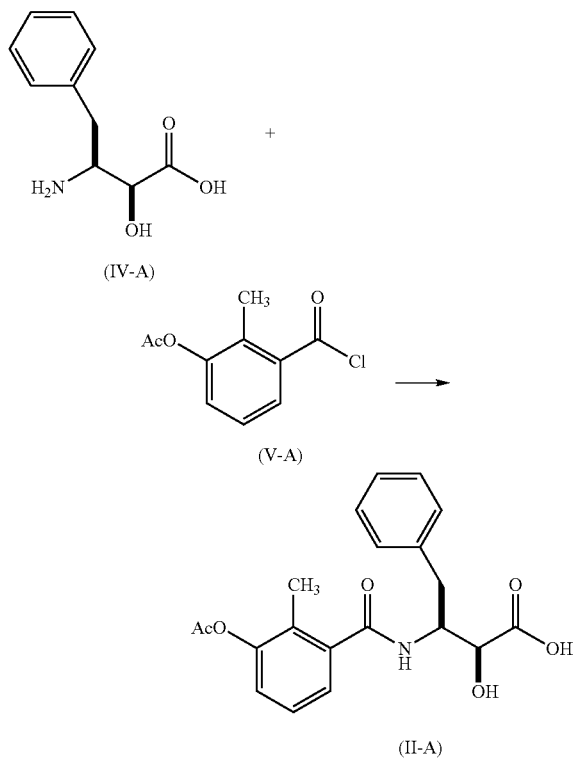

to afford a compound of formula (II-A);

(ii) reacting the compound of formula (II-A) with a compound of formula (III-A), or a salt or solvate thereof,

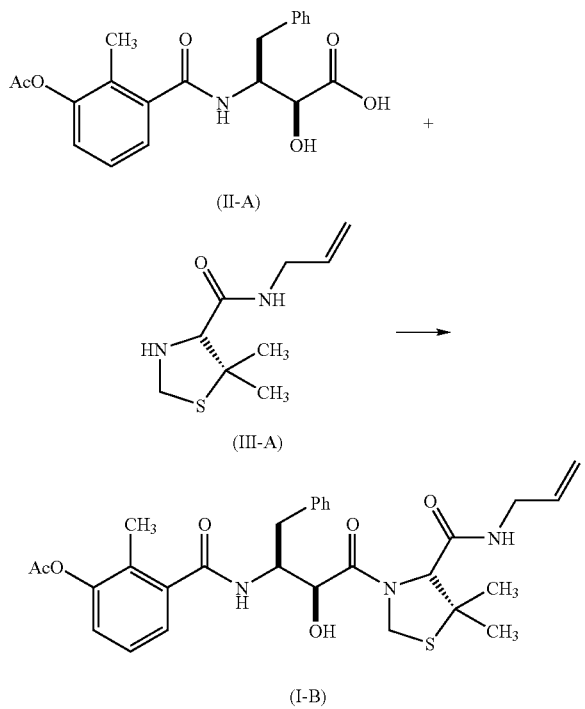

to afford a compound of formula (I-B); and (iii) deprotecting the compound of formula (I-B) to afford the compound of formula (I-C).

The HIV protease inhibitor compounds of this invention include prodrugs, the pharmaceutically active metabolites, and the pharmaceutically acceptable salts and solvates thereof. In preferred embodiments, the compounds of Formula I, prodrugs, pharmaceutically acceptable salts, and pharmaceutically active metabolites and solvates thereof demonstrate an HIV-protease inhibitory activity, corresponding to $K_i$ of at least 100 nM, an $EC_{50}$ of at least 10 mM or an $IC_{50}$ of at least 10 mM. Preferably, the compounds of this invention demonstrate an HIV-protease inhibitory activity, corresponding to a $K_i$ of at least 10 nM, an $EC_{50}$ of at least 1 mM or an $IC_{50}$ of at least 1 mM. More preferably, the compounds of this invention demonstrate an HIV-protease inhibitory activity against mutant strains of HIV, corresponding to a $K_i$ of at least 100 nM, an $EC_{50}$ of at least 10 mM or an $IC_{50}$ of at least 10 mM. Even more preferably, the compounds of this invention demonstrate protease inhibitory activity against mutant strains corresponding to a $K_i$ of at least 10 nM, an $EC_{50}$ of at least 1 mM or an $IC_{50}$ of at least 1 mM.

A "prodrug" is intended to mean a compound that is converted under physiological conditions or by solvolysis or metabolically to a specified compound that is pharmaceutically active. A prodrug may be a derivative of one of the compounds of this invention that contains a moiety, such as for example —$CO_2R$, —$PO(OR)_2$ or —$C=NR$, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for example, an amido, carboxylic acid, or hydroxyl moiety with a suitable reagent. A "pharmaceutically active metabolite" is intended to mean a pharmacologically active compound produced through metabolism in the body of a specified compound. Prodrugs and active metabolites of compounds of this invention of the above-described Formulas may be determined using techniques known in the art, for example, through metabolic studies. See, e.g., "Design of Prodrugs," (Bundgaard, ed.), 1985, Elsevier Publishers B.V., Amsterdam, The Netherlands. The following is an example of a prodrug that can be converted to the compound of this invention under physiological conditions, by solvolysis or metabolically:

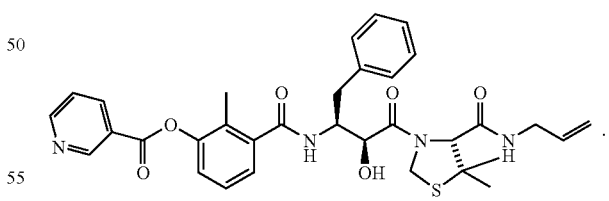

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates (mesylates), propanesulfonates, naphthalene-1-sulfonates, naphthalene-2-sulfonates, and mandelates. A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, and solvates may exist in different crystal forms, all of which are intended to be within the scope of the present invention and specified formulas.

The present invention is also directed to a method of inhibiting HIV protease activity, comprising contacting the protease with an effective amount of a compound of Formula I, or a pharmaceutically acceptable salt, prodrug, pharmaceutically active metabolite, or solvate thereof. For example, HIV protease activity may be inhibited in mammalian tissue by administering a compound of Formula I or a pharmaceutically acceptable salt, prodrug, pharmaceutically active metabolite, or solvate thereof. More preferably, the present method is directed at inhibiting HIV-protease activity. "Treating" or "treatment" is intended to mean at least the mitigation of a disease condition in a mammal, such as a human, that is alleviated by the inhibition of the activity of HIV proteases. The methods of treatment for mitigation of a disease condition include the use of the compounds in this invention in any conventionally acceptable manner, for example, as a prophylactic. The activity of the inventive compounds as inhibitors of HIV protease activity may be measured by any of the suitable methods known to those skilled in the art, including in vivo and in vitro assays. Examples of suitable assays for activity measurements are escribed herein. Administration of the compounds of the Formula I and their pharmaceutically acceptable prodrugs, salts, active metabolites, and solvates may be performed according to any of the generally accepted modes of administration available to those skilled in the art. Illustrative examples of suitable modes of administration include oral, nasal, parenteral, topical, transdermal, and rectal.

An inventive compound of Formula I or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use or mode of administration. Acceptable methods of preparing suitable pharmaceutical forms of the pharmaceutical compositions may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

The present invention includes pharmaceutical compositions useful for inhibiting HIV protease, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV protease, and a method of treating infection by HIV, or of treating AIDS or ARC. Additionally, the present invention is directed to a pharmaceutical composition comprising a therapeutically effective amount of a compound of the present invention in combination with a therapeutically effective amount of an HIV infection/AIDS treatment agent selected from:

1) an HIV/AIDS antiviral agent,
2) an anti-infective agent, and
3) an immunomodulator.

The compounds of the present invention may be administered in combination with an additional agent or agents for the treatment of a mammal, such as a human, that is suffering from an infection with the HIV virus, AIDS, AIDS-related complex (ARC), or any other disease or condition which is related to infection with the HIV virus. The agents that may be used in combination with the compounds of the present invention include, but are not limited to, those useful as HIV protease inhibitors, HIV reverse transcriptase inhibitors, non-nucleoside HIV reverse transcriptase inhibitors, inhibitors of HIV integrase, CCR5 inhibitors, HIV fusion inhibitors, compounds useful as immunomodulators, compounds that inhibit the HIV virus by an unknown mechanism, compounds useful for the treatment of herpes viruses, compounds useful as anti-infectives, and others as described below.

Compounds useful as HIV protease inhibitors that may be used in combination with the compounds of the present invention include, but are not limited to, 141 W94 (amprenavir), CGP-73547, CGP-61755, DMP-450, nelfinavir, ritonavir, saquinavir (invirase), lopinavir, TMC-126, BMS-232632 (atazanavir), palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, TMC-114, DPC-681, DPC-684, fosamprenavir calcium (Lexiva), benzenesulfonamide derivatives disclosed in WO 03053435, R-944, Ro-03-34649, VX-385, GS-224338, OPT-TL3, PL-100, SM-309515, AG-148, DG-35-VIII, DMP-850, GW-5950X, KNI-1039, L-756423, LB-71262, LP-130, RS-344, SE-063, UIC-94-003, Vb-19038, A-77003, BMS-182193, BMS-186318, SM-309515, and JE-2147.

Compounds useful as inhibitors of the HIV reverse transcriptase enzyme that may be used in combination with the compounds of the present invention include, but are not limited to, abacavir (1592U89), FTC, GS-840, lamivudine (3TC), adefovir dipivoxil, beta-fluoro-ddA, ddC (dideoxycytidine, zalcitabine), ddI (dideoxyinsine, didanosine), stavudine (d4T), zidovudine (AZT), tenofovir, amdoxovir, SPD-754, SPD-756, racivir, reverset (DPC-817), MIV-210 (FLG), beta-L-Fd4C (ACH-126443), MIV-310 (alovudine, FLT), dOTC, DAPD, and emtricitabine.

Compounds useful as non-nucleoside inhibitors of the HIV reverse transcriptase enzyme include, but are not limited to, efavirenz, HBY-097, nevirapine, TMC-120 (dapivirine), TMC-125, delaviradine, DPC-083, DPC-961, TMC-120, capravirine, and tricyclic pyrimidinone derivatives as disclosed in WO 03062238.

Compounds useful as CCR5 inhibitors that may be used in combination with the compounds of the present invention include, but are not limited to, TAK-779, SC-351125, SCH-D, UK-427857, PRO-140, and GW-873140 (Ono-4128, AK-602).

Compounds useful as inhibitors of HIV integrase enzyme that may be used in combination with the compounds of the present invention include, but are not limited to, 1,5-naphthyridine-3-carboxamide derivatives disclosed in WO 03062204, compounds disclosed in WO 03047564, compounds disclosed in WO 03049690, and 5-hydroxypyrimidine-4-carboxamide derivatives disclosed in WO 03035076.

Fusion inhibitors for the treatment of HIV that may be used in combination with the compounds of the present invention include, but are not limited to, T20, T-1249, AMD-3100, and fused tricyclic compounds disclosed in JP 2003171381.

Other compounds that are useful inhibitors of HIV that may be used in combination with the compounds of the present invention include, but are not limited to, Soluble CD4, TNX-355, PRO-542, BMS-806, tenofovir disoproxil fumarate, and compounds disclosed in JP 2003119137.

Compounds useful in the treatment or management of infection from viruses other than HIV that may be used in combination with the compounds of the present invention include, but are not limited to, acyclovir, penciclovir, HPMPC, oxetanocin G, AL-721, cidofovir, cytomegalovirus immune globin, cytovene, ganciclovir, famciclovir, Isis 2922, KNI-272, valaciclovir, and virazole ribavirin.

Compounds that act as immunomodulators and may be used in combination with the compounds of the present invention include, but are not limited to, AD-439, AD-519, Alpha Interferon, AS-101, bropirimine, acemannan, CL246, 738, EL 10, FP-21399, gamma interferon, granulocyte macrophage colony stimulating factor, IL-2, immune globulin intravenous, IMREG-1, IMREG-2, imuthiol diethyl dithio carbamate, alpha-2 interferon, methionine-enkephalin, MTP-PE, granulocyte colony stimulating sactor, remune, rCD4, recombinant soluble human CD4, interferon alfa-2, SK&F106528, soluble T4 yhymopentin, tumor necrosis factor (TNF), tucaresol, recombinant human interferon beta, and interferon alfa n-3.

Anti-infectives that may be used in combination with the compounds of the present invention include, but are not limited to, clindamycin with primaquine, fluconazole, pastill, ornidyl, eflornithine pentamidine, spiramycin, intraconazole-R51211, trimetrexate, daunorubicin, recombinant human erythropoietin, recombinant human growth hormone, megestrol acetate, testerone, and total enteral nutrition.

Other compounds that may be used in combination with the compounds of the present invention include, but are not limited to, acmannan, ansamycin, LM 427, AR177, BMS-232623, BMS-234475, CI-1012, curdlan sulfate, dextran sulfate, STOCRINE EL10, hypericin, lobucavir, novapren, peptide T octabpeptide sequence, trisodium phosphonoformate, probucol, and RBC-CD4.

In addition, the compounds of the present invention may be used in combination with compounds that act as inhibitors of metallo-matrix proteases, so-called MMP inhibitors.

The particular choice of an additional agent or agents will depend on a number of factors that include, but are not limited to, the condition of the mammal being treated, the particular condition or conditions being treated, the identity of the compound or compounds of the present invention and the additional agent or agents, and the identity of any additional compounds that are being used to treat the mammal. The particular choice of the compound or compounds of the invention and the additional agent or agents is within the knowledge of one of ordinary skill in the art.

The compounds of the present invention may be administered in combination with any of the above additional agents for the treatment of a mammal, such as a human, that is suffering from an infection with the HIV virus, AIDS, AIDS-related complex (ARC), or any other disease or condition which is related to infection with the HIV virus. Such a combination may be administered to a mammal such that a compound or compounds of the present invention are present in the same formulation as the additional agents described above. Alternatively, such a combination may be administered to a mammal suffering from infection with the HIV virus such that the compound or compounds of the present invention are present in a formulation that is separate from the formulation in which the additional agent is found. If the compound or compounds of the present invention are administered separately from the additional agent, such administration may take place concomitantly or sequentially with an appropriate period of time in between. The choice of whether to include the compound or compounds of the present invention in the same formulation as the additional agent or agents is within the knowledge of one of ordinary skill in the art.

Additionally, the compounds of the present invention may be administered to a mammal, such as a human, in combination with an additional agent that has the effect of increasing the exposure of the mammal to a compound of the invention. The term "exposure," as used herein, refers to the concentration of a compound of the invention in the plasma of a mammal as measured over a period of time. The exposure of a mammal to a particular compound can be measured by administering a compound of the invention to a mammal in an appropriate form, withdrawing plasma samples at predetermined times, and measuring the amount of a compound of the invention in the plasma using an appropriate analytical technique, such as liquid chromatography or liquid chromatography/mass spectroscopy. The amount of a compound of the invention present in the plasma at a certain time is determined and the concentration and time data from all the samples are plotted to afford a curve. The area under this curve is calculated and affords the exposure of the mammal to the compound. The terms "exposure," "area under the curve," and "area under the concentration/time curve" are intended to have the same meaning and may be used interchangeably throughout.

Among the agents that may be used to increase the exposure of a mammal to a compound of the present invention are those that can as inhibitors of at least one isoform of the cytochrome P450 (CYP450)enzymes. The isoforms of CYP450 that may be beneficially inhibited include, but are not limited to, CYP1A2, CYP2D6, CYP2C9, CYP2C 19 and CYP3A4. Suitable agents that may be used to inhibit CYP 3A4 include, but are not limited to, ritonavir.

Such a combination may be administered to a mammal such that a compound or compounds of the present invention are present in the same formulation as the additional agents described above. Alternatively, such a combination may be administered such that the compound or compounds of the present invention are present in a formulation that is separate from the formulation in which the additional agent is found. If the compound or compounds of the present invention are administered separately from the additional agent, such administration may take place concomitantly or sequentially with an appropriate period of time in between. The choice of whether to include the compound or compounds of the present invention in the same formulation as the additional agent or agents is within the knowledge of one of ordinary skill in the art.

The present invention also includes the use of a compound of the present invention as described above in the preparation of a medicament for (a) inhibiting HIV protease, (b) preventing or treating infection by HIV, or (c) treating AIDS or ARC.

The present invention further includes the use of any of the HIV protease inhibiting compounds of the present invention as described above in combination with one or more HIV infection/AIDS treatment agents selected from an HIV/AIDS antiviral agent, an anti-infective agent, and an immunomodulator for the manufacture of a medicament for (a) inhibiting HIV protease, (b) preventing or treating infection by HIV, or (c) treating AIDS or ARC, said medicament comprising an effective amount of the HIV protease inhibitor compound and an effective amount of the one or more treatment agents.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension. A dose of the pharmaceutical composition contains at least a therapeutically effective amount of the active compound (i.e., a compound of Formula I or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of HIV protease activity, by any known or suitable method of administering the dose, including: topically (for example, as an ointment or cream), orally, rectally (for example, as a suppository), parenterally (by injection) or continuously by intravaginal, intranasal, intrabronchial, intraaural, or intraocular infusion. A "therapeutically effective amount" is intended to mean the amount of an inventive agent that, when administered to a mammal in need thereof, is sufficient to effect treatment for disease conditions alleviated by the inhibition of the activity of one or more variant of the HIV protease. The amount of a given compound of the invention that will be therapeutically effective will vary depending upon factors such as the particular compound, the disease condition and the severity thereof, the identity of the mammal in need thereof, which amount may be routinely determined by artisans.

The compounds of this invention are also useful in the preparation and execution of screening assays for antiviral compounds. For example, the compounds of this invention are useful for isolating enzyme mutants that are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

General Synthetic Methods

Compounds of formula (I-A),

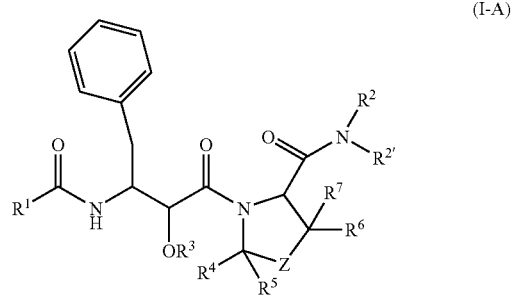

wherein $R^1$ is a 5- or 6-membered mono-cyclic carbocyclic or heterocyclic group, wherein said carbocyclic or heterocyclic group is saturated, partially unsaturated or fully unsaturated and is substituted by at least one hydroxyl, and Z, $R^2$, $R^{2'}$, $R^3$, $R^4$, $R^5$, $R^6$, and are as hereinbefore defined, may be prepared from compounds of formula (I-A) wherein $R^1$ is a 5- or 6-membered mono-cyclic carbocyclic or heterocyclic group, wherein said carbocyclic or heterocyclic group is saturated, partially unsaturated or fully unsaturated and is substituted by at least one substituent chosen from $C_{1-6}$ alkylcarbonyloxy, $C_{6-10}$ arylcarbonyloxy, and heteroarylcarbonyloxy. The $C_{1-6}$ alkylcarbonyloxy, $C_{6-10}$ arylcarbonyloxy, and heteroarylcarbonyloxy groups may be cleaved under conditions that directly provide the desired hydroxy substituted compounds of the invention. In general, the $C_{1-6}$ alkylcarbonyloxy, $C_{6-10}$ arylcarbonyloxy, and heteroarylcarbonyloxy groups may be cleaved under basic conditions, in a solvent that will not interfere with the desired transformation, and at a temperature that is compatible with the other reaction parameters, all of which are known to those of ordinary skill in the art. For example, appropriate bases include, but are not limited to, sodium bicarbonate, potassium bicarbonate, sodium carbonate, potassium carbonate, sodium hydroxide, potassium hydroxide, a sodium alkoxide such as sodium methoxide or sodium ethoxide, a potassium alkoxide such as potassium methoxide or potassium ethoxide, or a base formed in situ using an appropriate combination of reagents, such as a combination of a trialkyl or aryl amine in combination with an alkanol such as methanol. Or such a transformation may be accomplished using an acid that is known to those of skill in the art to be appropriate to cleave such a group without interfering with the desired transformation. Such acids include, but are not limited to, hydrogen halides such as hydrochloric acid or hydroiodic acid, an alkyl sulfonic acid such as methanesulfonic acid, an aryl sulfonic acid such as benzenesulfonic acid, nitric acid, sulfuric acid, perchloric acid, or chloric acid. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Finally, these transformations may be conducted at temperatures from −20° C. to 100° C., depending on the specific reactants and solvents and is within the skill of one of ordinary skill in the art. Further suitable reaction conditions may be found in T. Greene and P. Wuts, *Protective Groups in Organic Synthesis* (3$^{rd}$ ed.), John Wiley & Sons, NY (1999).

For example, the compound of Example A1 was prepared by cleaving an acetate protecting group using 4N hydrochloric acid in a mixture of methanol and 1,4-dioxane at room temperature.

situ from an appropriate combination of agents. Furthermore, such reactions may be performed in a solvent that is compatible with the reaction conditions and will not interfere with the desired transformation. For example, suitable solvents may include alkyl esters, alkylaryl esters, aryl esters, alkyl ethers, aryl ethers, alkylaryl esters, cyclic ethers, hydrocarbons, alcohols, halogenated solvents, alkyl nitriles, aryl nitriles, alkyl ketones, aryl ketones, alkylaryl ketones, or non-protic heterocyclic compounds. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetoni-

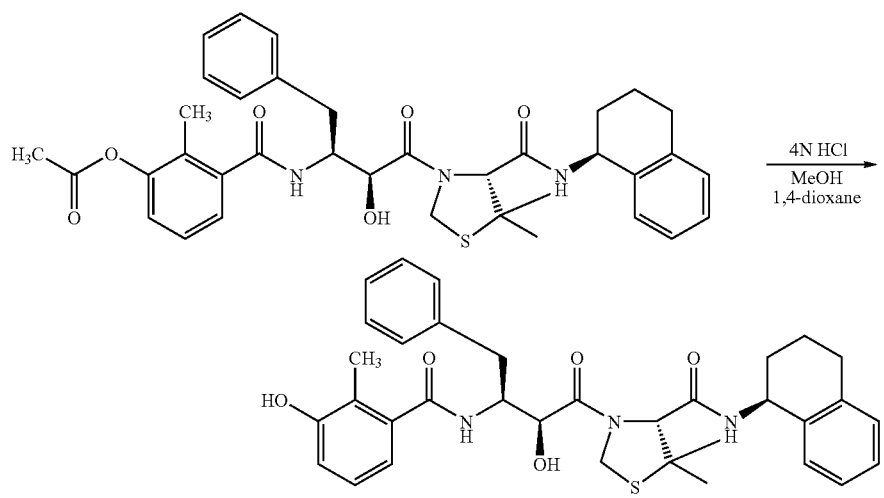

Example A1

Compounds of formula (I-A) wherein R$^3$ is hydrogen and Z, R$^1$, R$^2$, R$^{2'}$, R$^4$, R$^5$, R$^6$, and R$^7$, are as hereinbefore defined, may be prepared from compounds of formula (I-A) wherein R$^3$ is a hydroxyl protecting group. The choice of a suitable hydroxy protecting group is within the knowledge of one of ordinary skill in the art. Suitable hydroxyl protecting groups that are useful in the present invention include, but are not limited to, alkyl or aryl esters, alkyl silanes, aryl silanes or alkylaryl silanes, alkyl or aryl carbonates, benzyl groups, substituted benzyl groups, ethers, or substituted ethers. The various hydroxy protecting groups can be suitably cleaved utilizing a number of reaction conditions known to those of ordinary skill in the art. The particular conditions used will depend on the particular protecting group as well as the other functional groups contained in the subject compound. Choice of suitable conditions is within the knowledge of those of ordinary skill in the art.

For example, if the hydroxy protecting group is an alkyl or aryl ester, cleavage of the protecting group may be accomplished using a suitable base, such as a carbonate, a bicarbonate, a hydroxide, an alkoxide, or a base formed in trile, benzonitrile, acetone, 2-butanone, benzene, toluene, anisole, xylenes, and pyridine, or any mixture of the above solvents. Additionally, water may be used as a co-solvent in this transformation if necessary. Finally, such reactions may be performed at an appropriate temperature from −20° C. to 100° C., depending on the specific reactants used. The choice of a suitable temperature is within the knowledge of one of ordinary skill in the art. Further suitable reaction conditions may be found in T. Greene and P. Wuts, *Protective Groups in Organic Synthesis* (3$^{rd}$ ed.), John Wiley & Sons, NY (1999).

Additionally, if R$^3$ is an alkyl silane, aryl silane or alkylaryl silane, such groups may be cleaved under conditions known to those of ordinary skill in the art. For example, such silane protecting groups may be cleaved by exposure of the subject compound to a source of fluoride ions, such as the use of an organic fluoride salt such as a tetraalkylammonium fluoride salt, or an inorganic fluoride salt. Suitable fluoride ion sources include, but are not limited to, tetramethylammonium fluoride, tetraethylammonium fluoride, tetrapropylammonium fluoride, tetrabutylammonium fluoride, sodium fluoride, and potassium fluoride.

Alternatively, such silane protecting groups may be cleaved under acidic conditions using organic or mineral acids, with or without the use of a buffering agent. For example, suitable acids include, but are not limited to, hydrofluoric acid, hydrochloric acid, sulfuric acid, nitric acid, acetic acid, citric acid, and methanesulfonic acid. Such silane protecting groups may also be cleaved using appropriate Lewis acids. For example, suitable Lewis acids include, but are not limited to, dimethylbromo borane, triphenylmethyl tetrafluoroborate, and certain Pd (II) salts. Such silane protecting groups can also be cleaved under basic conditions that employ appropriate organic or inorganic basic compounds. For example, such basic compounds include, but are not limited to, sodium carbonate, potassium carbonate, sodium bicarbonate, potassium bicarbonate, sodium hydroxide, and potassium hydroxide. The cleavage of a silane protecting group may be conducted in an appropriate solvent that is compatible with the specific reaction conditions chosen and will not interfere with the desired transformation. Among such suitable solvents are, for example, alkyl esters, alkylaryl esters, aryl esters, alkyl ethers, aryl ethers, alkylaryl esters, cyclic ethers, hydrocarbons, alcohols, halogenated solvents, alkyl nitriles, aryl nitriles, alkyl ketones, aryl ketones, alkylaryl ketones, or non-protic heterocyclic compounds. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Finally, such reactions may be performed at an appropriate temperature from −20° C. to 100° C., depending on the specific reactants used. The choice of a suitable temperature is within the knowledge of one of ordinary skill in the art. Further suitable reaction conditions may be found in T. Greene and P. Wuts, *Protective Groups in Organic Synthesis* (3$^{rd}$ ed.), John Wiley & Sons, NY (1999).

When $R^3$ is a benzyl or substituted benzyl ether, cleavage of the protecting group may be accomplished by treating the subject compound with hydrogen in the presence of a suitable catalyst, oxidation with suitable compounds, exposure to light of particular wavelengths, electrolysis, treatment with protic acids, or treatment with Lewis acids. The choice of particular reagents to effect such a transformation will depend on the specific subject compound used and is within the skill of one of ordinary skill in the art. For example, such benzyl or substituted benzyl ethers may be cleaved using hydrogen gas in the presence of an appropriate catalyst. Suitable catalysts include, but are not limited to, 5% palladium on carbon, 10% palladium on carbon, 5% platinum on carbon, or 10% platinum on carbon. The choice of a particular catalyst and the amounts of catalyst, the amount of hydrogen gas, and the hydrogen gas pressure used to effect the desired transformation will depend upon the specific subject compound and the particular reaction conditions utilized. Such choices are within the skill of one of ordinary skill in the art. Furthermore, such benzyl and substituted benzyl ethers may be cleaved under oxidative conditions in which a suitable amount of an oxidizer is used. Such suitable oxidizers include, but are not limited to, dichlorodicyanoquinone (DDQ), ceric ammonium nitrate (CAN), ruthenium oxide in combination with sodium periodate, iron (III) chloride, or ozone. Additionally, such ethers may be cleaved using an appropriate Lewis acid. Such suitable Lewis acids include, but are not limited to, dimethylbromo borane, triphenylmethyl tetrafluoroborate, sodium iodide in combination with trifluoroborane-etherate, trichloroborane, or tin (IV) chloride. The cleavage of a benzyl or substituted benzyl ether protecting group may be conducted in an appropriate solvent that is compatible with the specific reaction conditions chosen and will not interfere with the desired transformation. Among such suitable solvents are, for example, alkyl esters, alkylaryl esters, aryl esters, alkyl ethers, aryl ethers, alkylaryl esters, cyclic ethers, hydrocarbons, alcohols, halogenated solvents, alkyl nitriles, aryl nitriles, alkyl ketones, aryl ketones, alkylaryl ketones, or non-protic heterocyclic compounds. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Finally, such reactions may be performed at an appropriate temperature from −20° C. to 100° C., depending on the specific reactants used. The choice of a suitable temperature is within the knowledge of one of ordinary skill in the art. Further suitable reaction conditions may be found in T. Greene and P. Wuts, *Protective Groups in Organic Synthesis* (3$^{rd}$ ed.), John Wiley & Sons, NY (1999).

When $R^3$ is methyl, cleavage of the protecting group may be accomplished by treating the subject compound with organic or inorganic acids or Lewis acids. The choice of a particular reagent will depend upon the type of methyl ether present as well as the other reaction conditions. The choice of a suitable reagent for cleaving a methyl ether is within the knowledge of one of ordinary skill in the art. Examples of suitable reagents include, but are not limited to, hydrochloric acid, sulfuric acid, nitric acid, para-toluenesulfonic acid, or Lewis acids such as boron trifluoride etherate. These reactions may be conducted in solvents that are compatible with the specific reaction conditions chosen and will not interfere with the desired transformation. Among such suitable solvents are, for example, alkyl esters, alkylaryl esters, aryl esters, alkyl ethers, aryl ethers, alkylaryl esters, cyclic ethers, hydrocarbons, alcohols, halogenated solvents, alkyl nitriles, aryl nitriles, alkyl ketones, aryl ketones, alkylaryl ketones, or non-protic heterocyclic compounds. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Finally, such reactions may be performed at an appropriate temperature from −20° C. to 100° C., depending on the specific reactants used. The choice of a suitable temperature is within the skill of one of ordinary skill in the art. Further suitable reaction conditions may be found in T. Greene and P. Wuts, *Protective Groups in Organic Synthesis* (3rd ed.), John Wiley & Sons, NY (1999).

When $R^3$ is a carbonate, cleavage of the protecting group may be accomplished by treating the subject compound with suitable basic compounds Such suitable basic compounds may include, but are not limited to, sodium carbonate, sodium bicarbonate, potassium carbonate, potassium bicarbonate, sodium hydroxide, or potassium hydroxide. The choice of a particular reagent will depend upon the type of carbonate present as well as the other reaction conditions. These reactions may be conducted in solvents that are compatible with the specific reaction conditions chosen and will not interfere with the desired transformation. Among such suitable solvents are, for example, alkyl esters, alkylaryl esters, aryl esters, alkyl ethers, aryl ethers, alkylaryl esters, cyclic ethers, hydrocarbons, alcohols, halogenated solvents, alkyl nitriles, aryl nitriles, alkyl ketones, aryl ketones, alkylaryl ketones, or non-protic heterocyclic compounds. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Finally, such reactions may be performed at an appropriate temperature from −20° C. to 100° C., depending on the specific reactants used. The choice of a suitable temperature is within the knowledge of one of ordinary skill in the art. Further suitable reaction conditions may be found in T. Greene and P. Wuts, *Protective Groups in Organic Synthesis* (3rd ed.), John Wiley & Sons, NY (1999).

Furthermore, compounds of formula I wherein $R^1$ is phenyl substituted by at least one group selected from hydroxy, and $R^3$ is hydrogen, may be prepared from compounds of formula I wherein $R^1$ is phenyl optionally substituted by at least one substituent independently chosen from $C_{1-6}$ alkylcarbonyloxy, $C_{6-10}$ arylcarbonyloxy, and heteroarylcarbonyloxy; and $R^3$ is a hydroxyl protecting group. In these compounds, the $R^1$ $C_{1-6}$ alkylcarbonyloxy, $C_{6-10}$ arylcarbonyloxy, and heteroarylcarbonyloxy group and the $R^3$ hydroxyl protecting group may be removed using reactions conditions in which both groups are removed concomitantly or they may be removed in step-wise fashion. For example, when $R^1$ is phenyl substituted by alkylcarbonyloxy and $R^3$ is an alkyl ester, both groups may be cleaved by reacting the subject compound with a base in an appropriate solvent and at an appropriate. temperature. The choice of a suitable base, solvent, and temperature will depend on the particular subject compound and the particular protecting groups being utilized. These choices are within the skill of one of ordinary skill in the art. For example, in compound (1), wherein $R^1$ is phenyl substituted with methylcarbonyloxy and methyl and $R^3$ is acetoxy, the methylcarbonyl and acetoxy protecting groups were cleaved concomitantly upon reacting (1) with potassium hydroxide in a mixture of methanol and acetonitrile to afford the desired compound, as shown below.

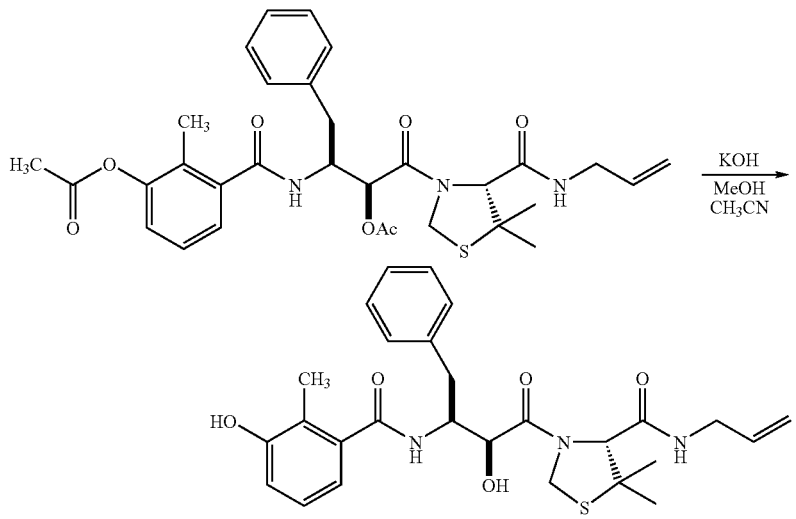

Alternatively, in compounds of formula (I-A) wherein R1 is phenyl substituted by at least one group selected from $C_{1-6}$ alkylcarbonyloxy, $C_{6-10}$ arylcarbonyloxy, and heteroarylcarbonyloxy, and $R^3$ is a hydroxyl protecting group, the $C_{1-6}$ alkylcarbonyloxy, $C_{6-10}$ arylcarbonyloxy, and heteroarylcarbonyloxy group and the $R^3$ hydroxyl protecting group may be cleaved in a stepwise manner to afford a compound of formula I wherein $R^1$ is phenyl substituted by hydroxy and $R^3$ is hydrogen. The choice of the $R^3$ hydroxyl protecting group and the conditions to affect its cleavage will depend upon the specific subject compound chosen and is within the knowledge of one of ordinary skill in the art. For example, in the compounds of formula (I-A) wherein $R^1$ is phenyl substituted by $C_{1-6}$ alkylcarbonyloxy and $R^3$ is a silane protecting group, the $R^3$ silane protecting group may be cleaved first by treatment of the subject compound with a fluoride source such as tetrabutylammonium fluoride in acetonitrile at room temperature, followed by cleavage of the $C_{1-6}$ alkylcarbonyloxy group in $R^1$ by treatment with a base such as potassium hydroxide in a mixture of methanol and acetonitrile at room temperature.

Compounds of formula (I-A) wherein Z, $R^1$, $R^2$, $R^{2'}$, $R^3$, $R^4$, $R^5$, $R^6$, and $R^7$, are as hereinbefore defined may be prepared by reacting a compound of formula (II), wherein $Y^1$ is a leaving group and $R^1$ and $R^3$ are as hereinbefore defined,

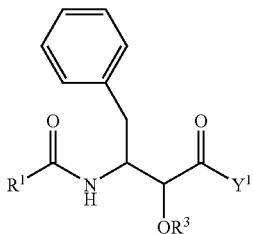

(II)

with a compound of formula (III),

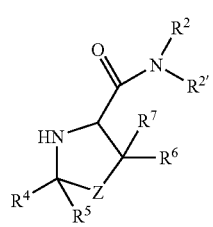

(III)

wherein Z, $R^2$, $R^{2'}$, $R^4$, $R^5$, $R^6$ and $R^7$ are as hereinbefore defined, or a salt or solvate thereof, to afford a compound of formula (I-A).

In general, these reactions may be performed in a solvent that does not interfere with the reaction, for example alkyl or aryl ethers, alkyl or aryl esters, aromatic and aliphatic hydrocarbons, non-competitive alcohols, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C., depending on the specific reactants, solvents, and other optional additives used. Such reactions may also be promoted by the addition of optional additives. Examples of such additives include, but are not limited to, hydroxybenztriazole (HOBt), hydroxyazabenzotriazole (HOAt), N-hydroxysuccinimide (HOSu), N-hydroxy-5-norbomene-endo-2,3-dicarboximide (HONB), 4-dimethylaminopyridine (DMAP). Whether these additives are necessary depends on the identity of the reactants, the solvent, and the temperature, and such a choice is within the knowledge of one of ordinary skill in the art.

In general, the leaving group $Y^1$ in the compounds of formula (II) should be such that it provides sufficient reactivity of the compounds of formula (II) with the compounds of formula (III). Compounds of formula (II) that contain such suitable leaving groups may be prepared, isolated and/or purified, and subsequently reacted with the compounds of formula (III). Alternatively, compounds of formula (II) with suitable leaving groups may be prepared and further reacted without isolation or further purification with the compounds of formula (III) to afford compounds of formula (I). Among suitable leaving groups, $Y^1$, are halides, aromatic heterocycles, sulfonic acid esters, anhydrides, or groups derived from the reaction of compounds of formula (II) wherein $Y^1$ is hydroxy with reagents such as carbodiimides or carbodiimide species. Examples of suitable leaving groups include, but are not limited to, chloride, iodide, imidazole, —OC(O)alkyl, —OC(O)aryl, —OC(O)Oalkyl, —OC(O)Oaryl, —OS(O$_2$)alkyl, —OS(O$_2$)aryl, —OPO(Oaryl)$_2$, —OPO(Oalkyl)$_2$, and those derived from the reaction of the compounds of formula (II) wherein $Y^1$ is —OH with carbodiimides. Other suitable leaving groups are known to those of ordinary skill in the art and may be found, for example, in Humphrey, J. M.; Chamberlin, A. R. *Chem. Rev.* 1997, 97, 2243; *Comprehensive Organic Synthesis*; Trost, B. M., Ed.; Pergamon: New York, 1991; Vol. 6, pp 301–434; and Comprehensive Organic Transformations; Larock, R. C.; VCH: New York, 1989, Chapter 9.

Compounds of formula (II) where in $Y^1$ is a halogen can be prepared from compounds of formula (II) wherein $Y^1$ is hydroxy by reaction with a suitable agent. For example, the compounds of formula (II) wherein $Y^1$ is chloro may be prepared from compounds of formula (II) wherein $Y^1$ is hydroxy by reaction with agents such as thionyl chloride or oxalyl chloride. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

The present invention specifically contemplates that the compounds of formula (I-A) may be prepared by reacting compounds of formula (III) with compounds of formula (II), wherein $R^3$ is hydrogen, an optionally substituted $C_{1-4}$ alkyl group, or a suitable protecting group, such as a $C_{1-6}$ alkylcarbonyl, $C_{6-10}$ arylcarbonyl, or heteroarylcarbonyl group. For example, as shown below, compound (2), wherein $R^3$ is methylcarboxy, was treated with thionyl chloride in a mixture of pyridine and acetonitrile and was then allowed to react with compound (3) to afford the desired compound (4), as shown below.

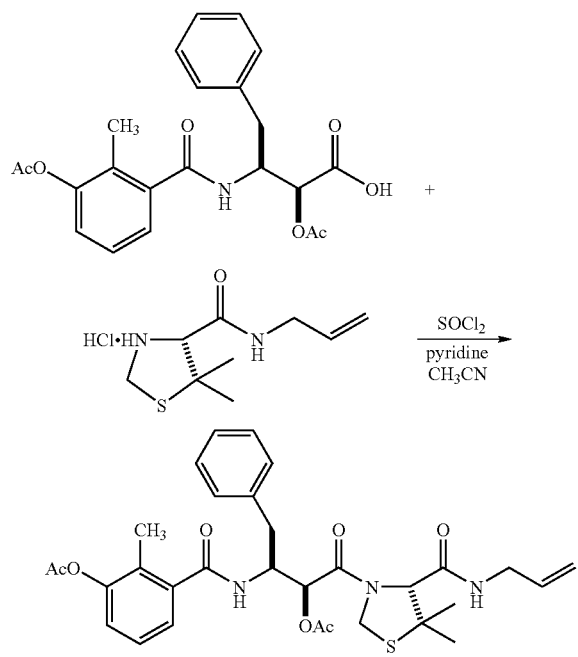

Alternatively, as shown below, compound (5) wherein $R^3$ is hydrogen, was allowed to react with compound (3) to afford the desired product, compound (6).

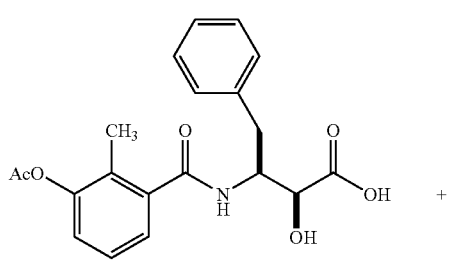

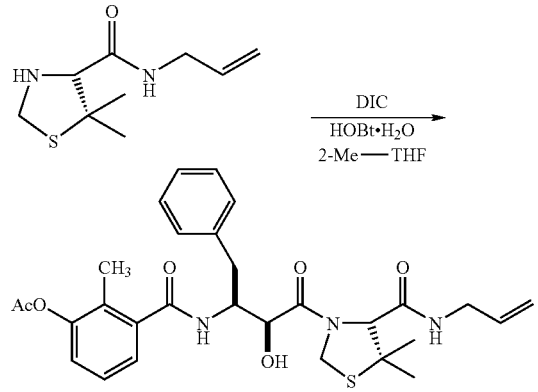

Whether $R^3$ in the compounds of formula (II) is hydrogen, an optionally substituted $C_{1-4}$ alkyl group, or a suitable protecting group is dependent on the specific product compounds desired and/or the specific reaction conditions used. Such choices are within the knowledge of one of ordinary skill in the art.

Compounds of formula (II) where in $Y^1$ is an aromatic heterocycle can be prepared from compounds of formula (II) wherein $Y^1$ is hydroxy by reaction with a suitable agent such as carbonyl diimidazole. These compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such knowledge is within the skill of one of ordinary skill in the art.

Compounds of formula (II) wherein $Y^1$ is —OC(O)alkyl or —OC(O)aryl may be prepared from compounds of formula (II) wherein $Y^1$ is hydroxy by reaction with suitable reagents such acyl halides, acyl imidazoles, or carboxylic acid under dehydrating conditions. Suitable reagents may include, but are not limited to, acetyl chloride, acetyl iodide formed in situ from acetyl chloride and sodium iodide, acetyl imidazole, or acetic acid under dehydrating conditions. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (II) wherein $Y^1$ is —OC(O)Oalkyl, —OC(O)Oaryl can be prepared from compounds of formula (II) wherein $Y^1$ is hydroxy by reaction with a suitable agents such as chloroformates of the formula ClC(O)Oalkyl or ClC(O)Oaryl. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (II) wherein $Y^1$ is —OS(O$_2$)alkyl or —OS(O$_2$)aryl can be prepared from compounds of formula (II) wherein $Y^1$ is hydroxy by reaction with a suitable agent such as an alkyl or aryl sulfonyl chloride. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Alternatively, compounds of formula (I) may be prepared by reaction of compounds of formula (II), wherein $Y^1$ is —OH, with compounds of formula (III) under dehydrating conditions, utilizing agents such as carbodiimides or carbodiimide derived species. Such suitable agents include, but are not limited to, dicyclohexylcarbodiimide, diisopropylcarbodiimide, 1-[3-(dimethylamino)propyl]-3-ethylcarbodiimide hydrochloride (EDC), 2-chloro-4,6-dimethoxy-1,3,5-triazine (CDMT), cyanuric chloride, 4-(4,6-dimethoxy-1,3,5-triazin-2-yl)-4-methylmorpholinium chloride, O-(7-azabenzotriazol-1-yl)-N,N,N',N'-tetramethyluronium hexafluorophosphate (HATU), carbonyldiimidazole (CDI), benzotriazole-1-yl-oxy-tris-(dimethylamino)-phosphonium-hexafluorophosphate (BOP), 2-ethoxy-1-ethoxycarbonyl-1,2-dihydroquinoline (EEDQ), 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrefluoroborate (TBTU), and 3-(diethoxyphosphoryloxy)-1,2,3-benzotriazin-4(3H)-one (DEPBT). These reactions may be performed in the presence of optional additives. Suitable additives include, but are not limited to, hydroxybenztriazole (HOBt), hydroxyazabenzotriazole (HOAt), N-hydroxysuccinimide (HOSu), N-hydroxy-5-norbornene-endo-2,3-dicarboximide (HONB), and 4-dimethylaminopyridine (DMAP). Whether these additives are necessary depends on the identity of the reactants, the solvent, and the temperature, and such choices are within the knowledge of one of ordinary skill in the art. For example, as shown below, compound (5) was treated with diisopropylcarbodiimide (DIC) in the presence of HOBt and in 2-methyltetrahydrofuran and was then allowed to react with compound (3) to afford the desired product.

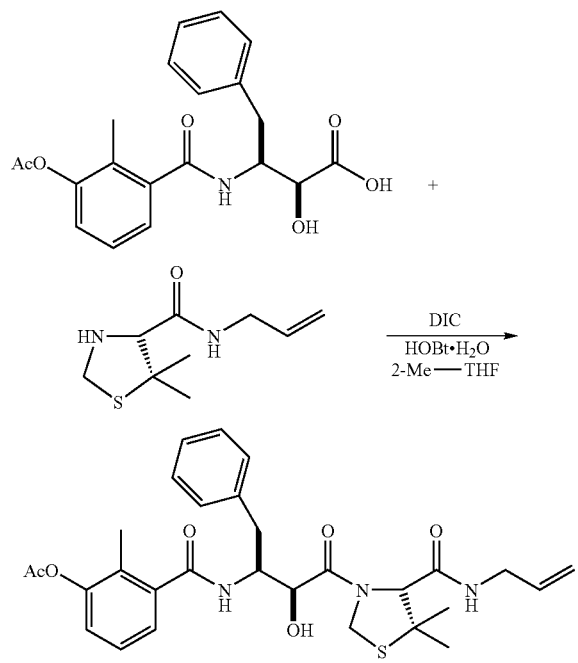

Compounds of formula (II), wherein $R^3$ is a suitable protecting group and $Y^1$ and $R^1$ are as hereinbefore defined, may be prepared from compounds of formula (II) wherein $R^3$ is hydrogen. The choice of a suitable protecting group is dependent upon the subject compound chosen and subsequent reaction conditions to which the compound of formula (II) will be subjected. Generally, $R^3$ in the compounds of formula II can be chosen from alkyl or aryl esters, alkyl silanes, aryl silanes, alkylaryl silanes, carbonates, optionally substituted benzyl ethers, or other substituted ethers. Such protecting groups can be introduced into the compounds of formula (II) wherein $R^3$ is hydrogen using methods known to those of ordinary skill in the art and as found in, for example, T. Greene and P. Wuts, *Protective Groups in Organic Synthesis* ($3^{rd}$ ed.), John Wiley & Sons, NY (1999). For example, as shown below, compound (2) was allowed to react with acetic anhydride in ethyl acetate and methanesulfonic acid at about 70° C. to afford compound (5).

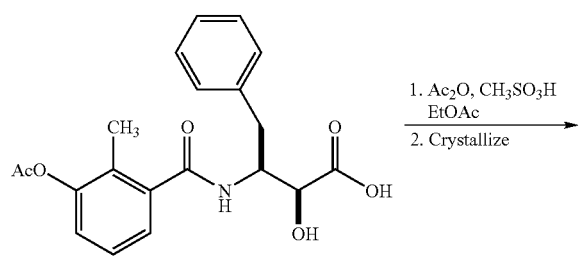

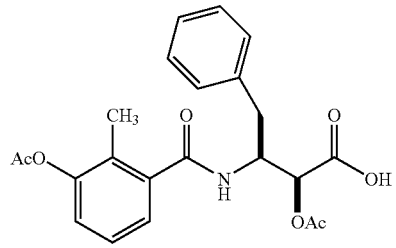

Compounds of formula (II), wherein $Y^1$ is hydroxy and $R^1$ and $R^3$ are as hereinbefore defined, can be prepared by reaction of compounds of formula (IV), wherein $Y^1$ and $R^3$ are as hereinbefore defined, with compounds of formula (V), wherein $R^1$ is as hereinbefore defined and $Y^2$ is hydroxy or a suitable leaving group, as shown below.

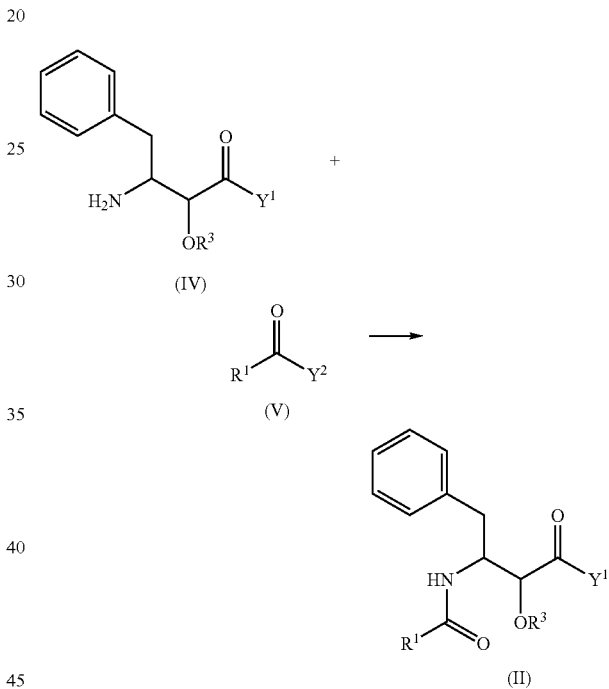

In general, these reactions may be performed in a solvent that does not interfere with the reaction, for example alkyl or aryl ethers, alkyl or aryl esters, aromatic and aliphatic hydrocarbons, non-competitive alcohols, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C., depending on the specific reactants, solvents, and other optional additives used. Such reactions may also be promoted by the addition of optional additives. Examples of such additives include, but are not limited to, hydroxybenztriazole (HOBt), hydroxyazabenzotriazole (HOAt), N-hydroxysuccinimide (HOSu), N-hydroxy-5-norbornene-endo-2,3-dicarboximide (HONB), and 4-dimethylaminopyridine (DMAP). Whether these additives are necessary depends on the identity of the reactants, the solvent, and the temperature. Such choices are within the knowledge of one of ordinary skill in the art.

In general, the leaving group $Y^2$ in the compounds of formula (V) should be such that it provides sufficient reactivity with the amine in the compounds of formula (IV). Compounds of formula (V) that contain such suitable leaving groups may be prepared, isolated and/or purified, and subsequently reacted with the compounds of formula (IV). Alternatively, compounds of formula (V) with suitable leaving groups may be prepared and further reacted without isolation or further purification with the compounds of formula (IV) to afford compounds of formula (II). Among suitable leaving groups in the compounds of formula (V) are halides, aromatic heterocycles, sulfonic acid esters, anhydrides, or groups derived from the reaction of compounds of formula (V) wherein $Y^2$ is hydroxy with reagents such as carbodiimides or carbodiimide species. Examples of suitable leaving groups include, but are not limited to, chloride, iodide, imidazole, —OC(O)alkyl, —OC(O)aryl, —OC(O)Oalkyl, —OC(O)Oaryl, —OS(O$_2$)alkyl, —OS(O$_2$)aryl, —OPO(Oaryl)$_2$, OPO(Oalkyl)$_2$, and those derived from the reaction of the compounds of formula V wherein $Y^2$ is —OH with carbodiimides. Other suitable leaving groups are known to those of ordinary skill in the art and may be found, for example, in Humphrey, J. M.; Chamberlin, A. R. *Chem. Rev.* 1997, 97, 2243; *Comprehensive Organic Synthesis*; Trost, B. M., Ed.; Pergamon: New York, 1991; Vol. 6, pp 301–434; and *Comprehensive Organic Transformations*; Larock, R. C.; VCH: New York, 1989, Chapter 9.

Compounds of formula (V) where in $Y^2$ is a halogen can be prepared from compounds of formula (V) wherein $Y^2$ is hydroxy by reaction with a suitable agent. For example, the compounds of formula (V) wherein $Y^2$ is chloro may be prepared from compounds of formula (V) wherein $Y^2$ is hydroxy by reaction with agents such as thionyl chloride or oxalyl chloride. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (IV) or they may be formed in situ and reacted with the compounds of formula (IV) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art. For example, as shown below, compound (7) was allowed to react with compound (8) in a mixture of tetrahydrofuran and water, in the presence of triethylamine, at room temperature to afford the desired compound (5).

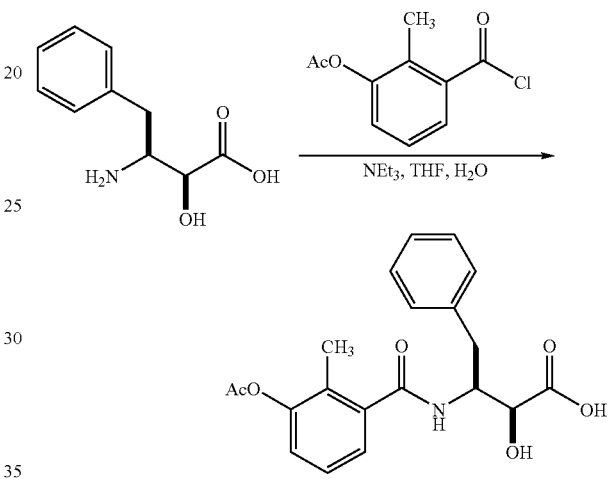

Compounds of formula (IV), wherein $Y^1$ is hydroxy and $R^3$ is as defined above, are either commercially available or can be prepared by methods known to those of skill in the art.

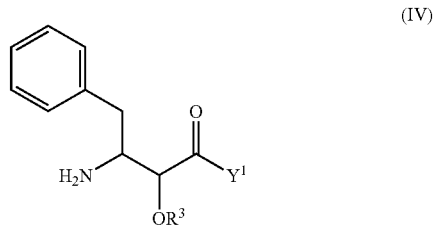

(IV)

For example, the compounds of formula (IV) can be prepared as shown in the scheme below. In general, an N-protected amino acid derivative is reduced to an aldehyde using reducing agents that are suitable for such a transformation. For example, suitable reducing agents are dialkyl aluminum hydride agents, such as diisobutyl aluminum hydride for example. Another method of preparing the compounds of formula (IV) is to reduce an appropriate carboxylic acid to an alcohol with a suitable reducing agent such as LiAlH$_4$ or BH$_3$ or NaBH$_4$ for example, followed by oxidation of the alcohol to the corresponding aldehyde with PCC, under Swern conditions or using pyr.SO$_3$/DMSO/NEt$_3$ for example Another method of preparing the compounds of formula (IV) is to reduce an appropriate carboxylic acid derivative, such as a Weinreb amide or an acyl imidazole, using a suitable reducing agent such as LiAlH$_4$ or diisobutyl aluminum hydride for example. Alternatively, the compounds of formula (IV) can be prepared by the preparation of an appropriate aldehyde by reduction of the corresponding acid chloride. Next, a compound is added to the aldehyde that is the equivalent of adding a carboxylate CO$_2$ anion. For example, cyanide can be added to the aldehyde to afford a cyanohydrin that can then be hydrolyzed under either acidic or basic conditions to afford the desired compound, (d). Alternatively, nitromethane may be added to the aldehyde under basic conditions to afford an intermediate that is then converted into the desired compound. These compounds can be prepared according to the following procedures. In those compounds where Y$^3$ is —CN, R. Pedrosa et al., *Tetrahedron Asymm.* 2001, 12, 347. For those compounds in which Y$^3$ is —CH$_2$NO$_2$, M. Shibasaki et al., *Tetrahedron Lett.* 1994, 35, 6123.

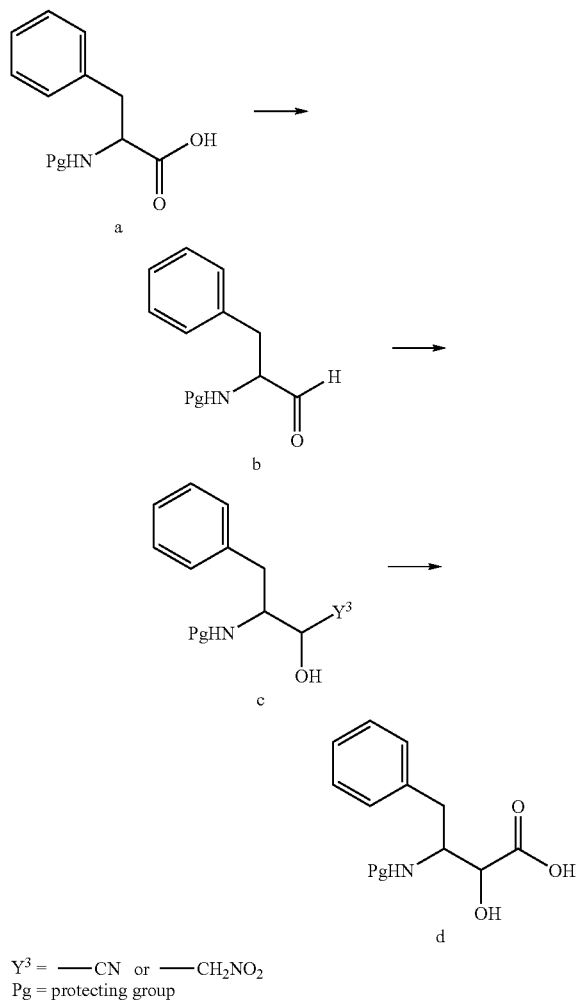

Y$^3$ = ——CN or ——CH$_2$NO$_2$
Pg = protecting group

Compounds of formula (V), wherein Y$^2$ is hydroxy and R$^1$ is as hereinbefore defined, are either commercially available or can be prepared by methods known to those of skill in the art. For example, such compounds can be prepared from the corresponding alcohols by oxidation with suitable reagents. Such oxidation agents include, but are not limited to, KMnO$_4$, pyridinium dichromate (PDC), H$_2$Cr$_2$O$_7$ (Jone's reagent), and 2,2,6,6-tetramethylpiperidinyl-2-oxyl (TEMPO)/NaClO$_2$.

Compounds of formula (III), wherein Z is S, O, SO, SO$_2$, CH$_2$, or CFH, and R$^2$, R$^{2'}$, R$^4$, R$^5$, R$^6$, and R$^7$ are as hereinbefore defined, are either commercially available or can be prepared according to methods known to those of skill in the art. For example, see Mimoto, T.; et. al. *J. Med. Chem.* 1999, 42, 1789; EP 0751145; and U.S. Pat. Nos. 5,644,028, 5,932,550, 5,962,640, and 6,222,043, which are hereby incorporated by reference.

Alternatively, the compounds of formula (I-A), wherein R$^1$ is phenyl optionally substituted by at least one substituent independently chosen from C$_{1-6}$ alkyl, hydroxyl, C$_{1-6}$ alkylcarbonyloxy, C$_{6-10}$ arylcarbonyloxy, and heteroarylcarbonyloxy, and Z, R$^2$, R$^{2'}$, R$^3$, R$^4$, R$^5$, R$^6$, and R$^7$ are as hereinbefore defined, may be prepared by reaction of compounds of formula (VI),

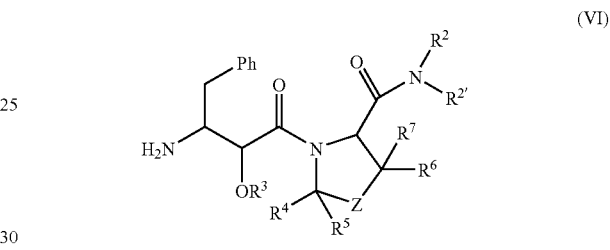

(VI)

wherein Z, R$^2$, R$^{2'}$, R$^3$, R$^4$, R$^5$, R$^6$, and R$^7$ are as hereinbefore defined with compounds of formula (V), wherein R$^1$ and Y$^2$ are as hereinbefore defined.

In general, these reactions may be performed in a solvent that does not interfere with the reaction, for example alkyl or aryl ethers, alkyl or aryl esters, aromatic and aliphatic hydrocarbons, non-competitive alcohols, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C., depending on the specific reactants, solvents, and other optional additives used. Such reactions may also be promoted by the addition of optional additives. Examples of such additives include, but are not limited to, hydroxybenztriazole (HOBt), hydroxyazabenzotriazole (HOAt), N-hydroxysuccinimide (HOSu), N-hydroxy-5-norbornene-endo-2,3-dicarboximide (HONB), and 4-dimethylaminopyridine (DMAP). Whether these additives are necessary depends on the identity of the reactants, the solvent, and the temperature. Such choices are within the knowledge of one of ordinary skill in the art.

In general, the leaving group $Y^2$ in the compounds of formula (V) should be such that it provides sufficient reactivity with the amino group in the compounds of formula (VI). Compounds of formula (V) that contain such suitable leaving groups may be prepared, isolated and/or purified, and subsequently reacted with the compounds of formula (VI). Alternatively, compounds of formula (V) with suitable leaving groups may be prepared and further reacted without isolation or further purification with the compounds of formula (VI) to afford compounds of formula (I). Among suitable leaving groups in the compounds of formula (V) are halides, aromatic heterocycles, sulfonic acid esters, anhydrides, or groups derived from the reaction of compounds of formula (V) wherein $Y^2$ is hydroxy with reagents such as carbodiimides or carbodiimide species. Examples of suitable leaving groups include, but are not limited to, chloride, iodide, imidazole, —OC(O)alkyl, —OC(O)aryl, —OC(O)Oalkyl, —OC(O)Oaryl, —OS(O$_2$)alkyl, —OS(O$_2$)aryl, —OPO(Oaryl)$_2$, —OPO(Oalkyl)$_2$, and those derived from the reaction of the compounds of formula (V), wherein $Y^2$ is —OH, with carbodiimides.

Compounds of formula (V) where in $Y^2$ is a halogen can be prepared from compounds of formula (V) wherein $Y^2$ is hydroxy by reaction with a suitable agent. For example, the compounds of formula (V) wherein $Y^2$ is chloro may be prepared from compounds of formula (V) wherein $Y^2$ is hydroxy by reaction with agents such as thionyl chloride or oxalyl chloride. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (VI) or they may be formed in situ and reacted with the compounds of formula (VI) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (VI),

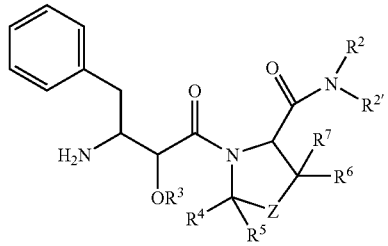

(VI)

wherein Z, $R^2$, $R^{2'}$, $R^3$, $R^4$, $R^5$, $R^6$, and $R^7$ are as hereinbefore defined, may be prepared from reaction of compounds of formula (VII),

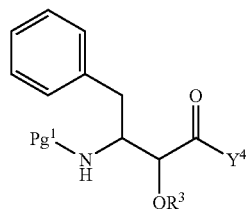

(VII)

wherein $Pg^1$ is a suitable nitrogen protecting group, $Y^4$ is hydroxy or a suitable leaving group, and $R^3$ is as hereinbefore defined, with a compound of formula (III), wherein Z, $R^2$, $R^{2'}$, $R^4$, $R^5$, $R^6$, and $R^7$ are as hereinbefore defined, or a salt or solvate thereof.

A suitable protecting group $Pg^1$ in the compounds of formula (VII) is one that is stable to subsequent reaction conditions in which the compounds of formula (VII) are allowed to react with the compounds of formula (III). Furthermore, such a protecting group should be chosen such that it can be removed after the compounds of formula (VII) have been allowed to react with the compounds of formula (III) to afford an intermediate compound that is subsequently deprotected to afford a compound of formula (VI). Suitable protecting groups include, but are not limited to, carbamates such as t-butyloxycarbonyl and benzyloxycarbonyl, imides such as phthaloyl, or suitable benzyl groups. Such protecting groups can be introduced into the compounds of formula (VII) and subsequently removed to provide compounds of formula (VI) according to methods known to those of ordinary skill in the art and as found in, for example, T. Greene and P. Wuts, *Protective Groups in Organic Synthesis* (3$^{rd}$ ed.), John Wiley & Sons, NY (1999).

In general, the leaving group $Y^4$ in the compounds of formula (VII) should be such that it provides sufficient reactivity with the amino group in the compounds of formula (III). Compounds of formula (VII) that contain such suitable leaving groups may be prepared, isolated and/or purified, and subsequently reacted with the compounds of formula (III). Alternatively, compounds of formula (VII) with suitable leaving groups may be prepared and further reacted without isolation or further purification with the compounds of formula (III) to afford compounds of formula (VI). Among suitable leaving groups in the compounds of formula (VII) are halides, aromatic heterocycles, sulfonic acid esters, anhydrides, or groups derived from the reaction of compounds of formula (VII) wherein $Y^4$ is hydroxy with reagents such as carbodiimides or carbodiimide species. Examples of suitable leaving groups include, but are not limited to, chloride, iodide, imidazole, —OC(O)alkyl, —OC(O)aryl, —OC(O)Oalkyl, —OC(O)Oaryl, —OS(O$_2$)alkyl, —OS(O$_2$)aryl, —OPO(Oaryl)$_2$, —OPO(Oalkyl)$_2$, and those derived from the reaction of the compounds of formula (VII), wherein Y$^4$ is —OH, with carbodiimides.

Compounds of formula (VII) where in Y$^4$ is a halogen can be prepared from compounds of formula (VII) wherein Y$^4$ is hydroxy by reaction with a suitable agent. For example, the compounds of formula (VII) wherein Y$^4$ is chloro may be prepared from compounds of formula (VII) wherein Y$^4$ is hydroxy by reaction with agents such as thionyl chloride or oxalyl chloride. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (VII) where in Y$^4$ is an aromatic heterocycle can be prepared from compounds of formula (VII) wherein Y$^4$ is hydroxy by reaction with a suitable agent such as carbonyl diimidazole. These compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the skill of one of ordinary skill in the art.

Compounds of formula (VII) wherein Y$^4$ is —OC(O)alkyl or —OC(O)aryl may be prepared from compounds of formula (VII) wherein Y$^4$ is hydroxy by reaction with suitable reagents such acyl halides, acyl imidazoles, or carboxylic acid under dehydrating conditions. Suitable reagents may include, but are not limited to, pivaloyl chloride, acetyl chloride, acetyl iodide formed in situ from acetyl chloride and sodium iodide, acetyl imidazole, or acetic acid under dehydrating conditions. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (VII) wherein Y$^4$ is —OC(O)Oalkyl, —OC(O)Oaryl can be prepared from compounds of formula (VII) wherein Y$^4$ is hydroxy by reaction with a suitable agents such as chloroformates of the formula Cl—C(O)Oalkyl or Cl—C(O)Oaryl. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (VII) wherein $Y^4$ is —OS(O$_2$)alkyl or —OS(O$_2$)aryl can be prepared from compounds of formula (VII) wherein $Y^4$ is hydroxy by reaction with a suitable agent such as an alkyl or aryl sulfonyl chloride. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (III) or they may be formed in situ and reacted with the compounds of formula (III) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Alternatively, compounds of formula (VI) may be prepared by reaction of compounds of formula (VII), wherein $Y^4$ is —OH, with compounds of formula (III) under dehydrating conditions using agents such as carbodiimides or carbodiimide derived species. Suitable agents include, but are not limited to, dicyclohexylcarbodiimide, diisopropylcarbodiimide, 1-[3-(dimethylamino)propyl]-3-ethylcarbodiimide hydrochloride (EDC), 2-chloro-4,6-dimethoxy-1,3,5-triazine (CDMT), cyanuric chloride, 4-(4,6-dimethoxy-1,3,5-triazin-2-yl)-4-methylmorpholinium chloride, O-(7-azabenzotriazol-1-yl)-N,N,N',N'-tetramethyluronium hexafluorophosphate (HATU), carbonyldiimidazole (CDI), benzotriazole-1-yl-oxy-tris-(dimethylamino)-phosphonium-hexafluorophosphate (BOP), 2-ethoxy-1-ethoxycarbonyl-1,2-dihydroquinoline (EEDQ), 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrefluoroborate (TBTU), and 3-(diethoxyphosphoryloxy)-1,2,3-benzotriazin-4(3H)-one (DEPBT). These reactions may be performed in the presence of optional additives. Suitable additives include, but are not limited to, hydroxybenztriazole (HOBt), hydroxyazabenzotriazole (HOAt), N-hydroxysuccinimide (HOSu), N-hydroxy-5-norbornene-endo-2,3-dicarboximide (HONB), and 4-dimethylaminopyridine (DMAP). Whether these additives are necessary depends on the identity of the reactants, the solvent, and the temperature. Such choices are within the knowledge of one of ordinary skill in the art.

Alternatively, the compounds of formula (I) may be prepared by reaction of a compound of formula (VIII),

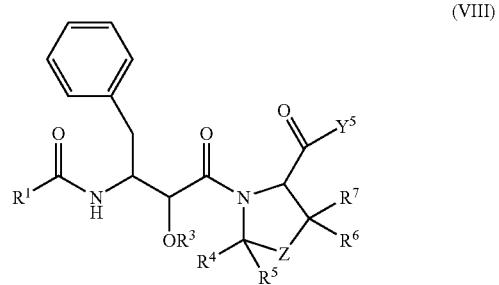

wherein $Y^5$ is hydroxy or a suitable leaving group, and Z, $R^1$, $R^3$, $R^4$, $R^5$, $R^6$, and $R^7$ are as hereinbefore defined, with a compound of formula (IX),

wherein $R^2$ and $R^{2'}$ are hereinbefore defined, or a salt or solvate thereof.

In general, the leaving group $Y^5$ in the compounds of formula (VIII) should be such that it provides sufficient reactivity with the amino group in the compounds of formula (IX). Compounds of formula (VIII) that contain such suitable leaving groups may be prepared, isolated and/or purified, and subsequently reacted with the compounds of formula (IX). Alternatively, compounds of formula (VIII) with suitable leaving groups may be prepared and further reacted without isolation or further purification with the compounds of formula (IX) to afford compounds of formula (I-A). Among suitable leaving groups in the compounds of formula (VIII) are halides, aromatic heterocycles, sulfonic acid esters, anhydrides, or groups derived from the reaction of compounds of formula (VIII) wherein $Y^5$ is hydroxy with reagents such as carbodiimides or carbodiimide species. Examples of suitable leaving groups include, but are not limited to, chloride, iodide, imidazole, —OC(O)alkyl, —OC(O)aryl, —OC(O)Oalkyl, —OC(O)Oaryl, —OS(O$_2$)alkyl, —OS(O$_2$)aryl, and those derived from the reaction of the compounds of formula (VIII), wherein Y$^5$ is —OH, with carbodiimides.

Compounds of formula (VIII) where in Y$^5$ is a halogen can be prepared from compounds of formula (VIII) wherein Y$^5$ is hydroxy by reaction with a suitable agent. For example, the compounds of formula (VIII) wherein Y$^5$ is chloro may be prepared from compounds of formula (VIII) wherein Y$^5$ is hydroxy by reaction with agents such as thionyl chloride or oxalyl chloride. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (IX) or they may be formed in situ and reacted with the compounds of formula (IX) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (VIII) where in Y$^5$ is an aromatic heterocycle can be prepared from compounds of formula (VIII) wherein Y$^5$ is hydroxy by reaction with a suitable agent such as carbonyl diimidazole. These compounds may be isolated and then further reacted with the compounds of formula (IX) or they may be formed in situ and reacted with the compounds of formula (IX) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (VIII) wherein Y$^5$ is —OC(O)alkyl or —OC(O)aryl may be prepared from compounds of formula (VIII) wherein Y$^5$ is hydroxy by reaction with suitable reagents such acyl halides, acyl imidazoles, or carboxylic acid under dehydrating conditions. Suitable reagents may include, but are not limited to, pivaloyl chloride, acetyl chloride, acetyl iodide formed in situ from acetyl chloride and sodium iodide, acetyl imidazole, or acetic acid under dehydrating conditions. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (IX) or they may be formed in situ and reacted with the compounds of formula (IX) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (VIII) wherein Y$^5$ is —OC(O)Oalkyl, —OC(O)Oaryl can be prepared from compounds of formula (VIII) wherein Y$^5$ is hydroxy by reaction with a suitable agents such as chloroformates of the formula Cl—C(O)Oalkyl or Cl—C(O)Oaryl. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (IX) or they may be formed in situ and reacted with the compounds of formula (IX) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Compounds of formula (VIII) wherein $Y^5$ is —$OS(O_2)$alkyl or —$OS(O_2)$aryl can be prepared from compounds of formula (VIII) wherein $Y^5$ is hydroxy by reaction with a suitable agent such as an alkyl or aryl sulfonyl chloride. These reactions may be performed in the presence of a suitable base such as sodium carbonate, sodium bicarbonate, potassium carbonate, potassium bicarbonate, sodium hydroxide, potassium hydroxide, a trialkylamine, triethylamine for example, or a heteroaromatic base, pyridine for example. The resulting compounds may be isolated and then further reacted with the compounds of formula (IX) or they may be formed in situ and reacted with the compounds of formula (IX) without isolation or further purification. These reactions may be performed in a solvent that does not interfere with the desired transformation. Among suitable solvents are alkyl or aryl ethers, alkyl or aryl esters, aromatic and aliphatic hydrocarbons, halogenated solvents, alkyl or aryl nitriles, alkyl or aryl ketones, aromatic hydrocarbons, or heteroaromatic hydrocarbons. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Furthermore, such reactions may be performed at temperatures from −20° C. to 100° C. The specific reaction conditions chosen will depend on the specific subject compound and reagents chosen. Such choices are within the knowledge of one of ordinary skill in the art.

Alternatively, compounds of formula I may be prepared by reaction of compounds of formula (VIII), wherein $Y^5$ is —OH, with compounds of formula (IX) under dehydrating conditions using agents such as carbodiimides or carbodiimide derived species Such suitable agents include, but are not limited to, dicyclohexylcarbodiimide, diisopropylcarbodiimide, 1-[3-(dimethylamino)propyl]-3-ethylcarbodiimide hydrochloride (EDC), 2-chloro-4,6-dimethoxy-1,3,5-triazine (CDMT), cyanuric chloride, 4-(4,6-dimethoxy-1,3,5-triazin-2-yl)-4-methylmorpholinium chloride, O-(7-azabenzotriazol-1-yl)-N,N,N',N'-tetramethyluronium hexafluorophosphate (HATU), carbonyldiimidazole (CDI), benzotriazole-1-yl-oxy-tris-(dimethylamino)-phosphonium-hexafluorophosphate (BOP), 2-ethoxy-1-ethoxycarbonyl-1,2-dihydroquinoline (EEDQ), 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrefluoroborate (TBTU), and 3-(diethoxyphosphoryloxy)-1,2,3-benzotriazin-4(3H)-one (DEPBT). These reactions may be performed in the presence of optional additives. Suitable additives include, but are not limited to, hydroxybenztriazole (HOBt), hydroxyazabenzotriazole (HOAt), N-hydroxysuccinimide (HOSu), N-hydroxy-5-norbornene-endo-2,3-dicarboximide (HONB), and 4-dimethylaminopyridine (DMAP). Whether these additives are necessary depends on the identity of the reactants, the solvent, and the temperature. Such choices are within the knowledge of one of ordinary skill in the art.

Compounds of formula (IX) are either commercially available or can be prepared by methods described herein or methods known to those of ordinary skill in the art.

Preferably, the inventive compounds are prepared by the methods of the present invention, including the General Methods shown below. When stereochemistry is not specified in chemical structures, either stereocenter may be utilized. The following abbreviations also apply: Boc (tert-butoxycarbonyl), Ac (acetyl), Cbz (benzyloxycarbonyl), DMB (2,4-dimethoxybenzyl), TBS (tert-butyldimethylsilyl), TBDPS (tert-butyldiphenylsilyl), Ms (methanesulfonate), Ts (toluenesulfonate), Bn (benzyl), and Tr (triphenylmethyl)

Various starting materials and other reagents were purchased from commercial suppliers, such as Aldrich Chemical Company or Lancaster Synthesis Ltd., and used without further purification, unless otherwise indicated.

In the examples described below, unless otherwise indicated, all temperatures in the following description are in degrees Celsius (°C.) and all parts and percentages are by weight, unless indicated otherwise.

The reactions set forth below were performed under a positive pressure of nitrogen, argon or with a drying tube, at ambient temperature (unless otherwise stated), in anhydrous solvents. All commercial reagents and solvents were used as received from their respective suppliers with the following exceptions: Tetrahydrofuran (THF) was distilled from sodium benzophenone ketyl prior to use. Dichloromethane ($CH_2Cl_2$) was distilled from calcium hydride prior to use. Flash chromatography was performed using silica gel 60 (Merck art. 9385). $^1$H-NMR spectra were recorded on a Bruker instrument operating at 300 MHz and $^{13}$C-NMR spectra were recorded at 75 MHz. NMR spectra are obtained as DMSO-$d_6$ or CDCl$_3$ solutions (reported in ppm), using chloroform as the reference standard (7.25 ppm and 77.00 ppm) or DMSO-$d_6$ ((2.50 ppm and 39.52 ppm)). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz. Alternatively, $^1$H NMR spectra were recorded at 300 MHz utilizing a Varian UNITY plus 300 spectrometer. Chemical shifts are reported in ppm (δ) downfield relative to internal tetramethylsilane, and coupling constants are given in Hertz. Infrared absorption spectra were recorded using a Perkin-Elmer 1600 series FTIR spectrometer. Alternatively, infrared spectra were recorded on a Perkin-Elmer FT-IR Spectrometer as neat oils, as KBr pellets, or as CDCl₃ solutions, and when reported are in wave numbers (cm⁻¹). Elemental analyses were performed by Atlantic Microlab, Inc., Norcross, Ga. Melting points are uncorrected.

Analytical thin-layer chromatography was performed on glass-backed silica gel 60° F. 254 plates (Analtech (0.25 mm)) and eluted with the appropriate solvent ratios (v/v). The reactions were assayed by high-pressure liquid chromotagraphy (HPLC) or thin-layer chromatography (TLC) and terminated as judged by the consumption of starting material. The TLC plates were visualized by UV, phosphomolybdic acid stain, or iodine stain. The mass spectra were obtained using LC/MS or APCI. All melting points are uncorrected.

All final products had greater than 95% purity (by HPLC at wavelengths of 220 nm and 254 nm).

In the following examples and preparations, "Et" means ethyl, "Ac" means acetyl, "Me" means methyl, "Ph" means phenyl, (PhO)₂POCl means chlorodiphenylphosphate, "HCl" means hydrochloric acid, "EtOAc" means ethyl acetate, "Na₂CO₃" means sodium carbonate, "NaOH" means sodium hydroxide, "NaCl" means sodium chloride, "NEt₃" means triethylamine, "THF" means tetrahydrofuran, "DIC" means diisopropylcarbodiimide, "HOBt" means hydroxy benzotriazole, "H₂O" means water, "NaHCO₃" means sodium hydrogen carbonate, "K₂CO₃" means potassium carbonate, "MeOH" means methanol, "i-PrOAc" means isopropyl acetate, "MgSO₄" means magnesium sulfate, "DMSO" means dimethylsulfoxide, "AcCl" means acetyl chloride, "CH₂Cl₂" means methylene chloride, "MTBE" means methyl t-butyl ether, "DMF" means dimethyl formamide, "SOCl₂" means thionyl chloride, "H₃PO₄" means phosphoric acid, "CH₃SO₃H" means methanesulfonic acid, "Ac₂O" means acetic anhydride, "CH₃CN" means acetonitrile, and "KOH" means potassium hydroxide.

All P2' amine variants mentioned in General Methods A–E described hereinbelow were either purchased and used directly or synthesized as follows.

Method A: Representative Procedure for Reduction of Ketones to Alcohols.

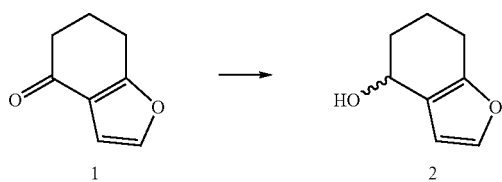

6,7-Dihydro-4-(5H)-benzofuranone (1) (1.00 g 7.34 mmol) was dissolved in methanol (55 mL). The mixture was cooled to 0° C. and NaBH₄ (0.31 g, 8.08 mmol) was added in portions. The reaction was stirred for 2 h at 0° C. at which time the methanol was evaporated. The residue was dissolved in EtOAc and poured into NaHCO₃ (saturated aqueous) and extracted with EtOAc (3×10 mL). The combined organic extracts were washed with brine (10 mL), passed over a short plug of Na₂SO₄, and concentrated in vacuo to give 2 (1.01 g, 99%, as a mixture of isomers) as a pale yellow, thick oil, which was of sufficient quality to be advanced to the next step without further purification. Rf (50% EtOAc/hexanes): 0.53.

Method B: Representative Procedure for Reduction of Acids to Alcohols

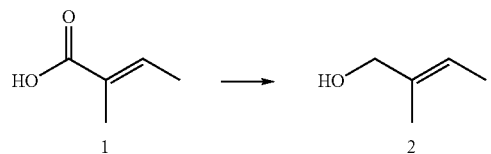

Tiglic acid (1) (20.0 g, 0.200 mol) was dissolved in ether (80 ml) and added dropwise over 30 min to a suspension of LiAlH₄ (15.0 g, 0.417 mol) in ether (80 ml) at 0° C. and the reaction mixture was allowed to warm to room temperature. After 3 h the mixture was re-cooled to 0° C. and quenched slowly by the addition of H₂O (15 ml), 15% NaOH (15 ml) and H₂O (15 ml). The reaction mixture was filtered to remove the granular precipitate and washed thoroughly with ether. The filtrate was washed successively with 1N HCl, NaHCO₃ (saturated aqueous), and brine. The combined organic layers were dried over MgSO₄ and concentrated in vacuo to give (E)-2-methyl-but-2-en-1-ol (2) as a clear oil (12.8 g, 74%).

Method C: Representative Procedure for Alkylation of Phenols Alcohols.

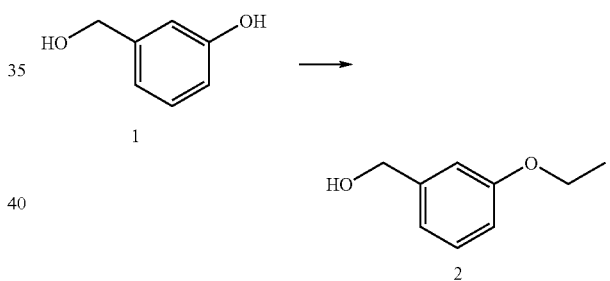

3-Hydroxybenzylalcohol (1) (0.500 g 4.03 mmol) was dissolved in DMF (2 mL) at ambient temperature. Ethyl bromide (0.900 mL, 12.1 mmol) and finely crushed K₂CO₃ (2.78 g, 20.1 mmol) were added and the reaction mixture was stirred for 5 h. The DMF was then removed in vacuo and the residue was partitioned between EtOAc and H₂O, and extracted with EtOAc (3×10 mL). The organic layers were washed with brine (10 mL) and passed over a short plug of Na₂SO₄. The solvents were removed in vacuo to give alcohol 2 (0.55 g, 90%) as a pale yellow, thick oil, which was of sufficient quality to be advanced to the next step without further purification. Rf (40% EtOAC/hexanes): 0.69.

Method D: Representative Procedure for Conversion of Alcohols to Amines.

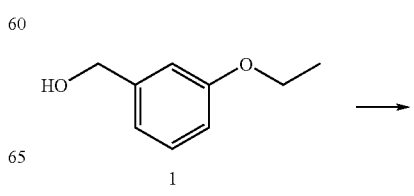

-continued

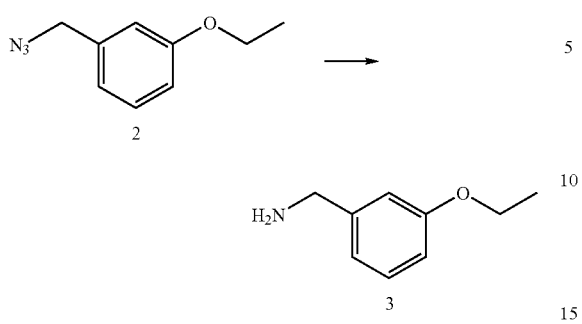

3-Ethoxy-phenyl-methanol (1) (1.23 g 8.08 mmol) was dissolved in CH$_2$Cl$_2$ (10 mL) at ambient temperature and diphenylphosphoryl azide (2.67 g, 9.70 mmol) and 1,8-diazabicyclo [5.4.0] undec-7-ene (1.45 mL, 9.70 mmol) were added. The mixture was stirred for 5 h at which time the CH$_2$Cl$_2$ was removed in vacuo and the crude residue was partitioned between EtOAc and H$_2$O and extracted with EtOAc (3×10 mL). The combined organic layers were washed with brine (10 mL), passed over a short plug of Na$_2$SO$_4$, and concentrated in vacuo to give a yellow oil that was loaded directly onto a flash silica gel column and was quickly eluted with 10% EtOAc/hexanes. The solvents were removed in vacuo to give azide 2 (1.43 g, 84%) as a colorless oil. Rf (30% EtOAc/hexanes): 0.79.

1-Azidomethyl-3-ethoxy-benzene (2) (1.19 g 6.71 mmol) was dissolved in MeOH (15 mL) and palladium 10% on activated carbon, wet (20% in weight) was added. The reaction was hydrogenated for 30 min at 40 PSI in a Parr Hydrogenator. The black suspension was then filtered through compacted celite and the methanol was removed in vacuo to give amine 3 (0.88 g, 88%) as a pale yellow, thick oil, which was of sufficient quality to be advanced to the coupling reactions without further purification.

Method E: Representative Procedure for Conversion of Alcohols to Bromides.

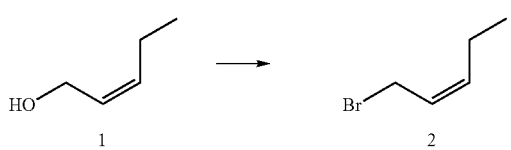

Cis-2-penten-1-ol (1) (1.00 g, 11.6 mmol) and carbon tetrabromide (3.85 g, 13.9 mmol) were dissolved in CH$_2$Cl$_2$ (75 mL). The mixture was cooled to 0° C. and triphenylphosphine (3.65 mL, 13.9 mmol) dissolved in CH$_2$Cl$_2$ (50 mL) was added dropwise. The mixture was allowed to warn to room temperature and was stirred overnight. The CH$_2$Cl$_2$ was removed in vacuo and the crude residue was loaded directly onto a flash silica gel column and eluted quickly with 20% EtOAc/hexanes. The solvents were removed in vacuo to give bromide 2 (1.53 g, 88%) as a colorless volatile oil. Rf (30% EtOAC/hexanes): 0.89.

Method F: Representative Procedure for Conversion of Bromides to Amines.

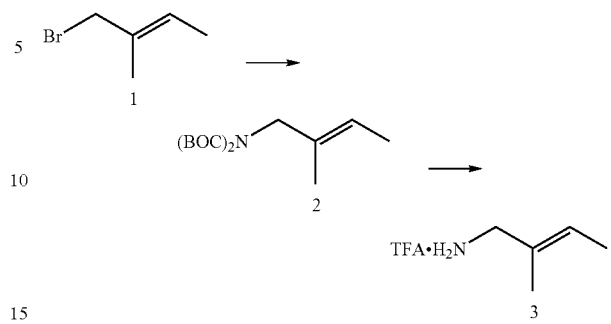

A mixture of bromide 1 (3.00 g, 20.1 mmol), di-tert-butyl-iminodicarboxylate (4.8 g, 22 mmol), and K$_2$CO$_3$ (3.10 g, 80.4 mmol) in DMF (30 ml) was stirred at ambient temperature overnight. The mixture was partitioned between 1N HCl and EtOAc. The organic layer was washed with H$_2$O and brine, then dried over NaSO$_4$. Concentration in vacuo afford a yellow oil which upon purification by flash column chromatography (hexanes to 5% EtOAc/Hexane gradient) yielded protected amine 2 as a clear oil (2.0 g, 35%).

A mixture of the diBOC amine 2 (2.0 g, 7.0 mmol), trifluoroacetic acid (2.7 ml, 35 mmol) and CH$_2$Cl$_2$ (40 ml) was stirred at ambient temperature overnight. The reaction mixture was concentrated in vacuo to give the TFA salt of (E)-2-methyl-but-2-enylamine (3).

Method G: Representative Procedure for Reduction of Aromatic Nitro Groups by Hydrogenation.

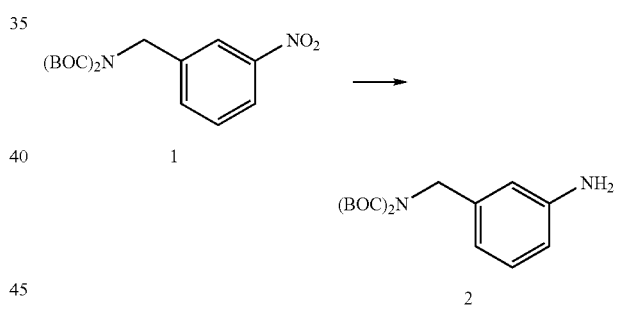

Compound 1 (2.04, 5.79 mmol) was dissolved in EtOAc (20 mL) and palladium 10% on activated carbon, wet (20% in weight) was added. The reaction was hydrogenated for 4 h at 45 PSI in a Parr Hydrogenator. The black suspension was then filtered through compacted celite and the methanol was removed in vacuo to give aniline 2 (1.65 g, 88%) as a pale yellow, thick oil, which was of sufficient quality to be advanced to the acetylation reaction without further purification.

Method H: Representative Procedure for Acetylation of Anilines.

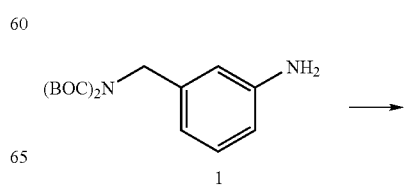

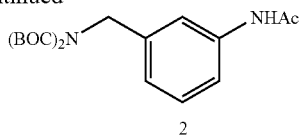

2

Aniline 1 (1.65 g, 5.12 mmol) was dissolved in CH$_2$Cl$_2$ (25 mL) at ambient temperature. Acetyl chloride (0.48 g, 6.14 mmol) and N,N-Diisopropylethylamine (0.79 g, 6.14 mmol) were added, and the reaction was stirred overnight. The CH$_2$Cl$_2$ was removed in vacuo and the crude residue was partitioned between EtOAc and 5% KHSO$_4$ and extracted with EtOAc (3×10 mL). The combined organic extracts were washed with NaHCO$_3$ (saturated aqueous, 10 mL), brine (10 mL), and dried over Na$_2$SO$_4$. The solvents were removed in vacuo to give an orange oil which was of sufficient quality to be advanced to the next step without further purification. Rf (50% EtOAC/hexanes): 0.42.

Method I: Representative Procedure for Reduction of Aldehydes to Amines.

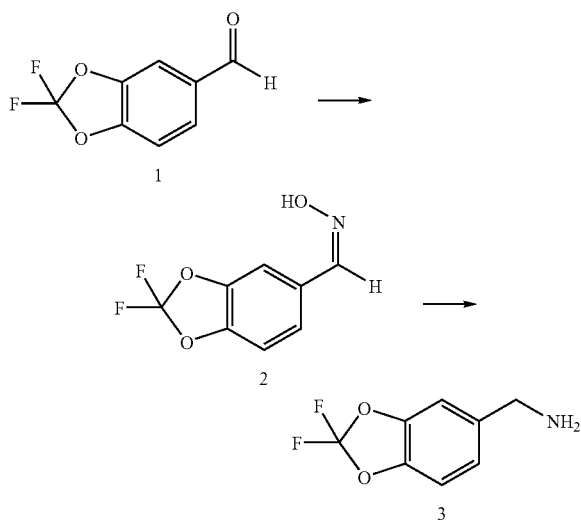

Hydroxyl amine hydrochloride (758 mg, 10.7 mmol) and pyridine (2.16 mL) was added to a solution of 2,2-difluoro-5-formyl benzodioxole (1) (2.00 g, 10.7 mmol) in MeOH (10 mL). After 18 hours the MeOH was removed in vacuo. The reaction mixture was diluted with EtOAc and was washed sequentially with H$_2$O, 10% w/v CUSO$_4$, and brine and then dried over MgSO$_4$. The solution was concentrated in vacuo. The hydroxy imine was purified by column chromatography using 20% EtOAc/Hexanes to give 1.37 g (64% yield) of a white solid. Imine was then subjected to LAH reduction as described above to provide amine 3.

The following amines were synthesized for the corresponding example numbers:

EXAMPLE A26

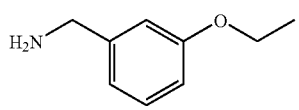

Amine was generated by alkylation of 3-hydroxybenzyl alcohol with ethyl bromide as describe in method C above followed by conversion of the alcohol to the amine as described in method D above provided desired amine.

EXAMPLE A43

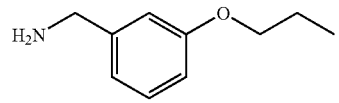

Amine was generated as described above for Example A43 using propylbromide as the alkylating agent.

EXAMPLE A33

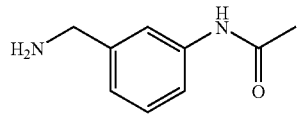

Amine was generated from displacement of bromide in 3-nitrobenzylbromide with di BOC amine as described in method F above. Reduction of the nitro moiety to the aniline (method G above) followed by acetylation (method H above) and BOC removal (method F above) provided desired amine.

EXAMPLE A36, EXAMPLE A37 and EXAMPLE A40

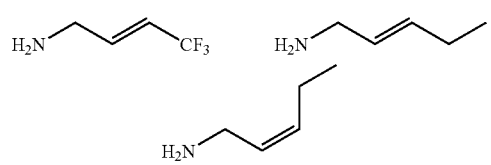

Amines were generated from conversion of the corresponding primary alcohols as described in method E above. Displacement of the bromide with di BOC amine and deprotection with TFA (method F above) provided the desired amines.

EXAMPLE A39

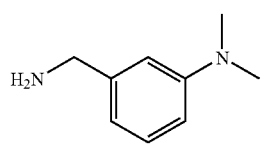

Amine was generated from 3-dimethylaminobenzyl alcohol as described in method D above.

EXAMPLE A34

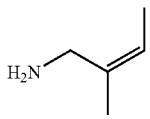

Amine was generated by reduction of the corresponding methyl ester to the primary alcohol (Wipf, *J. Org. Chem.* 1994, 59, 4875–86.). Conversion to the bromide (method E above) followed by displacement with diBOC amine and deprotection (method F above) provided desired amine.

EXAMPLE A35

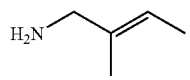

Amine was generated from the corresponding carboxylic acid. Reduction of the acid as described in method B above followed by bromide displacement as described in method E above gave the primary bromide. Conversion of the bromide to the primary amine followed the procedure described in method F above.

EXAMPLE A42

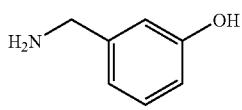

Amine was generated from 3-benzyloxybenzyl alcohol. Conversion to the azide and reduction of both the azide and benzyl protecting group were accomplished using method D as described above with longer hydrogenation time.

EXAMPLE A44

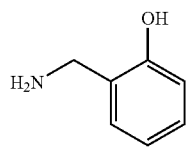

Amine was generated by LiAlH$_4$ reduction of 2-cyanophenol (Ludeman, S. M., et. al. *J. Med. Chem.* 1975, 18, 1252–3.).

EXAMPLE A50

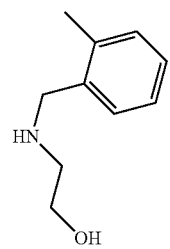

Amine was generated from the condensation of o-tolualdehyde with 2-aminoethanol followed by reduction with sodium borohydride (*Tetrahedron Assym.* 1997, 8, 2367–74.).

EXAMPLE A48

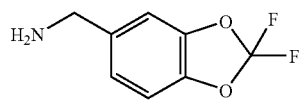

Amine was generated from the corresponding aldehyde by the reductive amination procedure described in method I above.

EXAMPLE A7

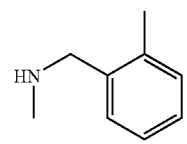

Amine was generated by a reductive amination with the corresponding aldehyde (*Arch. Pharm.* 1987, 320, 647–54.).

EXAMPLE A49

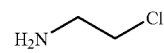

Amine was generated on the thiazolidine core as follows:

Diphenylchlorophosphate (1.0 ml, 4.2 mmol) followed by triethylamine (0.59 ml, 4.2 mmol) were added to a cooled 0° C. solution of BOC-DMTA 1 (1.0 g, 3.8 mmol) in EtOAc (10 ml). The mixture was stirred for 1 h and at which time triethylamine (0.59 ml, 4.2 mmol) and ethanolamine (0.25 ml, 4.2 mmol) were added. The reaction was left to stir overnight at ambient temperature and then partitioned between 1N HCl and EtOAc. The organic layer was washed with NaHCO$_3$(saturated aqueous) and brine. The organic layer was dried over Na$_2$SO$_4$ and concentrated in vacuo to a pale yellow oil 2. The oil was stirred with thionyl chloride (2 ml) for 45 min at room temperature. The mixture was concentrated in vacuo and the residual oil was partitioned between 1N NaOH and EtOAc. The organic layer was extracted with 1N HCl (2×20 ml). The combined aqueous layers were made basic with 1N NaOH and then extracted with EtOAc (3×60 ml). The organic layers were washed with brine, dried over Na$_2$SO$_4$ and concentrated in vacuo to give (R)-5,5-Dimethyl-thiazolidine-4-carboxylic acid (2-chloroethyl)-amide 3 as a clear oil (0.39 g, 55%).

The following amines were prepared as described:

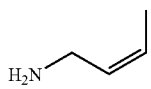

Example A31

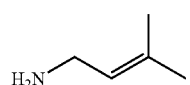

Example A32

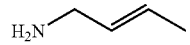

Example A38

The above amines were prepared according to Carlsen, H. J., *J. Heterocycle Chem.* 1997, 34, 797–806.

Example A41

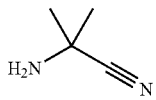

The above amine was prepared according to O'Brien, P. M., *J. Med. Chem.* 1994, 37, 1810–1822.

Example A7

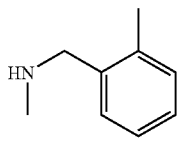

The above amine was prepared according to Weinheim, G. *Arch. Pharm.* 1987, 320, 647–654.

General Method A

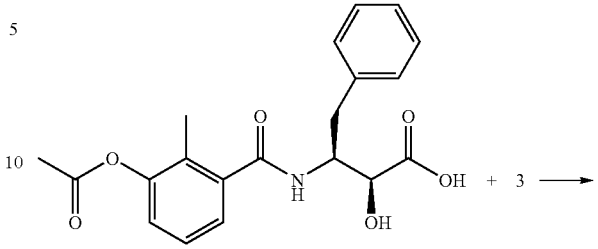

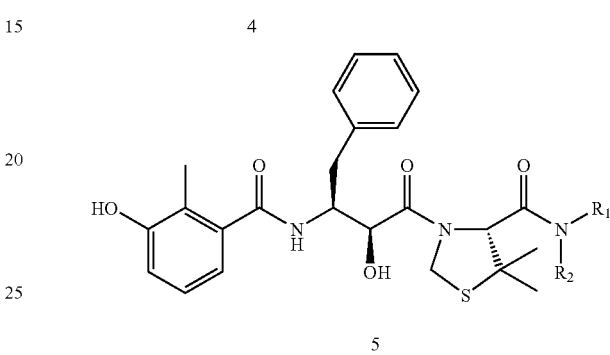

The synthesis of compounds with the general structure 5 is as follows. The boc-protected thiazolidine carboxylic acid 1 is coupled to the requisite amines 2 to yield amino amides 3 using a two step process. The process includes treatment of 1 with 2 in the presence of either diphenylchlorophosphate or HATU, followed by exposure to methane sulfonic acid. Final compounds 5 are obtained by a DCC-mediated coupling of 3 and 4 followed by deprotection of the P2 phenol. Final compounds were purified either by flash chromatography or preparative HPLC.

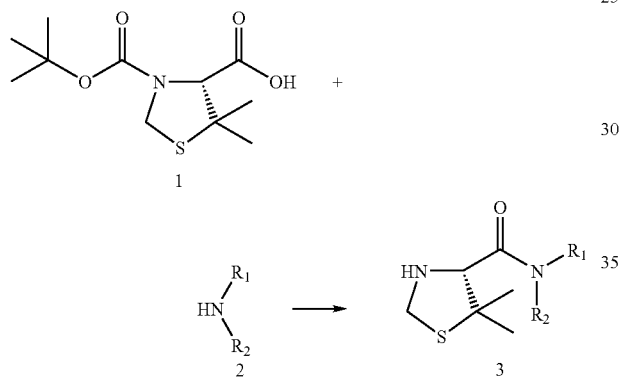

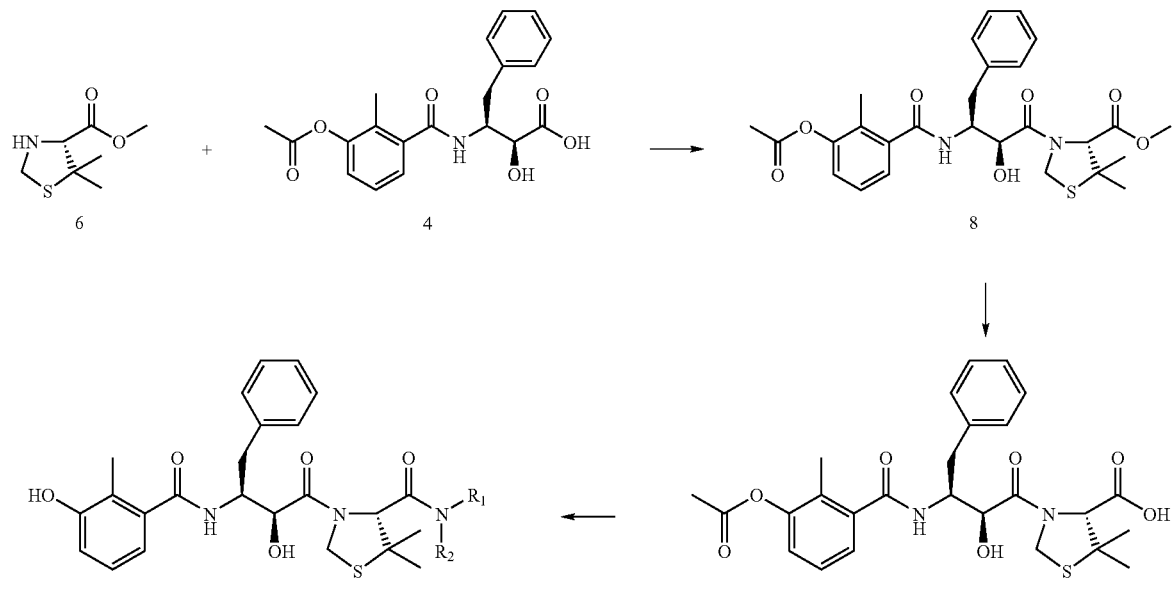

An alternative approach to the general structure 5 is as follows. The thiazolidine ester 6 is coupled to acid 7 under carbodiimide reaction conditions, resulting in product 8 which is converted to acid 9 by mild base hydrolysis. Acid 9 is combined with various amines, using diphenylphosphoryl azide, followed by cleavage of the P2 acetate to yield final compounds 5. The products were purified by either flash chromatography or preparative HPLC.

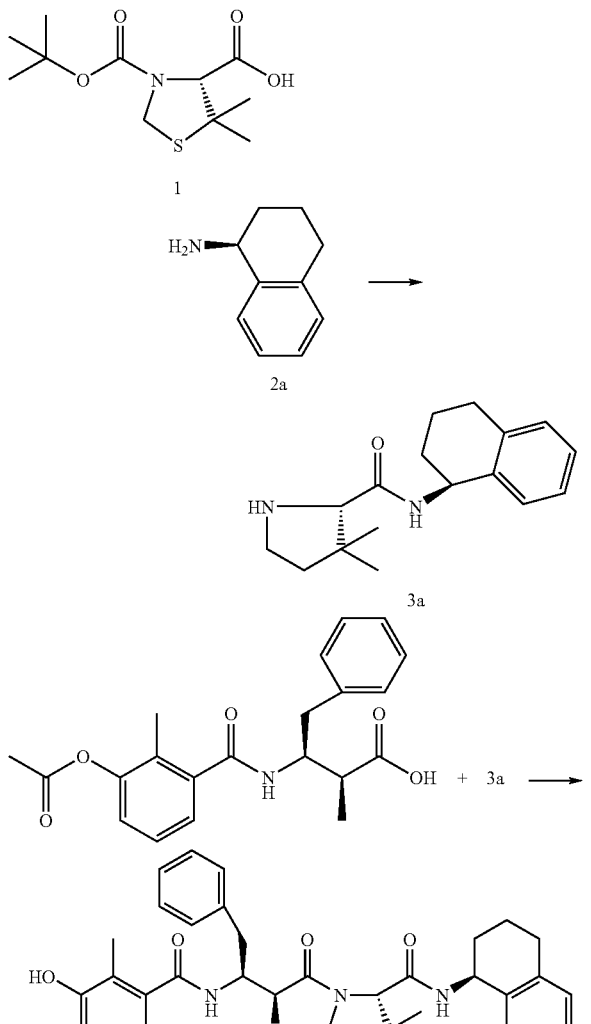

EXAMPLE A1

3-[2-Hydroxy-3-(3-hydroxy-2-methyl-benzoylamino)-4-phenyl-butyryl]-5,5-dimethyl-thiazolidine-4-carboxylic acid (1,2,3,4-tetrahydro-naphthalen-1-yl)-amide The title compound was prepared as follows. (R)-5,5-Dimethyl-thiazolidine-3,4-dicarboxylic acid 3-tert-butyl ester 1 (0.3 g, 1.15 mmol) was dissolved in EtOAc (3 mL) and cooled to 0° C. Diphenyl chlorophosphate (0.26 mL, 1.26 mmol) was added followed by TEA (0.18 mL, 1.26 mmol). The reaction was stirred at 0° C. for 1 h, and treated with (S)-1,2,3,4-Tetrahydro-1-naphthylamine (0.19 g, 1.26 mmol). The reaction mixture was stirred at room temperature overnight, then partitioned between 1N HCl (5 mL) and EtOAc (10 mL). The organic layer was washed with saturated NaHCO$_3$, brine, dried over Na$_2$SO$_4$ and concentrated to a light yellow oil. The resulting crude oil was dissolved in EtOAc (5 mL) and the cooled to 0° C. Methanesulfonic acid (0.36 mL, 5.32 mmol) was added and the solution was stirred at 0° C. for 15 minutes, then at room temperature for 1 h. The mixture was re-cooled to 0° C. and quenched with 5% Na$_2$CO$_3$ (5 mL) then extracted with EtOAc (10 mL). The organic layer was washed with brine, dried over Na$_2$SO$_4$ and concentrated in vacuo to give 3a as a yellow oil. The yellow oil 3a (0.34 g, 1.15 mmol) was dissolved in EtOAc (12 mL). AMB-AHPBA 4 (0.40 g, 1.09 mmol) was added followed by HOBt (0.15 g, 1.09 mmol). The mixture was stirred at room temperature 1 h, then cooled to 0° C. DCC (0.24 g, 1.15 mmol) was slowly added as solution in EtOAc (6 mL). The mixture was warmed to room temperature and stirred overnight. The mixture was filtered and the filtrate was washed with 1N HCl (10 mL), saturated NaHCO$_3$ (10 mL), brine (10 mL), dried over Na$_2$SO$_4$ and concentrated to give a crude white solid (contaminated with DCU). The DCU was removed by flash chromatography (30% to 50% EtOAc in hexanes) to provide a white solid, which was dissolved in MeOH (2 mL) and treated with 4N HCl in 1,4-dioxane (0.26 mL, 1.1 mmol). The reaction was stirred at room temperature overnight then partitioned between 1N HCl (10 mL) and EtOAc (10 mL). The organic layer was washed with saturated NaHCO$_3$, dried over Na$_2$SO$_4$ and concentrated to a residue which was purified by flash chromatography (60% EtOAc in hexanes) to provide the title compound as a white solid: mp=125–126° C.; IR (cm$^-$) 3320, 2932, 1704, 1644, 1530, 1454, 1361, 1284; $^1$H NMR (DMSO-d$_6$) δ 9.36 (s, 1H), 8.28 (d, J=8.6, 1H), 8.21 (d, J=8.8, 1H), 7.35–6.91 (m 10H), 6.76 (d, J=8.0, 1H), 6.54 (d, J=7.5, 1H), 5.34 (d, J=6.0, 1H), 5.13 (d, J=9.0, 1H), 5.02 (d, J=9.0, 1H), 4.60–4.30 (m, 4H), 2.81–2.68 (m, 4H), 1.81 (s, 3H), 1.78–1.60 (m, 4H), 1.48 (s, 3H), 1.45 (s, 3H); Anal. Calcd for C$_{34}$H$_{39}$N$_3$O$_5$S.1.5 H$_2$O: C, 64.95; H, 6.73; N, 6.68. Found: C, 64.88; H, 6.31; N, 6.18.

EXAMPLE A2

(R)-3-((2S,3R)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-methoxy-benzylamide

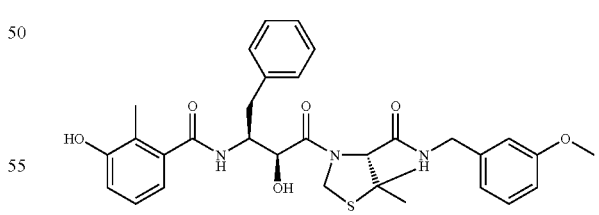

White solid: mp 108–110° C.; IR (neat, cm$^{-1}$) 3310, 2965, 1644, 1586, 1531, 1455, 1359, 1284; $^1$H NMR (DMSO-d$_6$) δ 9.37 (s, 1H), 8.40 (t, J=6.0, 1H), 8.09 (d, J=8.1, 1H), 7.31–6.52 (m, 12H), 5.49 (d, J=6.0, 1H), 5.12 (d, J=9.3, 1H), 5.00 (d, J=9.3, 1H), 4.44–4.35 (m, 3H), 4.42 (s, 1H), 4.09 (dd, J=15.0, 6.0, 1H), 3.69 (s, 3H), 2.87–2.67 (m, 2H), 1.82 (s, 3H), 1.49 (s, 3H), 1.34 (s, 3H); Anal. Calcd for C$_{32}$H$_{37}$N$_3$O$_6$S.0.75 H$_2$O: C, 63.50; H, 6.41; N, 6.94. Found: C, 63.60; H, 6.23; N, 6.80.

The following examples were prepared by the specific method outlined above using the requisite amine 2.

EXAMPLE A3

(R)-3-(2-Hydroxy-3-{[1-(3-hydroxy-2-methyl-phenyl)-methanoyl]-amino}-4-phenyl-butanoyl)-5,5-dimethyl-thiazolidine-4-carboxylic acid 2-methoxy-benzylamide

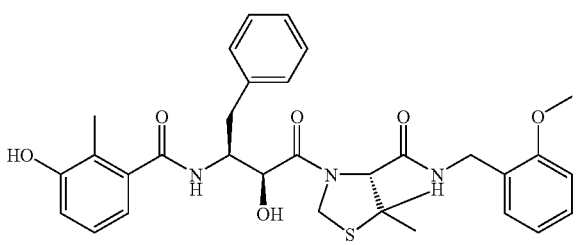

White solid: mp=123–125° C.; IR (cm$^{-1}$) 3318, 2965, 1644, 1525, 1495, 1464, 1286, 1246, 1120, 1030; $^1$H NMR (DMSO-d$_6$) δ 9.36 (s, 1H), 8.26 (t, J=5.9, 1H), 8.14 (d, J=8.0, 1H), 7.39–7.13 (m, 6H), 6.95–6.76 (m, 5H), 6.53 (d, J=7.5, 1H), 5.49 (d, J=6.0, 1H), 5.13 (d, J=9.0, 1H), 5.01 (d, J=9.0, 1H), 4.47 (s, 1H), 4.41–4.16 (m, 4H), 3.78 (s, 3H), 2.90–2.62 (m, 2H), 1.81 (s, 3H), 1.49 (s, 3H). 1.32 (s, 3H); Anal. Calcd for C$_{32}$H$_{37}$N$_3$O$_6$S.0.75 H$_2$O: C, 63.50; H, 6.41; N, 6.94. Found: C, 63.68; H, 6.20; N, 6.54.

EXAMPLE A4

3-(2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-trifluoromethyl-benzylamide

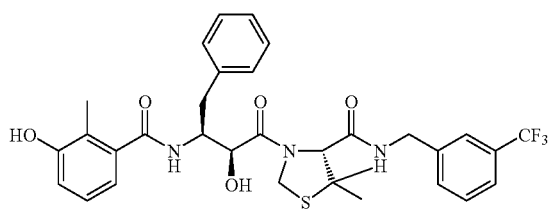

White solid: mp=108–110° C.; IR (cm$^{-1}$) 3308, 3065, 1646, 1540, 1456, 1362, 1329, 1284, 1165, 1125, 1074; $^1$H NMR (DMSO-d$_6$) δ 9.38 (s, 1H), 8.56 (t, J=6.0, 1H), 8.12 (d, J=8.2, 1H), 7.65 (s, 1H), 7.60–7.47 (m, 3H), 7.28–7.13 (m, 5H), 6.96–6.92 (m, 1H), 6.77 (d, J=8.0, 1H), 6.53 (d, J=7.5, 1H), 5.45 (d, J=6.0, 1H), 5.14 (d, J=9.0, 1H), 5.00 (d, J=9.2, 1H), 4.53–4.41 (m, 4H), 4.22 (dd, J=16.0, 6.0, 1H), 2.86–2.66 (m, 2H), 1.81 (s, 3H), 1.49 (s, 3H), 1.31 (s, 3H); Anal. Calcd for C$_{32}$H$_{34}$F$_3$N$_3$O$_5$S: C, 61.04; H, 5.44; N, 6.67. Found: C, 61.03; H, 5.56; N, 6.51.

EXAMPLE A5

3-(2-Hydroxy-3-{[1-(3-hydroxy-2-methyl-phenyl)-methyanoyl]amino}-4-phenyl-butanoyl)-5,5-dimethyl-thiazolidine-4-carboxlic acid fluoro trifluoromethyl-benzylamide

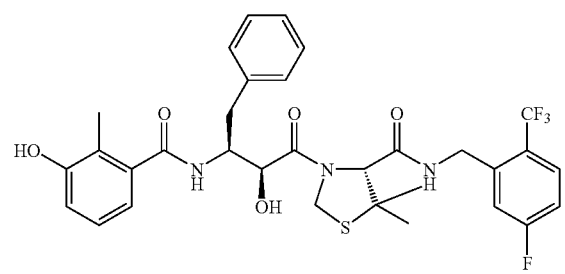

$^1$H NMR (DMSO-d$_6$) δ 9.33 (s, 1H), 8.69 (t, J=5.6, 1H), 8.12–6.56 (m, 11H), 5.50 (d, J=6.0, 1H), 5.22 (d, J=9.3, 1H), 5.06 (d, J=9.3, 1H), 4.60–4.36 (m, 5H), 4.50 (s, 1H), 2.89–2.67 (m, 2H), 1.83 (s, 3H), 1.55 (s, 3H), 1.39 (s, 3H); Anal. Calcd for C$_{32}$H$_{33}$N$_3$O$_5$SF$_4$: C, 59.34; H, 5.14; N, 6.49; S, 4.95. Found: C, 59.06; H, 5.31; N, 6.22; S, 4.66.

EXAMPLE A6

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 4-methoxy-benzylamide

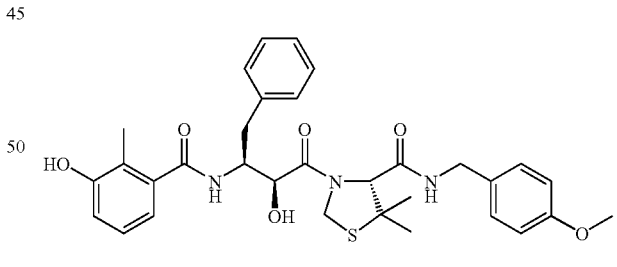

IR (neat cm$^{-1}$) 3335, 2920, 1641, 1516, 1463, 1374, 1285, 1249, 1172, 1118; $^1$H NMR (DMSO-$d_6$) δ 9.38 (s, 1H), 8.37 (t, J=5.5, 1H), 8.12 (d, J=8.2, 1H), 7.33–7.13 (m, 7H), 6.94 (t, J=7.7, 1H), 6.84–6.79 (m, 3H), 6.54 (d, J=7.0, 1H), 5.48 (d, J=6.6, 1H), 5.12 (d, J=9.2, 1H), 5.00 (d, J=9.2, 1H), 4.49–4.42 (m, 3H), 4.32 (dd, J=6.2, 14.8, 6., 1H), 4.09 (dd, J=14.8, 5.3, 1H), 3.67 (s, 3H), 2.87–2.68 (m, 2H), 1.82 (s, 3H), 1.48 (s, 3H), 1.32 (s, 3H); HRMS (ESI) m/z calcd for C$_{32}$H$_{37}$N$_3$O$_6$SNa (M+Na)$^+$ 614.2301, found 614.2305; Anal. Calcd for C$_{32}$H$_{37}$N$_3$O$_6$S.0.75 H$_2$O: C, 63.50; H, 6.41; N, 6.94. Found: C, 63.65; H, 6.43; N, 6.74.

EXAMPLE A7

3-[2-Hydroxy-3-(3-hydroxy-2-methyl-benzoylamino)-4-phenyl-butyryl]-5,5-dimethyl-thiiazolidine-4-carboxylic acid methyl-(2-methyl-benzyl)-amide

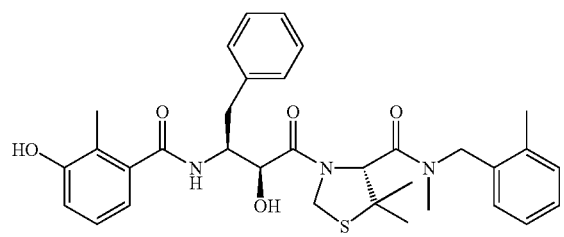

$^1$H NMR (DMSO-d$_6$) δ 9.36 (s, 1H), 8.44 (t, J=7.98, 1H), 8.13–8.07 (m, 2H), 7.34–7.13 (m, 9H), 6.93 (t, J=7.9, 1H), 6.78 (d, J=7.7, 1H), 6.53 (d, J=7.1, 1H), 5.58 (d, J=6.8, 1H), 5.45 (d, J=7.0, 1H), 5.12 (dd J=7.8 8.2 1H), 4.51–4.31(m, 6H), 2.86–2.67 (m, 2H), 2.19 (s, 3H), 1.81 (s, 3H), 1.51 (s, 3H), 1.34 (s, 3H); Anal. Calcd for C$_{33}$H$_{39}$N$_3$O$_5$S.0.37 H$_2$O: C, 66.45; H, 6.72; N, 7.15. Found: C, 66.34; H, 7.28; N, 7.45.

EXAMPLE A8

3-[2-Hydroxy-3-(3-hydroxy-2-methyl-benzoylamino)-4-phenyl-butyryl]-5,5-dimethyl-thiiazolidine-4-carboxylic acid methyl-(3-methyl-thiophen-2-ylmethyl)-amide

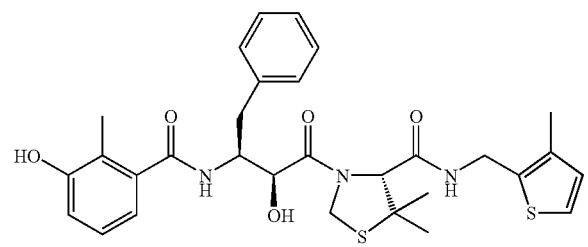

IR (neat or KBr cm$^-$) 3150, 3000, 2942, 2187, 1712, 1600, 1567, 1505; $^1$H NMR (DMSO-d$_6$) δ 9.36 (s, 1H), 8.44 (t, J=7.98, 1H), 8.13–8.07 (m, 2H), 7.34–7.13 (m, 5H), 6.93 (t, J=7.9, 1H), 6.78 (d, J=7.7, 1H), 6.53 (d, J=7.1, 1H), 5.45 (d, J=7.0, 1H), 5.12 (dd, J=7.8, 8.2 1H), 4.51–4.31(m, 4H), 2.86–2.67 (m, 2H), 2.19 (s, 3H), 1.81 (s, 3H), 1.51 (s, 3H), 1.34 (s, 3H); Anal. Calcd for C$_{30}$H$_{35}$N$_3$O$_5$S$_2$: calculated C, 61.94; H, 6.06; N, 7.22. Found C, 62.38; H, 6.23, N, 7.17.

EXAMPLE A9

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 4-trifluoromethyl-benzylamide

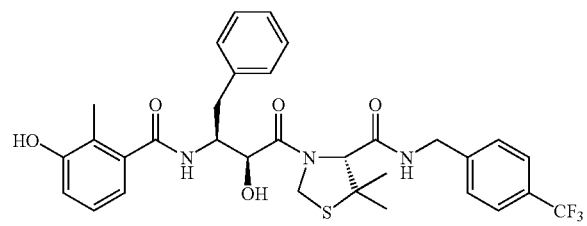

IR (neat cm$^{-1}$) 3343, 2931, 1543, 1530, 1454, 1326, 1122; $^1$H NMR (DMSO-d$_6$) δ 9.38 (s, 1H), 8.57 (t, J=5.0, 1H), 8.15 (d, J=8.4, 1H), 7.59 (d, J=8.2, 2H), 7.50 (d, J=8.2, 2H), 7.28–7.13 (m, 5H), 6.93 (t, J=7.5, 1H), 6.77 (d, J=7.7, 1H), 6.54 (d, J=7.3, 1H), 5.50 (s br, 1H), 5.15 (d, J=9.2, 1H), 5.02 (d, J=9.2, 1H), 4.47–4.21 (m, 5H), 2.85–2.67 (m, 2H), 1.81 (s, 3H), 1.51 (s, 3H), 1.34 (s, 3H);); HRMS (ESI) m/z calcd for C$_{32}$H$_{34}$F$_3$N$_3$O$_5$SNa (M+Na)$^+$ 652.2063, found 652.2044; Anal. Calcd for C$_{32}$H$_{34}$F$_3$N$_3$O$_5$S.0.25 H$_2$O: C, 60.60; H, 5.48; N, 6.63. Found: C, 60.50; H, 5.29; N, 6.48.

EXAMPLE A10

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2-oxo-2-phenyl-ethyl)-amide

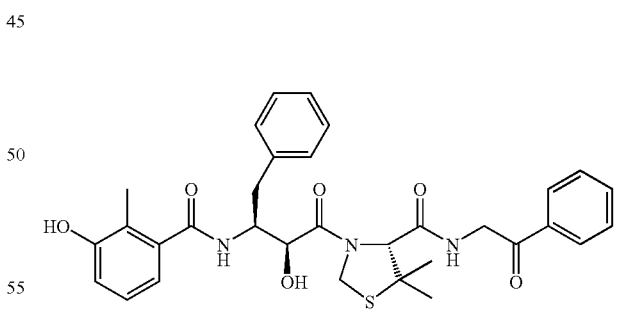

$^1$H NMR (DMSO-d$_6$) δ 9.39 (s, 1H), 8.36 (t, J=4.8, 1H), 8.15 (d, J=8.1, 1H), 7.98 (d, J=7.4, 1H), 7.65 (m, 1H), 7.52 (m, 2H), 7.32–7.11 (m, 6H), 6.93 (t, J=7.9, 1H), 6.76 (d, J=7.9, 1H), 6.54 (d, J=7.5, 1H), 5.42 (d, J=6.4, 1H), 5.08 (d, J=9.3, 1H), 5.02 (d, J=9.0, 1H), 4.78–4.30 (m, 5H), 2.84–2.66 (m, 2H), 1.81 (s, 3H), 1.57 (s, 3H), 1.45 (s, 3H); HRMS (ESI) m/z calcd for C$_{32}$H$_{35}$N$_3$O$_6$SNa (M+Na)$^+$ 612.2139, found 612.2141.

EXAMPLE A11

3-(2-Hydroxy-3-{[1-(3-hydroxy-2-methyl-phenyl)-methanoyl-amino}-4-phenyl-butanoyl-5,5-dimethyl-thiazolidine-4-carboxylic acid 3-fluoro-4-trifluoromethyl-benzylamide

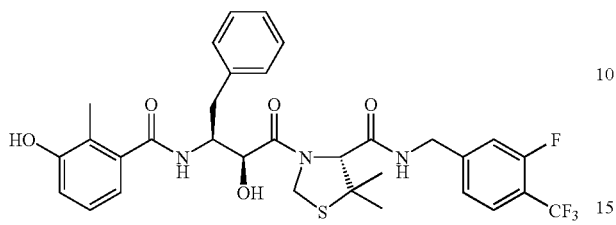

$^1$H NMR (DMSO-d$_6$) δ 9.34 (s, 1H), 8.62 (t, J=5.9, 1H), 8.09–6.54 (m, 11H), 5.45 (s br, 1H), 5.18 (d, J=9.2, 1H), 5.03 (d, J=9.2, 1H), 4.55–4.00 (m, 5H), 4.45 (s, 1H), 2.86–2.49 (m, 2H), 1.82 (s, 3H), 1.53 (s, 3H), 1.36 (s, 3H); Anal. Calcd for C$_{32}$H$_{33}$N$_3$O$_5$SF$_4$: C, 59.34; H, 5.14; N, 6.49; S, 4.95. Found: C, 59.14; H, 5.29; N, 6.21; S, 4.67.

EXAMPLE A12

3-(2-Hydroxy-3-{[1-(3-hydroxy-2-methyl-phenyl)-methanoyl-amino}-4-phenyl-butanoyl)-5,5-dimehtyl-thiazolidine-4-carboxylic acid-2-trifluoromethyl-4-fluoro-benzylamide

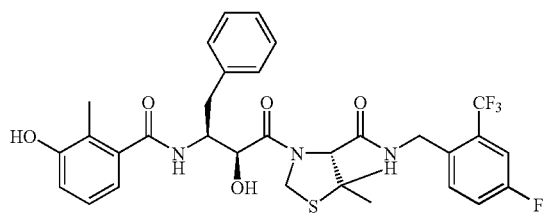

$^1$H NMR (DMSO-d$_6$) δ 9.33 (s, 1H), 8.65 (t, J=5.9, 1H), 8.12–6.54 (m, 11H), 5.45 (d, J=6.9, 1H), 5.18 (d, J=9.2, 1H), 5.05 (d, J=9.2, 1H), 4.59–4.34 (m, 5H), 4.50 (s, 1H), 2.85–2.67 (m, 2H), 1.82 (s, 3H), 1.53 (s, 3H), 1.37 (s, 3H); Anal. Calcd for C$_{32}$H$_{33}$N$_3$O$_5$SF$_4$: C, 59.34; H, 5.14; N, 6.49; S, 4.95. Found: C, 59.26; H, 5.35; N, 6.23; S, 4.69.

EXAMPLE A13

3-[2-Hydroxy-3-(3-hydroxy-2-methyl-benzoylamino)-4-phenyl-butyryl]-5,5-dimethyl-thiazolidine-4-carboxylic acid 4-methanesulfonyl-benzamide

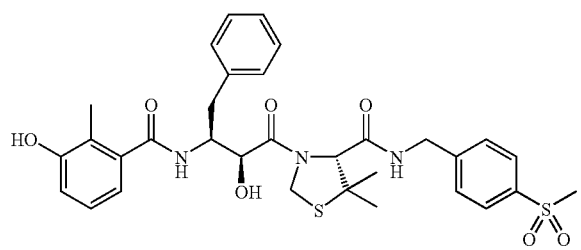

$^1$H NMR (DMSO-d$_6$) δ 9.38 (s, 1H), 8.37 (t, J=5.5, 1H), 8.12 (d, 1H, J=8.2, 1H), 7.33–7.13 (m, 7H), 6.94 (t, 1H, J=7.7, 1H), 6.84–6.79 (m, 3H), 6.54 (d, 1H, J=7.3, 1H), 5.48 (d, J=6.6, 1H), 5.12 (d, J=9.2, 1H), 5.00 (d, 1H, J=9.2, 1H), 4.49–4.42 (m, 3H), 4.32 (dd, J=14.8, 6.2, 1H), 4.09 (dd, 1H, J=14.8, 5.3, 1H), 3.47 (s, 3H), 2.87–2.68 (m, 2H), 1.82 (s, 3H), 1.48 (s, 3H), 1.32 (s, 3H); Anal. Calcd for C$_{32}$H$_{37}$N$_3$O$_7$S$_2$: C, 60.07; H, 5.83; N, 6.57. Found C, 60.25; H, 6.13; N, 6.74.

EXAMPLE A14

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid allylamide

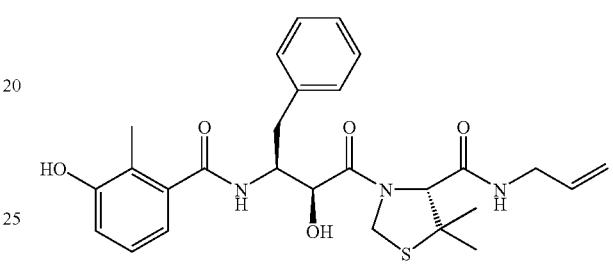

IR (neat cm$^{-1}$) 3342, 2966, 1637, 1531, 1460, 1366, 1284, 1108; $^1$H NMR (DMSO-d$_6$) δ 9.36 (s, 1H), 8.13–8.07 (m, 2H), 7.34–7.13 (m, 5H), 6.93 (t, J=7.9, 1H), 6.78 (d, J=7.7, 1H), 6.53 (d, J=7.0, 1H), 5.82–5.70 (m, 1H), 5.46 (d, J=6.6, 1H), 5.23–4.97 (m, 4H), 4.40 (m, 3H), 3.81–3.59 (m, 2H), 2.86–2.67 (m, 2H), 1.81 (s, 3H), 1.50 (s, 3H), 1.35 (s, 3H); HRMS (ESI) m/z calcd for C$_{27}$H$_{33}$N$_3$O$_5$S Na (M+Na)$^+$ 534.2039, found 534.2062; Anal. Calcd for C$_{27}$H$_{33}$N$_3$O$_5$S: C, 63.38; H, 6.50; N, 8.21. Found: C, 63.68; H, 6.57; N, 8.29.

EXAMPLE A15

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 4-dimethylamino-benzylamide

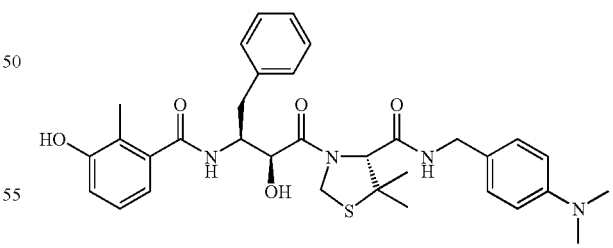

IR (neat cm$^{-1}$) 3331, 2931, 1643, 1519, 1455, 1349, 1284; $^1$H NMR (DMSO-d$_6$) δ 9.37 (s, 1H), 8.26 (m, 1H), 8.12 (d, J=7.1, 1H), 7.38–6.92 (m, 8H), 6.78 (t, J=7.9, 1H), 6.60 (d, J=8.6, 1H), 6.55 (d, J=7.3, 1H), 6.42 (d, J=8.2, 1H), 5.46 (d, J=6.0, 1H), 5.11 (d, J=9.3, 1H), 5.00 (d, J=9.3, 1H), 4.45 (m, 3H), 4.25 (m, 1H), 4.03 (m, 1H), 2.80 (s, 3H), 2.87–2.73 (m, 2H), 1.82 (s, 3H), 1.48 (s, 3H), 1.32 (s, 3H); HRMS (ESI) m/z calcd for C$_{33}$H$_{40}$N$_4$O$_5$SNa (M+Na)$^+$ 627.2612, found 627.2607.

EXAMPLE A16

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 4-amino-benzylamide

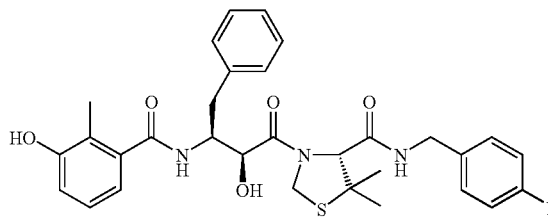

Pale yellow solid: mp=107–109° C.; IR (cm$^{-1}$) 3378, 2919, 1631, 1518, 1453, 1382, 1281, 1121; $^1$H NMR (DMSO-d$_6$) δ 9.36 (s, 1H), 8.21 (t, J=6.0, 1H), 7.40–7.10 (m, 6H), 8.12 (d, J=8.1, 1H), 6.92 (d, J=8.4, 2H), 6.77 (d, J=7.2, 1H), 6.54 (d, J=7.2, 1H), 6.44 (d, J=8.4, 2H), 5.44 (d, J=6.0, 1H), 5.10 (d, J=9.2, 1H), 4.99 (d, J=9.2, 1H), 4.90 (s, 2H), 4.50–4.32 (m, 3H), 4.22–3.93 (m, 2H), 2.90–2.60 (m, 2H), 1.81 (s, 3H), 1.47 (s, 3H), 1.31 (s, 3H); Anal. Calcd for C$_{31}$H$_{36}$N$_4$O$_5$S.0.25 H$_2$O: C, 64.06; H, 6.33; N, 9.64. Found: C, 64.17; H, 6.38; N, 9.60.

EXAMPLE A17

3-(2-Hydroxy-3-{[1-(3-hydroxy-2-methyl-phenyl)-methanoyl]-amino}-4-phenyl-butanoyl)-5,5-dimethyl-thiazolidine-4-carboxylic acid prop-2-ynylamide

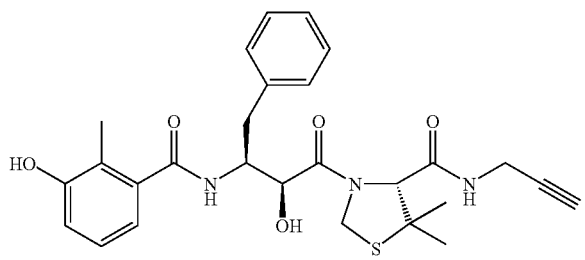

$^1$H NMR (DMSO-d$_6$) δ 9.33 (s, 1H), 8.38 (t, J=5.5, 1H), 8.08(d, J=8.3, 1H), 7.35–6.53 (m, 8H), 5.46 (d, J=6.6, 1H), 5.10 (d, J=9.2, 1H), 5.02 (d, J=9.2, 1H), 4.44–4.40 (m, 1H), 4.40 (s, 1H), 3.85 (m, 3H), 3.08 (t, J=2.5, 1H), 2.88–2.68 (m, 2H), 1.82 (s, 3H), 1.51 (s, 3H), 1.37 (s, 3H); Anal. Calcd for C$_{27}$H$_{31}$N$_3$O$_5$S: C, 63.63; H, 6.13; N, 8.24; S, 6.29. Found: C, 63.50; H, 6.33; N, 7.81; S, 5.68.

EXAMPLE A18

3-(2-Hydroxy-3-{[1-(3-hydroxy-2-methyl-phenyl)-methanoylamino}-4-phenyl-butanoyl)]-5,5-dimethyl-thiazolidine-4-carboxylic acid (2-methylsulfanyl-phenyl)-amide

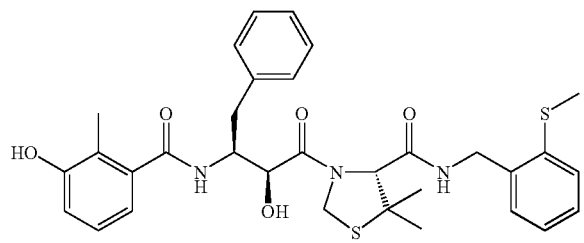

$^1$H NMR (DMSO-d$_6$) δ 9.33 (s, 1H), 8.41 (t, J=5.7, 1H), 8.10 (d, J=8.3, 1H), 8.09–6.54 (m, 12H), 5.46 (d, J=6.6, 1H), 5.14 (d, J=9.2, 1H), 5.04 (d, J=9.2, 1H), 4.50–4.02 (m, 4H), 4.50 (s, 1H), 2.89–2.69 (m, 2H), 2.51 (s, 3H), 1.84 (s, 3H), 1.53 (s, 3H), 1.39 (s, 3H); Anal. Calcd for C$_{32}$H$_{37}$N$_3$O$_5$S$_2$: C, 63.24; H, 6.14; N, 6.91. Found: C, 63.01; H, 6.30; N, 6.53.

EXAMPLE A19

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid phenethyl-amide

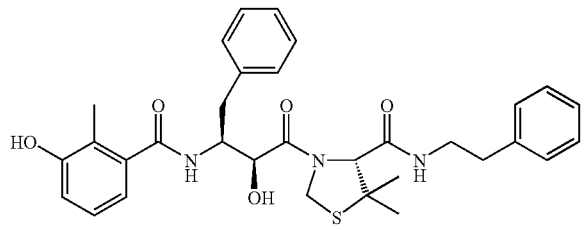

$^1$H NMR (DMSO-d$_6$) δ 9.41 (s, 1H), 8.38 (t, J=4.8, 1H), 8.16 (d, J=8.1, 1H), 8.01 (d, J=7.4, 1H), 7.64 (m, 1H), 7.52 (m, 2H), 7.32–7.11 (m, 6H), 6.93 (t, J=7.9, 1H), 6.76 (d, J=7.9, 1H), 6.54 (d, J=7.5, 1H), 5.42 (d, J=6.4, 1H), 5.10 (d, J=9.3, 1H), 5.05 (d, J=9.0, 1H), 4.80–4.32 (m, 5H), 2.84–2.66 (m, 4H), 1.80 (s, 3H), 1.56 (s, 3H), 1.45 (s, 3H); Anal. Calcd for C$_{32}$H$_{37}$N$_3$O$_5$S: C, 66.76; H, 6.48; N, 7.30. Found C, 66.50; H, 6.56; N, 7.23.

EXAMPLE A20

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid ((S)-1-phenyl-ethyl)-amide

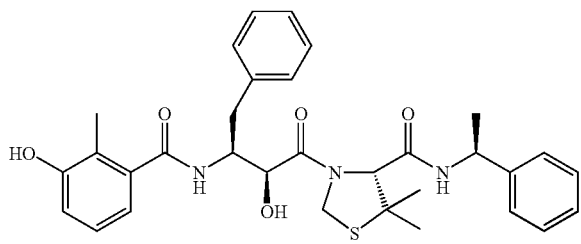

White solid: mp 114–115° C.; IR (neat, cm$^{-1}$) 3306, 2971, 1643, 1531, 1451, 1372, 1284, 1211, 1107; $^1$H NMR (DMSO-d$_6$) δ 9.36 (s, 1H), 8.45 (d, J=8.2, 1H), 8.19 (d, J=8.2, 1H), 7.32–7.18 (m, 10H), 6.96–6.91 (m, 1H), 6.76 (d, J=8.1, 1H), 6.54 (d, J=7.5, 1H), 5.36 (d, J=7.2, 1H), 5.08 (d, J=9.7, 1H), 5.01 (d, J=9.7, 1H), 4.95–4.85 (m, 2H), 4.48 (s, 1H), 4.45–4.30 (m, 1H), 2.80–2.60 (m, 2H), 1.79 (s, 3H), 1.47 (s, 3H), 1.36 (d, J=7.2, 3H), 1.30 (d, J=7.0, 3H); Anal. Calcd for C$_{32}$H$_{37}$N$_3$O$_5$S.0.25 H$_2$O: C, 66.24; H, 6.51; N, 7.24. Found C, 66.30; H, 6.56; N, 6.89.

EXAMPLE A21

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid ((R)-1-phenyl-ethyl)-amide

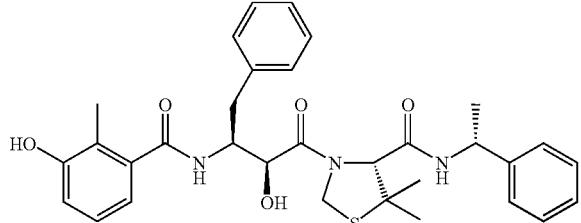

White solid: mp 114–115° C.; IR (neat, cm$^{-1}$) 3299, 1643, 1583, 1520, 1454, 1377, 1284, 1104; $^1$H NMR (DMSO-d$_6$) δ 9.35 (s, 1H), 8.36 (d, J=8.2, 1H), 8.15 (d, J=8.2, 1H), 7.44–7.13 (m, 10H), 6.96–6.91 (m, 1H), 6.75 (d, J=8.1, 1H), 6.52 (d, J=6.7, 1H), 5.38 (d, J=6.9, 1H), 5.15 (d, J=9.7, 1H), 4.99 (d, J=9.7, 1H), 5.28–4.74 (m, 1H), 4.52(s, 1H), 4.49–4.35 (m, 2H), 2.80–2.60 (m, 2H), 1.79 (s, 3H), 1.50 (s, 3H), 1.38 (s, 3H), 1.34 (d, J=7.0, 3H); Anal. Calcd for C$_{32}$H$_{37}$N$_3$O$_5$S.0.25 H$_2$O: C, 66.24; H, 6.51; N, 7.24. Found: C, 66.38; H, 6.52; N, 7.30.

EXAMPLE A22

3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (benzo[1,3]dioxol-5-ylmethyl)-amide

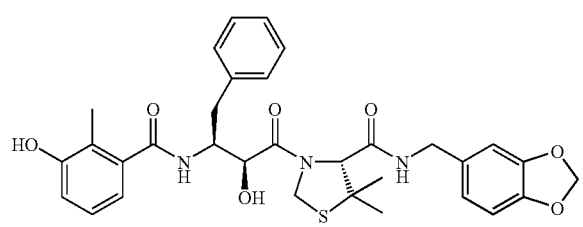

IR (neat or KBr cm$^{-1}$) 3302, 2922, 2351, 2333, 1768, 1750, 1646, 1537; $^1$H NMR (DMSO-d$_6$) δ 9.36 (s, 1H), 8.44 (s, 1H), 8.13 (d, J=7.9 1H), 7.34–7.13 (m, 5H), 6.99–6.77 (m, 4H), 6.78 (d, J=7.7, 1H), 5.93 (d, J=7.1, 2H), 5.15 (d, J=7.0, 1H), 5.08 (d, J=7.8, 1H), 4.43 (d, J=9.32, 2H), 4.34 (m, 2H), 4.12(d, J=6.18, 1H), 4.08 (d, J=6.08, 1H), 2.86–2.67 (m, 2H), 2.55 (s, 1H), 1.81 (s, 3H), 1.51 (s, 3H), 1.39 (s, 3H); Anal. Calcd C$_{32}$H$_{35}$N$_3$O$_7$S.0.65 TFA.1.0 H$_2$O: C, 57.31; H, 5.44; N, 6.02. Found: C, 57.58; H, 5.47; N, 5.85.

EXAMPLE A23

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid allyl-methyl-amide

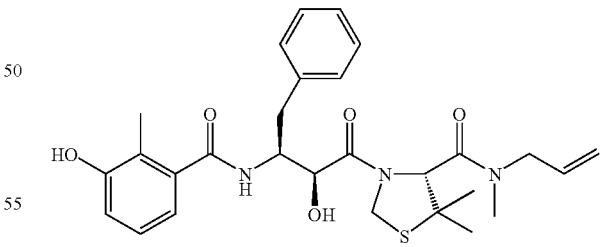

IR (neat, cm$^{-1}$) 3380, 2943, 1637, 1460, 1284, $^1$H NMR (DMSO-d$_6$) δ 9.37 (s, 1H), 8.24 (d, J=8.4, 1H), 7.34–7.15 (m, 5H), 6.94 (t, J=7.5, 1H), 6.77 (d, J=7.7, 1H), 6.53 (d, J=7.5, 1H), 5.99 (m, 1H), 5.70–5.65 (m, 1H), 5.49–5.00 (m, 5H), 4.30–3.85 (m, 4H), 3.08 (s, 3H), 2.78–2.65 (m, 2H), 1.80 (s, 3H), 1.58 (s, 3H), 1.38 (s, 3H); HRMS (ESI) m/z calcd for C$_{28}$H$_{35}$N$_3$O$_5$SNa (M+Na)$^+$ 548.2190, found 548.2178.

EXAMPLE A24

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid fluoro-trifluoromethyl-benzylamide

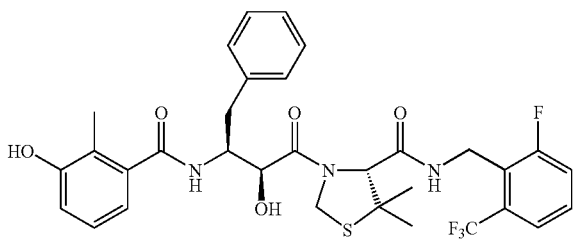

$^1$H NMR (DMSO-d$_6$) δ 9.34 (s, 1H), 8.32 (t, J=6.0, 1H), 8.20 (d, J=8.4, 1H), 7.70–7.56 (m, 3H), 7.37 (d, J=6.9, 2H), 7.27 (t, J=7.5, 2H), 7.18 (t, J=7.4, 1H), 6.97 (t, J=7.0, 1H), 6.79 (d, J=7.0, 1H), 6.58 (d, J=6.6, 1H), 5.15 (d, J=9.0, 1H), 5.02 (d, J=9.0, 1H), 4.60–4.48 (m, 3H), 4.48–4.32 (m, 2H), 2.88–2.65 (m, 2H), 1.83 (s, 3H), 1.48 (s, 3H), 1.34 (s, 3H); HRMS (ESD m/z calcd for C$_{32}$H$_{33}$N$_3$O$_5$SF$_4$Na (M+Na)$^+$ 670.1969, found 670.1999; Anal. Calcd for C$_{32}$H$_{33}$N$_3$O$_5$S F$_4$.1 H$_2$O, 0.3 TFA: C, 55.94; H, 5.08; N, 6.00. Found: C, 55.74; H, 4.98; N, 5.94.

EXAMPLE A25

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-trifluoromethoxy-benzylamide

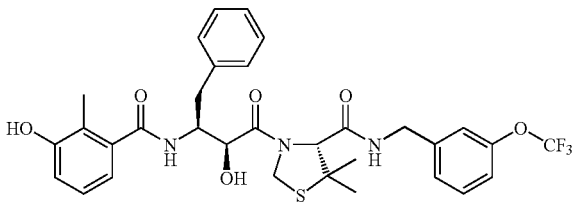

White solid: mp=102–105° C.; IR (cm$^{-1}$) 3306, 2966, 1644, 1586, 1520, 1216, 1166; $^1$H NMR (DMSO-d$_6$) δ 9.38 (s, 1H), 8.53 (t, J=6.0, 1H), 8.12 (d, J=8.1, 1H), 7.40–7.13 (m, 9H), 6.96–6.91 (m, 1H), 6.77 (d, J=8.2, 1H), 6.54 (d, J=7.7, 1H), 5.48 (d, J=6.4, 1H), 5.13 (d, J=9.2, 1H), 5.00 (d, J=9.2, 1H), 4.46–3.97 (m, 5H), 2.87–2.67 (m, 2H), 1.81 (s, 3H), 1.50 (s, 3H), 1.30 (s, 3H); Anal. Calcd for C$_{32}$H$_{34}$F$_3$N$_3$O$_6$S.0.25 H$_2$O: C, 59.11; H, 5.35; N, 6.46. Found: C, 58.91; H, 5.40; N, 6.30.

EXAMPLE A26

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-ethoxy-benzylamide

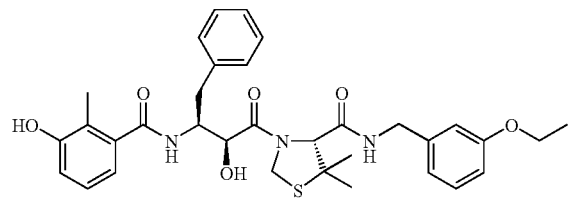

White solid: mp=105–107° C.; IR (cm$^{-1}$) 3322, 3063, 2978, 1643, 1585, 1538, 1454, 1354, 1265, 1159, 1050; $^1$H NMR (DMSO-d$_6$) δ 9.38 (s, 1H), 8.40 (t, J=5.6, 1H), 8.11 (d, J=8.2, 1H), 7.30–6.70 (m, 11H), 6.53 (d, J=7.5, 1H), 5.48 (d, J=5.9, 1H), 5.11 (d, J=8.9, 1H), 5.00 (d, J=8.9, 1H), 4.50–4.20 (m, 4H), 4.07 (dd, J=15.0, 5.3, 1H), 3.94 (dd, J=14.0, 6.9, 2H), 2.90–2.62 (m, 2H), 1.81 (s, 3H), 1.49 (s, 3H), 1.34 (s, 3H), 1.25 (t, J=6.9, 3H); Anal. Calcd for C$_{33}$H$_{39}$N$_3$O$_6$S.0.75 H$_2$O: C, 64.01; H, 6.59; N, 6.79. Found: C, 63.89; H, 6.27; N, 6.44.

EXAMPLE A27

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid methyl-prop-2-ynyl-amide

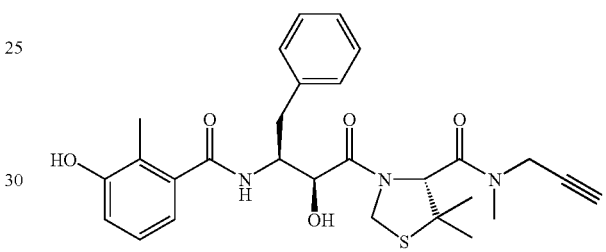

IR (neat, cm$^{-1}$) 3378, 1643, 1461, 1279, 1108, $^1$H NMR (DMSO-d$_6$) δ 9.37 (s, 1H), 8.21 (d, J=9.2, 1H), 7.33–7.13 (m, 5H), 6.94 (t, J=7.7, 1H), 6.78 (d, J=8.1, 1H), 6.52 (d, J=7.0, 1H), 5.45 (d, J=6.8, 1H), 5.16 (d, J=9.2, 1H), 5.02 (d, J=9.2, 1H), 4.98 (s, 1H), 4.47–4.13 (s, 3H), 4.03–3.92 (m, 1H), 3.17 (s, 3H), 2.88 (s, 1H), 2.79–2.50 (m, 2H), 1.80 (s, 3H), 1.57 (s, 3H), 1.36 (s, 3H); Anal. Calcd for C$_{28}$H$_{33}$N$_3$O$_5$S.0.6H$_2$O: C, 62.95; H, 6.45; N, 7.86. Found: C, 62.95; H, 6.39; N, 7.69.

EXAMPLE A28

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2-methyl-allyl)-amide

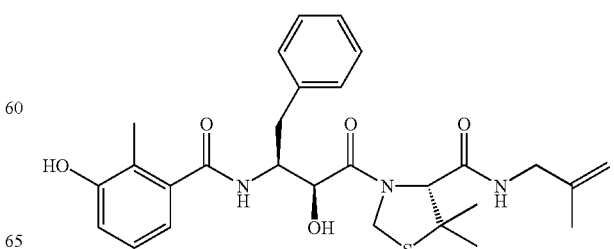

¹H NMR (DMSO-d₆) δ 9.33, (s, 1H), 8.18–7.79 (m, 2H), 7.39–7.12 (m, 5H), 6.92 (t, J=8.1, 1H), 6.75 (d, J=8.1, 1H), 6.53 (d, J=7.0, 1H), 5.09 (d, J=9.2, 1H), 4.96 (d, J=9.2, 1H), 4.96 (d, J=9.2, 1H), 4.70 (s, 1H), 4.43 (s, 1H), 4.40 (br s, 2H) 3.81–3.49 (m, 4H), 2.85–2.65 (m, 2H), 1.82 (s, 3H), 1.63 (s, 3H), 1.49 (s, 3H), 1.35 (s, 3H); Anal. Calcd for $C_{28}H_{35}N_3O_5S$: C, 63.97; H, 6.71; N, 7.99. Found: C, 63.85; H, 6.92; N, 7.65.

EXAMPLE A29

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-amino-benzylamide

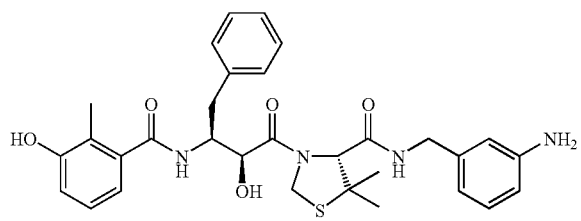

IR (neat, cm⁻¹) 3401, 2943, 1643, 1525, 1461, 1373; ¹H NMR (DMSO-d₆) δ 9.36 (s, 1H), 8.28 (t, J=8.0, 1H), 8.12 (d, J=8.9, 1H), 7.33–6.37 (m, 12H), 5.45 (d, J=7.0, 1H), 5.10 (d, J=8.9, 1H), 4.99 (d, J=8.9, 1H), 4.50–4.35 (m, 3H), 4.30–3.90 (m, 2H), 2.90–2.70 (m, 2H), 2.06 (s, 2H), 1.81 (s, 3H), 1.48 (s, 3H), 1.33 (s, 3H); Anal. Calcd for $C_{31}H_{36}N_4O_5S \cdot 0.5 H_2O$: C, 63.57; H, 6.37; N, 9.57. Found: C, 63.59; H, 6.38; N, 9.58.

EXAMPLE A30

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid cyanomethylamide

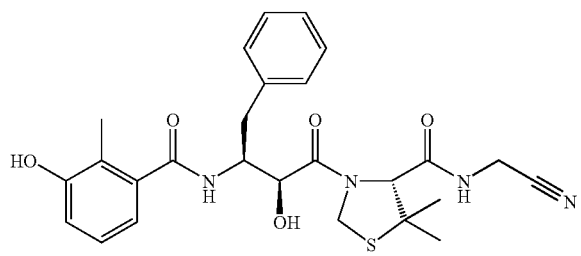

¹H NMR (DMSO-d₆) δ 9.34 (s, 1H), 8.65 (s, 1H), 8.15 (m, 1H), 7.42–7.19 (m, 5H), 6.94 (t, J=7.9, 1H), 6.81 (d, J=7.9, 1H), 6.62 (d, J=7.9, 1H), 5.22 (d, J=9.7, 1H), 5.05 (d, J=9.7, 1H), 4.61–4.36 (m, 4H), 3.01–2.71 (m, 4H), 1.84 (s, 3H), 1.47 (s, 3H), 1.34 (s, 3H); Anal. Calcd for $C_{26}H_{30}N_4O_5S$: C, 61.16; H, 5.92; N, 10.97. Found: C, 61.24; H, 6.14; N, 10.62.

EXAMPLE A31

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (Z)-but-2-enylamide

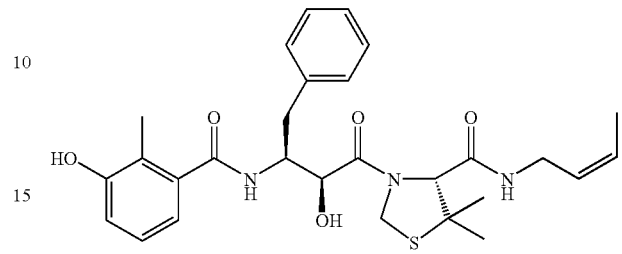

¹H NMR (DMSO-d₆) δ 9.37 (s, 1H), 8.35 (m, 1H), 8.12 (m, 1H), 7.15–6.98 (m, 6H), 6.77 (d, J=7.7, 1H), 6.68 (d, J=7.5, 1H), 5.60–5.33 (m, 3H), 5.18 (d, J=9.2, 1H), 5.02 (d, J=9.2, 1H), 4.52–4.39 (m, 3H), 3.79–3.68 (m, 2H), 2.92–2.62 (m, 2H), 1.80 (s, 3H), 1.61 (d, J=6.9, 3H), 1.51 (s, 3H), 1.38 (s, 3H); Anal. Calcd for $C_{28}H_{35}N_3O_5S$: C, 63.97; H, 6.71; N, 7.99. Found: C, 63.73; H, 6.75; N, 7.83.

EXAMPLE A32

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (3-methyl-but-2-enyl)-amide

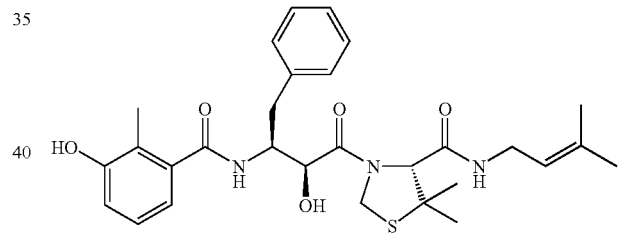

¹H NMR (DMSO-d₆) δ 9.33 (s, 1H), 8.19 (d, J=8.6, 1H), 7.96 (s br, 1H), 7.39–7.18 (m, 5H), 6.91 (t, J=7.6, 1H), 6.79 (d, J=7.9, 1H), 6.55 (d, J=7.1, 1H), 5.41 (m br, 1H), 5.21 (m, 2H), 5.02 (d, J=9.1, 1H), 4.57–4.37 (m, 3H), 3.79–3.61 (m, 2H), 2.90–2.71 (m, 2H), 1.81 (s, 3H), 1.63 (s, 6H), 1.52 (s, 3H), 1.40 (s, 3H); Anal. Calcd for $C_{29}H_{37}N_3O_5S$: C, 64.54; H, 6.91; N, 7.79. Found: C, 64.75; H, 6.82; N, 7.43.

EXAMPLE A33

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-acetylamino-benzylamide

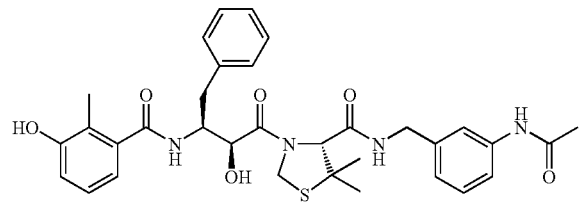

White solid: mp=145–147° C.; IR (neat, cm$^{-1}$) 3378, 2919, 1637, 1514, 1461, 1361; $^1$H NMR (DMSO-d$_6$) δ 9.87 (s, 1H), 9.36 (s, 1H), 8.45–8.40 (m, 1H), 8.12 (d, J=7.9, 1H), 7.49–6.91 (m, 10H), 6.77 (d, J=7.9, 1H), 6.55 (d, J=7.9, 1H), 5.49 (d, J=7.0, 1H), 5.10 (d, J=9.3, 1H), 5.00 (d, J=9.3, 1H), 4.44–3.95 (m, 5H), 2.90–2.62 (m, 2H), 2.00 (s, 3H), 1.80 (s, 3H), 1.48 (s, 3H), 1.32 (s, 3H); Anal. Calcd for C$_{32}$H$_{38}$N$_4$O$_6$S.1.5 H$_2$O: C, 61.38; H, 6.40; N, 8.68. Found: C, 61.49; H, 6.14; N, 8.35.

EXAMPLE A34

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid ((Z)-2-methyl-but-2-enyl)-amide

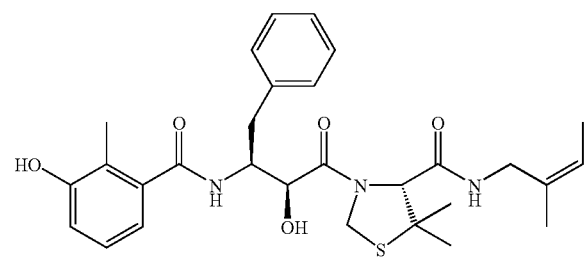

$^1$H NMR (DMSO-d$_6$) δ 9.36 (s, 1H), 8.16 (d, J=8.4, 1H), 8.00 (t, J=5.3, 1H), 7.36–7.13 (m, 5H), 6.94 (t, J=7.7, 1H), 6.77 (d, J=8.1, 1H), 6.53 (d, J=7.3, 1H), 5.37 (d, J=5.7, 1H), 5.24 (m, 1H), 5.12 (d, J=9.0, 1H), 5.00 (d, J=9.0, 1H), 4.48–4.39 (m, 3H), 3.71 (d, J=3.7, 2H), 2.82–2.65 (m, 2H), 1.80 (s, 3H), 1.61 (m, 6H), 1.49 (s, 3H), 1.35 (s, 3H); HRMS (ESI) m/z calcd for C$_{29}$H$_{37}$N$_3$O$_5$SNa (M+Na)$^{30}$ 562.2346, found 562.2360; Anal. Calcd for C$_{29}$H$_{37}$N$_3$O$_5$S: C, 64.54; H, 6.91; N, 7.79. Found: C, 64.33; H, 6.92; N, 7.60.

EXAMPLE A35

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid ((E)-2-methyl-but-2-enyl)-amide

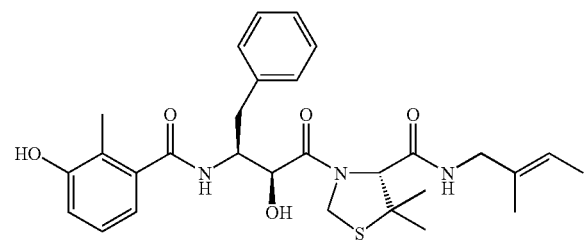

$^1$H NMR (DMSO-d$_6$) δ 9.37(s, 1H), 8.11 (d, J=8.2, 1H), 7.96 (t, J=5.5, 1H), 7.34–7.13 (m, 5H), 6.94 (t, J=7.7, 1H), 6.77 (d, J=8.1, 1H), 6.53 (d, J=7.3, 1H), 5.44 (d, J=6.6, 1H), 5.34 (d, J=6.6, 1H), 5.10 (d, J=9.0, 1H), 4.98 (d, J=9.1, 1H), 4.47–4.36 (m, 3H), 3.71 (dd, J=14.7, 6.6, 1H), 3.46 (dd, J=14.5, 4.8, 1H), 2.85–2.67 (m, 2H), 1.81 (s, 3H), 1.50 (m, 9H), 1.35 (s, 3H); HRMS (ESI) m/z calcd for C$_{29}$H$_{37}$N$_3$O$_5$SNa (M+Na)$^{30}$ 562.2346, found 562.2220.

EXAMPLE A36

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (E)-pent-2-enylamide

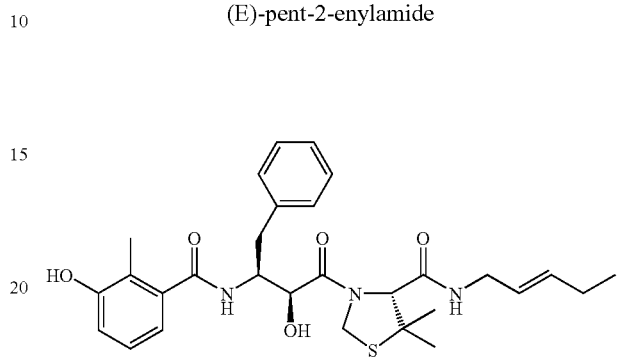

White solid: mp=113–115° C.; IR (neat, cm$^{-1}$) 3315, 2964, 1643, 1584, 1530, 1454, 1371, 1283, 1104, 969; $^1$H NMR (DMSO-d$_6$) δ 9.35 (s, 1H), 8.11 (d, J=8.2, 1H), 8.02 (t, J=5.6, 1H), 7.33–7.13 (m, 5H), 6.96–6.90 (m, 1H), 6.76 (d, J=8.2, 1H), 6.52 (d, J=7.5, 1H), 5.66–5.56 (m, 1H), 5.43(d, J=6.8, 1H), 5.38–5.31 (m, 1H), 5.10 (d, J=8.9, 1H), 4.99 (d, J=8.9, 1H), 4.47–4.39 (m, 2H), 4.38 (s, 1H), 3.72–3.53 (m, 2H), 2.84–2.66 (m, 2H), 1.98–1.83 (m, 2H), 1.80 (s, 3H), 1.48 (s, 3H), 1.34 (s, 3H), 0.87 (t, J=7.3, 3H); Anal. Calcd for C$_{29}$H$_{37}$N$_3$O$_5$S.0 5 H$_2$O: C, 63.48; H, 6.98; N, 7.66. Found: C, 63.30; H, 7.00; N, 7.28.

EXAMPLE A37

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (Z)-pent-2-enylamide

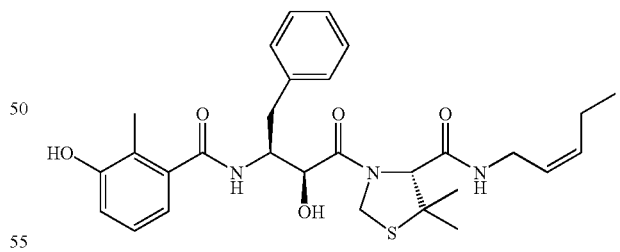

White solid: mp=112–113° C.; IR (neat, cm$^{-1}$) 3320, 2965, 1659, 1643, 1538, 1455, 1372, 1285, 1210, 1105, 1048; $^1$H NMR (DMSO-d$_6$) δ 9.35 (s, 1H), 8.11 (d, J=7.9, 1H), 8.03 (t, J=5.3, 1H), 7.35–7.13 (m, 5H), 6.96–6.90 (m, 1H), 6.76 (d, J=8.1, 1H), 6.53 (d, J=7.3, 1H), 5.42 (d, J=6.7, 1H), 5.37–5.35 (m, 1H), 5.29–5.23 (m, 1H), 5.09 (d, J=9.2, 1H), 4.99 (d, J=9.2, 1H), 4.45–4.38 (m, 2H), 4.36 (s, 1H), 3.80–3.62 (m, 2H), 2.84–2.70 (m, 2H), 2.07–1.97 (m, 2H), 1.80 (s, 3H), 1.48 (s, 3H), 1.34 (s, 3H), 0.90 (t, J=7.5, 3H); Anal. Calcd for C$_{29}$H$_{37}$N$_3$O$_5$S.0 5 H$_2$O: C, 63.48; H, 6.98; N, 7.66. Found: C, 63.60; H, 6.92; N, 7.48.

EXAMPLE A38

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (E)-but-2-enylamide

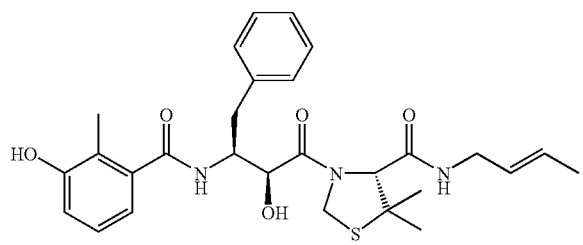

$^1$H NMR (DMSO-d$_6$) δ 9.39 (s, 1H), 8.19 (m br, 1H), 8.03 (m br, 1H), 7.40–7.16 (m, 5H), 6.94 (t, J=7.1, 1H), 6.79 (d, J=7.7, 1H), 6.55 (d, J=7.5, 1H), 5.64–5.31 (m, 3H), 5.19 (d, J=9.2, 1H), 5.02 (d, J=9.2, 1H), 4.55–4.38 (m, 3H), 3.80–3.69 (m, 2H), 2.84–2.70 (m, 2H), 1.80 (s, 3H), 1.61 (s br, 3H), 1.51 (s, 3H), 1.39 (s, 3H); Anal. Calcd for C$_{28}$H$_{35}$N$_3$O$_5$S: C, 63.73; H, 7.07; N, 7.96. Found: C, 63.41; H, 7.23; N, 7.71.

EXAMPLE A39

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-dimethylamino-benzylamide

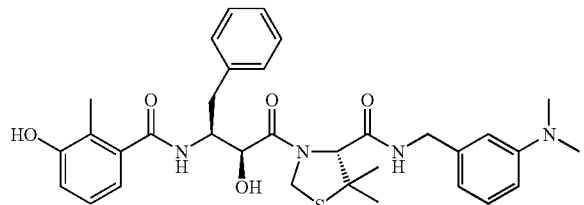

White solid: mp=105–106° C.; IR (neat, cm$^{-1}$) 2219, 2966, 1732, 1644, 1585, 1531, 1494, 1454, 1373, 1264, 1047; $^1$H NMR (DMSO-d$_6$) δ 9.37 (s, 1H), 8.33 (t, J=6.1, 1H), 8.08 (d, J=8.1, 1H), 7.32–6.52 (m, 12H), 5.54 (d, J=6.0, 1H), 5.10 (d, J=9.2, 1H), 4.99 (d, J=9.2, 1H), 4.43–4.31 (m, 4H), 4.03 (dd, J=15.3, 5.3, 1H), 2.84 (s, 6H), 2.84–2.67 (m, 2H), 1.81 (s, 3H), 1.49 (s, 3H), 1.35 (s, 3H). Anal. Calcd for C$_{33}$H$_{40}$N$_4$O$_5$S.0.1 H$_2$O: C, 65.35; H, 6.68; N, 9.24. Found: C, 65.49; H, 6.67; N, 9.30.

EXAMPLE A40

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid ((E)-4,4,4-trifluoro-but-2-enyl)-amide

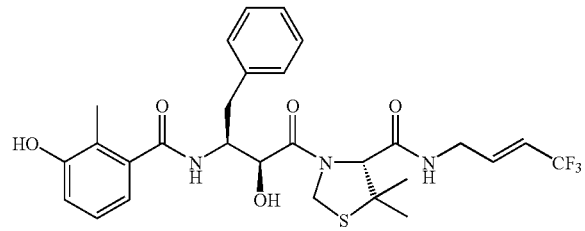

White foam; IR (neat, cm$^{-1}$) 3332, 1661, 1641, 1584, 1531, 1443, 1280, 1119; $^1$H NMR (DMSO-d$_6$) δ 9.36 (s, 1H), 8.32 (t, J=5.6, 1H), 8.15 (d, J=8.4, 1H), 7.35–7.12 (m, 5H), 7.00–6.90 (m, 1H), 6.77 (d, J=7.3, 1H), 6.52 (d, J=7.3, 1H), 6.49–6.40 (m, 1H), 6.08–6.00 (m, 1H), 5.49(d, J=6.4, 1H), 5.15 (d, J=9.2, 1H), 5.01 (d, J=9.2, 1H), 4.50–4.40 (m, 2H), 4.38 (s, 1H), 4.10–3.90 (m, 1H), 3.80–3.70 (m, 1H), 2.90–2.60 (m, 2H), 1.80 (s, 3H), 1.51 (s, 3H), 1.34 (s, 3H); Anal. Calcd for C$_{28}$H$_{32}$F$_3$N$_3$O$_5$S: C, 58.02; H, 5.56; N, 7.25. Found: C, 58.37; H, 5.70; N, 6.91.

EXAMPLE A41

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (1-cyano-1,1-dimethyl-methyl)-amide

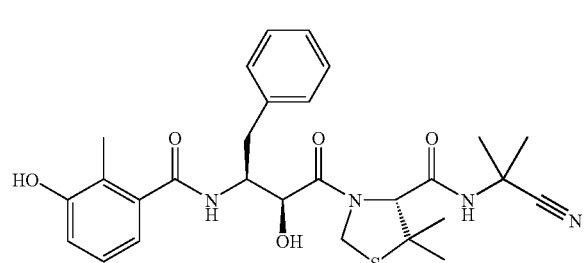

$^1$H NMR (DMSO-d$_6$) δ 9.39 (s, 1H), 8.31–8.12 (m, 2H), 7.38–7.17 (m, 5H), 6.97 (t, J=7.3, 1H), 6.79 (d, J=7.7, 1H), 6.59 (d, J=7.4, 1H), 5.41 (m br, 1H), 5.21 (d, J=9.2, 1H), 5.00 (d, J=9.2, 1H), 4.58–4.35 (m, 3H), 2.85–2.62 (m, 2H), 1.81 (s, 3H), 1.62 (s, 6H), 1.47 (s, 3H), 1.39 (s, 3H); Anal. Calcd for C$_{28}$H$_{34}$N$_4$O$_5$S: C, 62.43; H, 6.36; N, 10.40. Found: C, 62.12; H, 6.55; N, 10.13.

EXAMPLE A42

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-hydroxy-benzylamide

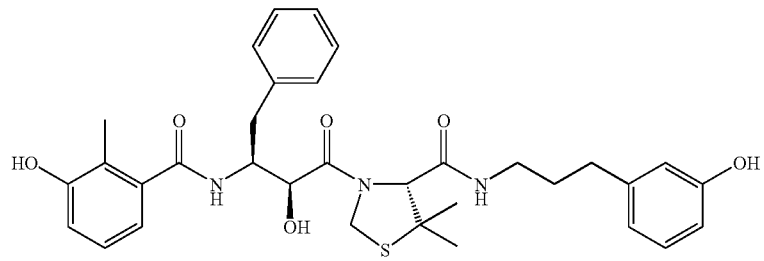

$^1$H NMR (DMSO-d$_6$) δ 9.37 (s, 1H), 9.30 (s, 1H), 8.35 (t, J=5.9, 1H), 8.11 (d, J=8.1, 1H), 7.33–7.15 (m, 5H), 7.04 (t, J=7.7, 1H), 6.94 (t, J=7.9, 1H), 6.77 (d, J=8.1, 1H), 6.70–6.54 (m, 4H), 5.49 (s br, 1H), 5.11 (d, J=9.2, 1H), 5.00 (d, J=9.3, 1H), 4.43 (m, 3H), 4.27 (dd, J=15.2, 6.0, 1H), 4.07 (dd, J=15.0, 5.5, 1H), 2.88–2.67 (m, 2H), 1.82 (s, 3H), 1.49 (s, 3H), 1.33 (s, 3H); Anal. Calcd for C$_{31}$H$_{35}$N$_3$O$_6$S.H$_2$O: C, 62.50; H, 6.26; N, 7.05. Found: C, 62.66; H, 6.19; N, 6.83.

EXAMPLE A43

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 3-propoxy-benzylamide

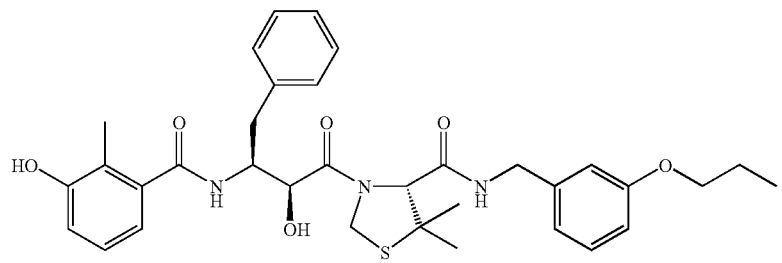

White foam; IR (cm$^{-1}$) 3319, 2966, 1644, 1585, 1531, 1454, 1373, 1264, 1047; $^1$H NMR (DMSO-d$_6$) δ 9.37 (s, 1H), 8.40 (t, J=5.8, 1H), 8.10 (d, J=8.4, 1H), 7.31–6.71 (m, 11H), 6.53 (d, J=7.3, 1H), 5.46 (d, J=6.4, 1H), 5.12 (d, J=9.2, 1H), 5.00 (d, J=9.2, 1H), 4.50–4.20 (m, 4H), 4.11–3.83 (m, 3H), 2.90–2.62 (m, 2H), 1.81 (s, 3H), 1.72–1.60 (m, 2H), 1.49 (s, 3H), 1.34 (s, 3H), 0.92 (t, J=7.3, 3H). Anal. Calcd for C$_{34}$H$_{41}$N$_3$O$_6$S.0.25 H$_2$O: C, 65.42; H, 6.70; N, 6.73. Found: C, 65.49; H, 6.67; N, 6.70.

EXAMPLE A44

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 2-hydroxy-benzylamide

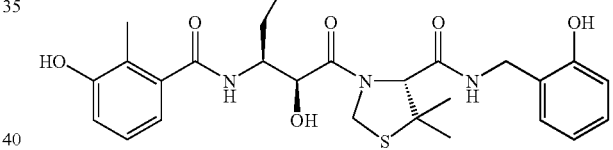

$^1$H NMR (DMSO-d$_6$) δ 9.50 (s, 1H), 9.36 (s, 1H), 8.33 (t, J=5.5, 1H), 8.14 (d, J=8.2, 1H), 7.32–7.12 (m, 6H), 7.04–6.91 (m, 2H), 6.76 (m, 2H), 6.68 (t, J=7.5, 1H), 6.54 (d, J=7.5, 1H), 5.46 (d, J=6.6, 1H), 5.13 (d, J=9.2, 1H), 5.01 (d, J=9.3, 1H), 4.47 (m, 3H), 4.28–4.19 (m, 2H), 2.86–2.67 (m, 2H), 1.82 (s, 3H), 1.49 (s, 3H), 1.32 (s, 3H); HRMS (ESI) m/z calcd for C$_{31}$H$_{36}$N$_3$O$_6$S (M+H)$^{30}$ 578.2325, found 578.2325.

EXAMPLE A45

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (3,3,3-trifluoro-propyl)-amide

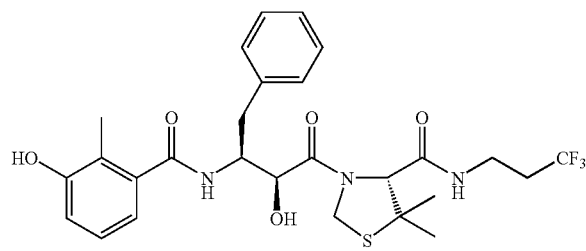

$^1$H NMR (DMSO-$d_6$) δ 9.36 (s, 1H), 8.20 (t, J=5.5, 1H), 8.13 (d, J=8.2, 1H), 7.34–7.13 (m, 5H), 6.93 (t, J=7.7, 1H), 6.76 (d, J=8.1, 1H), 6.08 (d, J=7.5, 1H), 5.44 (d, J=6.8, 1H), 5.10 (d, J=9.2, 1H), 5.05 (d, J=9.2, 1H), 4.48–4.38 (m, 2H), 4.35 (s, 1H), 3.32–3.25 (m, 2H), 2.75–2.70 (m, 2H), 2.44–2.35 (m, 2H), 1.80 (s, 3H), 1.49 (s, 3H), 1.34 (s, 3H); HRMS (ESI) m/z calcd for $C_{27}H_{33}N_3O_5SF_3$ (M+H)[30] 568.2093, found 568.2118.

EXAMPLE A46

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid methyl-propyl-amide

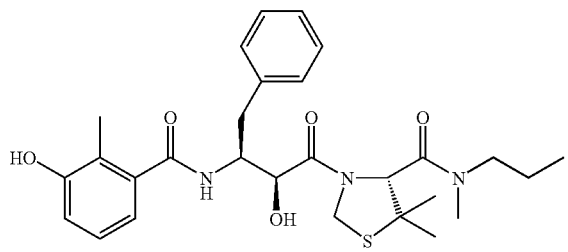

White solid: mp=108–110° C.; IR (cm$^{-1}$) 3325, 2964, 1637, 1522, 1456, 1372, 1284; $^1$H NMR (DMSO-$d_6$) δ 9.35 (s, 1H), 8.22 (d, J=8.6, 1H), 7.34–7.12 (m, 5H), 6.96–6.90 (m, 1H), 6.77–6.75 (m, 1H), 6.53–6.50 (m, 1H), 5.46 (d, J=6.4, 1H), 5.18–4.70 (m, 3H), 4.48–4.20 (m, 2H), 3.31 (s, 3H), 2.90–2.50 (m, 2H), 1.80 (s, 3H), 1.80–1.77 (m, 2H), 1.56 (s, 3H), 1.56–1.36 (m, 2H), 1.37 (s, 3H), 0.79 (t, J=7.5, 3H). Anal. Calcd for $C_{28}H_{37}N_3O_5S \cdot 1.0\ H_2O$: C, 61.63; H, 7.20; N, 7.60. Found: C, 62.03; H, 6.93; N, 7.33.

EXAMPLE A47

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid 4-trifluoromethoxy-benzylamide

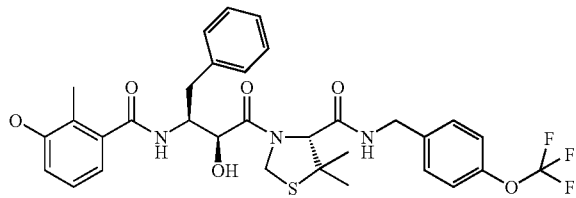

White solid: $^1$H NMR (DMSO) δ 9.37 (s, 1H), 8.51 (t, J=5.9, 1H), 8.13 (d, J=7.3, 1H), 7.39 (d, J=8.6, 1H), 7.32–7.10 (m, 8H), 7.00–6.90 (m, 1H), 6.76 (d, J=8.2, 1H), 6.53 (d, J=7.3, 1H), 5.49 (d, J=6.6, 1H), 5.14 (d, J=9.3, 1H), 5.00 (d, J=9.3, 1H), 4.49–4.37 (m, 4H), 4.17 (dd, J=15.0, 5.7, 1H), 2.90–2.64 (m, 2H), 1.81 (s, 3H), 1.49 (s, 3H), 1.32 (s, 3H); HRMS (ESI) m/z calcd for $C_{32}H_{35}N_3O_6F_3S$ (M+H)[30] 646.2199, found 646.2184.

EXAMPLE A48

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2,2-difluoro-benzo[1,3]dioxol-5-ylmethyl)-amide

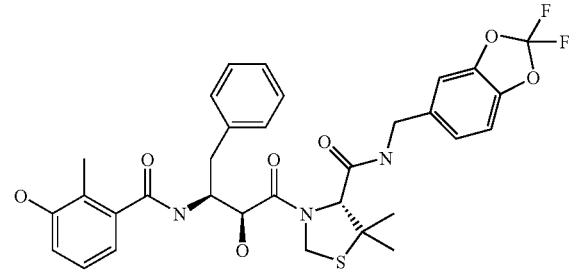

$^1$H NMR (DMSO-$d_6$) δ 9.36 (s, 1H), 8.55 (t, J=5.8, 1H), 8.14 (d, J=8.4, 1H), 7.29–7.11 (m, 8H), 6.94 (t, J=7.8, 1H), 6.77 (d, J=7.9, 1H), 6.54 (d, J=7.4, 1H), 5.58 (d, J=8.2, 1H), 5.17 (d, J=9.2, 1H), 5.02 (d, J=9.2, 1H), 4.49–4.39 (m, 3H), 4.43 (s, 1H), 4.21 (dd, J=5.4, 15.3, 1H), 2.83 (m, 1H), 2.71 (dd, J=13.5, 10.7, 1H), 2.20 (s, 3H), 1.51 (s, 3H), 1.34 (s, 3H); HRMS (ESI) m/z calcd for $C_{32}H_{34}F_2N_3O_7S$ (M+H)[30] 642.2086, found 642.2099; Anal. Calcd for $C_{32}H_{33}F_2N_3O_7S$: C, 59.90; H, 5.18; N, 6.55. Found: C, 60.01; H, 5.27; N, 6.29.

EXAMPLE A49

(R)-3-[(2S,3S)-2-Hydroxy-3-(3-hydroxy-2-methyl-benzoylamino)-4-phenyl-butyryl]-5,5-dimethyl-thiazolidine-4-carboxylic acid (2-chloro-ethyl)-amide

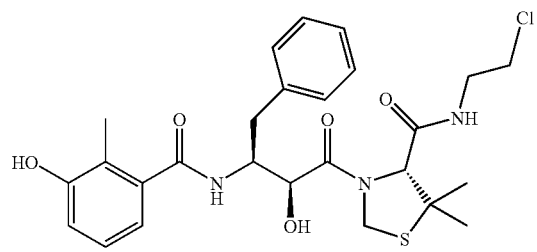

$^1$H NMR (DMSO-d$_6$) δ 9.40 (s, 1H), 8.31 (t, 1H, J=5.5), 8.17 (d, 1H, J=8.4), 7.37–7.16 (m, 5H), 6.96 (t, 1H, J=7.9), 6.79 (d, 1H, J=8.1), 6.55 (d, 1H, J=7.5), 5.47 (d, 1H, J=6.8), 5.11 (d, 1H, J=9.3), 5.03 (d, 1H, J=9.3), 4.50–4.45 (m, 2H), 4.41 (s, 1H), 3.64–3.58 (m, 2H), 3.46–3.34 (m, 2H), 2.86–2.69 (m, 2H), 1.82 (s, 3H), 1.53 (s, 3H), 1.40 (s, 3H). Exact mass calculated for C$_{26}$H$_{33}$N$_3$O$_5$SCl (M+H)$^{30}$ 534.1829, found 534.1841.

EXAMPLE A50

(R)-3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2-hydroxy-ethyl)-(2-methyl-benzyl)-amide

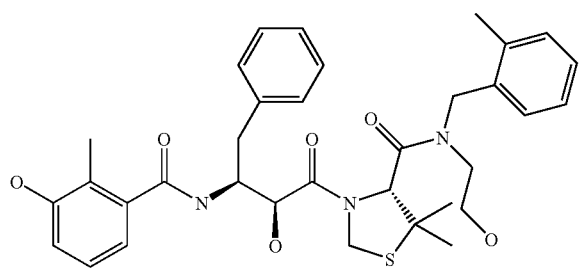

$^1$H NMR (DMSO-d$_6$) δ 9.38 (s, 1H), 8.29 (d, J=8.4, 1H), 7.42–6.87 (m, 10H), 6.78 (d, J=7.1, 1H), 6.55 (d, J=6.8, 1H), 5.44 (d, J=6.8, 1H), 5.26 (d, J=10.0, 1H), 5.08 (s, 1H), 5.04 (d, J=9.2, 1H), 4.82–4.67 (m, 2H), 4.55–4.24 (m, 3H), 3.67 (m, 2H), 3.47 (m, 2H), 2.78 (m, 2H), 2.24 (s, 3H), 1.82 (s, 3H), 1.61 (s, 3H), 1.45 (s, 3H); HRMS (ESI) m/z calcd for C$_{34}$H$_{42}$N$_3$O$_6$S (M+H)$^{30}$ 620.2794, found 620.2798; Anal. Calcd for C$_{34}$H$_{41}$N$_3$O$_6$S.1 H$_2$O: C, 64.03; H, 6.80; N, 6.59. Found: C, 63.66; H, 6.40; N, 6.59.

EXAMPLE A51

3-[2-Hydroxy-3-(3-hydroxy-2-methyl-benzoylamino)-4-phenyl-butyryl]-5,5-dimethyl-thiiazolidine-4-carboxylic acid methyl-(2-ethyl-benzyl)-amide

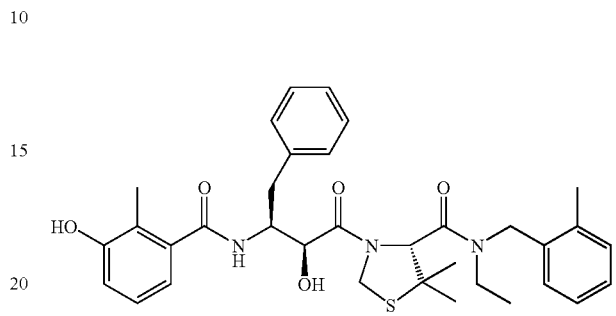

White solid: $^1$H NMR (DMSO-d$_6$) δ 9.40 (s, 1H), 8.45 (t, J=7.99, 1H), 8.10 (d, J=8.1, 1H), 7.41–6.91 (m, 12H), 6.62 (d, J=7.8, 1H), 5.41 (d, J=6.8, 1H), 5.12 (dd, J=8.1, 7.8, 1H), 4.44–4.35 (m, 3H), 4.42 (s, 1H), 2.91–2.67 (m, 2H), 2.54–2.21 (q, J=6.89, 2H), 2.1 (s, 3H), 1.88 (s, 3H), 1.56 (t, J=6.90, 3H), 1.49 (s, 3H), 1.34 (s, 3H); Anal. (C$_{34}$H$_{41}$N$_3$O$_5$S.0.75 H$_2$O) calculated C (62.34), H (6.43), N (6.23), found C (62.72), H (6.52), N (5.97). HRMS (ESI) m/z calcd for 604.2845, found 604.2845.

EXAMPLE A52

3-((2S,3S)-2-Hydroxy-3-{[1-(3-hydroxy-2-methyl-phenyl)-methanoyl]-amino}-4-phenyl-butanoyl)-5,5-dimethyl-thiazolidine-4-carboxylic acid (2-methylamino-ethyl)-amide

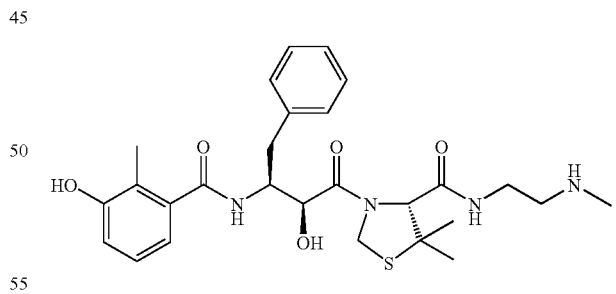

White solid: $^1$H NMR (DMSO-d$_6$) δ 9.40 (s, 1H), 8.45–8.01 (m, 1H), 7.41–7.13 (m, 12H), 6.98 (t, J=7.8, 1H), 6.78 (d, J=6.85, 1H), 6.55 (d, J=6.99, 1H), 5.41 (m, 1H), 5.12–4.98 (m, 2H), 4.44–4.35 (m, 2H), 3.15 (m, 2H), 2.91–2.67 (m, 2H), 1.84 (s, 3H), 1.66 (q, J=8.2, 4H), 1.34 (s, 3H); Anal. (C$_{27}$H$_{36}$N$_4$O$_5$S.0.50 H$_2$) calculated C (60.31), H (6.94), N (10.42), found C (60.59), H (6.50), N (8.08). HRMS (ESI) m/z calcd for 556.2771, found 556.2770.

115

General Method B

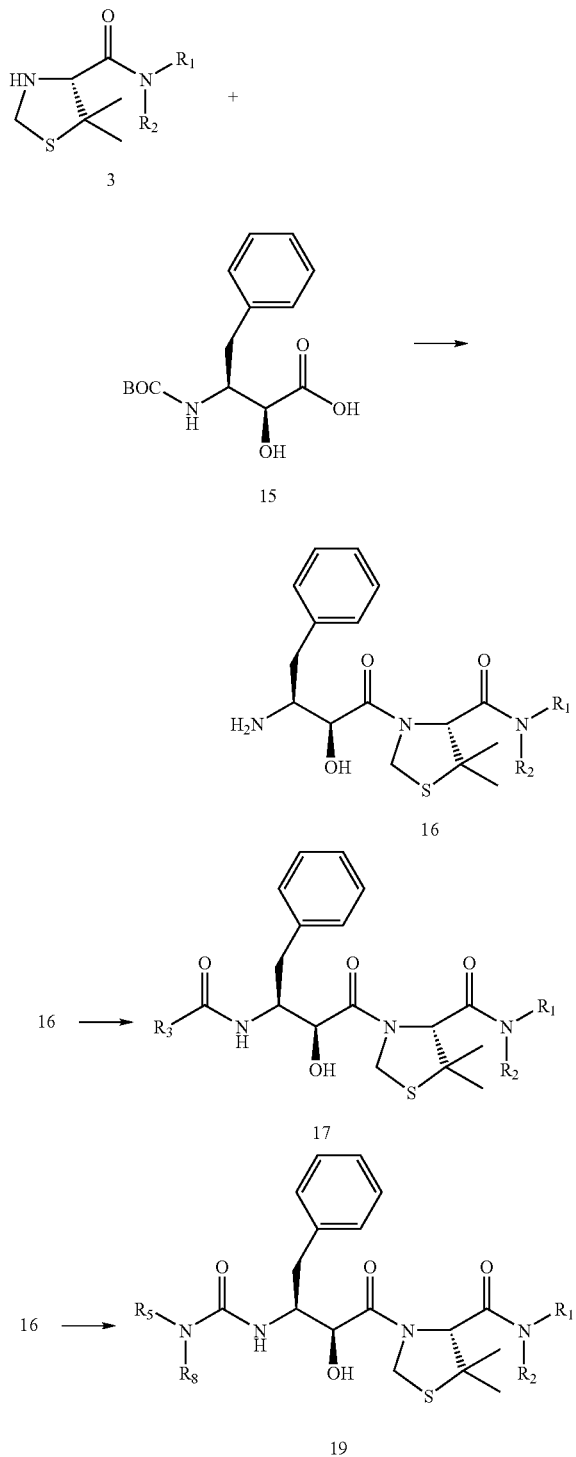

Amides of the general structure 3 (synthesized in the same manor as in the Methods A section) are coupled to boc-protected acid 15, and exposed to methane sulfonic acid to yield amines 16. Subjecting amines 16 to the reaction conditions depicted yielded a series of amides 17 and ureas 19.

116

Synthesis of amines of the general type 16.

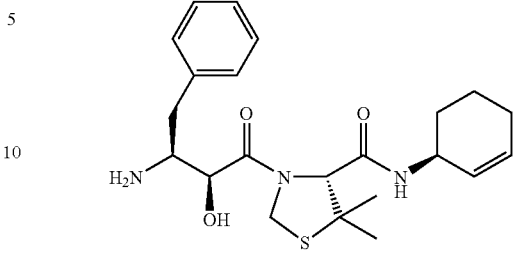

The title compound was prepared as follows. (R)-5,5-Dimethyl-thiazolidine-3,4-dicarboxylic acid 3-tert-butyl ester 1 (1.95 g, 7.47 mmol) was dissolved in EtOAc (25 mL) and cooled to 0° C. Diphenyl chlorophosphate (1.71 mL, 8.23 mmol) was added followed by TEA (1.14 mL, 8.23 mmol). The reaction was stirred at 0° C. for 1 h, and treated with (S)-Cyclohex-2-enylamine (0.8 g, 8.23 mmol). The reaction mixture was stirred at room temperature overnight, then partitioned between 1N HCl (25 mL) and EtOAc (30 mL). The organic layer was washed with saturated $NaHCO_3$, brine, dried over $Na_2SO_4$ and concentrated to a yellow oil. The resulting oil (2.54 g, 7.47 mmol) was dissolved in EtOAc (30 mL) and then cooled to 0° C. Methanesulfonic acid (2.27 mL, 33.62 mmol) was added and the solution was stirred at 0° C. for 15 minutes, then at room temperature for 4 h. The mixture was re-cooled to 0° C. and quenched with 10% $Na_2CO_3$ (30 mL) then extracted with EtOAc (30 mL). Organic layer was washed with brine, dried over $Na_2SO_4$ and concentrated in vacuo to give a yellow oil 3. The resulting yellow oil (1.86 g, 7.74 mmol) was dissolved in EtOAc (77 mL). BOC-AHPBA 4 (2.29 g, 7.74 mmol) was added followed by HOBt (1.05 g, 7.74 mmol). The mixture was stirred at room temperature 1 h, then cooled to 0° C. DCC (1.60 g, 7.74 mmol) was slowly added as solution in EtOAc (30 mL). The mixture was allowed to gradually warm to room temperature and stirred overnight. The mixture was filtered and the filtrate was washed with 1N HCl (40 mL), saturated $NaHCO_3$ (40 mL), brine (40 mL), dried over $Na_2SO_4$ and concentrated to give a crude white solid (contaminated with DCU). The DCU was removed by flash chromatography (30% to 50% EtOAc in hexanes) to provide a white solid (4 g, 7.73 mmol), which was dissolved in EtOAc (30 mL) and then cooled to 0° C. Methanesulfonic acid (2.35 mL, 34.76 mmol) was added and the solution was stirred at 0° C. for 15 minutes, then at room temperature for 3 h. The mixture was re-cooled to 0° C. and quenched with 10% $Na_2CO_3$ (35 mL) then extracted with EtOAc (30 mL). Organic layer was washed with brine, dried over $Na_2SO_4$ and concentrated in vacuo to give a material which was recrystalized from 60% EtOAc in hexanes to provide the titled compound (2.41 g, 80%) as a white solid. $^1$H NMR (DMSO-$d_6$) δ 8.21 (d, J=8.1, 1H), 7.31–7.17 (m, 5H), 5.80 (d, J=5.6, 1H), 5.52–5.48 (m, 2H), 5.30–5.25 (m, 2H), 4.89 (s, 2H), 4.26 (s, 1H), 4.21–4.00 (m, 3H), 3.15–2.70 (m, 2H), 2.50–2.00 (m, 2H), 2.00–1.00 (m, 4H), 1.49 (s, 3H), 1.31 (s, 3H); Anal. Calcd for $C_{22}H_{31}N_3O_3S$: C, 63.28; H, 7.48; N, 10.06. Found: C, 63.40; H, 7.20; N, 9.98.

The following amines a–h were prepared by the specific method outlined above using the requisite amine.

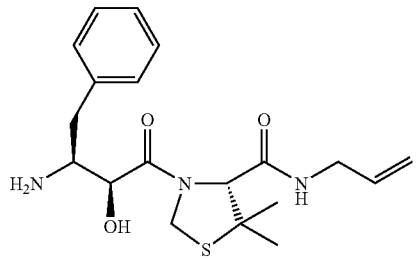

16a

¹H NMR (DMSO-d₆) δ 8.36 (t, J=6.0, 1H), 7.36–7.14 (m, 5H), 5.70 (m, 1H), 5.34 (s br, 1H), 5.12 (d, J=17.0, 1H), 4.96–4.88 (m, 3H), 4.34 (s, 1H), 4.10 (d, J=7.0, 1H), 3.80–3.55 (m, 2H), 3.06 (d, J=13.0, 1H), 2.87 (t, J=9.0, 1H), 2.38 (dd, J=13.0, 10.0, 1H), 1.52 (s, 3H), 1.33 (s, 3H).

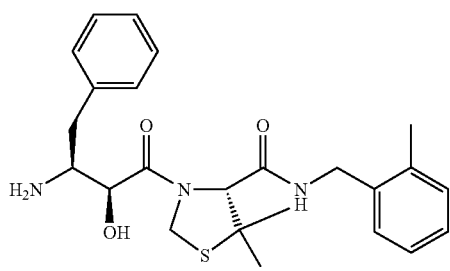

16b

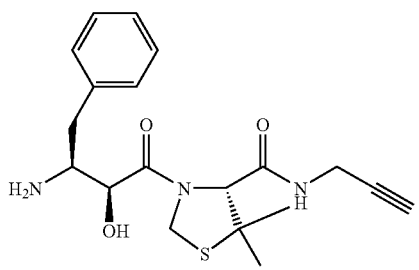

16c

¹H NMR (DMSO-d₆) δ 8.69 (t, J=5.3, 1H), 7.34–7.14 (m, 5H), 5.34 (s br, 1H), 4.90 (s, 2H), 4.29 (s, 1H), 4.08 (d, J=7.0, 1H), 3.90–3.70 (m, 2H), 3.07 (dd, J=13.4, 2.5, 1H), 2.96 (t, J=2.6, 1H), 2.88, (ddd, J=9.8, 8.0, 2.8, 1H), 2.37 (dd, J=13.2, 9.9, 1H), 1.50 (s, 3H), 1.32 (s, 3H).

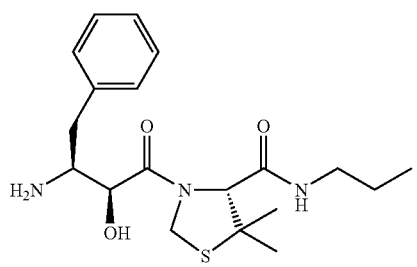

16d

¹H NMR (DMSO-d₆) δ 8.13 (t, J=5.4, 1H), 7.35–7.15 (m, 5H), 5.28 (d, J=8.1, 1H), 4.79 (m, 2H), 4.27 (s, 1H), 4.07 (t, J=7.1, 1H), 3.10–2.71 (m, 4H), 2.37 (dd, J=13.2, 9.9, 1H), 1.49 (s, 3H), 1.34 (m, 2H), 1.33 (s, 3H), 0.77 (t, J=7.4, 3H).

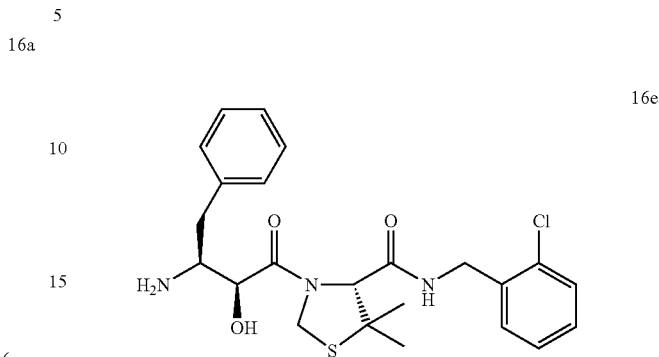

16e

Isolated yield: 84%; MS (APCI, m/z): 461, 463 (M+H)

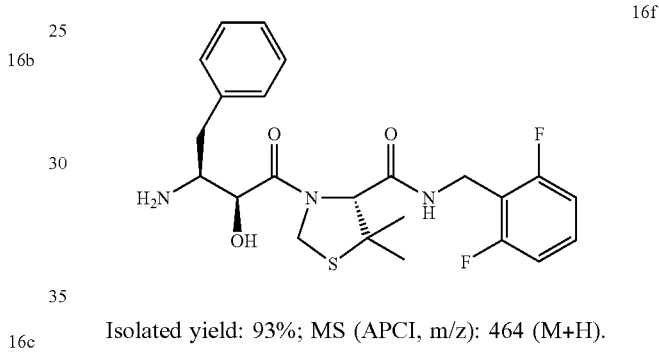

16f

Isolated yield: 93%; MS (APCI, m/z): 464 (M+H).

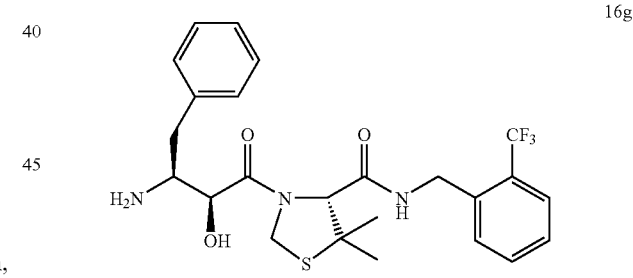

16g

Isolated yield: 86%; MS (APCI, m/z): 496 (M+H).

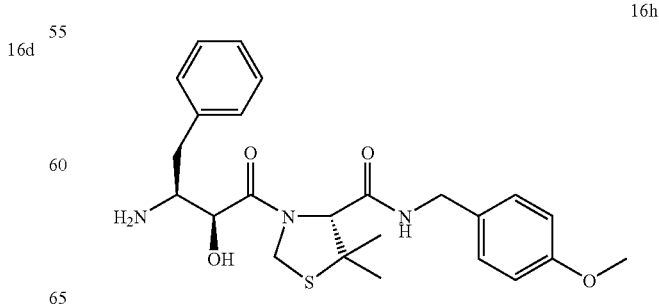

16h

Isolated yield: 87%. MS-APCI (m/z+): 458.

Synthesis of Final Products of the General Type 17 from 16a–h,

General Methods:

Amide formation—To a solution of acid, amine 16 and HOBT in $CH_2Cl_2$ was added EDC and the solution stirred overnight at room temperature. The solution was concentrated in vacuo and the residue dissolved in ethyl acetate and a small portion of water. The solution was washed with saturated $NH_4Cl$ or 0.5N HCl (2×), saturated $NaHCO_3$ (2×), brine (1×), dried with $MgSO_4$ and concentrated in vacuo. The resulting residue subjected to flash silica gel chromatography or preparative HPLC to afford the desired product.

Urea formation #1—The corresponding amine and isocyanate (1.1–1.2 eq.) were taken in dichloromethane and stirred at room temperature under nitrogen. (1.5 hr to overnight). The solvent was then removed in vacuo and the resulting residue subjected to flash silica gel chromatography or preparative HPLC to afford the desired product.

Urea formation #2—The corresponding amine was dissolved in $CH_2Cl_2$ and treated with diisopropylethylamine (1.5 eq.) and phosgene (1 eq., 20% soln. in toluene) at −78° C. The resulting solution was warmed to room temperature and treated with the amine of general structure 16. The resulting residue subjected to flash silica gel chromatography or preparative HPLC to afford the desired product.

Specific Urea Synthesis

EXAMPLE B1

3-(2-hydroxy-3-{[1-(3-hydroxy-pyrrolidin-yl)-methanoyl]-amino}-4-phenyl-butanoyl)-5,5-dimethyl-thiazolidine-4-carboxylic acid-2-methyl-benzylamide

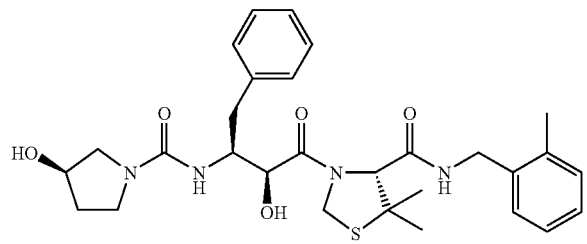

(R)-Pyrrolidin-3-ol (0.21 g, 2.40 mmol) was dissolved in dry $CH_2Cl_2$ (15 mL) and cooled to −78° C. under argon with magnetic stirring. To this solution was added Diisopropylethylamine (0.63 mL, 3.63 mmol) followed by Phosgene as a 20% solution in toluene (1.2 mL, 2.40 mmol). The resulting yellow solution was stirred for 20 min at −78° C. then allowed to warm to room temperature. The solution was concentrated and re-dissolved in dry $CH_2Cl_2$ (5 mL) and THF (5 mL). To this was added Diisopropylethylamine (0.31 mL, 1.81 mmol) followed by 16c. The result was stirred for 16 h at 23° C. then diluted with EtOAc (50 mL). The mixture was washed sequentially with 10% citric acid (1×50 mL), saturated $NaHCO_3$ (1×50 mL), $H_2O$ (1×50 mL). The organics were dried over $Na_2SO_4$, filtered, and concentrated. The residue was purified by flash column chromatography (5% MeOH in EtOAc) to yield the title compound (0.12 g, 18%) as a white foam.

$^1$H NMR (DMSO-$d_6$) δ 8.38 (t, J=5.7, 1H), 7.34–7.09 (m, 10H), 5.99 (d, J=8.3, 1H), 5.04 (d, J=9.5, 1H), 4.96 (d, J=9.5, 1H), 4.49 (s, 1H), 4.48–4.38 (m, 3H), 4.22–3.83 (m, 4H), 3.29–3.04 (m, 3H), 2.77–2.70 (m, 2H), 2.28 (s, 3H), 1.52 (s, 3H), 1.32 (s, 3H), 1.82–1.69 (m, 2H); HRMS (ESI) m/z calcd for $C_{29}H_{38}N_4O_5SNa$ (M+Na)$^{30}$ 577.2455, found 577.2440; Anal. Calcd for $C_{29}H_{38}N_4O_5S.2H_2O$: C, 58.96; H, 7.17; N, 9.48; S, 5.43. Found: C, 58.90; H, 6.40; N, 9.23; S, 5.24.

The following examples were prepared by the corresponding specific method outlined above using the requisite P2 fragment.

EXAMPLE B2

Isoxazole-5-carboxylic acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

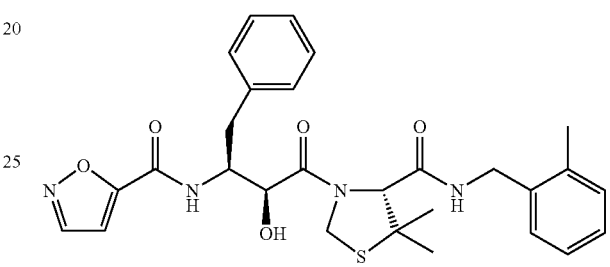

White solid: mp=82–84° C.; IR (neat, cm$^{-1}$) 3313, 2967, 1656, 1538, 1454, 1372, 1283, 1211, 1108, 916; $^1$H NMR (DMSO-$d_6$) δ 8.91 (d, J=8.6, 1H), 8.67 (d, J=2.0, 1H), 8.35 (t, J=5.0, 1H), 7.31–7.08 (m, 9H), 7.03 (d, J=2.0, 1H), 5.63 (d, J=6.9, 1H), 5.02 (d, J=8.6, 1H), 4.97 (d, J=8.6, 1H), 4.60–4.30 (m, 4H), 4.14–4.00 (m, 1H), 2.90–2.75 (m, 2H), 2.23 (s, 3H), 1.49 (s, 3H), 1.28 (s, 3H); HRMS (ESI) m/z calcd for $C_{28}H_{32}N_4O_5SNa$ (M+Na)$^{30}$ 559.1986, found 559.1994; Anal. Calcd for $C_{28}H_{32}N_4O_5S.0.5H_2O$: C, 61.63; H, 6.10; N, 10.27. Found: C, 61.40; H, 5.91; N, 9.97.

EXAMPLE B3

Isoxazole-3-carboxylic acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

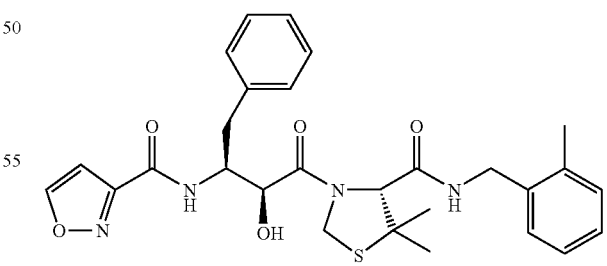

White solid; IR (neat, cm$^{-1}$) 3436, 1643, 1537, 1425, 1378; $^1$H NMR (DMSO-$d_6$) δ 9.03 (s, 1H), 8.66 (d, J=8.7, 1H), 8.32 (t, J=5.3, 1H), 7.30–7.11 (m, 9H), 6.79 (s, 1H), 5.67 (d, J=6.8, 1H), 4.97 (s, 2H), 4.47–4.32 (m, 4H), 4.09 (dd, J=15.0, 5.0, 1H), 2.84 (m, 2H), 2.24 (s, 3H), 1.49 (s, 3H), 1.34 (m, 3H); HRMS (ESI) m/z calcd for $C_{28}H_{32}N_4O_5SNa$ (M+Na)$^{30}$ 559.1986, found 559.1980.

EXAMPLE B4

5-Chloro-isoxazole-3-carboxylic acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

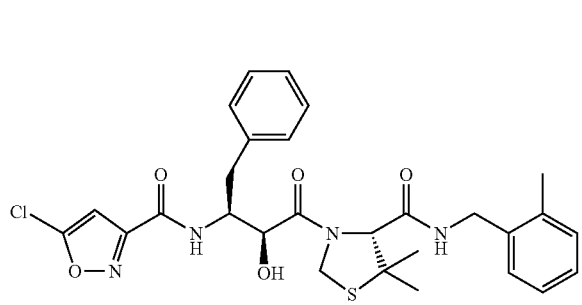

White solid; IR (neat, cm$^{-1}$) 3320, 2969, 1657, 1547, 1434, 1372, 1266; $^1$H NMR (DMSO-d$_6$) δ 8.74 (d, J=8.2, 1H), 8.29 (t, J=5.5, 1H), 7.28–7.08 (m, 9H), 6.90 (s, 1H), 5.72 (d, J=7.1, 1H), 4.96 (s, 2H), 4.44 (m, 3H), 4.32 (dd, J=15.2, 6.0, 1H), 4.09 (dd, J=15.2, 4.6, 1H), 2.85 (m, 2H), 2.83 (s, 3H), 1.49 (s, 3H), 1.33 (s, 3H); HRMS (ESI) m/z calcd for C$_{28}$H$_{31}$N$_4$O$_5$SClNa (M+Na)$^{30}$ 593.1596, found 593.1569.

EXAMPLE B5

(R)-3-{(2S,3S)-2-Hydroxy-4-phenyl-3-[(1-thiophen-2-yl-methanoyl)-amino]-butanoyl}-5,5-dimethyl-thiazolidine-4-carboxylic acid 2-methyl-benzylamide

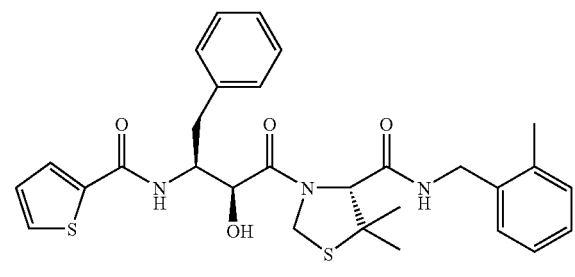

White solid: mp=98–101° C.; IR (neat, cm$^{-1}$) 3416, 1644, 1538, 1455, 1372, 1291, 1107; $^1$H NMR (DMSO-d$_6$) δ 8.56 (d, J=8.0, 1H), 8.38 (t, J=4.8, 1H), 7.85 (d, J=3.5, 1H), 7.69 (d, J=4.8, 1H), 7.36–7.08 (m, 10H), 5.38 (d, J=7.2, 1H), 5.10 (d, J=8.8, 1H), 4.98 (d, J=8.8, 1H), 4.54–4.20 (m, 5H), 2.90–2.70 (m, 2H), 2.25 (s, 3H), 1.49 (s, 3H), 1.34 (s, 3H); HRMS (ESI) m/z calcd for C$_{29}$H$_{33}$N$_3$O$_4$S$_2$Na (M+Na)$^+$ 574.1805, found 574.1818; Anal. Calcd for C$_{29}$H$_{33}$N$_3$O$_4$S$_2$.0.75H$_2$O: C, 61.62; H, 6.15; N, 7.43. Found: C, 61.31; H, 5.97; N, 7.28.

EXAMPLE B6

(R)-3-{(2S,3S)-2-Hydroxy-4-phenyl-3-[(1-thiophen-3-yl-methanoyl)-amino]-butanoyl}-5,5-dimethyl-thiazolidine-4-carboxylic acid 2-methyl-benzylamide

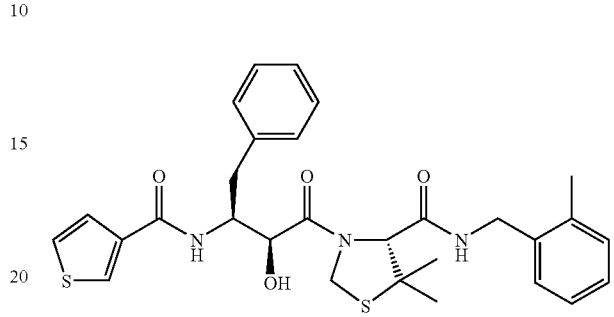

White solid: mp=98–100° C.; IR (neat, cm$^{-1}$) 3312, 3086, 2966, 1644, 1538, 1455, 1372, 1286, 1109; $^1$H NMR (DMSO-d$_6$) δ 8.42–8.34 (m, 2H), 8.14 (m, 1H), 7.54–7.06 (m, 11H), 5.74 (d, J=9.3, 1H), 5.35 (d, J=6.8, 1H), 4.99 (d, J=9.3, 1H), 4.53 (d, J=3.0, 1H), 4.50 (s, 1H), 4.42 (dd, J=15.0, 7.0, 1H), 4.40–4.30 (m, 1H), 4.15 (dd, J=15.0, 5.0, 1H), 2.90–2.70 (m, 2H), 2.26 (s, 3H), 1.50 (s, 3H), 1.35 (s, 3H); HRMS (ESI) m/z calcd for C$_{29}$H$_{33}$N$_3$O$_4$S$_2$Na (M+Na)$^{30}$ 574.1805, found 574.1789; Anal. Calcd for C$_{29}$H$_{33}$N$_3$O$_4$S$_2$.1H$_2$O: C, 61.14; H, 6.19; N, 7.38. Found: C, 60.74; H, 5.90; N, 7.15.

EXAMPLE B7

(R)-3-{(2S,3S)-2-Hydroxy-4-phenyl-3-[((S)-1-tetrahydro-furan-2-yl-methanoyl)-amino]-butanoyl}-5,5-dimethyl-thiazolidine-4-carboxylic acid 2-methyl-benzylamide

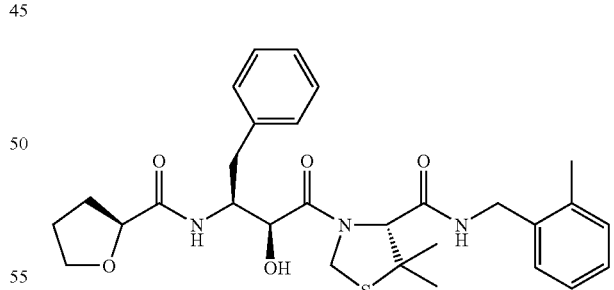

White solid: mp=82–84° C.; IR (neat, cm$^{-1}$) 3314, 2969, 1651, 1531, 1456, 1372, 1109, 1071; $^1$H NMR (DMSO-d$_6$) δ 8.35 (t, J=6.0, 1H), 7.60 (d, J=9.2, 1H), 7.31–7.09 (m, 9H), 5.45 (d, J=6.8, 1H), 4.97 (d, J=9.5, 1H), 4.93 (d, J=9.5, 1H), 4.46 (s, 1H), 4.41–4.07 (m, 4H), 3.77–3.65 (m, 3H), 2.78–2.64 (m, 2H), 2.26 (s, 3H), 2.00–1.80 (m, 1H), 1.60 (m, 1H), 1.49 (s, 3H), 1.44–1.38 (m, 2H), 1.34 (s, 3H); HRMS (ESI) m/z calcd for C$_{29}$H$_{37}$N$_3$O$_5$SNa (M+Na)$^{30}$ 562.2346, found 562.2345; Anal. Calcd for C$_{29}$H$_{37}$N$_3$O$_5$S.0.5 H$_2$O: C, 63.48; H, 6.98; N, 7.66. Found: C, 63.61; H, 6.85; N, 7.58.

EXAMPLE B8

3-(2-hydroxy-3-{[1-(3-hydroxy-pyrrolidin-yl)-methanoyl]-amino}-4-phenyl-butanoyl)-5,5-dimethyl-thiazolidine-4-carboxylic acid-2-methyl-benzylamide

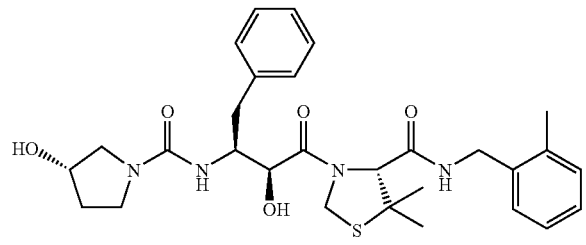

¹H NMR (DMSO-d₆) δ 8.38 (t, J=5.5, 1H), 7.34–7.09 (m, 10H), 5.99 (d, J=8.2, 1H), 5.04 (d, J=9.5, 1H), 4.96 (d, J=9.5, 1H), 4.49 (s, 1H), 4.48–4.38 (m, 3H), 4.35–4.16 (m, 3H), 4.00 (m, 1H), 3.29–3.04 (m, 3H), 2.78–2.70 (m, 2H), 2.28 (s, 3H), 1.83–1.65 (m, 2H), 1.52 (s, 3H), 1.36 (s, 3H); HRMS (ESI) m/z calcd for C₂₉H₃₈N₄O₅SNa (M+Na)³⁰ 577.2455, found 577.2473; Anal. Calcd for C₂₉H₃₈N₄O₅S.2H₂O: C, 58.96; N, 9.48. Found: C, 58.68; N, 9.11.

EXAMPLE B9

(R)-3-{(2S,3S)-2-Hydroxy-4-phenyl-3-[((R)-1-tetrahydro-furan-2-yl-methanoyl)-amino]-butanoyl}-5,5-dimethyl-thiazolidine-4-carboxylic acid 2-methyl-benzylamide

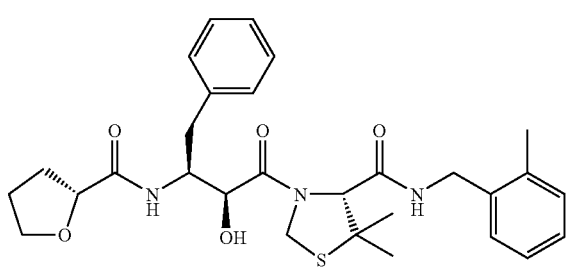

White solid; IR (neat, cm⁻¹) 3324, 2959, 2873, 1724, 1651, 1526, 1455, 1372, 1289, 1073; ¹H NMR (DMSO-d₆) δ 8.35 (t, J=4.9, 1H), 7.77 (d, J=8.9, 1H), 7.52–7.09 (m, 9H), 5.51 (d, J=6.6, 1H), 4.97–4.89 (m, 2H), 4.52–3.66 (m, 8H), 2.90–2.60 (m, 2H), 2.25 (s, 3H), 1.99–1.63 (m, 4H), 1.48 (s, 3H), 1.33 (s, 3H); HRMS (ESI) m/z calcd for C₂₉H₃₇N₃O₅SNa (M+Na)³⁰ 562.2346, found 562.2366. Anal. Calcd for C₂₉H₃₇N₃O₅S.0.25 H₂O: C, 64.01; H, 6.95; N, 7.72. Found: C, 64.20; H, 6.90; N, 7.82.

EXAMPLE B10

3,5-Dimethyl-isoxazole-4-carboxylic acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

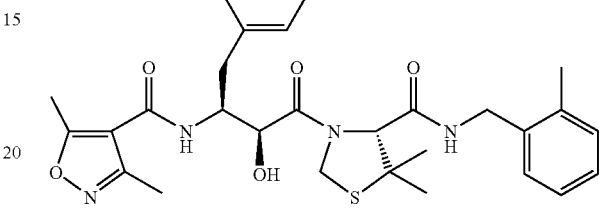

Isolated yield: 92%; 1H-NMR (400 MHz, dmso-d₆): δ 8.38 (t, 1H), 8.13 (d, 1H), 7.04–7.35 (m, 10H), 5.52 (d, 1H), 5.09 (d, 1H), 5.0 (d, 1H), 4.53 (m, 1H), 4.5 (s, 1H), 4.48 (m, 2H), 4.17 (dd, 1H), 2.87 (dd, 1H), 2.7 (q, 1H), 2.26 (s, 6H), 2.09 (s, 3H), 1.52 (s, 3H), 1.35 (s, 3H); IR (KBr in cm-1): 3313, 1643, 1521, 743; MS (APCI, m/z): 565 (M+H), 519, 265; C30H36N4O5S1.0.69 H₂O Calculated: C, 62.43, H, 6.53, N, 9.71, Observed: C, 63.81, H, 6.43, N, 9.92; HPLC: Rf (min.) 20.167; Purity: 98%.

EXAMPLE B11

2,4-Dimethyl-thiazole-5-carboxylic acid {1-benzyl-3-[5,5-dimethyl-4-(2-methyl-benzylcarbamoyl)-thiazolidin-3-yl]-2-hydroxy-3-oxo-propyl}-amide

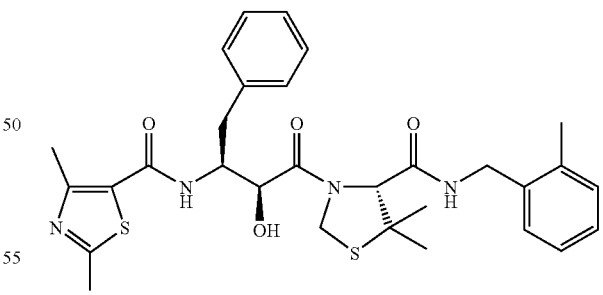

Isolated yield: 80%; 1H-NMR (400 MHz, dmso-d₆): δ 8.35 (t, 1H), 8.14 (d, 1H), 7.0–7.35 (m, 10H), 5.48 (d, 1H), 5.04 (d, 1H), 5.0 (d, 1H), 4.52 (m, 1H), 4.4 (s, 1H), 4.35 (m, 2H), 4.14 (dd, 1H), 2.78 (d, 2H), 2.57 (s, 3H), 2.30 (s, 3H), 2.26 (s, 3H), 1.48 (s, 3H), 1.35 (s, 3H); IR (KBr in cm-1): 3310, 1641, 1534, 743; MS (APCI, m/z): 581 (M+H), 317, 265, 259; C30H36N4O4S2.0.39 H₂O Calculated: C, 61.30, H, 6.31, N, 9.53, Observed: C, 62.04, H, 6.25, N, 9.65; HPLC: Rf (min.) 19.613; Purity: 98%.

EXAMPLE B12

(R)-3-{(2S,3S)-2-Hydroxy-3-[(1-methyl-1H-pyrrole-2-carbonyl)-amino]-4-phenyl-butyryl}-5,5-dimethyl-thiazolidine-4-carboxylic acid 2-methyl-benzylamide

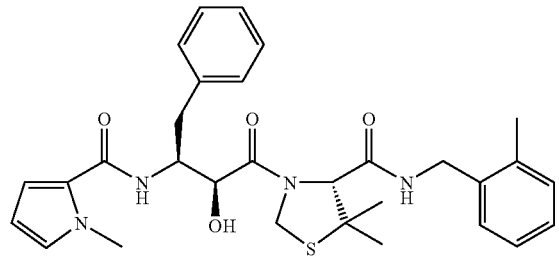

Isolated yield: 82%; 1H-NMR (400 MHz, dmso-$d_6$): δ 8.35 (t, 1H), 7.91 (d, 1H), 7.35–7.04 (m, 10H), 6.78 (s, 2H), 5.96 (s, 1H), 5.35 (d, 1H), 5.13 (s, 1H), 5.0 (d, 1H), 4.48 (s, 2H), 4.38 (dd, 1H), 4.30 (m, 1H), 4.13 (dd, 1H), 3.7 (s, 3H), 2.8 (m, 2H), 2.26 (s, 3H), 1.52 (s, 3H), 1.35 (s, 3H); IR (KBr in cm-1): 3324, 1639, 1538, 735; MS (APCI, m/z): 549 (M+H), 503, 382, 285; C30H36N4O4S1.2.44 H$_2$O Calculated: C, 60.80, H, 6.95, N, 9.45, Observed: C, 65.67, H, 6.61, N, 10.21; HPLC: Rf (min.) 20.745; Purity: 100%.

EXAMPLE B13

(R)-3-{(2S,3S)-3-[(1,5-Dimethyl-1H-pyrazole-4-carbonyl)-amino]-2-hydroxy-4-phenyl-butyryl}-5,5-dimethyl-thiazolidine-4-carboxylic acid 2-methyl-benzylamide

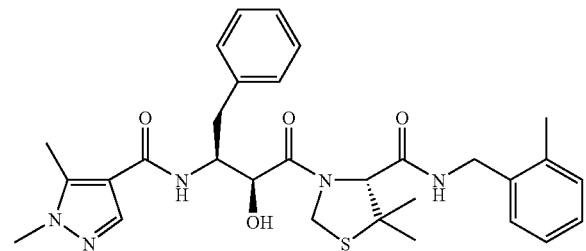

Isolated yield: 68%; 1H-NMR (400 MHz, dmso-$d_6$): δ 8.30 (t, 1H), 7.83 (d, 1H), 7.31–7.04 (m, 10H), 6.30 (s, 1H), 5.48 (d, 1H), 4.92 (s, 2H), 4.30–4.48 (m, 4H), 4.17 (dd, 1H), 3.7 (s, 3H), 2.74 (m, 2H), 2.26 (s, 3H), 2.18 (s, 3H), 1.48 (s, 3H), 1.30 (s, 3H); IR (KBr in cm-1): 3313, 1645, 1532, 744; MS (APCI, m/z): 564 (M+H), 300, 272; C30H37N5O4S1.0.5 H$_2$O Calculated: C, 62.86, H, 6.69, N, 12.22, Observed: C, 63.92, H, 6.62, N, 12.42; HPLC: Rf (min.) 19.724; Purity: 100%.

EXAMPLE B14

3-{(S)-3-[(5-Chloro-1,3-dimethyl-1H-pyrazole-4-carbonyl)-amino]-2-hydroxy-4-phenyl-butyryl}-5,5-dimethyl-thiazolidine-4-carboxylic acid 2-methyl-benzylamide Isolated yield: 92%; 1H-NMR (400 MHz, dmso-$d_6$): δ 8.35 (t, 1H), 7.74 (d, 1H), 7.30–7.0 (m, 10H), 5.44 (d, 1H), 4.96 (q, 2H), 4.48 (m, 1H), 4.35 (m, 2H), 4.13 (dd, 1H), 2.74 (m, 2H), 2.22 (s, 3H), 2.09 (s, 3H), 1.48 (s, 3H), 1.26 (s, 3H); IR (KBr in cm-1): 3438, 3313, 1693, 1649, 1513, 1372, 754; MS (APCI, m/z): 598 (M+H), 334, 276, 174; C30H36N5O4S1Cl1.0.17 H2O Calculated: C, 59.93, H, 6.09, N, 11.65, Observed: C, 60.24, H, 6.07, N, 11.71; HPLC: Rf (min.) 19.829; Purity: 100%.

EXAMPLE B15

2-Amino-4-methyl-thiazole-5-carboxylic acid {(S)-1-benzyl-3-[5,5-dimethyl-4-(2-methyl-benzylcarbamoyl)-thiazolidin-3-yl]-2-hydroxy-3-oxo-propyl}-amide

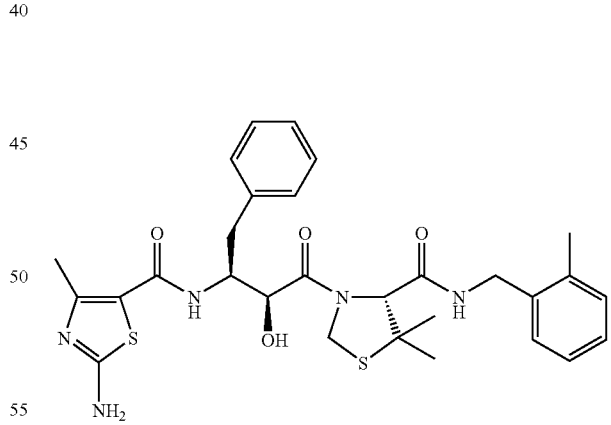

Isolated yield: 42%; 1H-NMR (400 MHz, dmso-$d_6$): δ 8.48 (brs, 1H), 8.35 (brs, 1H), 7.44 (d, 1H), 7.35–7.04 (m, 9H), 6.91 (s, 1H), 5.37 (d, 1H), 4.96 (q, 2H), 4.48–4.0 (m, 5H), 2,96 (m, 2H), 2.22 (2, 3H), 2.13 (s, 3H), 1.48 (s, 3H), 1.30 (s, 3H); IR (KBr in cm-1): 3307, 1625, 1495; MS (APCI, m/z): 582 (M+H), 442, 318; C29H35N5O4S2Cl1 Calculated: C, 60.13, H, 6.5, N, 10.82, Observed: C, 59.87, H, 6.06, N, 12.04; HPLC: Rf (min.) 17.981; Purity: 98%.

EXAMPLE B16

3-[2-Hydroxy-3-(2-methyl-benzoylamino)-4-phenyl-butyryl]-5,5-dimethyl-thiazolidine-4-carboxylic acid 2-methyl-benzylamide

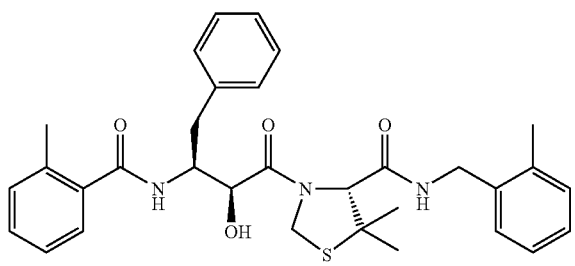

Isolated yield: 76%; 1H-NMR (400 MHz, dmso-d$_6$): δ 8.31 (t, 1H), 8.22 (d, 1H), 7.32–7.04 (m, 13H), 5.48 (d, 1H), 5.13 (d, 1H), 5.0 (d, 1H), 4.48 (s, 2H), 4.38 (dd, 2H), 4.09 (dd, 1H), 2.83 (d, 1H), 2.70 (t, 1H), 2.26 (s, 3H), 2.01 (s, 3H), 1.48 (s, 3H), 1.33 (s, 3H); IR (KBr in cm-1): 3309, 1641, 1520, 742; MS (APCI, m/z): 560 (M+H), 514, 296, 265; C32H37N3O4S1. 0.64 H2O Calculated: C, 67.40, H, 6.59, N, 7.37, Observed: C, 68.79, H, 6.49, N, 7.52; HPLC: Rf (min.) 21.024; Purity: 98%.

EXAMPLE B17

3-[3-(2,3-Dimethyl-benzoylamino)-2-hydroxy-4-phenyl-butyryl]-5,5-dimethyl-thiazolidine-4-carboxylic acid 2-methyl-benzylamide

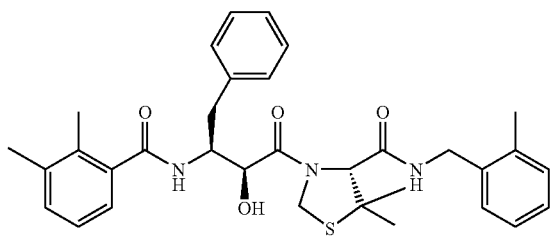

Isolated yield: 72%; 1H-NMR (400 MHz, dmso-d$_6$): δ 8.33 (t, 1H), 8.22 (d, 1H), 7.35–6.83 (m, 12H), 5.48 (d, 1H), 5.13 (d, 1H), 5.04 (d, 1H), 4.48–4.30 (m, 4H), 4.09 (dd, 1H), 2.84 (d, 1H), 2.70 (t, 1H), 2.26 (s, 3H), 2.17 (s, 3H), 1.87 (s, 3H), 1.48 (s, 3H), 1.30 (s, 3H); IR (KBr in cm-1): 3307, 1640, 1515, 743; MS (APCI, m/z): 574 (M+H), 528, 310, 265; C33H39N3O4S1. 0.54 H2O Calculated: C, 68.05, H, 6.76, N, 7.21, Observed: C, 69.20, H, 6.76, N, 7.34; HPLC: Rf (min.) 21.449; Purity: 99%.

EXAMPLE B18

6-Oxo-1,4,5,6-tetrahydro-pyridazine-3-carboxylic acid {1-benzyl-3-[5,5-dimethyl-4-(2-methyl-benzylcarbamoyl)-thiazolidin-3-yl]-2-hydroxy-3-oxo-propyl}-amide

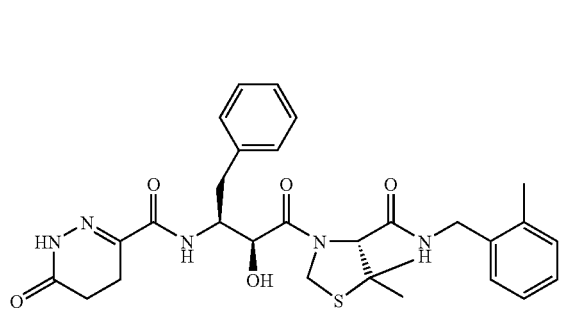

Isolated yield: 67%; 1H-NMR (400 MHz, dmso-d$_6$): δ 8.35 (t, 1H), 8.09 (d, 1H), 7.30–7.0 (m, 10H), 5.6 (d, 1H), 4.91 (d, 1H), 4.83 (d, 1H), 4.44 (s, 1H), 4.30 (m, 3H), 4.17 (dd, 1H), 2.78 (d, 2H), 2.61 (t, 2H), 2.30 (t, 2H), 2.22 (s, 3H), 1.48 (s, 3H), 1.30 (s, 3H); IR (KBr in cm-1): 3306, 1650, 1521, 742; MS (APCI, m/z): 566 (M+H), 520, 265; C29H35N5O5S1. 0.7 H2O Calculated: C, 60.23, H, 6.34, N, 12.11, Observed: C, 61.57, H, 6.24, N, 12.38; HPLC: Rf (min.) 18.455; Purity: 97%.

EXAMPLE B19

2,4-Dimethyl-5-oxo-2,5-dihydro-isoxazole-3-carboxylic acid {1-benzyl-3-[5,5-dimethyl-4-(2-methyl-benzylcarbamoyl)-thiazolidin-3-yl]-2-hydroxy-3-oxo-propyl}-amide

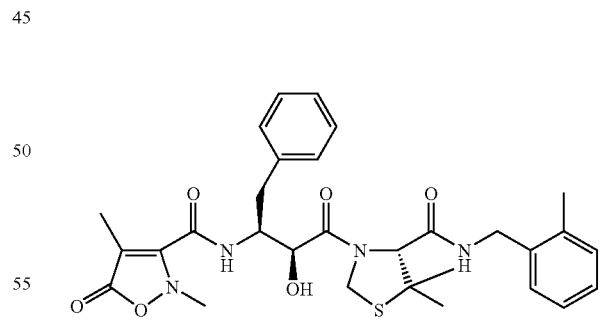

Isolated yield: 73%; 1H-NMR (400 MHz, dmso-d$_6$): δ 8.91 (d, 1H), 8.35 (t, 1H), 7.30–7.04 (m, 9H), 5.70 (d, 1H), 5.0 (d, 2H), 4.44 (s+m, 3H), 4.31 (dd, 1H), 4.13 (dd, 1H), 2.91 (s+m, 4H), 2.65 (t, 1H), 2.22 (s, 3H), 1.52 (s, 3H), 1.48 (s, 3H), 1.30 (s, 3H); IR (KBr in cm-1): 3325, 2932, 1729, 1649, 1527, 742; MS (APCI, m/z): 581 (M+H), 539, 493, 225; C30H36N4O6S1 Calculated: C, 62.29, H, 5.61, N, 9.19, Observed: C, 62.05, H, 6.25, N, 9.65; HPLC: Rf (min.) 19.638; Purity: 100%.

EXAMPLE B20

(R)-3-((2S,3S)-2-Hydroxy-3-{[1-(3-hydroxy-2,4-dimethyl-phenyl)-methanoyl]-amino}-4-phenyl-butanoyl)-5,5-dimethyl-thiazolidine-4-carboxylic acid allylamide

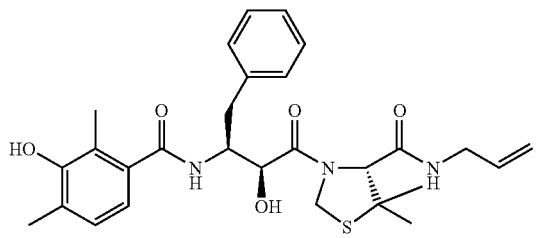

$^1$H NMR (DMSO-d$_6$) δ 8.23 (s, 1H), 8.10–8.03 (m, 2H), 7.33–7.12 (m, 5H), 6.85 (d, J=7.7, 1H), 6.51 (d, J=7.7, 1H), 5.82–5.70 (m, 1H), 5.44 (d, J=6.8, 1H), 5.22–4.97 (m, 4H), 4.50–4.30 (m, 3H), 3.84–3.60 (m, 2H), 2.84–2.66 (m, 2H), 2.13 (s, 3H), 1.85 (s, 3H), 1.49 (s, 3H), 1.35 (s, 3H); HRMS (ESI) m/z calcd for C$_{28}$H$_{36}$N$_3$O$_5$S (M+H)$^{30}$ 526.2376, found 526.2380; Anal. Calcd for C$_{29}$H$_{35}$N$_3$O$_5$S.0.2 TFA: C, 62.19; H, 6.47; N, 7.66. Found: C, 62.27; H, 6.78; N, 7.26.

EXAMPLE B21

3-(2-Hydroxy-3-{[1-(3-hydroxy-2,4-dimethyl-phenyl)-methyanoyl]-amino}-4-phenyl-butznoyl)-5,5-dimethyl-thiazolidine-4-carboxylic acid prop-2-ynylamide

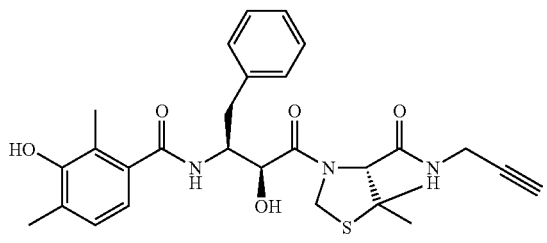

$^1$H NMR (DMSO-d$_6$) δ 8.40 (t, J=5.4, 1H), 8.22 (s, 1H), 8.02 (d, J=8.2, 1H), 7.35–6.52 (m, 7H), 5.44 (d, J=6.8, 1H), 5.10 (d, J=9.1, 1H), 5.02 (d, J=9.1, 1H), 4.46–4.40 (m, 2H), 4.40 (s, 1H), 3.86 (s br, 2H), 3.08 (t, J=1.8, 1H), 2.82–2.72 (m, 2H), 2.15 (s, 3H), 1.88 (s, 3H), 1.51 (s, 3H), 1.37 (s, 3H); HRMS (ESI) m/z calcd for C$_{28}$H$_{34}$N$_3$O$_5$S (M+H)$^{30}$ 524.2219, found 524.2219; Anal. Calcd for C$_{28}$H$_{33}$N$_3$O$_5$S.0.5H$_2$O: C, 63.13; H, 6.43; N, 7.89; S, 6.02. Found: C, 62.80; H, 6.64; N, 7.71; S, 5.69.

EXAMPLE B22

3-{2-Hydroxy-3-[(1-methyl-1H-pyrrole-2-carbonyl)-amino]-4-phenyl-butyryl}-5,5-dimethyl-thiazolidine-4-carboxylic acid 2-chloro-benzylamide

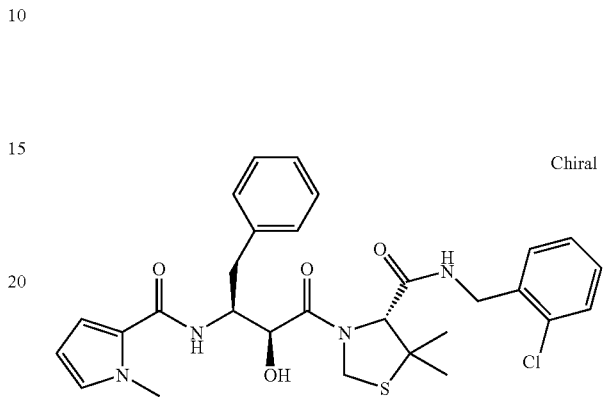

Isolated yield: 50%; 1H-NMR (400 MHz, dmso-d$^6$): 6.40–7.40 (m, 11H), 6.00 (m, 1H), 4.20–5.20 (m, 7H), 3.71, 3.54 (s 3H), 2.70–2.90 (m, 2H), 1.52 (d, J=2.0 Hz, 3H), 1.32 (d, J=2.1 Hz, 3H); MS (APCI, m/z): 570 (M+H).

EXAMPLE B23

3,5-Dimethyl-isoxazole-4-carboxylic acid {1-benzyl-3-[4-(2-chloro-benzylcarbamoyl)-5,5-dimethyl-thiazolidin-3-yl]-2-hydroxy-3-oxo-propyl}-amide

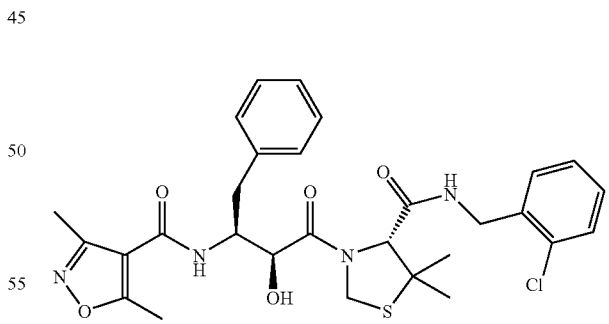

Isolated yield: 55%; 1H-NMR (400 MHz, dmso-d$^6$): 7.00–7.40 (m, 9H), 4.36–5.08 (m, 7H), 2.70–2.90 (m, 2H), 2.34, 2.25 (s, 3H), 2.18, 2.12 (s, 3H), 1.56 (d, J=8.5 Hz, 3H), 1.35 (d, J=6.2 Hz, 3H); MS (APCI, m/z): 586 (M+H); C$_{29}$H$_{33}$ClN$_4$O$_5$S. 0.42H$_2$O Calculated: C, 58.77, H, 5.75, N, 9.45, Observed: C, 58.37, H, 5.73, N, 9.19.

EXAMPLE B24

3-{2-Hydroxy-3-[(1-methyl-1H-pyrrole-2-carbonyl)-amino]-4-phenyl-butyryl}-5,5-dimethyl-thiazolidine-4-carboxylic acid 2,6-difluoro-benzylamide

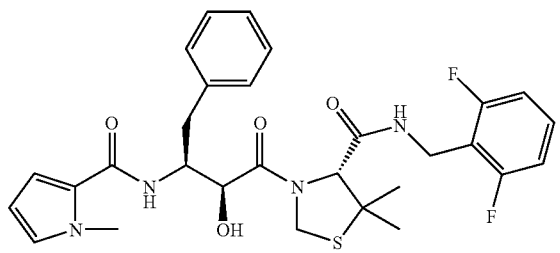

Isolated yield: 75%; 1H-NMR (400 MHz, dmso-d$^6$): 6.40–7.40 (m, 10H), 6.00 (m, 1H), 4.20–5.20 (m, 7H), 3.64, 3.61 (s 3H), 2.70–2.90 (m, 2H), 1.52, 1.49 (s, 3H), 1.33, 1.29 (s, 3H); MS (APCI, m/z): 571 (M+H); $C_{29}H_{32}F_2N_4O_4S$ Calculated: C, 61.04, H, 5.65, N, 9.82, Observed: C, 60.86, H, 5.94, N, 9.71.

EXAMPLE B25

3,5-Dimethyl-isoxazole-4-carboxylic acid {1-benzyl-3-[4-(2,6-difluoro-benzylcarbam yl)-5,5-dimethyl-thiazolidin-3-yl]-2-hydroxy-3-oxo-propyl}-amide

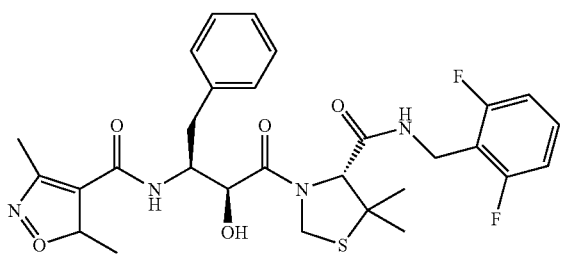

Isolated yield: 75%; 1H-NMR (400 MHz, dmso-d$^6$): 6.60–7.40 (m, 8H), 4.26–5.08 (m, 7H), 2.70–2.90 (m, 2H), 2.32, 2.28 (s, 3H), 2.16, 2.13 (s, 3H), 1.56, 1.53 (s, 3H), 1.37, 1.34 (s, 3H); MS (APCI, m/z): 587 (M+H); $C_{29}H_{32}F_2N_4O_5S$ Calculated: C, 59.37, H, 5.50, N, 9.55, Observed: C, 59.12, H, 5.88, N, 9.50.

EXAMPLE B26

3-{2-Hydroxy-3-[(1-methyl-1H-pyrrole-2-carbonyl)-amino]-4-phenyl-butyryl}-5,5-dimethyl-thiazolidine-4-carboxylic acid 2-trifluoromethyl-benzylamide

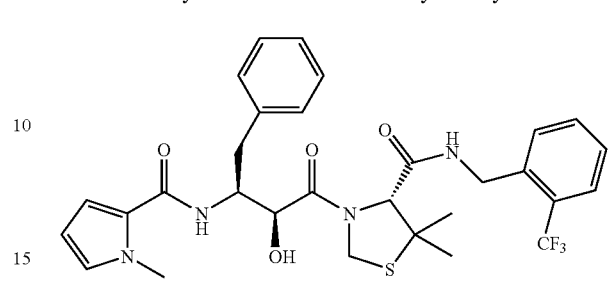

Isolated yield: 83%; 1H-NMR (400 MHz, dmso-d$^6$): 6.40–7.60 (m, 11H), 6.00 (m, 1H), 4.20–5.20 (m, 7H), 3.70, 3.54 (s 3H), 2.70–2.90 (m, 2H), 1.52 (s, 3H), 1.36, 1.29 (s, 3H); MS (APCI, m/z): 619 (M+H); $C_{30}H_{33}F_3N_4O_4S$ Calculated: C, 59.79, H, 5.52, N, 9.30, Observed: C, 59.42, H, 5.55, N, 9.06.

EXAMPLE B27

3,5-Dimethyl-isoxazole-4-carboxylic acid {1-benzyl-3-[5,5-dimethyl-4-(2-trifluoromethyl-benzylcarbamoyl)-thiazolidin-3-yl]-2-hydroxy-3-oxo-propyl}-amide

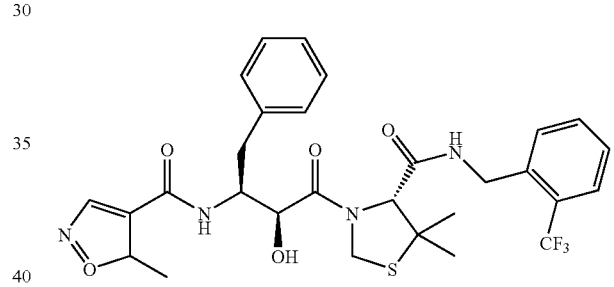

Isolated yield: 93%; 1H-NMR (400 MHz, dmso-d$^6$): 7.05–7.60 (m, 9H), 4.36–5.08 (m, 7H), 2.70–2.90 (m, 2H), 2.30, 2.21 (s, 3H), 2.15, 2.05 (s, 3H), 1.54, 1.52 (s, 3H), 1.39, 1.32 (s, 3H); MS (APCI, m/z): 619 (M+H); $C_{30}H_{33}F_3N_4O_5S$ Calculated: C, 58.24, H, 5.38, N, 9.06, Observed: C, 57.87, H, 5.68, N, 9.02.

EXAMPLE B28

N-[(1S,2S)-3-(4-Allylcarbamoyl-5,5-dimethyl-thiazolidin-3-yl)-1-benzyl-2-hydroxy-3-oxo-propyl]-nicotinamide

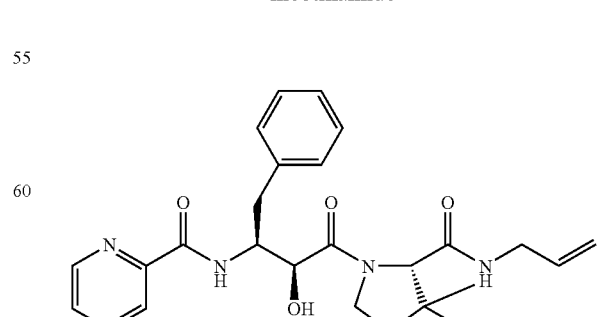

White solid: ¹H NMR (DMSO-d₆) δ 8.81 (d, J=8.6, 1), 8.77 (d, J=6.2, 1H), 8.12 (m, 1H), 7.99 (m, 1H), 7.63 (m, 1H), 7.32–7.12 (m, 7H), 5.78 (m, 1H), 5.18 (m, 2H), 4.56(m, 3H), 4.40 (m, 4H), 2.87–2.67 (m, 2H), 1.49 (s, 3H), 1.34 (s, 3H); Anal. (C₂₆H₃₂N₄O₄S.0.5 H₂O.0.5 TFA) calculated C (57.65), H (6.36), N (10.19), found C (57.73), H (5.91), N (10.15). HRMS (ESI) m/z calcd for 483.2075, found 497.2066.

EXAMPLE B29

3-[2-Hydroxy-3-(4-methoxy-2-methyl-benzoylamino)-4-phenyl-butyryl]-5,5-dimethyl-thiazolidine-4-carboxylic acid 2-methyl-benzylamide

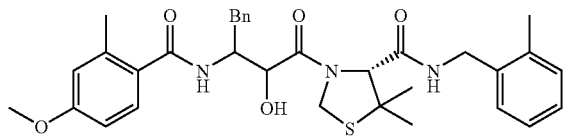

Isolated yield: 56%. ¹H NMR (400 MHz, DMSO-d₆): δ 8.32 (t, 1H), 8.09 (d, 1H), 7.33–7.27 (m, 3H), 7.23–7.19 (m, 2H), 7.15–7.08 (m, 5H), 6.69 (d, 2H), 5.46 (d, 1H), 5.13 (d, 1H), 4.99 (d, 1H), 4.49 (s, 2H), 4.41–4.36 (m, 2H), 4.10 (dd, 1H), 3.71 (s, 3H), 2.84–2.81 (m, 1H), 2.72 (t, 1H), 2.24 (s, 3H), 2.07 (s, 3H), 1.48 (s, 3H), 1.33 (s, 3H); MS-APCI (m/z+): 326, 590 (M+H). HPLC: Rf(min.) 21.26; Purity: 100%; C₃₃H₃₉N₃O₅S₁.0.4 H₂O: calcd: C, 66.40, H, 6.72, N, 7.04, found: C, 66.38, H, 6.71, N, 6.94.

EXAMPLE B30

(R)-3-{(2S,3S)-2-Hydroxy-4-phenyl-3-[(1-o-tolyl-methanoyl)-amino]-butanoyl}-5,5-dimethyl-thiazolidine-4-carboxylic acid propylamide

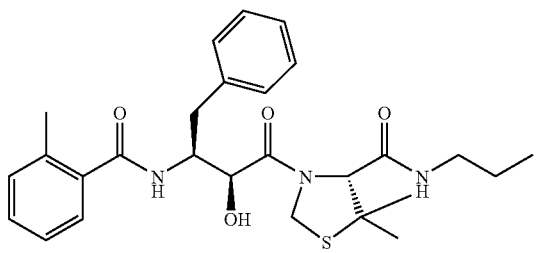

IR (neat, cm⁻¹) 3318, 2964, 1642, 1530, 1445, 1372, ¹H NMR (DMSO) δ 8.21 (d, J=8.4, 1H), 7.90 (t, J=5.6, 1H), 7.35–7.07 (m, 9H), 5.45 (d, J=6.8, 1H), 5.09 (d, J=9.2, 1H), 5.00 (d, J=9.2, 1H), 4.50–4.38 (m, 2H), 4.37 (s, 1H), 3.01 (q, J=6.9, 2H), 2.90–2.60 (m, 2H), 2.02 (s, 3H), 1.49 (s, 3H), 1.44–1.35 (m, 2H), 1.34 (s, 3H), 0.82 (t, J=7.5, 3H); HRMS (ESI) m/z calcd for C₂₇H₃₆N₃O₄S (M+H)³⁰ 498.2424, found 498.2427.

EXAMPLE B31

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic acid propylamide

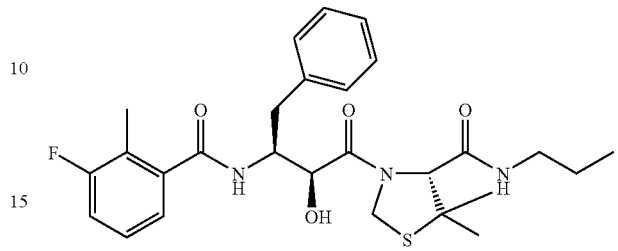

White solid: ¹H NMR (DMSO) δ 8.34 (d, J=8.1, 1H), 7.91 (t, J=5.9, 1H), 7.40–7.10 (m, 7H), 6.93 (d, J=6.9, 1H), 5.51 (d, J=6.2, 1H), 5.08 (d, J=8.8, 1H), 5.00 (d, J=8.8, 1H), 4.50–4.39 (m, 2H), 4.38 (s, 1H), 3.00 (dd, J=12.3, 5.9, 2H), 2.90–2.60 (m, 2H), 1.89 (s, 3H), 1.49 (s, 3H), 1.40–1.34 (m, 2H), 1.34 (s, 3H), 0.82 (t, J=7.7, 3H); HRMS (ESI) m/z calcd for C₂₇H₃₅N₃O₄FS (M+H)³⁰ 516.2332, found 516.2339.

EXAMPLE B32

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic acid 3-methoxy-benzylamide

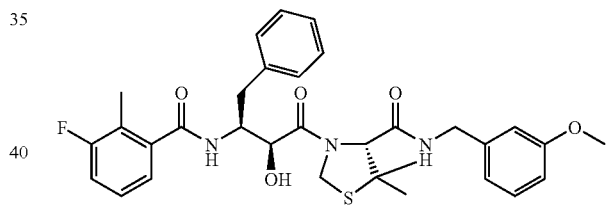

White solid: ¹H NMR (DMSO) δ 8.43 (t, J=5.9, 1H), 8.34 (d, J=8.1, 1H), 7.31–6.72 (m, 12H), 5.57 (d, J=6.8, 1H), 5.12 (d, J=9.3, 1H), 5.01 (d, J=9.3, 1H), 4.50–4.30 (m, 4H), 4.12 (dd, J=15.7, 5.9, 1H), 3.69 (s, 3H), 2.95–2.62 (m, 2H), 1.90 (s, 3H), 1.49 (s, 3H), 1.34 (s, 3H); HRMS (ESI) m/z calcd for C₃₂H₃₇N₃O₅SF (M+H)⁺ 594.2434, found 594.2438.

EXAMPLE B33

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic acid allylamide

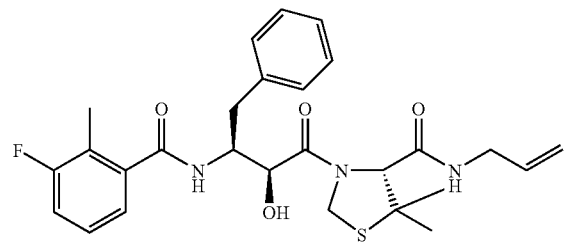

White solid: ¹H NMR (DMSO) δ 8.34 (d, J=8.3, 1H), 8.10 (t, J=5.7, 1H), 7.40–6.90 (m, 8H), 5.81–5.69 (m, 1H), 5.54 (d, J=6.6, 1H), 5.30–4.90 (m, 4H), 4.50–4.35 (m, 3H), 3.80–3.65 (m, 2H), 2.90–2.60 (m, 2H), 1.89 (s, 3H), 1.49 (s, 3H), 1.35 (s, 3H); HRMS (ESI) m/z calcd for $C_{27}H_{33}N_3O_4SF$ $(M+H)^{30}$ 514.2182, found 514.2176.

EXAMPLE B34

3-[(2S,3S)-2-Hydroxy-3-(3-hydroxy-2,5-dimethyl-benzoylamino)-4-phenyl-butyryl]-5,5-dimethyl-thiazolidine-4-carboxylic acid allylamide

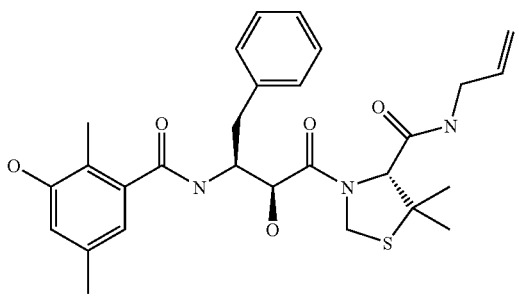

¹H NMR (DMSO-$d_6$) δ 9.23 (s, 1H), 8.09 (m, 2H), 7.35–7.17 (m, 5H), 6.60 (s, 1H), 6.37 (s, 1H), 5.74 (m, 1H), 5.41 (br s, 1H), 5.20 (dd, J=17.2, 1.6, 1H), 5.11 (d, J=9.2, 1H), 5.02 (dd, J=10.2, 1.5, 1H), 5.00 (d, J=9.1, 1H), 4.46–4.37 (m, 3H), 3.79 (ddd, J=15.9, 5.5, 5.3, 1H), 3.63 (ddd, J=15.9, 5.4, 5.3, 1H), 2.82 (dd, J=13.9, 0.3, 1H), 2.71 (dd, J=13.6, 10.7, 1H), 2.16 (s, 3H), 1.76 (s, 3H), 1.51 (s, 3H), 1.36 (s, 3H); Anal. Calcd for $C_{28}H_{35}N_4O_5S.0.3H_2O$: C, 63.32; H, 6.76; N, 7.91, Found: C 63.35; H, 6.70; N, 7.71.

EXAMPLE B35

3-[(2S,3S)-3-(5-Fluoro-3-hydroxy-2-methyl-benzoylamino)-2-hydroxy-4-phenyl-butyryl]-5,5-dimethyl-thiazolidine-4-carboxylic acid allylamide

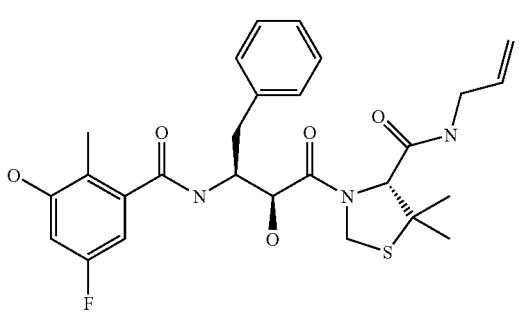

¹H NMR (DMSO-$d_6$) δ 9.94 (s, 1H), 8.23 (d, J=8.2, 1H), 8.10 (t, J=5.6, 1H), 7.33–7.17 (m, 5H), 6.58 (dd, J=10.6, 2.5, 1H), 6.32 (dd, J=8.8, 2.5, 1H), 5.78 (m, 1H), 5.54 (br s, 1H), 5.21 (dd, J=17.2, 1.7, 1H), 5.10 (d, J=9.1, 1H), 5.03 (dd, J=10.2, 1.5, 1H), 5.01 (d, J=9.1, 1H), 4.50–4.42 (m, 3H), 3.78 (ddd, J=15.9, 5.4, 5.4, 1H), 3.63 (ddd, J=15.9, 5.4, 5.3, 1H), 2.84 (dd, J=14.5, 3.3, 1H), 2.70 (dd, J=13.5, 10.3, 1H), 1.75 (s, 3H), 1.50 (s, 3H), 1.36 (s, 3H); Anal. Calcd for $C_{27}H_{32}FN_3O_5S.0.3H_2O$: C, 60.61; H, 6.14; N, 7.85, Found: C, 60.63; H, 6.08; N, 8.07.

EXAMPLE B36

(R)-3-((2S,3S)-3-{[1-(3-Fluoro-2-methyl-phenyl)-methanoyl]-amino}-2-hydroxy-4-phenyl-butanoyl)-5,5-dimethyl-thiazolidine-4-carboxylic acid 2-methyl-benzylamide

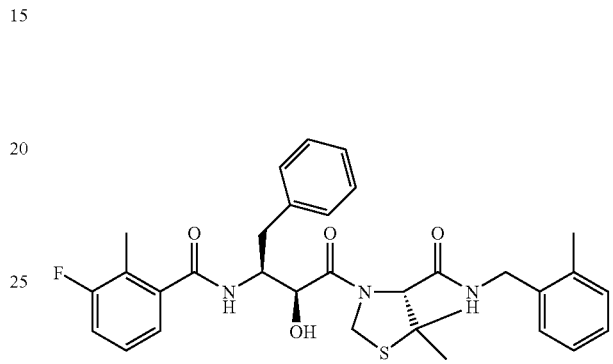

¹H NMR (DMSO) δ 8.85–8.35 (m, 2H), 7.38–6.90 (m, 12H), 5.55 (d, J=5.9, 1H), 5.12 (d, J=9.2, 1H), 5.01 (d, J=9.2, 1H), 4.58–4.32 (m, 4H), 4.10 (dd, J=15.0, 4.6, 1H), 2.92–2.62 (m, 2H), 2.24 (s, 3H), 1.90 (s, 3H), 1.49 (s, 3H), 1.34 (s, 3H); HRMS (ESI) m/z calcd for $C_{32}H_{37}N_3O_4FS$ $(M+H)^{30}$ 578.2489, found 578.2486; Anal. Calcd for $C_{32}H_{36}N_3O_4FS.0.2$ EtOAc: C, 66.17; H, 6.37; N, 7.06. Found: C, 66.30; H, 6.54; N, 6.74.

EXAMPLE B37

(R)-3-((2S,3S)-3-{[1-(4-Fluoro-2-methyl-phenyl)-methanoyl]-amino}-2-hydroxy-4-phenyl-butanoyl)-5,5-dimethyl-thiazolidine-4-carboxylic acid 2-methyl-benzylamide

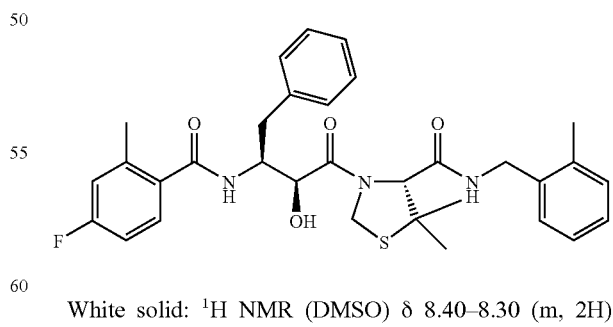

White solid: ¹H NMR (DMSO) δ 8.40–8.30 (m, 2H), 7.35–6.90 (m, 12H), 5.53 (d, J=6.8, 1H), 5.13 (d, J=9.0, 1H), 5.00 (d, J=9.0, 1H), 4.48 (s, 1H), 4.47–4.45 (m, 2H), 4.38 (dd, J=15.0, 5.9, 1H), 4.10 (dd, J=15.0, 4.8, 1H), 2.90–2.62 (m, 2H), 2.24 (s, 3H), 2.04 (s, 3H), 1.48 (s, 3H), 1.33 (s, 3H); HRMS (ESI) m/z calcd for $C_{32}H_{37}N_3O_4SF$ $(M+H)^{30}$ 578.2463, found 578.2489.

EXAMPLE B38

Nicotinic acid 3-[(1S,2S)-3-((R)-4-allylcarbamoyl-5,5-dimethyl-thiazolidin-3-yl)-1-benzyl-2-hydroxy-3-oxo-propylcarbamoyl]-2-methyl-phenyl ester

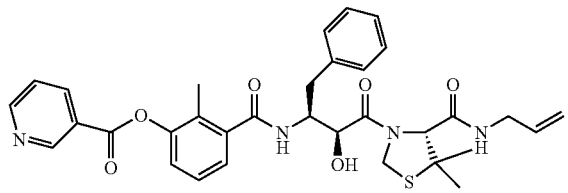

White solid: $^1$H NMR (DMSO) δ 9.26 (dd, J=2.0, 0.9, 1H), 8.90 (dd, J=5.6, 2.0, 1H), 8.47 (dt, J=7.9, 2.0, 1H), 8.40 (d, J=8.2, 1H), 8.1 (t, J=5.7, 1H), 7.65 (ddd, J=7.9, 5.6, 0.9, 1H), 7.40–7.10 (m, 8H), 5.82–5.68 (m, 1H), 5.6 (d, J=6.2, 1H), 5.30–4.90 (m, 4H), 4.50–4.40 (m, 2H), 4.40 (s, 1H), 3.80–3.70 (m, 2H), 3.00–2.60 (m, 2H), 1.85 (s, 3H), 1.49 (s, 3H), 1.34 (s, 3H).

EXAMPLE B39

(R)-3-[(2S,3S)-2-Hydroxy-3-(4-hydroxy-2-methyl-benzoylamino)-4-phenyl-butyryl]-5,5-dimethyl-thiazolidine-4-carboxylic acid 2-methyl-benzylamide

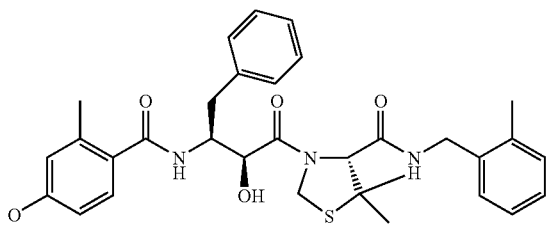

White solid: $^1$H NMR (DMSO) δ 9.55 (s, 1H), 8.32 (t, J=4.9, 1H), 8.00 (d, J=8.4, 1H), 7.36–7.00 (m, 10H), 6.54–6.48 (m, 2H), 5.44 (d, J=6.6, 1H), 5.13 (d, J=9.2, 1H), 4.99 (d, J=9.2, 1H), 4.50–4.32 (m, 4H), 4.11 (dd, J=15.0, 4.8, 1H), 3.50–2.80 (m, 2H), 2.25 (s, 3H), 2.04 (s, 3H), 1.49 (s, 3H), 1.33 (s, 3H); Anal. Calcd for $C_{32}H_{37}N_3O_5S \cdot 0.25 H_2O$: C, 66.24; H, 6.51; N, 7.24. Found: C, 66.25; H, 6.55; N, 7.35.

EXAMPLE B40

6-Amino-pyridine-2-carboxylic acid {(1S,2S)-1-benzyl-3-[(R)-5,5-dimethyl-4-(2-methyl-benzylcarbamoyl)-thiazolidin-3-yl]-2-hydroxy-3-oxo-propyl}-amide

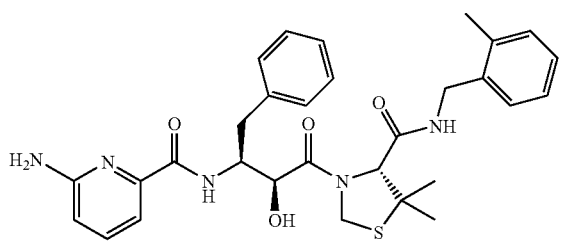

$^1$H NMR (DMSO-$d_6$) δ 8.44 (d, 1H, J=5.6), 8.36 (d, 1H, J=9.3), 7.69–7.49 (t, 1H, J=7.7), 7.34–7.06 (m, 10H), 6.61 (d, 1H, J=8.4), 6.27 (br s, 2H) 5.47 (d, 1H, J=7.1), 5.00 (m, 2H), 4.54–4.43 (m, 2H), 4.50 (s, 1H), 4.38 (dd, 1H, J=6.4, 15.2), 4.19 (dd, 1H, J=4.6, 14.7), 2.87–2.65 (m, 2H), 2.28 (s, 3H), 1.53 (s, 3H), 1.38 (s, 3H). Exact mass calculated for $C_{30}H_{36}N_5O_4S$ (M+H)[30] 562.2488, found 562.2493.

EXAMPLE B41

{(1S,2S)-1-Benzyl-3-[(R)-5,5-dimethyl-4-(2-methyl-benzylcarbamoyl)-thiazolidin-3-yl]-2-hydroxy-3-oxo-propyl}-2,3-dichloro-isonicotinamide

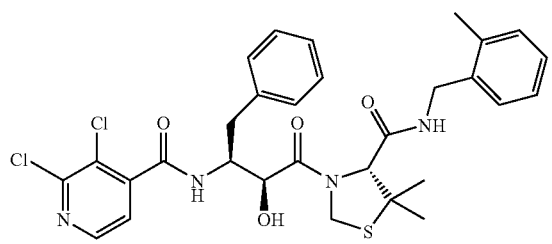

$^1$H NMR (DMSO-$d_6$) δ 8.89 (d, 1H, J=8.42), 8.40 (t, 1H, J=5.5), 8.38 (d, 1H, J=4.8), 7.30–7.08 (m, 10H), 5.58 (d, 1H, J=7.3), 5.07 (d, 1H, J=8.8), 5.00 (d, 1H, J=8.8), 4.54–4.50 (m, 1H), 4.51 (s, 1H), 4.43–4.36 (m, 2H), 4.16 (dd, 1H, J=5.1, 15.0), 2.89–2.85 (m, 1H), 2.71–2.63 (m, 1H), 2.26 (s, 3H), 1.50 (s, 3H), 1.35s (s, 3H). Exact mass calculated for $C_{30}H_{33}N_4O_4SCl_2$ (M+H)[30] 615.1600, found 615.1581. Anal. Calcd for $C_{30}H_{32}N_4O_4SCl_2$: C, 58.54; H, 5.24; N, 9.10. Found: C, 58.48; H, 5.10; N, 8.80.

EXAMPLE B42

{(1S,2S)-1-Benzyl-3-[(R)-5,5-dimethyl-4-(2-methyl-benzylcarbamoyl)-thiazolidin-3-yl]-2-hydroxy-3-oxo-propyl}-3-chloro-isonicotinamide

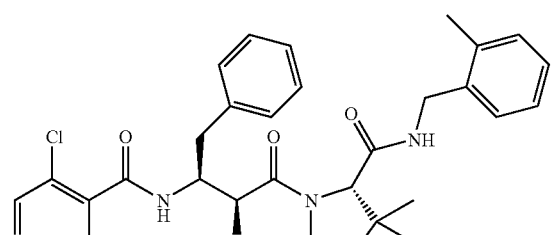

$^1$H NMR (DMSO-$d_6$) δ 8.82 (d, 1H, J=8.6), 8.62 (s, 1H), 8.52 (d, 1H, J=4.9), 8.39 (d, 1H, J=5.1), 7.29–7.09 (m, 10H), 5.54 (d, 1H, J=7.1), 5.09 (d, 1H, J=9.0), 4.99 (d, 1H, J=9.0), 4.56–4.49 (m, 1H), 4.51 (s, 1H), 4.44–4.37 (m, 2H), 4.15 (dd, 1H, J=5.1, 15.0), 2.88–2.83 (m, 1H), 2.74–2.65 (m, 1H), 2.26 (s, 3H), 1.50 (s, 3H), 1.35s (s, 3H). Exact mass calculated for $C_{30}H_{33}N_4O_4SCl$ (M)[30] 581.1989, found 581.1983.

EXAMPLE B43

(R)-3-[(2S,3S)-2-Hydroxy-3-(3-hydroxy-2,5-dimethyl-benzoylamino)-4-phenyl-butyryl]-5,5-dimethyl-thiazolidine-4-carboxylic acid 2-methyl-benzylamide

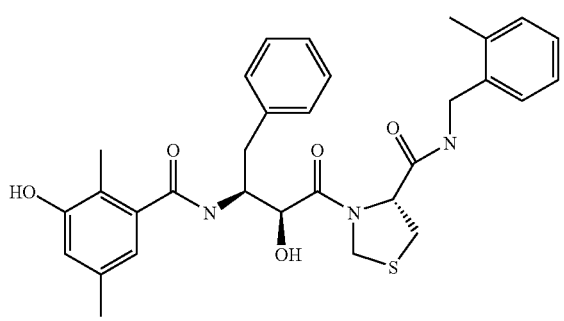

$^1$H NMR (DMSO-d$_6$) δ 9.24 (s, 1H), 8.31 (t, J=5.6, 1H), 8.10 (d, J=8.2, 1H), 7.34–7.09 (m, 9H), 6.60 (s, 1H), 6.38 (s, 1H), 5.42 (br s, 1H), 5.14 (d, J=9.1, 1H), 5.01 (d, J=9.1, 1H), 4.50 (s, 1H), 4.50–4.37 (m, 3H), 4.11 (dd, J=15.1, 4.7, 1H), 2.76 (m, 2H), 2.26 (s, 3H), 2.16 (s, 3H), 1.77 (s, 3H), 1.50 (s, 3H), 1.35 (s, 3H); HRMS (ESI) m/z calcd for C$_{33}$H$_{40}$N$_3$O$_5$S (M+H)$^{30}$ 590.2689, found 590.2676; Anal. Calcd for C$_{33}$H$_{39}$N$_3$O$_5$S.0.3 H$_2$O: C, 66.60; H, 6.71; N, 7.06. Found: C, 66.65; H, 6.69; N, 7.05.

EXAMPLE B44

N-{(1S,2S)-1-Benzyl-3-[5,5-dimethyl-4-(2-methyl-benzylcarbamoyl)-thiazolidin-3-yl]-2-hydroxy-3-oxo-propyl}-2-methyl-nicotinamide

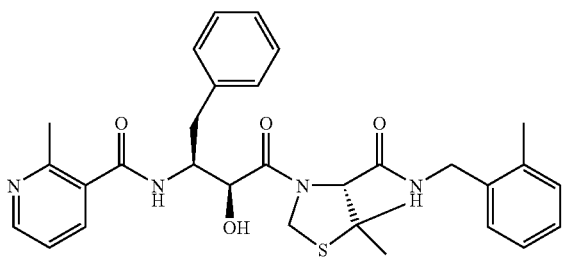

White solid: $^1$H NMR (DMSO-d$_6$) δ 8.53–8.33 (m, 2H), 7.47 (d, J=7.82, 1H), 7.38–7.10 (m, 12H), 5.62 (d, J=7.94, 1H), 5.18 (dd, J=9.6, 7.6, 2H), 4.43–4.37 (m, 3H), 4.17 (dd, J=7.81, 6.99, 1H), 2.87–2.67 (m, 2H), 2.28 (s, 3H), 2.21(s, 3H), 1.49 (s 3H), 1.34 (s, 3H); Anal. (C$_{31}$H$_{36}$N$_4$O$_4$S.1.0 H$_2$O.1.0 MeCN) calculated C (63.95), H (6.67), N (11.30), found C (63.94), H (6.75), N (11.26). HRMS (ESI) m/z calcd for 561.2544, found 561.2556.

EXAMPLE B45

Pyridine-2-carboxylic acid {(1S,2S)-1-benzyl-3-[5,5-dimethyl-4-(2-methyl-benzylcarbamoyl)-thiazolidin-3-yl]-2-hydroxy-3-oxo-propyl}-amide

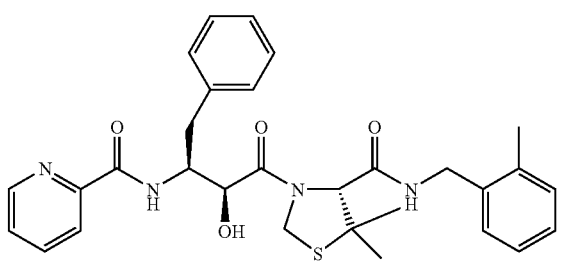

White solid: $^1$H NMR (DMSO-d$_6$) δ 8.89 (d, J=7.86,), 8.66 (d, J=4.2, 1H), 8.39 (t, J=6.54, 1H), 7.89 (m 2H), 7.32–7.12 (m, 9H), 5.68 (d, J=7.28, 1H), 5.03 (dd J=9.7, 8.3, 2H), 4.56(m 3H), 4.40 (d, J=7.5, 1H), 4.35 (d, J=7.5, 1H), 4.21 (d, J=6.7, 1H), 2.87–2.67 (m, 2H), 2.25 (s 3H), 1.49 (s, 3H), 1.34 (s, 3H); Anal. (C$_{30}$H$_{34}$N$_4$O$_4$S.0.1 H$_2$O.0.1 EtOAc) calculated C (65.52), H (6.33), N (10.05), found C (65.78), H (6.69), N (9.66). HRMS (ESI) m/z calcd for 547.2380, found 547.2373.

EXAMPLE B46

Pyridine-2–5-hydroxy-carboxylic acid{(1S,2S)-1-benzyl-3-[5,5-dimethyl-4-(2-methyl-benzylcarbamoyl)-thiazolidin-3-yl]-2-hydroxy-3-oxo-propyl}-amide

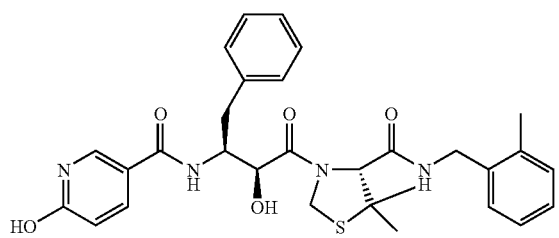

White solid: $^1$H NMR (DMSO-d$_6$) δ 8.89 (d, J=7.9, 1), 8.66 (d, J=4.2, 1H), 8.39 (t, J=6.54, 1H), 7.89 (m 2H), 7.32–7.12 (m, 9H), 5.68 (d, J=7.2, 1H), 5.03 (dd J=9.7, 8.3, 2H), 4.56(m 3H), 4.40 (d, J=7.5, 1H), 4.35 (d, J=7.5, 1H), 4.21 (d, J=6.7, 1H), 2.87–2.67 (m, 2H), 2.25 (s 3H), 1.49 (s, 3H), 1.34 (s, 3H); Anal. (C$_{30}$H$_{34}$N$_4$O$_5$S.0.5 H$_2$O.0.5 EtOAc) calculated C (62.29), H (6.42), N (9.91), found C (62.53), H (6.84), N (10.10). HRMS (ESI) m/z calcd for 563.2325, found 563.2328.

EXAMPLE B47

N-{(1S,2S)-1-Benzyl-3-[5,5-dimethyl-4-(2-methyl-benzylcarbamoyl)-thiazolidin-3-yl]-2-hydroxy-3-oxo-propyl}-nicotinamide

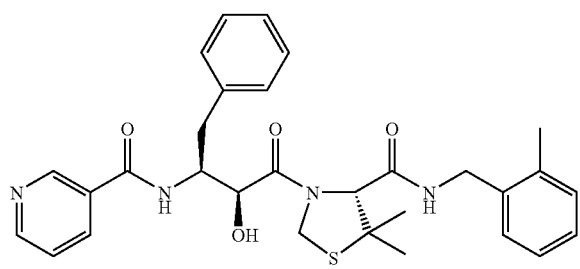

White solid $^1$H NMR (DMSO-d$_6$) δ 8.89 (d, J=7.9, 1H), 8.66 (d, J=4.2, 1H), 8.39 (t, J=6.54, 1H), 7.89 (m 2H), 7.32–7.12 (m, 9H), 5.68 (d, J=7.3, 1H), 5.03 (dd J=9.7, 8.3, 2H), 4.56(m 3H), 4.40 (d, J=7.5, 1H), 4.35 (d, J=7.5,1H), 4.21 (d, J=6.7, 1H), 2.87–2.67 (m, 2H), 2.25 (s 3H), 1.49 (s, 3H), 1.34 (s, 3H); Anal. (C$_{30}$H$_{34}$N$_4$O$_4$S.0.5 H$_2$O.0.5 MeCN) calculated C (64.61), H (6.39), N (10.94), found C (65.02), H (6.58), N (10.90). HRMS (ESI) m/z calcd for 547.2372, found 547.2379.

EXAMPLE B48

N-{(1S,2S)-1-Benzyl-3-[5,5-dimethyl-4-(2-methyl-benzylcarbamoyl)-thiazolidin-3-yl]-2-hydroxy-3-oxo-propyl}-nicotinamide

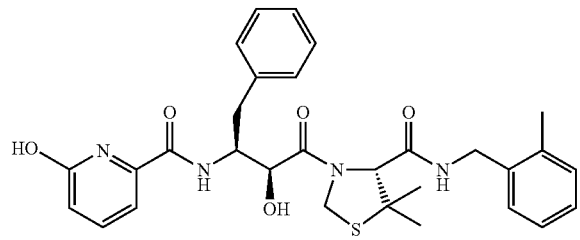

White solid: $^1$H NMR (DMSO-d$_6$) δ 8.89 (d, J=7.9, 1H), 8.66 (d, J=4.2, 1H), 8.39 (t, J=6.54, 1H), 7.89 (m 2H), 7.32–7.12 (m, 9H), 5.68 (d, J=7.28, 1H), 5.03 (dd J=9.7, 8.3, 2H), 4.56 (m, 3H), 4.40 (d, J=7.5, 1H), 4.35 (d, J=7.5, 1H), 4.21 (d, J=6.7, 1H), 2.87–2.67 (m, 2H), 2.25 (s 3H), 1.49 (s, 3H), 1.34 (s, 3H); Anal. (C$_{30}$H$_{34}$N$_4$O$_5$S.1.3 H$_2$O) calculated C (61.42), H (6.32), N (9.49), found C (61.64), H (6.17), N (9.12). HRMS (ESI) m/z calcd for 563.2326, found 563.2328.

EXAMPLE B49

N-[(1S,2S)-3-(4-Allylcarbamoyl-5,5-dimethyl-thiazolidin-3-yl)-1-benzyl-2-hydroxy-3-oxo-propyl]-2-methyl-nicotinamide

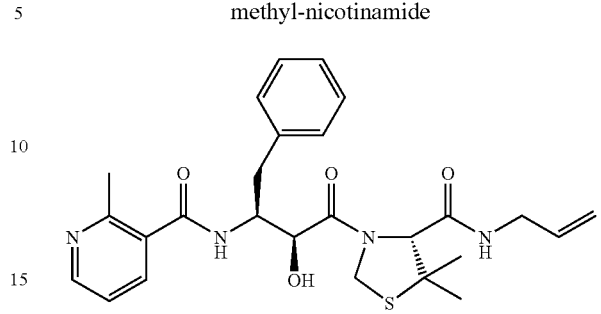

White solid: $^1$H NMR (DMSO-d$_6$) δ 8.58 (m, 1H), 8.29 (d, J=7.54, 1H), 7.78 (d, J=7.88, 2H), 7.32–7.12 (m, 7H), 5.78 (m, 1H), 5.18 (dd J=9.7, 8.3, 2H), 4.56(m, 3H), 4.40 (m, 4H), 2.87–2.67 (m, 2H), 2.25 (s 3H), 1.49 (s, 3H), 1.34 (s, 3H); Anal. (C$_{26}$H$_{32}$N$_4$O$_4$S.0.5 H$_2$O.0.5 TFA) calculated C (57.68), H (6.66), N (8.31), found C (57.66), H (6.18), N (8.77). HRMS (ESI) m/z calcd for 497.2232, found 497.2223.

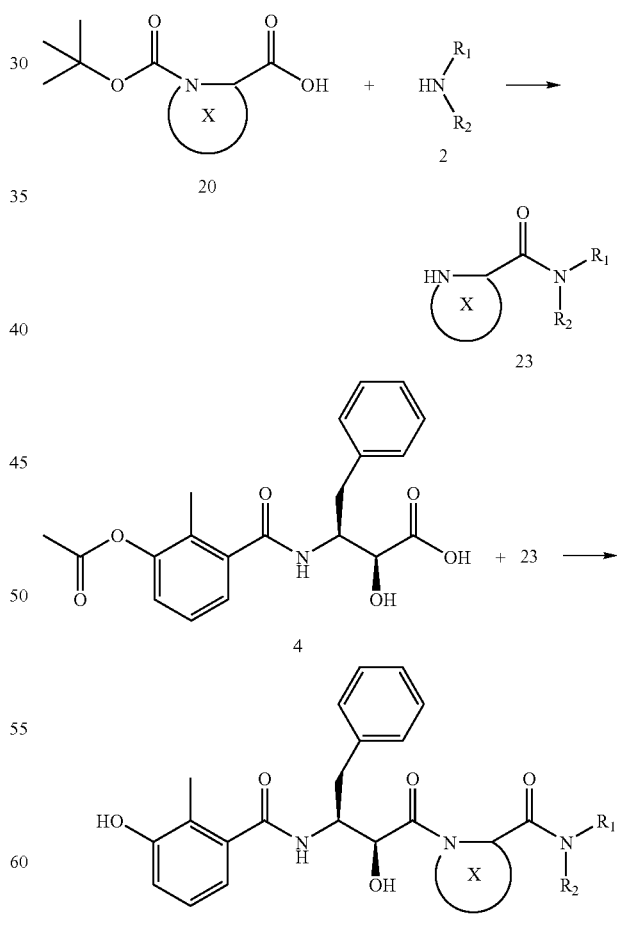

The synthesis of compounds with the general structure 24 is as follows. The boc-protected carboxylic acids 20a–f are coupled to the requisite amines 2 to yield amino amides 23 using a two step process. The process includes treatment of 20 with 2 in the presence of either diphenyl chlorophosphate or EDCI, followed by exposure to HCl or methane sulfonic acid. Final compounds 24 are obtained by a DCC-mediated coupling of 23 and 4 followed by deprotection of the P2 phenol. Final compounds were purified either by flash chromatography or preparative HPLC.

Na$_2$SO$_4$ and concentrated in vacuo. The crude was used without further purification unless otherwise noted.

4N HCl Boc deprotection—To a solution of Boc-amine in dioxane was added 4N HCl solution in dioxane and the solution stirred overnight at room temperature. The solution was poured into saturated NaHCO$_3$ and the product was extracted into ethyl acetate. The organic solution was Additional General Method C

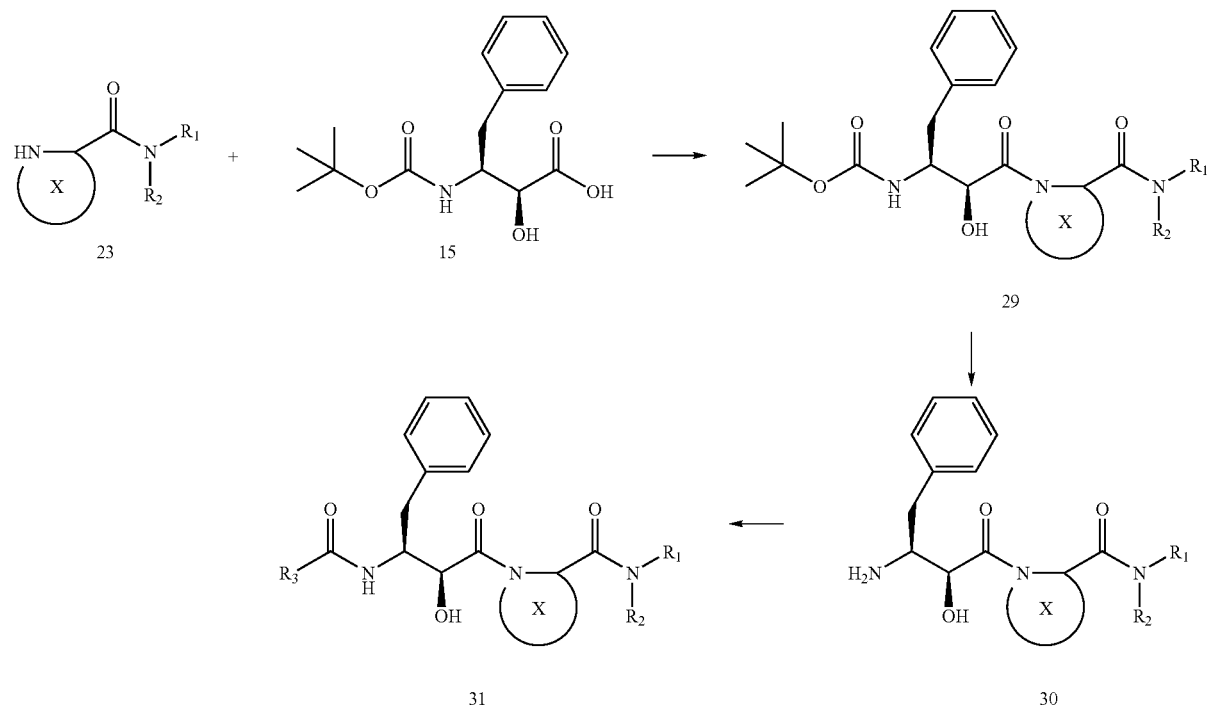

The synthesis of compounds of the general structure 31 (where P2 is not 2-methyl-3-hydroxy benzamide) is as follows. Amino amides of the general structure 23 were coupled to the Boc-acid intermediate 15 using DCC coupling conditions. The resulting intermediate 29 was deprotected under acidic conditions to yield amine of the general structure 30. Final compounds were obtained by modification of amine 30 by methods described in General Methods B section to give P2 amides and ureas.

Methods Used for Synthesis of Compounds with P1 Variations.

EDCI coupling—To a solution of acid, amine and HOBT in CH$_2$Cl$_2$ was added EDCI and the solution stirred overnight at room temperature. The solution was concentrated in vacuo and the residue dissolved in ethyl acetate and a small portion of water. The solution was washed with saturated NH$_4$Cl (2×), saturated NaHCO$_3$ (2×), brine (1×), dried with MgSO$_4$ and concentrated in vacuo. The crude used without further purification unless otherwise noted.

DCC coupling—A solution of acid, amine and HOBT was prepared in ethyl acetate. To the solution was then added DCC in an EtOAc solution at 0° C. and the mixture was stirred overnight at room temperature. The mixture was filtered and the filtrate was concentrated in vacuo. The residue dissolved in ethyl acetate washed with saturated NH$_4$Cl (1×), saturated NaHCO$_3$ (1×), brine (1×), dried over washed with brine, dried over Na$_2$SO$_4$ and concentrated in vacuo. The crude was used without further purification unless otherwise noted.

MeSO$_3$H Boc deprotection—To a solution of Boc-amine in ethyl acetate at 0° C. was added methane sulfonic acid and the solution stirred 3–6 h at room temperature. The solution was cooled to 0° C. and sufficient saturated NaHCO$_3$ was added to quench the acid. The solution was diluted with ethyl acetate, washed with saturated NaHCO$_3$ and brine, dried over Na$_2$SO$_4$ and concentrated in vacuo. The crude used without further purification unless otherwise noted.

KCN Phenolic acetate deprotection—A solution of phenolic acetate and KCN in ethanol was heated at 50° C. overnight. The solution was concentrated in vacuo. The residue was purified by flash chromatography eluted with 0 to 5% methanol in CH$_2$Cl$_2$ unless otherwise noted.

NaOMe/MeOH Phenolic acetate deprotection—0.5 N NaOCH$_3$/MeOH Phenolic acetate deprotection—A solution of phenolic acetate in EtOAc and methanol was cooled to 0° C. in an ice bath. 0.5 N NaOCH$_3$/MeOH was then added dropwise and then stirred at 0° C. for 1.5–2 hrs following addition. Additional EtOAc was then added, the 0.15 N HCl (4.5 eq.) added dropwise. The phases were separated and organic phase washed with 2.5% Na$_2$CO$_3$ aqueous solution, then with 0.1 N HCl/brine (2:1), followed with brine, dried with MgSO$_4$ and concentrated in vacuo. The resulting residue subjected to flash silica gel chromatography to afford the desired product unless otherwise noted.

HCl/MeOH Phenolic acetate deprotection—To a solution of phenolic acetate in methanol was added 4N HCl in dioxane and the solution stirred at room temperature ca. 4 h. The solution was concentrated in vacuo. The residue was purified by flash chromatography eluted with 0 to 5% methanol in CH$_2$Cl$_2$ unless otherwise noted.

Fragments of the General Structure 20.

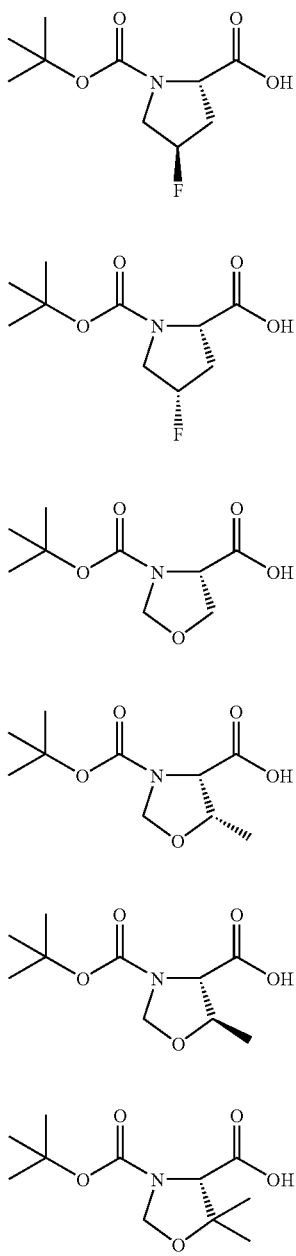

20b

20c

20d

20e

20f

Source of Boc-carboxylic Acids 20a–f

Boc-acids 20a and 20b were prepared following the procedure of Demange, L.; Ménez, A.; Dugave, C. *Tet. Lett.* 1998, 39, 1169.

Boc-acids 20c, 20d, 20e and 20f were prepared following the procedure of Karanewsky, D.; et al. *J. Med. Chem.* 1990, 33, 1459.

Specific Method C

EXAMPLE C1

(S)-4,4-Difluoro-1-[(2S,3S)-2-hydroxy-3-(3-hydroxy-2-methyl-benzoylamino)-4-phenyl-butyryl]-pyrrolidine-2-carboxylic acid 2-methyl-benzylamide.

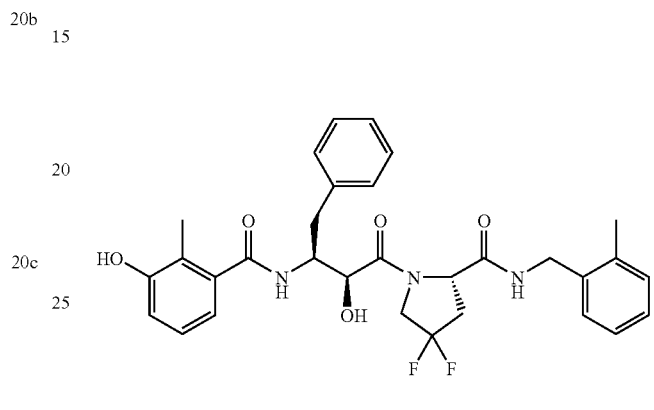

The title compound was prepared according to general methods using the corresponding Boc-protected pyrrolidinic acid (0.96 g, 3.8 mmol), o-methylbenzyl amine (0.57 mL, 4.6 mmol), HOBT (0.62 g, 4.6 mmol), EDCI (0.88 g, 4.6 mmol), CH$_2$Cl$_2$ (50 mL). To give the crude Boc-amide (MS-APCI (m/z+): 355, 255) (1.35 g, 3.8 mmol). The Boc was removed using the general 4N HCl Boc deprotection. 4N HCl in 1,4-dioxane (5 mL), 1,4-dioxane (5 mL). The result was amino amide of general structure 23. Isolated yield: 0.79 g (71%, 2 steps). $^1$H NMR (400 MHz, DMSO-d$_6$): δ 9.02 (t, 1H), 7.24–7.14 (m, 4H), 4.55 (t, 1H), 4.35 (dd, 1H), 4.30 (dd, 1H), 3.73 (m, 2H), 2.94 (m, 2H), 2.52 (m, 1H), 2.27 (s, 3H); $^{19}$F NMR (376 MHz, DMSO-d$_6$): δ −95.3 (dq, J=235, 15 Hz, 1F), −96.5 (dq, J=235, 12 Hz, 1F); MS-APCI (m/z+): 255.

Amino amide 23 (100 mg, 0.34 mmol) was coupled to carboxylic acid 4 (140 mg, 0.38 mmol) using the general DCC coupling method outlined above. HOBT (51 mg, 0.38 mmol), DCC (78 mg, 0.38 mmol), TEA (50 µL, 0.36 mmol), CH$_2$Cl$_2$ (10 mL). The crude was purified by chromatography eluted with 10% acetone in CH$_2$Cl$_2$. Isolated yield: 0.13 g (63%). MS-APCI (m/z+): 608. This material was subjected to the general KCN phenolic acetate deprotection conditions (130 mg, 0.21 mmol), KCN (1 mg, 15 µmol), ethanol (10 mL). The crude was precipitated from diethyl ether and ethyl acetate with hexanes at −78° C. Isolated yield: 0.10 g (84%). $^1$H NMR (400 MHz, DMSO-d$_6$): δ 9.37 (s, 1H), 8.36 (t, 1H), 8.16 (d, 1H), 7.32–7.09 (m, 9H), 6.93 (t, 1H), 6.76 (d, 1H), 6.54 (d, 1H), 5.49 (d, 1H), 4.66 (dd, 1H), 4.34–4.15 (m, 6H), 2.85–2.65 (m, 3H), 2.40 (m, 1H), 2.22 (s, 3H), 1.79 (s, 3H); $^{19}$F NMR (376 MHz, DMSO-d$_6$): δ −98.7 (m, 2F); MS-APCI (m/z+): 566; HPLC Purity: 100%; Rf (min.) 19.01; Anal. C$_{31}$H$_{33}$N$_3$O$_5$F$_2$·0.3 H$_2$O C, H, N calcd: C, 65.21, H, 5.93, N, 7.36; found: C, 65.1 1, H, 5.90, N, 7.17.

EXAMPLE C2

(2S,4R)-4-Fluoro-1-[(2S,3S)-2-hydroxy-3-(3-hydroxy-2-methyl-benzoylamino)-4-phenyl-butyryl]-pyrrolidine-2-carboxylic acid 2-methyl-benzylamide

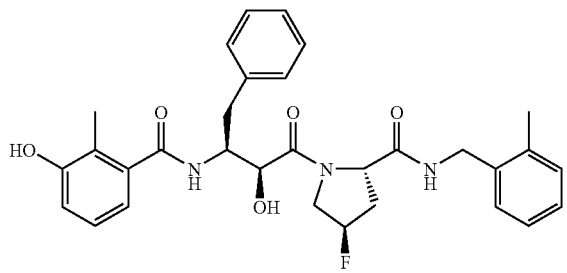

Isolated material was subjected to flash silica gel chromatography, eluting with EtOAc/hexanes (50/50) then with EtOAc EtOAc/hexanes (4:1) to afford the title compound. $^1$H NMR (400 MHz, DMSO-$d_6$): δ 9.37 (s, 1H), 8.46 (t, 1H), 8.21 (d, 1H), 7.34 (d, 2H), 7.26 (d, 2H), 7.21 (t, 2H), 7.15–7.07 (m, 3H), 6.94 (t, 1H), 6.76 (d, 1H), 6.56 (d, 1H), 5.51+5.38 (bs+bs, 1H), 5.06 (d, 1H), 4.58 (t, 1H), 4.45 (dd, 1H), 4.35–4.27 (m, 2H), 4.21–4.09 (m, 3H), 3.94–3.91+3.84–3.81 (m+m, 1H), 2.69 (d, 2H), 2.23 (s, 3H), 2.19–2.01 (m, 1H), 1.83 (s, 3H); MS-APCI (m/z+): 548; HPLC: Rf (min.) 18.72; Purity: 96%. Anal. $C_{31}H_{34}N_3O_5F.0.3\ H_2O$ calcd: 67.33, 6.31, 7.60, found: 67.37, 6.25, 7.35.

EXAMPLE C3

(2S,4S)-4-Fluoro-1-[(2S,3S)-2-hydroxy-3-(3-hydroxy-2-methyl-benzoylamino)-4-phenyl-butyryl]-pyrrolidine-2-carboxylic acid 2-methyl-benzylamide

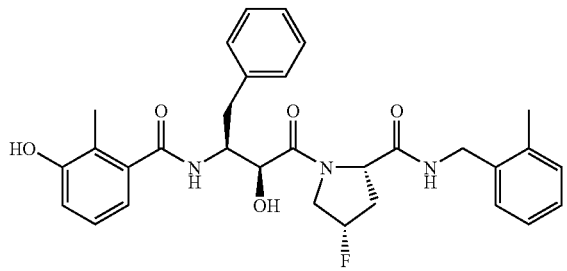

Isolated material was subjected to flash silica gel chromatography, eluting with EtOAc/hexanes (50/50) then with EtOAc to afford the title compound. $^1$H NMR (400 MHz, DMSO-$d_6$): δ 9.37 (s, 1H), 8.21 (d, 1H), 7.96 (t, 1H), 7.29 (d, 2H), 7.23 (t, 2H), 7.18–7.13 (m, 2H), 7.10–7.04 (m, 3H), 6.90 (t, 1H), 6.75 (d, 1H), 6.52 (d, 1H), 5.55 (d, 1H), 5.45+5.32 (bs+bs, 1H), 4.54 (d, 1H), 4.42–4.36 (m, 1H), 4.29–4.40 (m, 5H), 2.98 (t, 1H), 2.73 (t, 1H), 2.32–2.21 (m, 2H), 2.19 (s, 3H), 1.78 (s, 3H); MS-APCI (m/z+): 548; HPLC: Rf (min.) 18.21; Purity: 99%; Anal. $C_{31}H_{34}N_3O_5F.0.5\ H_2O$ calcd: 66.89, 6.34, 7.55, found: 66.85, 6.22, 7.41.

EXAMPLE C4

(S)-3-((2S,3S)-2-Hydroxy-3-{[1-(3-hydroxy-2-methyl-phenyl)-methanoyl]-amino}-4-phenyl-butanoyl)-oxazolidine-4-carboxylic acid 2-methyl-benzylamide

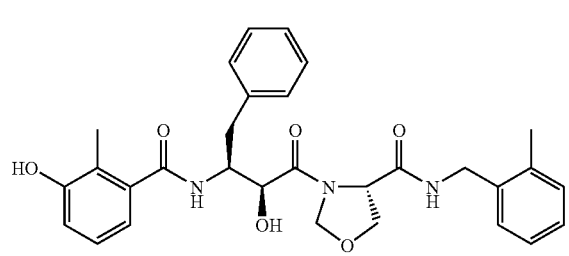

White solid; $^1$H NMR (DMSO-$d_6$) δ 9.36 (s, 1H), 8.80 (dd, J=8.8, 4.8, 1H), 8.30 (t, J=5.5, 1H), 8.12 (d, J=8.6, 1H), 7.30–7.13 (m, 9H), 6.96 (t, J=7.9, 1H), 6.76 (d, J=7.9, 1H), 6.55 (d, J=7.2, 1H), 5.74 (d, J=8.8, 1H), 5.31 (d, J=3.8, 1H), 5.23 (d, J=4.2, 1H), 4.49 (dd, J=6.6, 6.5, 1H), 4.33–4.11 (m, 5H), 2.94–2.68 (m, 2H), 2.24 (s, 3H), 1.78 (s, 3H); HRMS (ESI) m/z calcd for $C_{30}H_{34}N_3O_6$ (M+H)$^{30}$ 532.2448, found 532.2450.

EXAMPLE C5

(4S,5R)-3-((2S,3S)-2-Hydroxy-3-{[1-(3-hydroxy-2-methyl-phenyl)-methanoyl]-amino}-4-phenyl-butanoyl)-5-methyl-oxazolidine-4-carboxylic acid 2-methyl-benzylamide

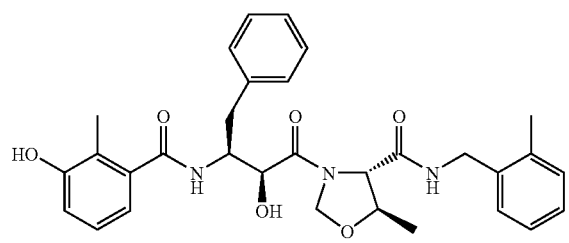

White solid; $^1$H NMR (DMSO-$d_6$) δ 9.38 (s, 1H), 8.51 (t, J=6.0, 1H), 8.15 (d, J=8.4, 1H), 7.33–7.13 (m, 9H), 6.96 (t, J=7.7, 1H), 6.79 (d, J=8.2, 1H), 6.58 (d, J=7.3, 1H), 5.69 (d, J=5.7, 1H), 5.50 (d, J=4.6, 1H), 5.10 (d, J=4.8, 1H), 4.39–4.22 (m, 4H), 4.11–4.01 (m, 2H), 2.90 (m, 1H), 2.74 (m, 1H), 2.27 (s, 3H), 1.82 (s, 3H), 1.37 (d, J=5.9, 1H); HRMS (ESI) m/z calcd for $C_{31}H_{36}N_3O_6$ (M+H)$^{30}$ 546.2604, found 546.2595.

EXAMPLE C6

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic acid 2-methyl-benzylamide

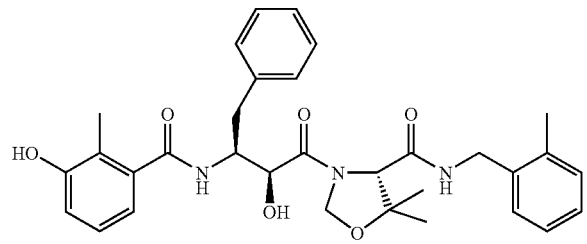

White solid; $^1$H NMR (DMSO-$d_6$) δ 9.34 (s, 1H), 8.32 (t, J=5.8, 1H), 8.11 (J=9.0, 1H), 7.31–7.10 (m, 9H), 6.93 (t, J=7.9, 1H), 6.76 (d, J=8.1, 1H), 6.55 (d, J=6.5, 1H), 5.73 (d, J=4.0, 1H), 5.46 (d, J=4.1, 1H), 5.23 (d, J=3.9, 1H), 4.39–4.32 (m, 2H), 4.18 (m, 3H), 2.92 (m, 1H), 2.69 (m, 1H), 2.27 (s, 3H), 1.81 (s, 3H), 1.28 (s, 3H), 1.18 (s, 3H); HRMS (ESI) m/z calcd for $C_{32}H_{38}N_3O_6$ (M+H)$^{30}$ 560.2761, found 560.2759; Anal. Calcd for $C_{32}H_{37}N_3O_6 \cdot 0.5\ H_2O$: C, 67.59; H, 6.74; N, 7.39. Found: C, 67.74; H, 6.75; N, 7.16.

EXAMPLE C7

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic acid propylamide

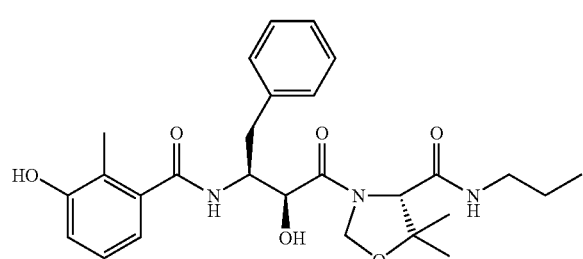

$^1$H NMR (DMSO-$d_6$) δ 9.37 (s, 1H), 8.12 (d, J=9.3, 1H), 7.93 (t, J=5.6, 1H), 7.34–7.18 (m, 5H), 6.96 (t, J=8.1, 1H), 6.79 (d, J=8.1, 1H), 6.56 (d, J=7.1, 1H), 5.73 (d, J=6.2, 1H), 5.44 (d, J=4.0, 1H), 5.24 (d, J=3.8, 1H), 4.36 (m, 1H), 4.18 (m, 1H), 4.11 (s, 1H), 3.10–2.92 (m, 3H), 2.75–2.66 (m, 1H), 1.80 (s, 3H), 1.46–1.39 (m, 2H), 1.31 (s, 3H), 1.22 (s, 3H), 0.86 (t, J=7.2, 3H); HRMS (ESI) m/z calcd for $C_{27}H_{36}N_3O_6$ (M+H)$^{30}$ 498.2604, found 498.2590.

EXAMPLE C8

(4S,5S)-3-((2S,3S)-2-Hydroxy-3-{[1-(3-hydroxy-2-methyl-phenyl)-methanoyl]-amino}-4-phenyl-butanoyl)-5-methyl-oxazolidine-4-carboxylic acid 2-methyl-benzylamide

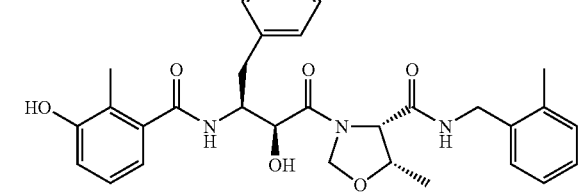

White solid; $^1$H NMR (DMSO-$d_6$) δ 9.36 (s, 1H), 8.26 (t, J=5.5, 1H), 8.09 (d, J=8.8, 1H), 7.30–7.08 (m, 9H), 6.93 (t, J=7.7, 1H), 6.76 (d, J=7.9, 1H), 6.56 (d, J=7.5, 1H), 5.72 (d, J=6.4, 1H), 5.55 (d, J=3.7, 1H), 5.08 (d, J=3.8, 1H), 4.40–4.33 (m, 3H), 4.26–4.11 (m, 3H), 3.10–2.89 (m, 1H), 2.78–2.67 (m, 1H), 2.26 (s, 3H), 1.78 (s, 3H), 1.15 (d, J=6.2, 3H); HRMS (ESI) m/z calcd for $C_{31}H_{36}N_3O_6$ (M+H)$^{30}$ 546.2604, found 546.2592.

EXAMPLE C9

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic acid 5-fluoro-2-methyl-benzylamide

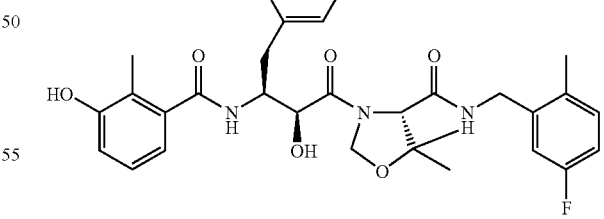

White solid; $^1$H NMR (DMSO-$d_6$) δ 9.35 (s, 1H), 8.41 (t, J=5.6, 1H), 8.12 (d, J=8.9, 1H), 7.28–7.08 (m, 8H), 6.95–6.90 (m, 1H), 6.76 (d, J=8.1, 1H), 6.55 (d, J=7.2, 1H), 5.78 (d, J=6.1, 1H), 5.47 (d, J=3.8, 1H), 5.24 (d, J=3.8, 1H), 4.40–4.25 (m, 2H), 4.20–4.10 (m, 3H), 3.00–2.60 (m, 2H), 2.22 (s, 3H), 1.77 (s, 3H), 1.30 (s, 3H), 1.19 (s, 3H); Anal. Calcd for $C_{32}H_{36}N_3O_6F$: C, 66.54; H, 6.28; N, 7.27. Found: C, 66.37; H, 6.20; N, 7.21.

EXAMPLE C10

(S)-3-((2S,3S)-2-Hydroxy-3-{[1-(3-hydroxy-2-methyl-phenyl)-methanoyl]-amino}-4-phenyl-butanoyl)-5,5-dimethyl-oxazolidine-4-carboxylic acid cyanomethyl-amide

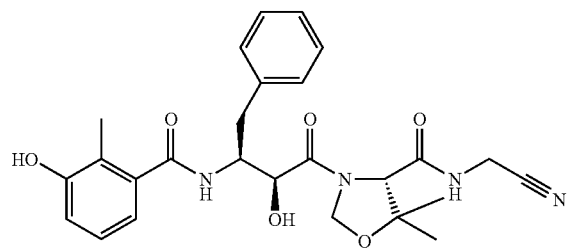

White solid; $^1$H NMR (DMSO-$d_6$) δ 9.36 (s, 1H), 8.72 (t, J=5.3, 1H), 8.11 (d, J=9.0, 1H), 7.29–7.16 (m, 5H), 6.94 (t, J=7.7, 1H), 6.76 (d, J=8.1, 1H), 6.50 (d, J=7.5, 1H), 5.85 (d, J=6.0, 1H), 5.49 (d, J=4.0, 1H), 5.23 (d, J=3.9, 1H), 4.35 (m, 1H), 4.18–4.12 (m, 3H), 4.11 (s, 1H), 2.92 (m, 1H), 2.70 (m, 1H), 1.76 (s, 3H), 1.29 (s, 3H), 1.19 (s, 3H); HRMS (ESI) m/z calcd for $C_{26}H_{31}N_4O_6$ (M+H)[30] 495.2244, found 495.2239.

EXAMPLE C11

(S)-3-((2S,3S)-3-{[1-(3-Fluoro-2-methyl-phenyl)-methanoyl]-amino}-2-hydroxy-4-phenyl-butanoyl)-5,5-dimethyl-oxazolidine-4-carboxylic acid 2-methyl-benzylamide

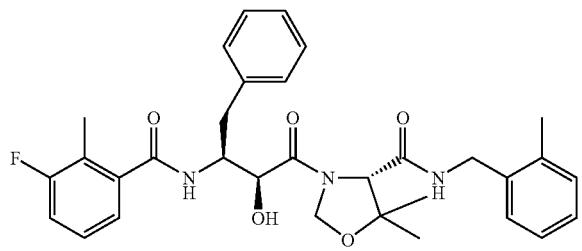

$^1$H NMR (DMSO-$d_6$) δ 8.34 (m, 2H), 7.30–7.13 (m, 11H), 6.95 (d, J=7.1, 1H), 5.82 (d, J=6.4, 1H), 5.45 (d, J=3.9, 1H), 5.23 (d, J=4.0, 1H), 4.38–4.31 (m, 2H), 4.18–4.15 (m, 3H), 2.96 (m, 1H), 2.67 (m, 1H), 2.26 (s, 3H), 1.87 (s, 3H), 1.28 (s, 3H), 1.18 (s, 3H); HRMS (ESI) m/z calcd for $C_{32}H_{37}N_3O_5F$ (M+H)[30] 562.2717, found 562.2713.

General Methods D

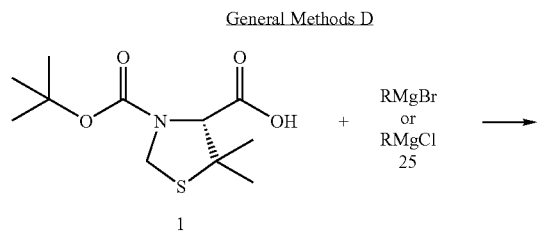

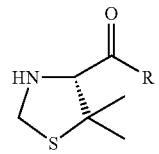

26

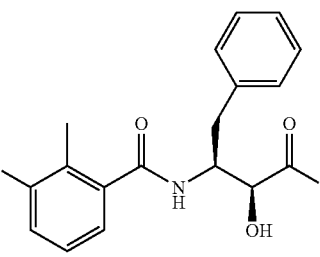

4

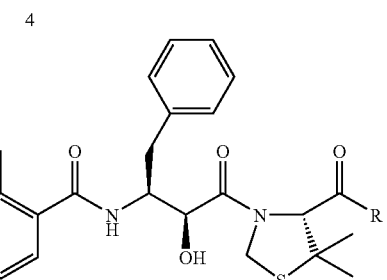

27

The synthesis of compounds with the general structure 27 is as follows. The boc-protected thiazolidine carboxylic acid 1 is converted to amino-ketones 26 with requisite grignard reagents 25 in the presence of oxalyl chloride. Final compounds 27 are obtained by a DCC-mediated coupling of 26 and 4 followed by deprotection of the P2 phenol. Final compounds were purified either by flash chromatography or preparative HPLC.

Specific Method D

EXAMPLE D1

N-[(1S,2S)-1-Benzyl-3-((R)-5,5-dimethyl-4-pent-4-enoyl-thiazolidin-3-yl)-2-hydroxy-3-oxo-propyl]-3-hydroxy-2-methyl-benzamide

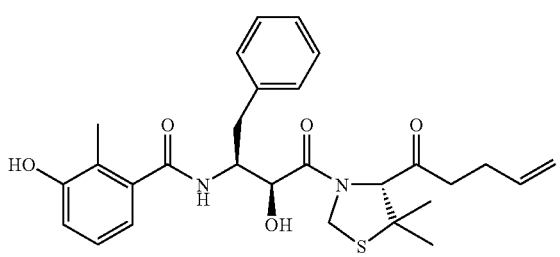

The title compound was prepared as follows. (R)-5,5-Dimethyl-thiazolidine-3,4-dicarboxylic acid 3-tert-butyl ester 1 (1.0 g, 3.80 mmol) was dissolved in benzene (10 mL) and cooled to 0° C. with magnetic stirring. Two drops of DMF were added followed by a drop wise addition of oxalyl chloride (0.33 mL, 3.80 mmol). When gas evolution ceased, the solution was concentrated to a yellow/red residue. The material was dissolved in dry THF (10 mL) and cooled to −78° C. with magnetic stirring. The grignard reagent, 3-butenylmagnesium bromide (7.7 mL, 3.80 mmol) was added dropwise over 10 min. The result was stirred at −78° C. for 1 h then at −55° C. for 30 min. The reaction was quenched at −55° C. with sat NH$_4$Cl soln.(3 mL) and then poured into H$_2$O (50 mL). The mixture was extracted with EtOAc (2×50 mL). The combined organics were washed with brine (1×100 mL), dried over Na$_2$SO$_4$, filtered, and concentrated. The result was the amino ketone 26 that was sufficiently pure to use in the subsequent step. The clear oil 26 (0.24 g, 1.15 mmol) was dissolved in EtOAc (10 mL). AMB-AHPBA 4 (0.40 g, 1.09 mmol) was added followed by HOBt (0.15 g, 1.09 mmol). The mixture was stirred at room temperature 1h, then cooled to 0° C. DCC (0.24 g, 1.15 mmol) was slowly added as solution in EtOAc (6 mL). The mixture was warmed to room temperature and stirred overnight. The mixture was filtered and the filtrate was washed with 1N HCl (10 mL), saturated NaHCO$_3$ (10 mL), brine (10 mL), dried over Na$_2$SO$_4$ and concentrated to give a crude white solid (contaminated with DCU). The DCU was removed by flash chromatography (30% to 50% EtOAc in hexanes) to provide a white solid, which was dissolved in MeOH (2 mL) and treated with 4N HCl in 1,4-dioxane (0.26 mL, 1.1 mmol). The reaction was stirred at room temperature overnight then partitioned between 1N HCl (10 mL) and EtOAc (10 mL). The organic layer was washed with saturated sat. NaHCO$_3$ (1×25 mL) dried over Na$_2$SO$_4$, filtered, and concentrated to a residue which was purified by flash chromatography (60% EtOAc in hexanes) to provide the title compound as a white amorphous solid: $^1$H NMR (DMSO-d$_6$) δ 9.36 (s, 1H), 8.23 (d, J=8.1, 1H), 7.35–7.14 (m, 5H), 6.96 (t, J=7.5, 1H), 6.78 (d, J=8.2, 1H), 6.52 (d, J=7.5, 1H), 5.81–5.69 (m. 2H), 5.32 (d, J=9.7, 1H), 5.11–5.91 (m, 3H), 4.40 (m, 3H), 2.89–2.61 (m, 4H), 2.37–2.14 (m, 2H), 1.81 (s, 3H), 1.55 (s, 3H), 1.30 (s, 3H); Anal. Calcd for C$_{28}$H$_{34}$N$_2$O$_5$S: C, 65.86; H, 6.71; N, 5.49. Found: C, 65.52; H, 6.55; N, 5.81.

The following examples were synthesized using the specific method outlined above using the appropriate grignard reagent for the desired compound.

EXAMPLE D2

N-{1-Benzyl-3-[5,5-dimethyl-4-(4,4,4-trifluoro-butanoyl)-thiazolidin-3-yl]-2-hydroxy-3-oxo-propyl}-3-hydroxy-2-methyl-benzamide

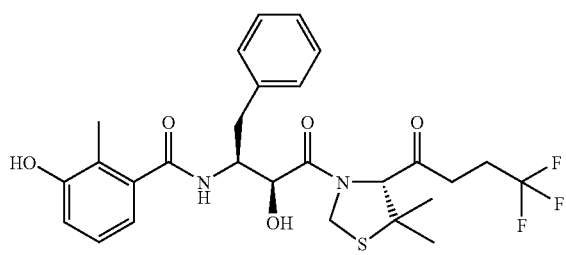

$^1$H NMR (DMSO-d$_6$) δ 9.34 (s, 1H), 8.16 (d, 1H, J=8.6), 7.29–6.49 (m, 8H), 5.88 (d, 1H, J=6.1), 5.33 (d, 1H, J=9.5), 5.10 (d, 1H, J=9.5), 4.56 (s br, 3H), 2.98–2.57 (m, 6H), 1.74 (s, 3H), 1.55 (s, 3H), 1.30 (s, 3H); HRMS (ESI) m/z calcd for C$_{27}$H$_{32}$N$_2$O$_5$SF$_3$ (M+H)$^{30}$ 553.1984, found 553.1984; Anal. Calcd for C$_{27}$H$_{31}$N$_2$O$_5$SF$_3$.0.5H$_2$O: C, 58.59; H, 5.66; N, 5.06; S, 5.79. Found: C, 58.96; H, 6.02; N, 5.58; S, 5.33.

EXAMPLE D3

N-{1-Benzyl-2-hydroxy-3-[4-(4-methoxy-butanoyl)-5,5-dimethyl-thiazolidin-3-yl]-3-oxo-propyl}-3-hydroxy-2-methyl-benzamide

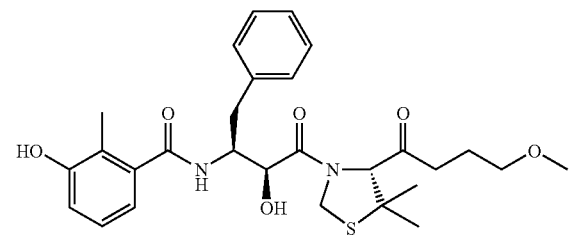

$^1$H NMR (DMSO-d$_6$) δ 9.34 (s, 1H), 8.18 (d, 1H, J=8.2), 7.32–6.51 (m, 8H), 5.56 (d, 1H, J=7.8), 5.26 (d, 1H, J=9.5), 5.08 (d, 1H, J=9.5), 4.45–4.38 (m, 2H), 4.36 (s, 1H), 3.15 (s, 3H), 2.93–2.61 (m, 2H), 1.87–1.00 (m, 6H), 1.80 (s, 3H), 1.55 (s, 3H), 1.36 (s, 3H); HRMS (ESI) m/z calcd for C$_{28}$H$_{37}$N$_2$O$_6$S (M+H)$^{30}$ 529.2165, found 529.2372; Anal. Calcd for C$_{28}$H$_{36}$N$_2$O$_6$S.0.5H$_2$O: C, 62.55; H, 6.94; N, 5.21; S, 5.96. Found: C, 62.89; H, 7.32; N, 5.96; S, 5.59.

EXAMPLE D4

(R)-3-[(2S, 3S)-2-Hydroxy-3-(3-hydroxy-2,5-dimethyl-benzoylamino)-4-phenyl-butyryl]-5,5-dimethyl-thiazolidine-4-carboxylic acid allylamide

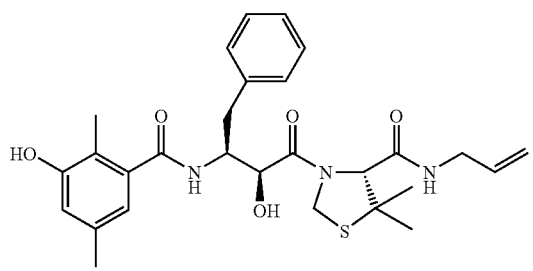

White solid: $^1$H NMR (DMSO-d$_6$) δ 9.23 (s, 1H), 8.09 (m, 2H), 7.35–7.17 (m, 5H), 6.60 (s, 1H), 6.37 (s, 1H), 5.82–5.68 (m, 1H), 5.41 (br s, 1H), 5.20 (dd, 1H, J=1.6, 17.2), 5.11 (d, 1H, J=9.2), 5.02 (dd, 1H, J=1.5, 10.2), 5.00 (d, 1H, J=9.1), 4.46–4.37 (m, 3H), 3.79 (ddd, 1H, J=5.3, 5.5, 15.9), 3.63 (ddd, 1H, J=5.4, 5.3, 15.9), 2.82 (dd, 1H, J=0.3, 13.9), 2.71 (dd, 1H, J=10.7, 13.6), 2.16 (s, 3H), 1.76 (s, 3H), 1.51 (s, 3H), 1.36 (s, 3H); HRMS (ESI) m/z calcd for C$_{28}$H$_{36}$N$_3$O$_5$S (M+H)$^{30}$ 526.6670, found 526.2376; Anal. Calcd for C$_{28}$H$_{35}$N$_3$O$_5$S.0.3 H$_2$O: C, 63.32; H, 6.76; N, 7.91, Found: C, 63.35; H, 6.70; N, 7.71.

Combinatorial Chemistry Approach to HIV Protease P2' Inhibitors

General Method E

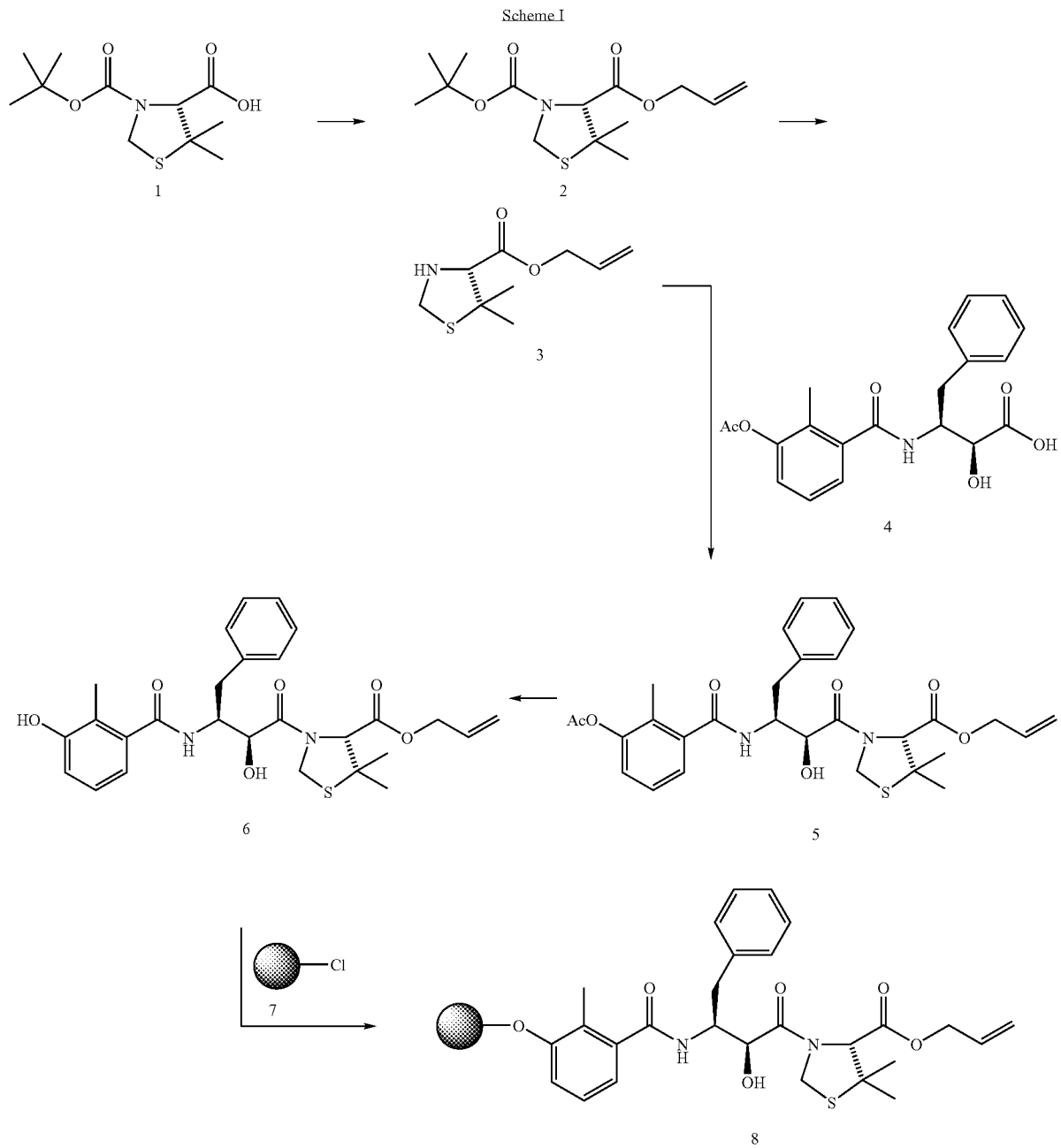

The combinatorial building block, 8, is prepared using the following method. The boc-protected thiazolidine carboxylic acid, 1, is treated with allyl bromide in the presence of NaHCO$_3$ to yield the boc-protected thiazolidine allyl ester, 2. Deprotection of boc-protected allyl ester, 2, with HCl (g) in EtOAc gives the HCl salt of the thiazolidine allyl ester amine, 3, which is treated with TEA and coupled to 4 in the presence of HOBT and DCC to give the building block precursor, 5. Deprotection of the building block, 5, with 4N HCl yields the phenol, 6. Loading the building block, 6, on to activated cross-linked trityl chloride polystyrene beads, 7, was accomplished in the following manner. The polystyrene cross-linked trityl alcohol was activated to the trityl chloride, 7, by treatment with 20% acetyl chloride in anhydrous CH$_2$Cl$_2$ at room temperature. The trityl chloride beads were combined with the phenol 6 in the presence of Hunig's base in anhydrous CH$_2$Cl$_2$ to yield the substrate loaded polystyrene beads 8. Intermediates were purified either by flash chromatography or preparative HPLC.

Scheme II

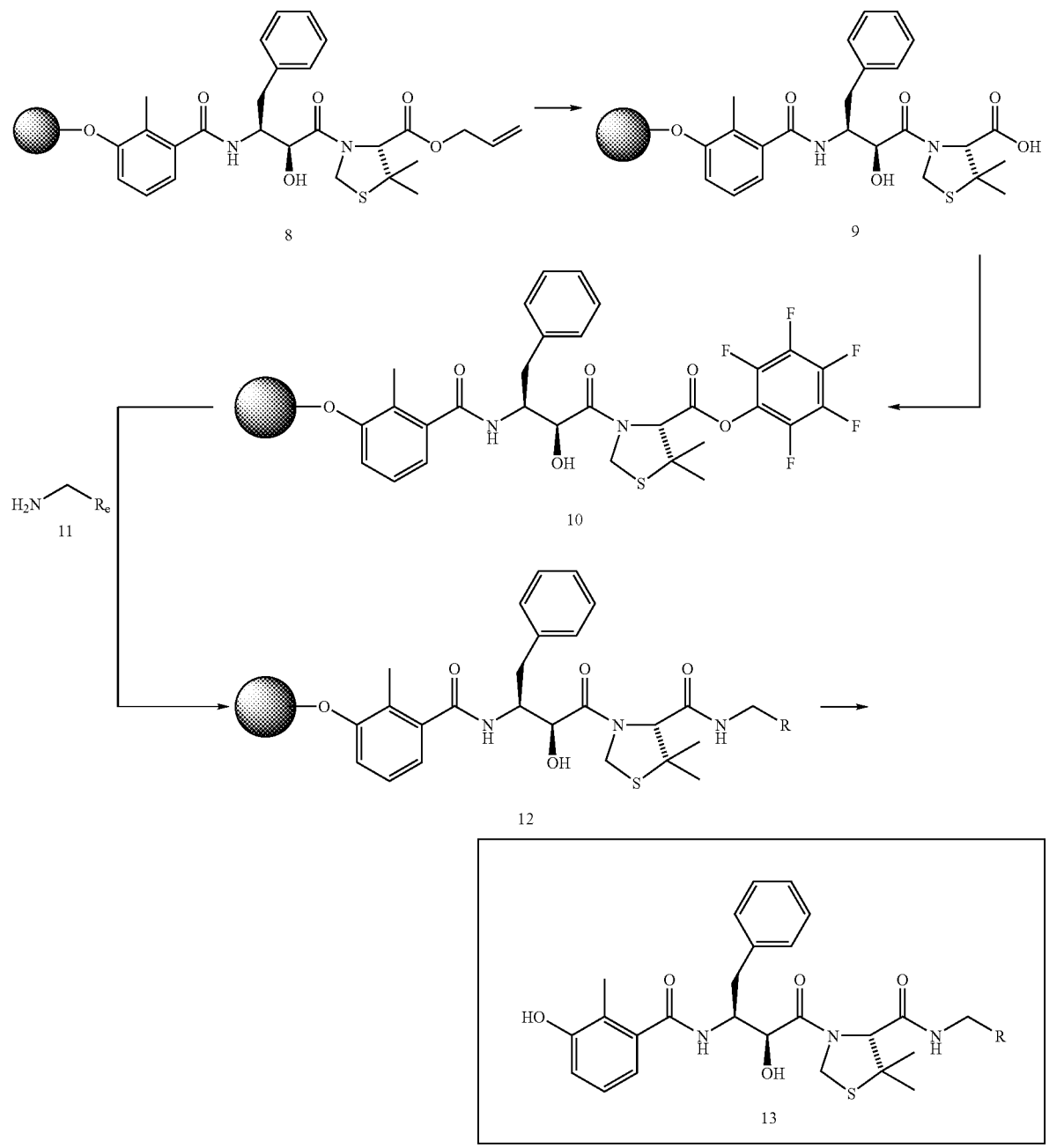

The synthesis of the HIV protease combinatorial library was carried out in the following fashion. The allyl ester was removed by treatment with Pd[PPh$_3$]$_4$ and NMM in anhydrous THF to give carboxylate 9, which was treated with pentafluorophenol, pentafluorophenol trifluoromethyl acetate and pyridine in DMF to yield the pentafluoro ester, 10. The pentafluoro ester 10 was treated with various primary amines in a 96-well plate format to give amides 12. The final products were cleaved from the polystyrene crowns with TFA to give products 13. Each product was analyzed by LCMS and HPLC. The following table typifies compounds synthesized by this combinatorial method.

TABLE 1

| P2' | Expected Mass (LCMS) | Observed Mass | % Inhibition |
|---|---|---|---|
| HO–CH(CH$_3$)–CH$_2$–NH$_2$ | 529 | 552(Na$^+$) | 38 |

TABLE 1-continued

| P2' | Expected Mass (LCMS) | Observed Mass | % Inhibition |
|---|---|---|---|
| H₂N−CH₂CH₂−N(CH₃)H | 528 | 529(MH⁺) | 4 |
| H₂N−CH₂CH₂−C₆H₄−OH | 591 | 614(Na⁺) | 18 |
| (CH₃)₃C−CH₂CH₂−NH₂ | 555 | 578(Na⁺) | 19 |
| H₂N−CH₂CH₂−C₆H₃(OMe)₂ | 635 | 658(Na⁺) | 5 |
| ClH | 656 | 656(MH⁺) | 8 |

TABLE 1-continued

| P2' | Expected Mass (LCMS) | Observed Mass | % Inhibition |
|---|---|---|---|
| H₂N−CH₂CH₂−C₆H₄−NO₂ | | | |
| H₂N−CH₂−C₆H₄−CH₃ | 575 | 598(Na⁺) | 86 |
| (CH₃)₃C−CH₂−NH₂ | 541 | 564(Na⁺) | 63 |
| H₂N−CH₂CH₂CH₂−OH | 529 | 552(Na⁺) | 49 |

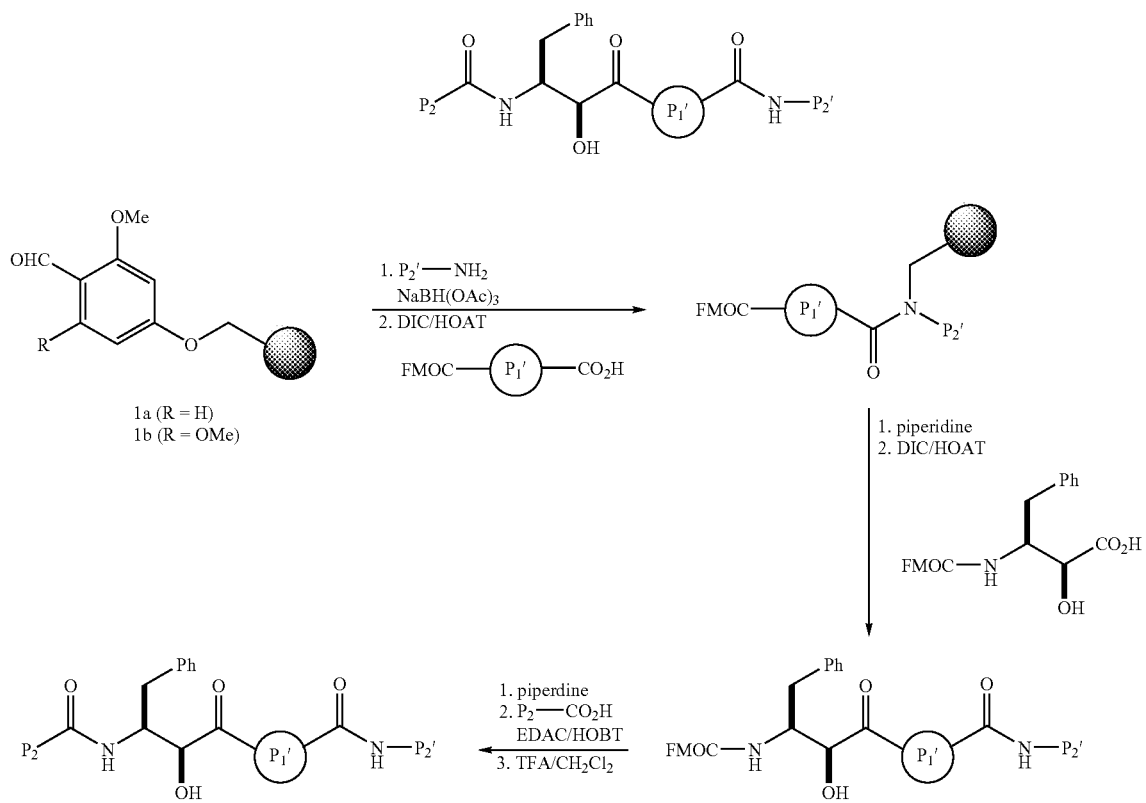

Scheme 3: Solid Phase Synthesis Of HIV Protease Inhibitors (AG 1776 Analogs)

The solid phase combinatorial synthesis of HIV protease inhibitors was performed using the IRORI Directed Sorting Technology. Commercial 4-formyl-3-methoxyphenoxymethyl polystyrene resin 1a (PS-MB-CHO, Argonaut Technologies) or 4-formyl-3,5-dimethoxyphenoxymethyl polystyrene resin 1b (PL-FDMP resin, Polymer Laboratories) was loaded into individual Minikans.

Step A. Reductive Amination With $P_2'$ Amines

To separate flasks containing sorted MiniKans was added DCM (3 mL/MiniKan). The appropriate primary $P_2'$ amine (3 eq), sodium triacetoxyborohydride (5 eq), and acetic acid (3 eq) were added, and the mixtures were placed under argon, agitated with periodic venting at room temperature for 1–2 hours, and allowed to react overnight. For resin 1a, the filtrates were poured off and the MiniKans were washed with DCM, MeOH (2×), DCM (2×), $Et_3N$/DCM (1:3, 3×), DCM (2×), MeOH (3×), and DCM (4×). For resin 1b, a washing sequence of DCM, MeOH (2×), DCM (2×), $Et_3N$/DCM (1:3, 3×), DCM (2×), DMF, 1M NaOH/DMF (1:5, 3×), DMF (3×), MeOH (3×), and DCM (3×) was used. The MiniKans were dried under vacuum and taken on in Step B.

Step B. Peptide Coupling With $P_1'$ Amino Acids

To separate flasks containing the sorted MiniKans was added DMF (3 mL/MiniKan). The appropriate FMOC-protected amino acid (2.5 eq) and 1-hydroxy-7-azabenzotriazole (HOAT) (3 eq) were added and mixed until dissolved, and 1,3-diisopropylcarbodiimide (DIC) (3 eq) was added. The containers were placed under argon and agitated at room temperature overnight. The filtrates were poured off, and the MiniKans were washed with DMF (3×), MeOH (3×), DCM (2×), and DMF (2×). The MiniKans were taken directly on to Step C.

Step C. FMOC Deprotection

A container of MiniKans in DMF and piperidine (25%) with a total reaction volume of 3 mL/MiniKan was agitated under argon at room temperature for 45 minutes. The filtrate was removed, and the reaction procedure was repeated. The MiniKans were filtered and washed with DMF (3×), MeOH (2×), DCM (3×), and DMF, and taken directly on to Step D.

Step D. Peptide Coupling With FMOC-APNS

FMOC-Allophenylnorstatine (APNS) (3 eq) was added to the flask of MiniKans in DMF (3 mL/MiniKan). After dissolution, HOAT (3.5 eq) and DIC (3.5 eq) were added. The mixture was placed under argon and agitated at room temperature overnight. The reaction was filtered and the MiniKans were washed with DMF (3×), MeOH (3×), DCM (3×), and DMF. FMOC deprotection was carried out as in Step C, and the MiniKans were washed with DMF (3×), MeOH (2×), DCM (3×), dried under vacuum and taken on to Step E or F.

Step E. Peptide Coupling With $P_2$ Acids

To separate flasks containing the sorted MiniKans in DMF (3 mL/MiniKan) was added the appropriate $P_2$ acid (3 eq), HOBT hydrate (4 eq), and (3-(dimethylamino)propyl)ethylcarbodiimide hydrochloride (EDAC) (3.5 eq). The reaction was agitated under argon at room temperature for 3 hours. After filtration, the MiniKans were washed with DMF (3×), MeOH (3×), and DCM (3×), dried under vacuum, and taken on to Step G.

Step F. Cleavage and Processing Of The HIV Analogs

The individual MinKans were sorted into cleavage racks and a solution of 25% TFA in DCM (3 mL/MinKan) was added. The racks were agitated for 1.5 hours. The individual filtrates and DCM rinses were collected, concentrated, and purified by HPLC to provide the final compounds.

TABLE 2

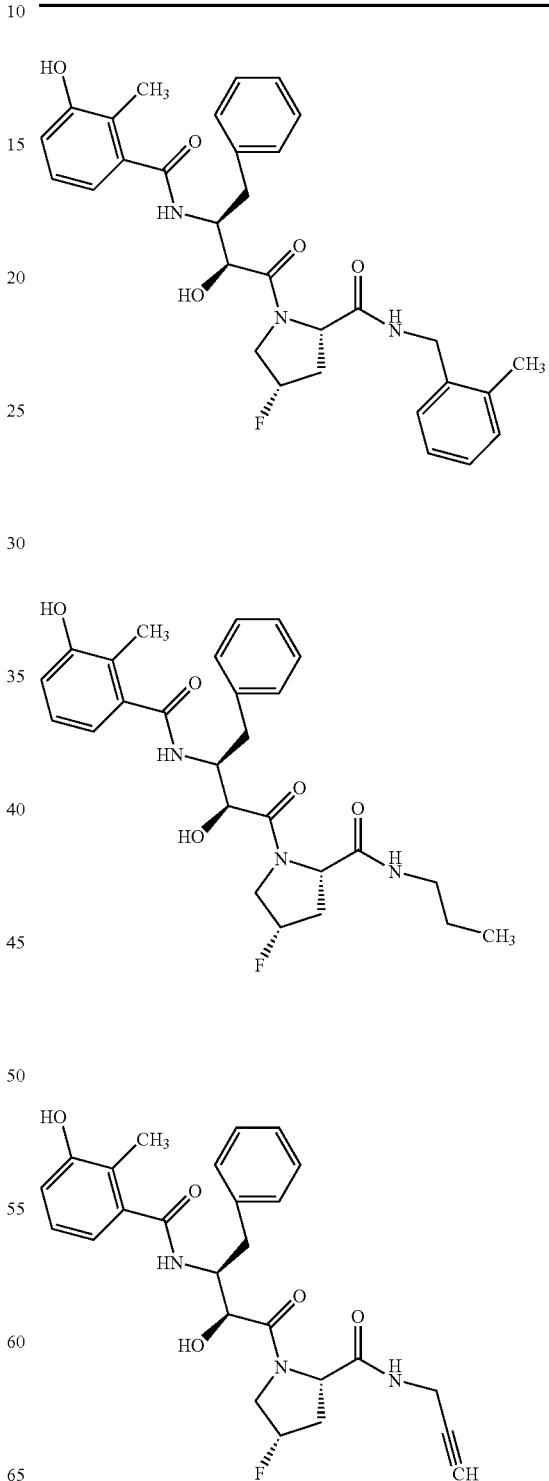

TABLE 2-continued
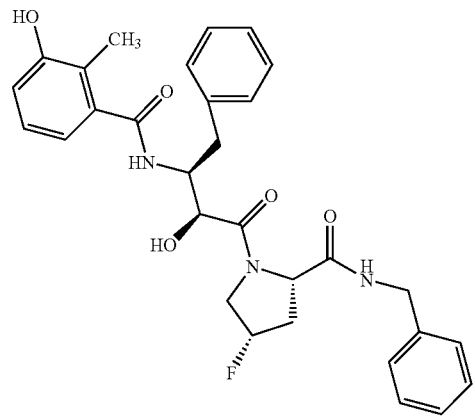
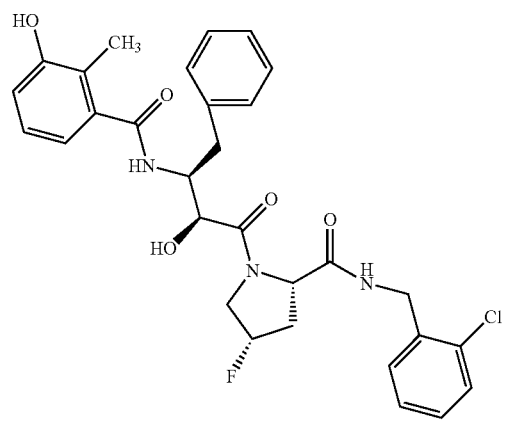
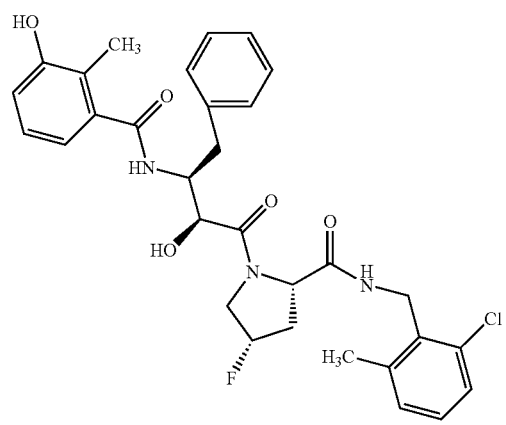
TABLE 2-continued
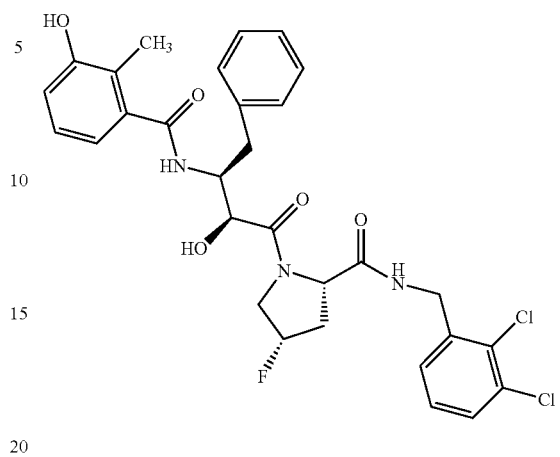
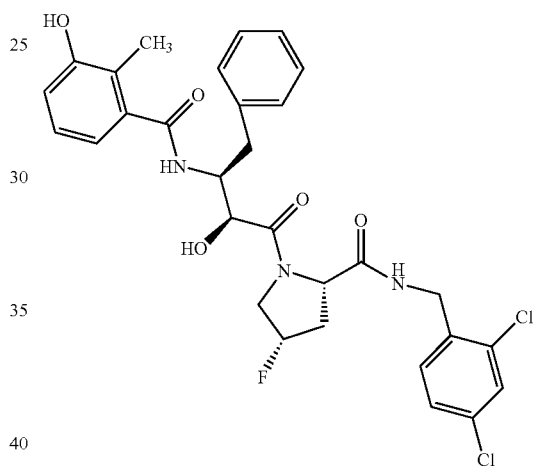
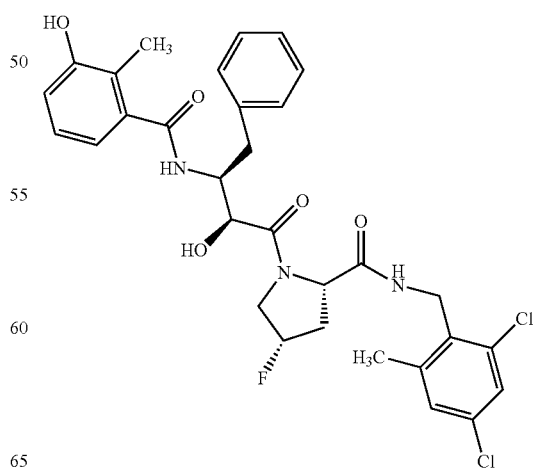

TABLE 2-continued
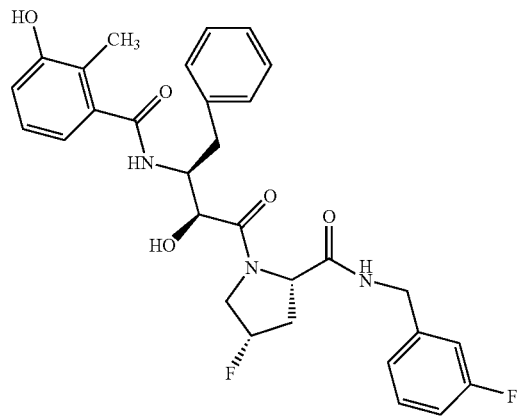
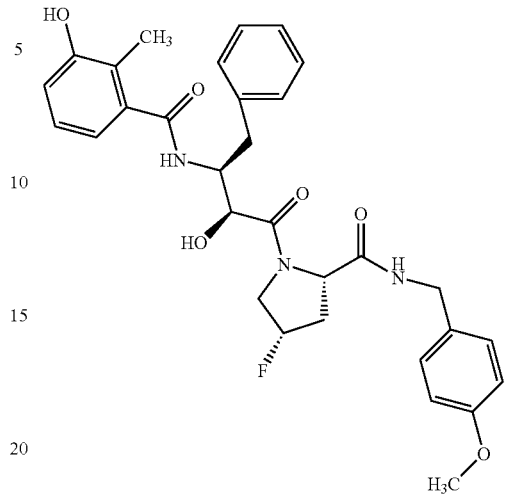
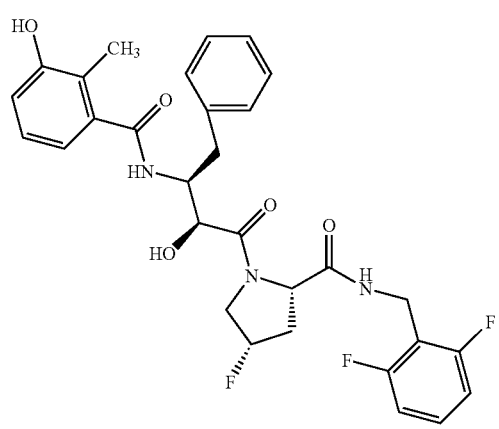
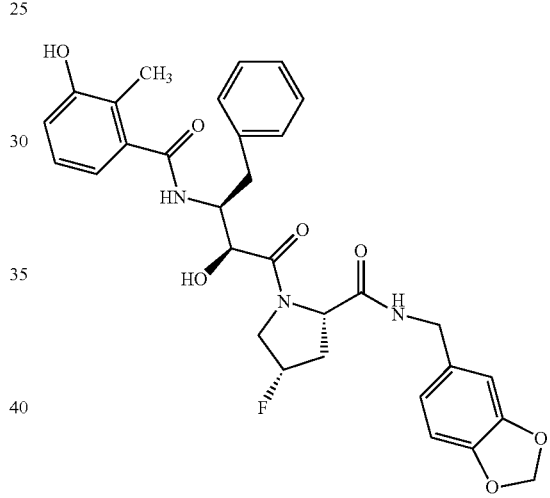
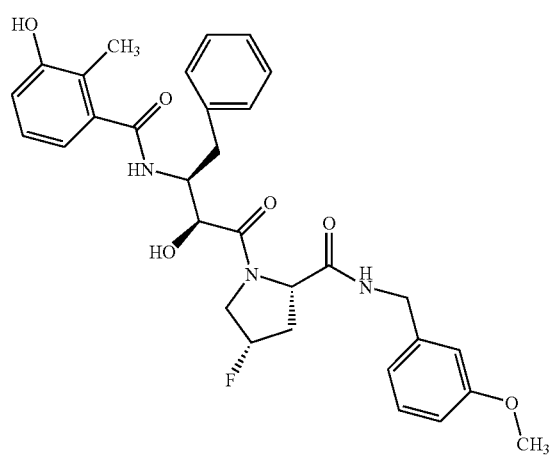
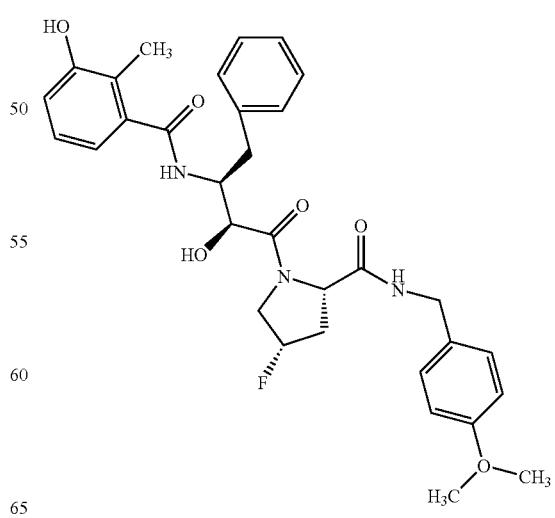

TABLE 2-continued
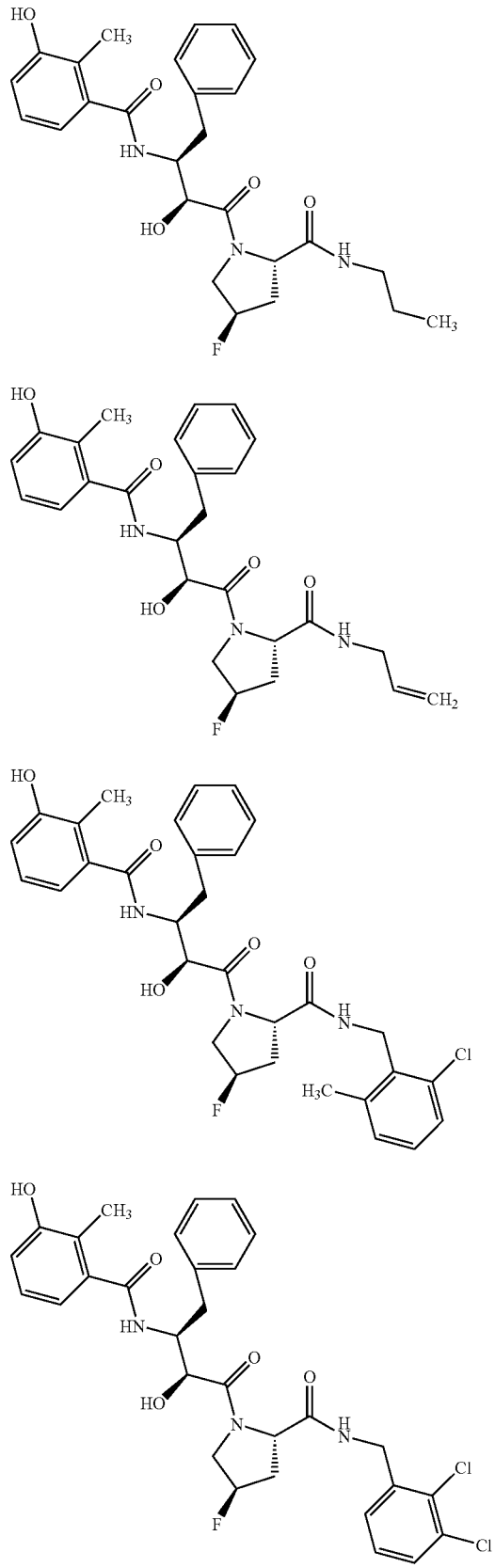
TABLE 2-continued
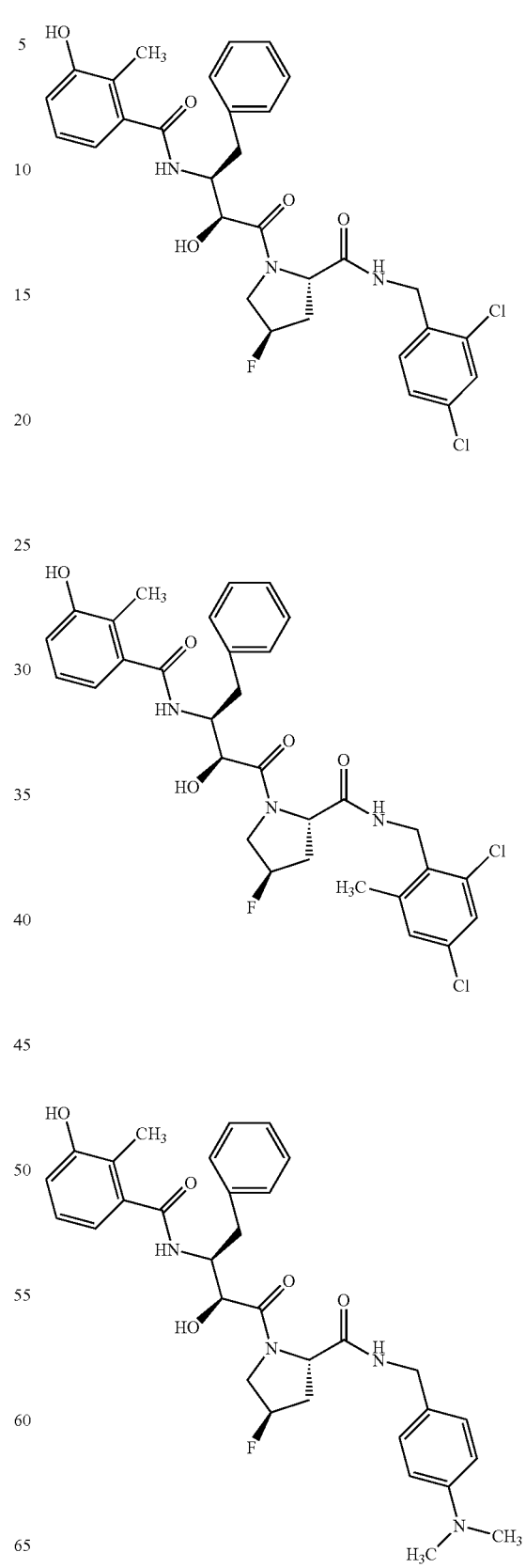

TABLE 2-continued
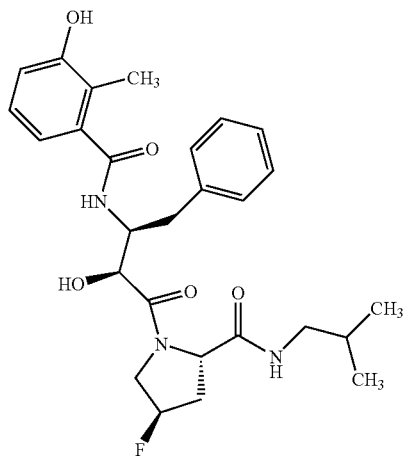
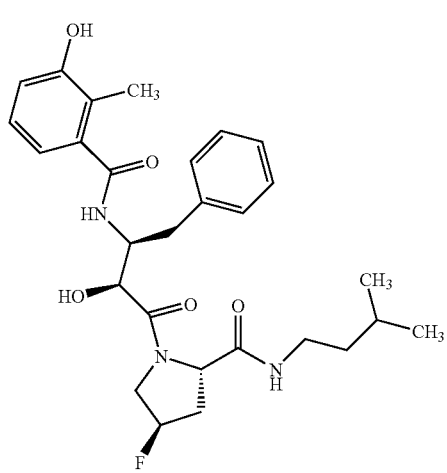
TABLE 2-continued
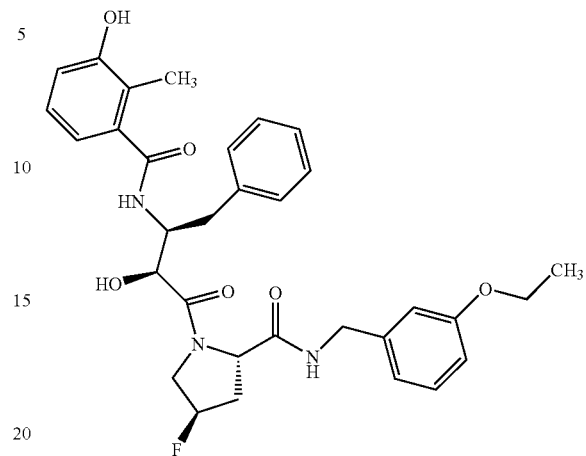
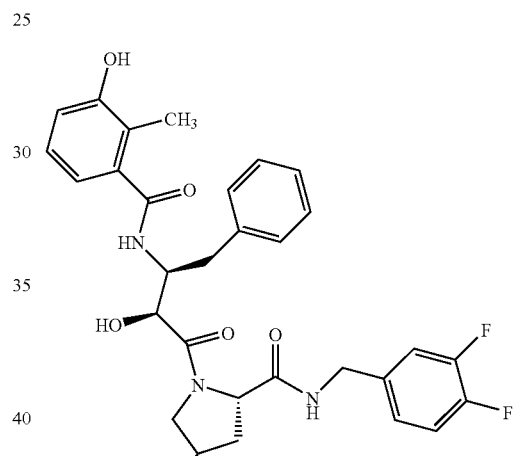
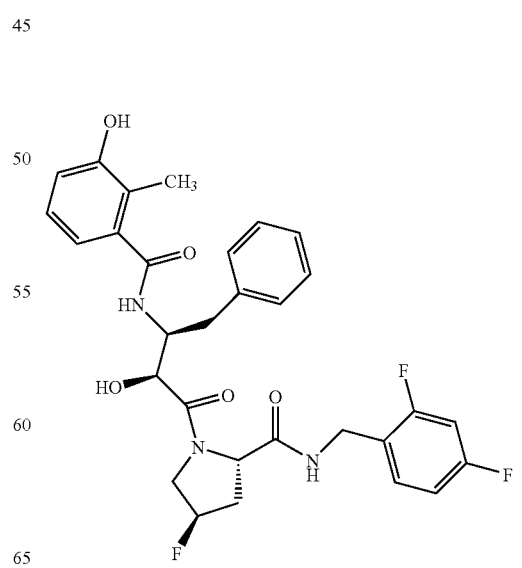

TABLE 2-continued
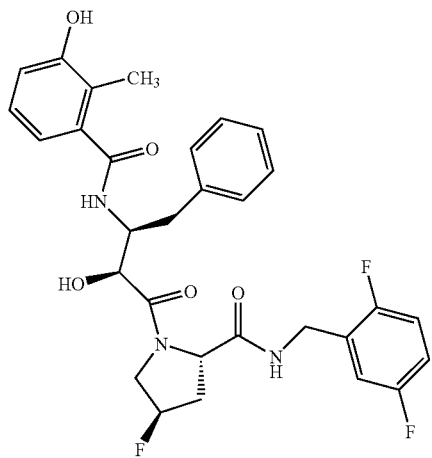
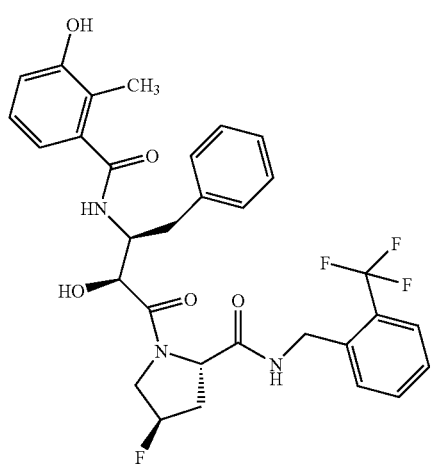
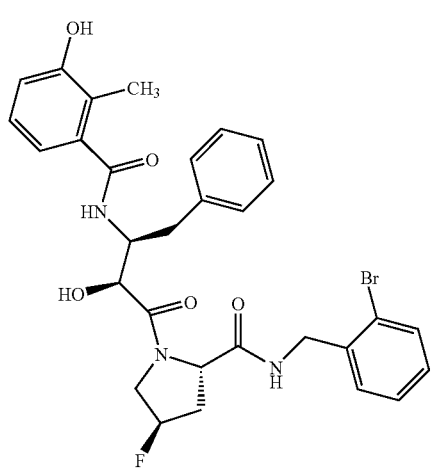
TABLE 2-continued
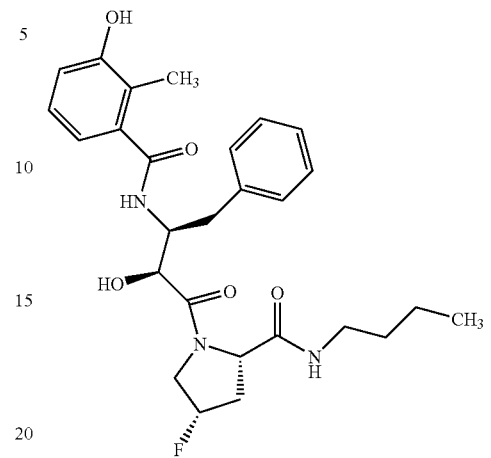
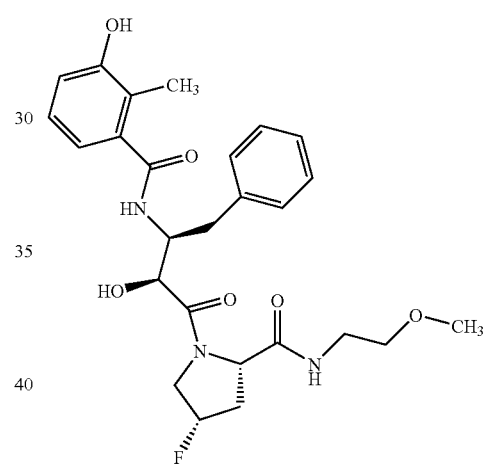
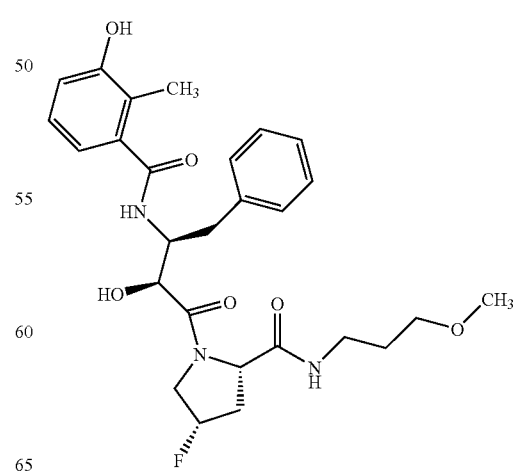

TABLE 2-continued
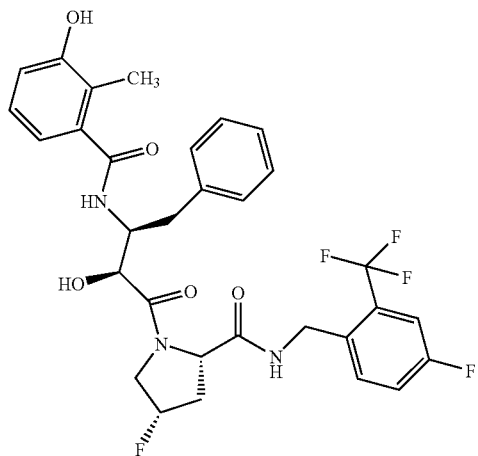
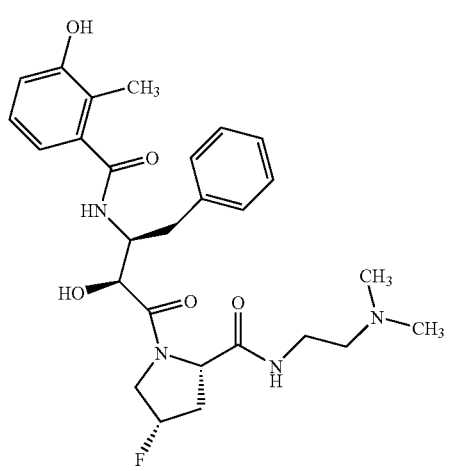
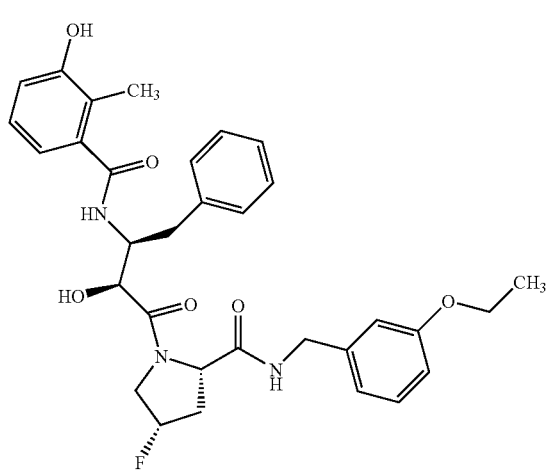
TABLE 2-continued
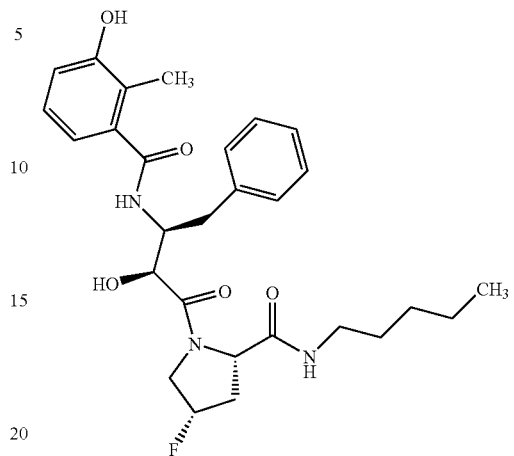
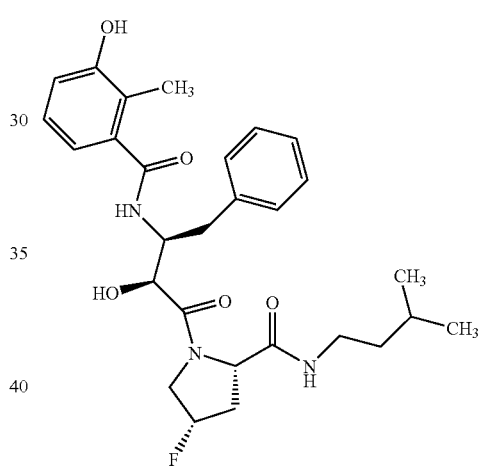
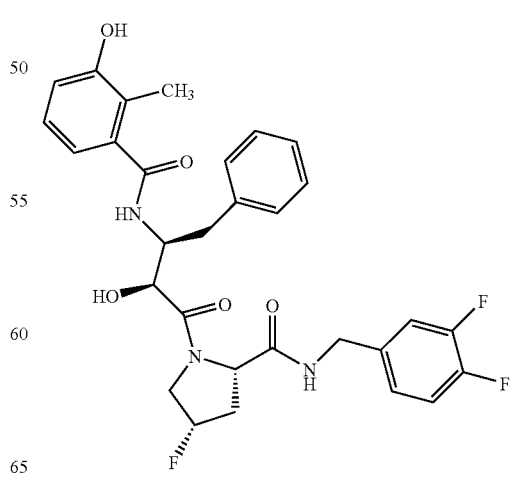

TABLE 2-continued
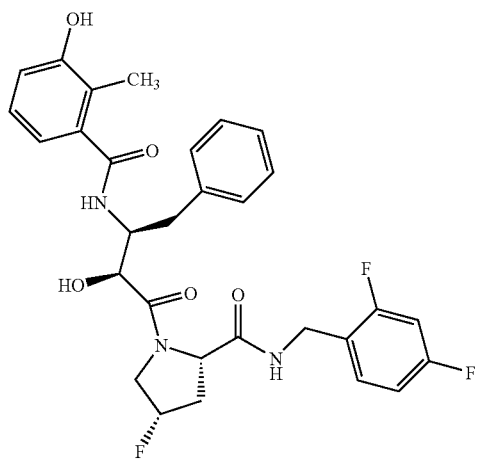
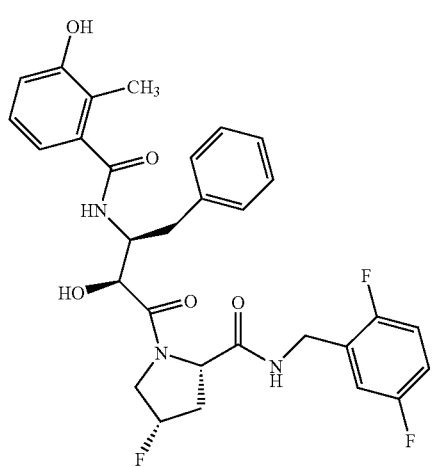
TABLE 2-continued
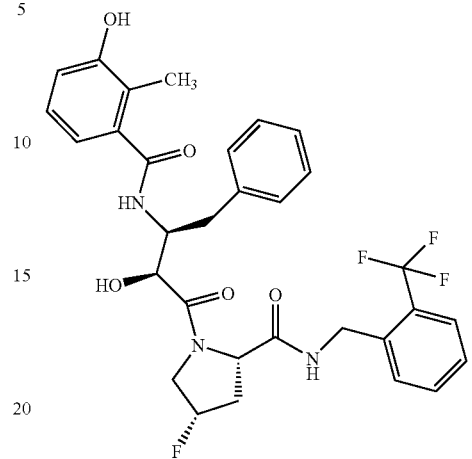
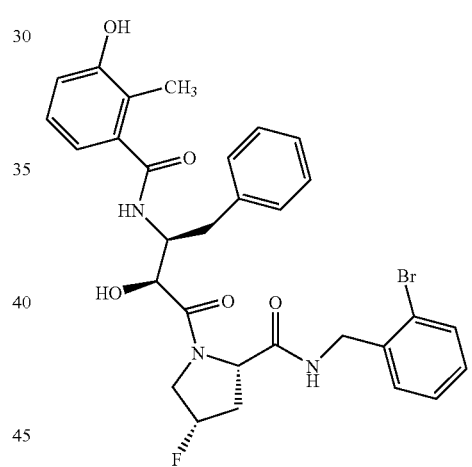
Scheme 3: Solid Phase Synthesis Of HIV Protease Inhibitors
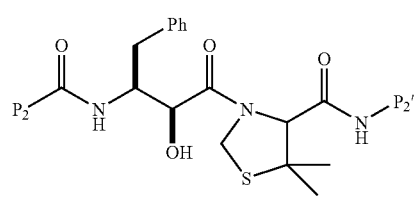

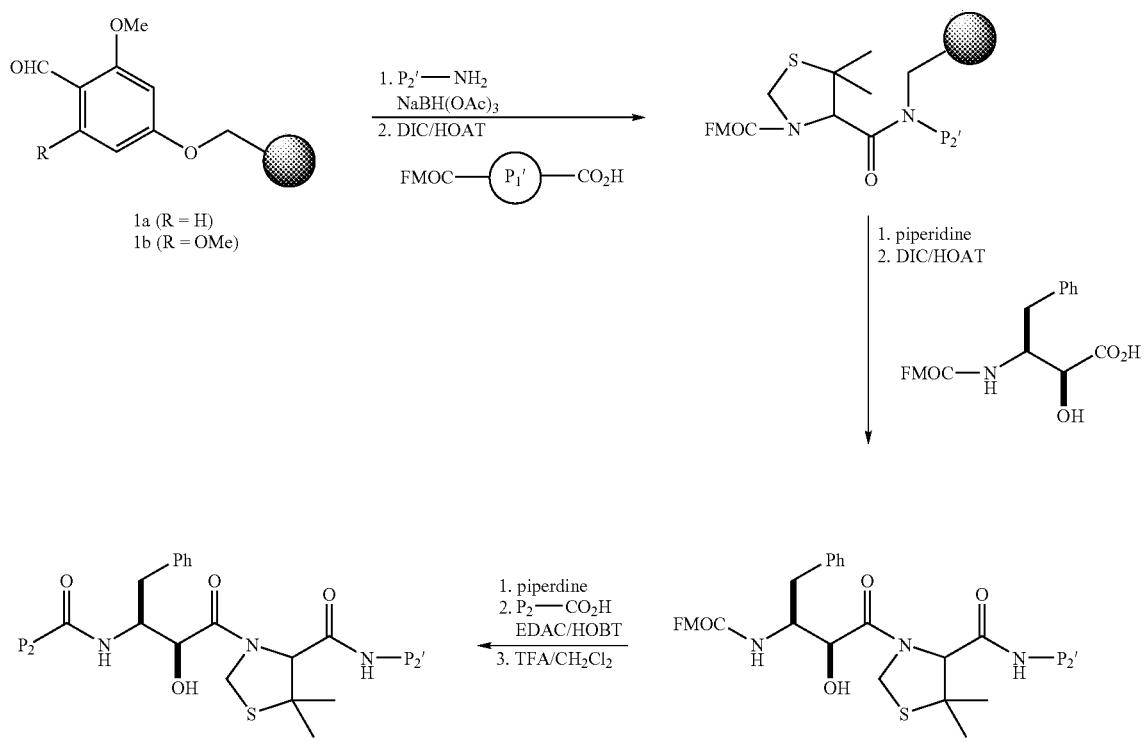

Scheme 3 Experimental

The solid phase combinatorial synthesis of HIV protease inhibitors was performed using the IRORI Directed Sorting Technology. Commercial 4-formyl-3-methoxyphenoxymethyl polystyrene resin 1a (PS-MB-CHO, Argonaut Technologies) or 4-formyl-3,5-dimethoxyphenoxymethyl polystyrene resin 1b (PL-FDMP resin, Polymer Laboratories) was loaded into individual Minikans.

Step A. Reductive Amination With $P_2'$ Amines

To separate flasks containing sorted MiniKans was added DCM (3 mL/MiniKan). The appropriate primary $P_2'$ amine (3 eq), sodium triacetoxyborohydride (5 eq), and acetic acid (3 eq) were added, and the mixtures were placed under argon, agitated with periodic venting at room temperature for 1–2 hours, and allowed to react overnight. For resin 1a, the filtrates were poured off and the MiniKans were washed with DCM, MeOH (2×), DCM (2×), Et$_3$N/DCM (1:3, 3×), DCM (2×), MeOH (3×), and DCM (4×). For resin 1b, a washing sequence of DCM, MeOH (2×), DCM (2×), Et$_3$N/DCM (1:3, 3×), DCM (2×), DMF, 1M NaOH/DMF (1:5, 3×), DMF (3×), MeOH (3×), and DCM (3×) was used. The MiniKans were dried under vacuum and taken on in Step B.

Step B. Peptide Coupling With $P_1'$ Amino Acids

To separate flasks containing the sorted MiniKans was added DMF (3 mL/MiniKan). The appropriate FMOC-protected amino acid (2.5 eq) and 1-hydroxy-7-azabenzotriazole (HOAT) (3 eq) were added and mixed until dissolved, and 1,3-diisopropylcarbodiimide (DIC) (3 eq) was added. The containers were placed under argon and agitated at room temperature overnight. The filtrates were poured off, and the MiniKans were washed with DMF (3×), MeOH (3×), DCM (2×), and DMF (2×). The MiniKans were taken directly on to Step C.

Step C. FMOC Deprotection

A container of MiniKans in DMF and piperidine (25%) with a total reaction volume of 3 mL/MiniKan was agitated under argon at room temperature for 45 minutes. The filtrate was removed, and the reaction procedure was repeated. The MiniKans were filtered and washed with DMF (3×), MeOH (2×), DCM (3×), and DMF, and taken directly on to Step D.

Step D. Peptide Coupling With FMOC-APNS

FMOC-Allophenylnorstatine (APNS) (3 eq) was added to the flask of MiniKans in DMF (3 mL/MiniKan). After dissolution, HOAT (3.5 eq) and DIC (3.5 eq) were added. The mixture was placed under argon and agitated at room temperature overnight. The reaction was filtered and the MiniKans were washed with DMF (3×), MeOH (3×), DCM (3×), and DMF. FMOC deprotection was carried out as in Step C, and the MiniKans were washed with DMF (3×), MeOH (2×), DCM (3×), dried under vacuum and taken on to Step E or F.

Step E. Peptide Coupling With $P_2$ Acids

To separate flasks containing the sorted MiniKans in DMF (3 mL/MiniKan) was added the appropriate $P_2$ acid (3 eq), HOBT hydrate (4 eq), and (3-(dimethylamino)propyl)ethylcarbodiimide hydrochloride (EDAC) (3.5 eq). The reaction was agitated under argon at room temperature for 3 hours. After filtration, the MiniKans were washed with DMF (3×), MeOH (3×), and DCM (3×), dried under vacuum, and taken on to Step G.

Step F. Cleavage and Processing Of The HIV Analogs

The individual MinKans were sorted into cleavage racks and a solution of 25% TFA in DCM (3 mL/MinKan) was added. The racks were agitated for 1.5 hours. The individual filtrates and DCM rinses were collected, concentrated, and purified by HPLC to provide the final compounds.

TABLE 3
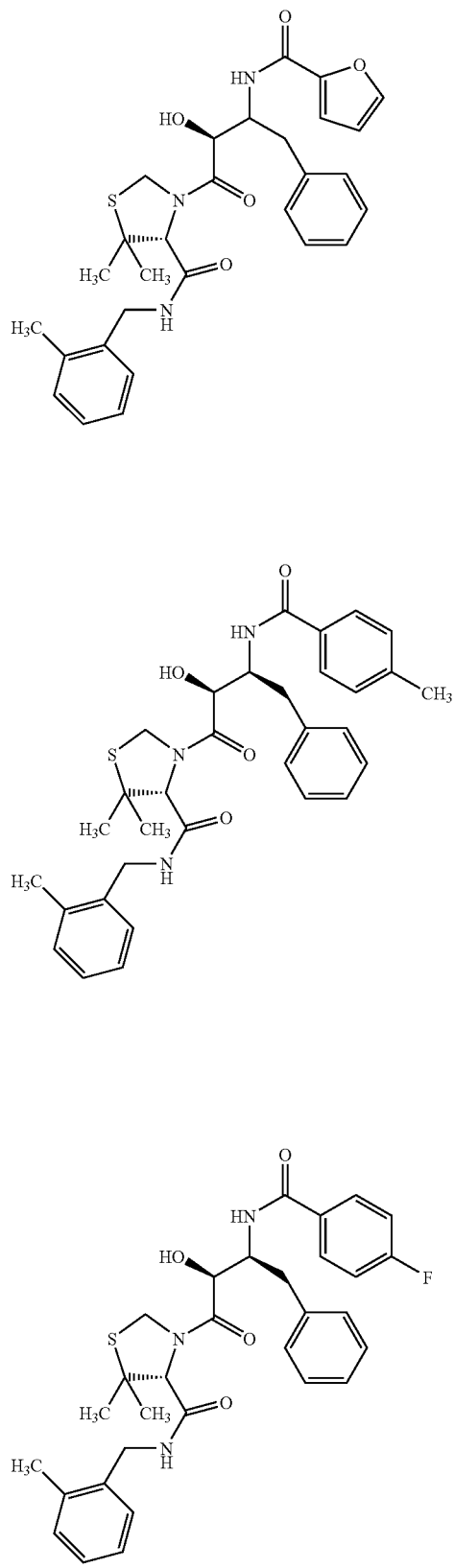
TABLE 3-continued
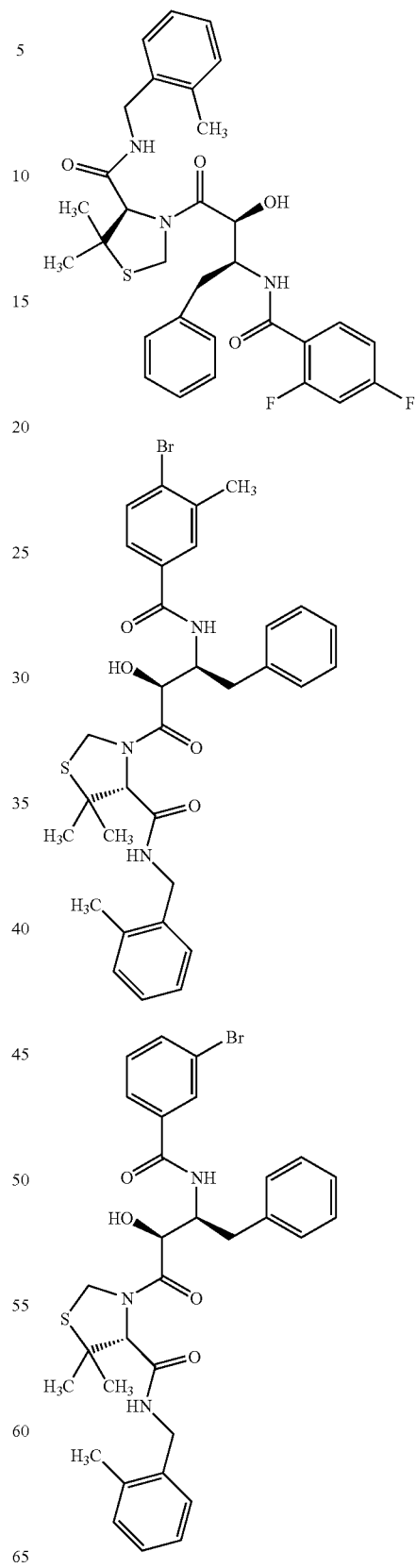

TABLE 3-continued
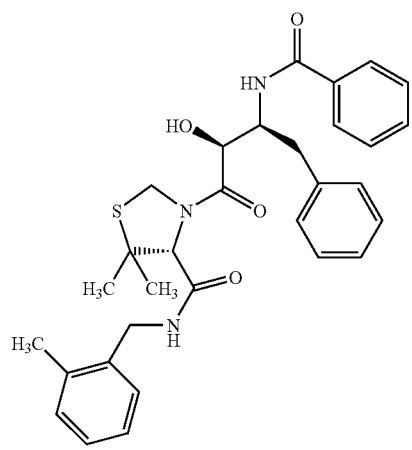
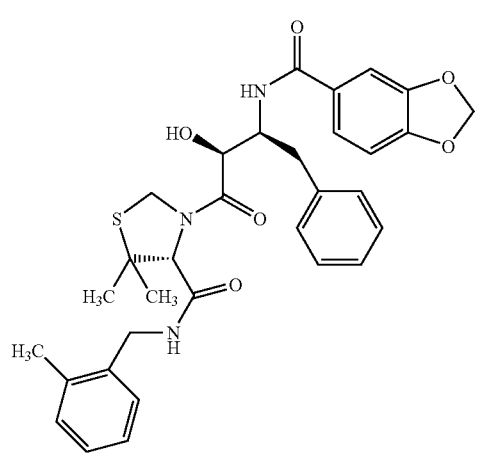
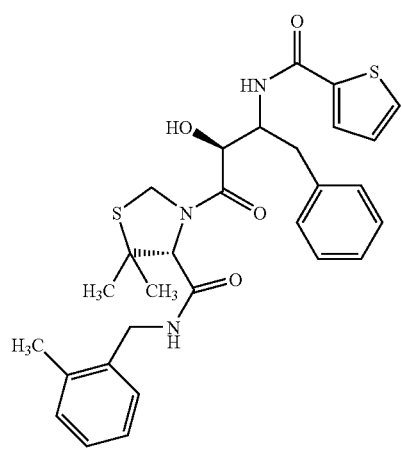
TABLE 3-continued
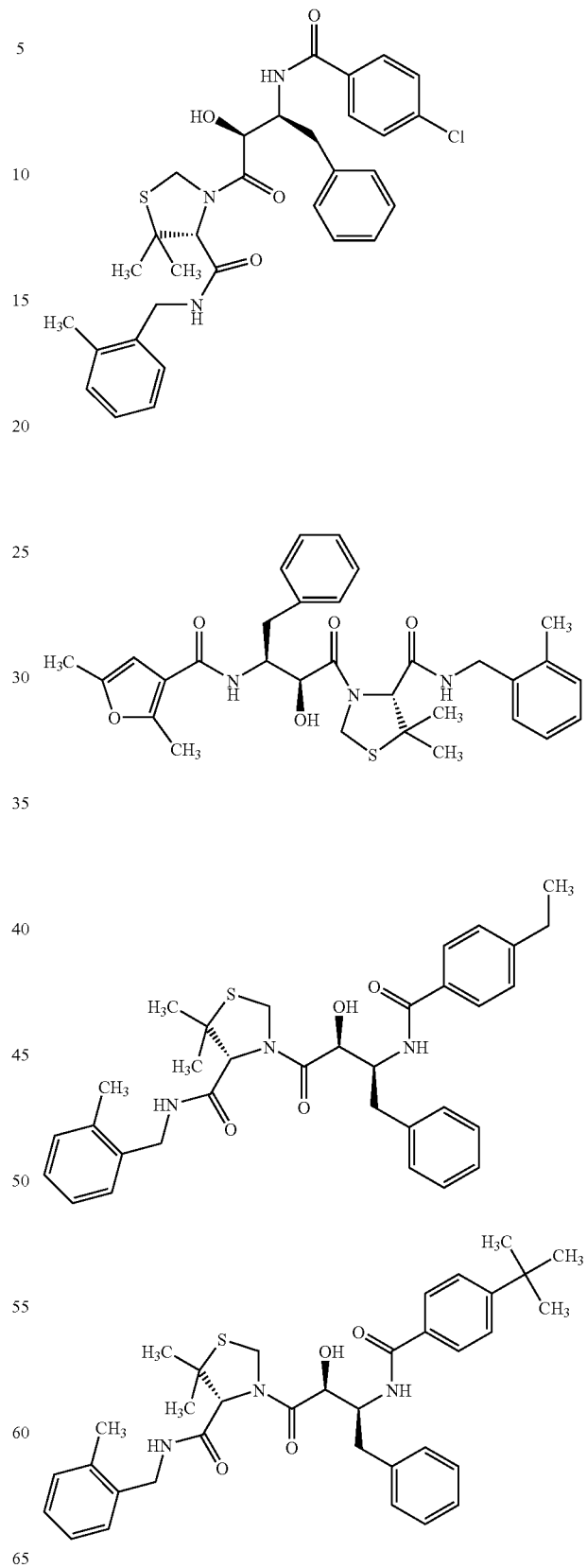

TABLE 3-continued
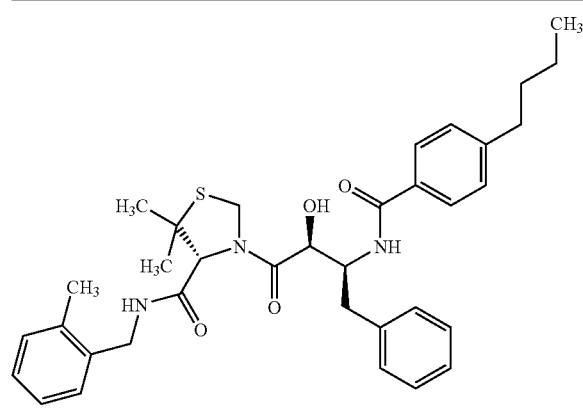
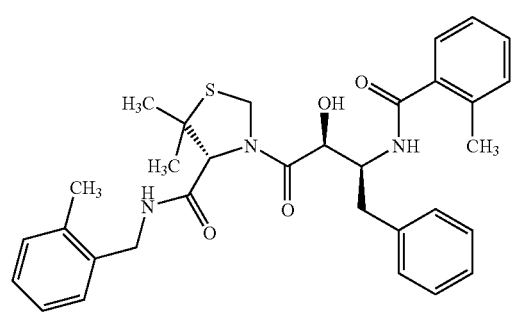
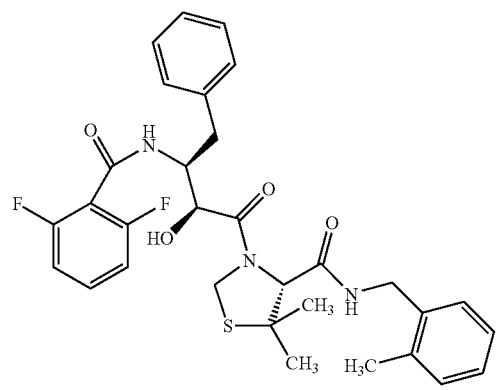
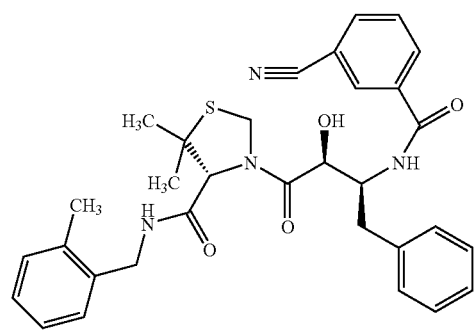
TABLE 3-continued
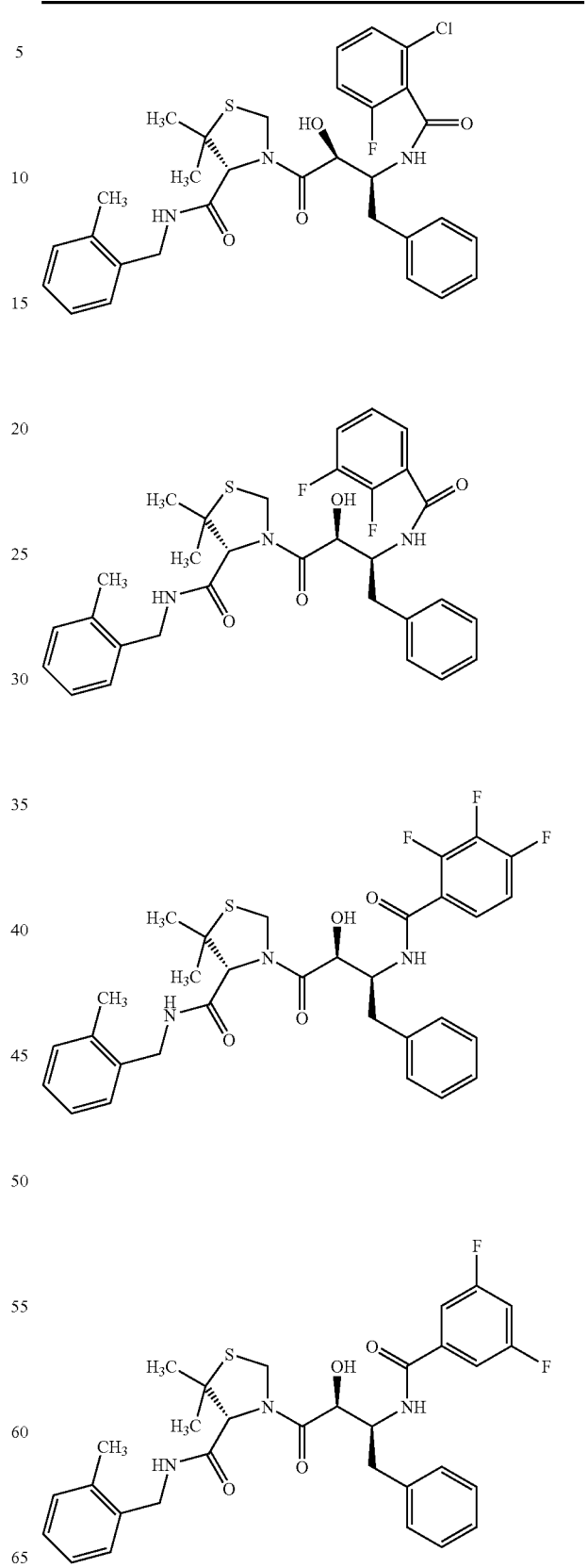

TABLE 3-continued
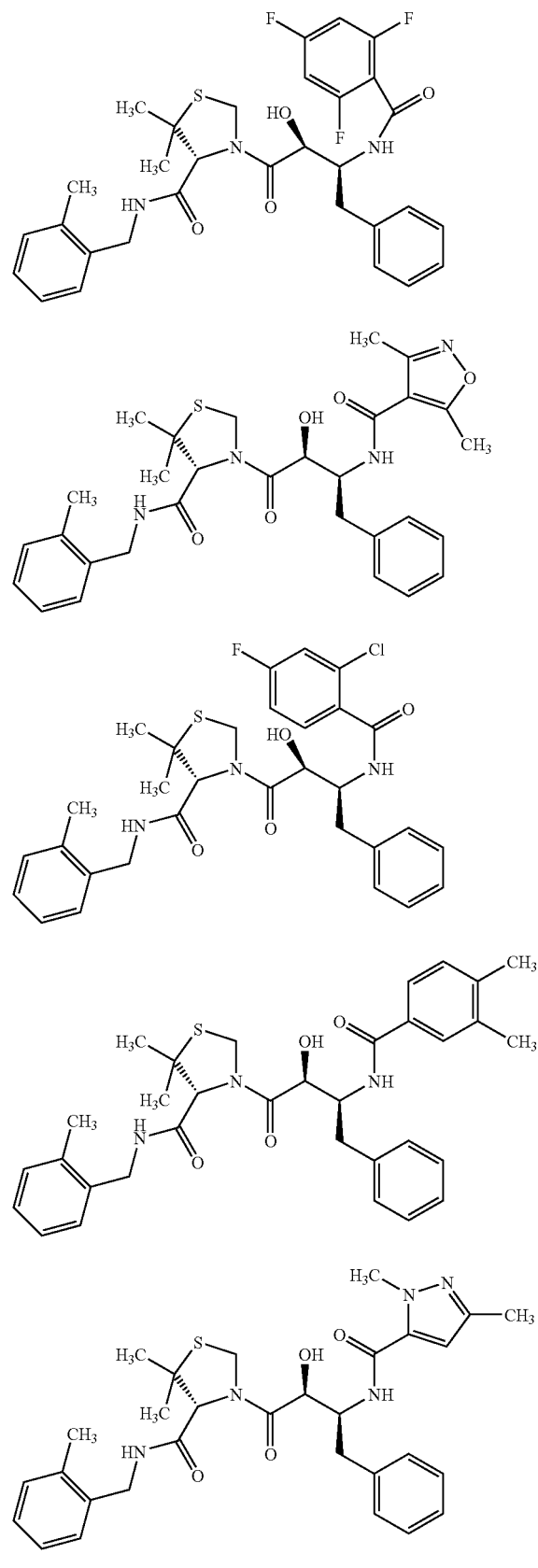
TABLE 3-continued
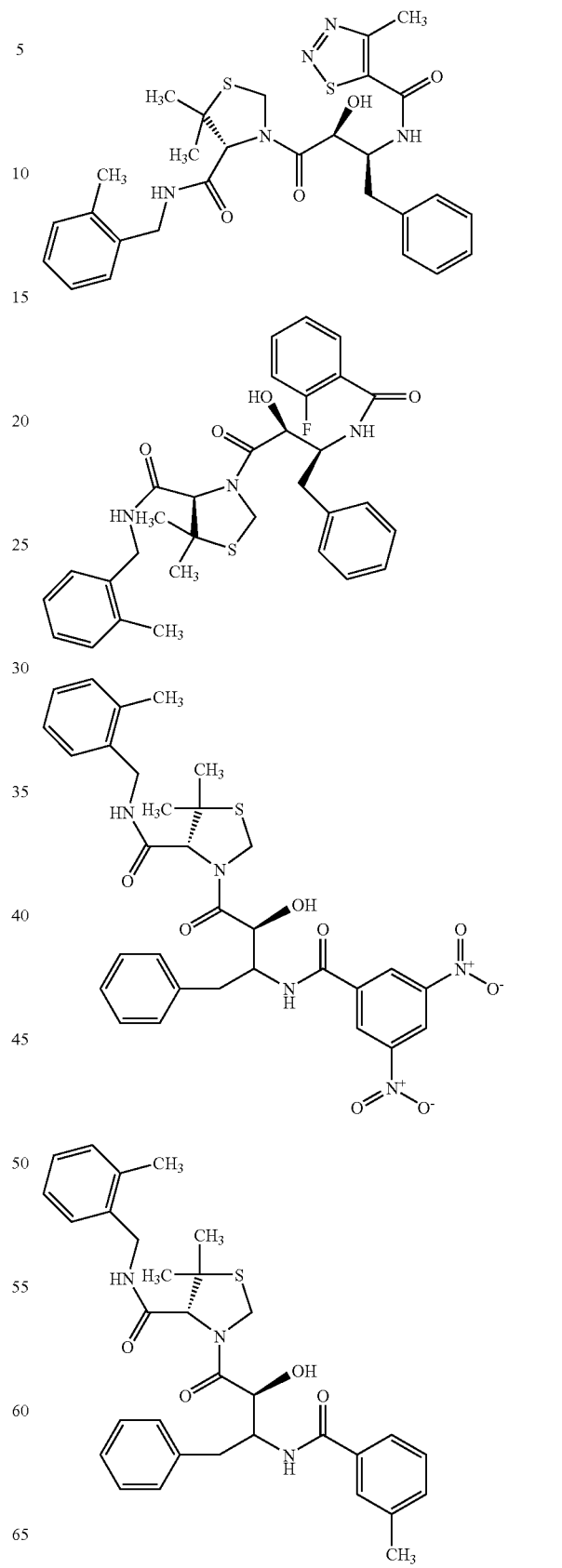

TABLE 3-continued
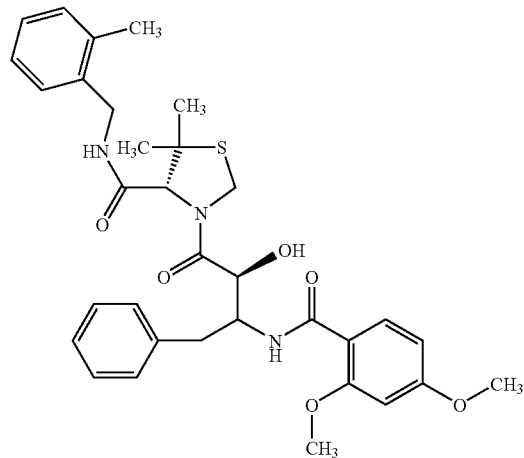
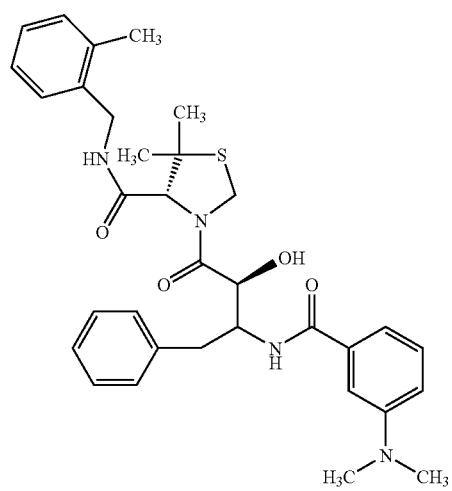
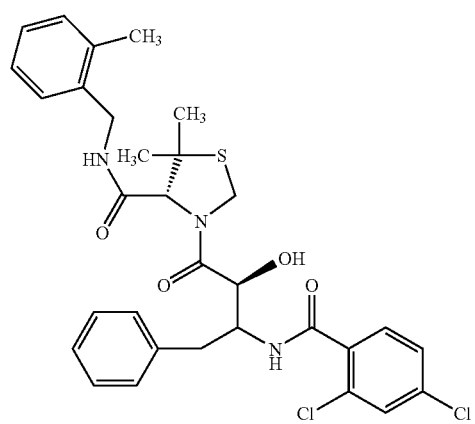
TABLE 3-continued
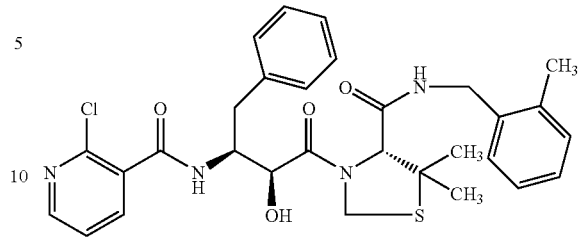
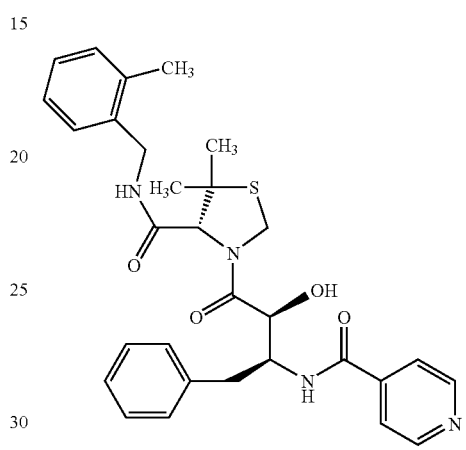
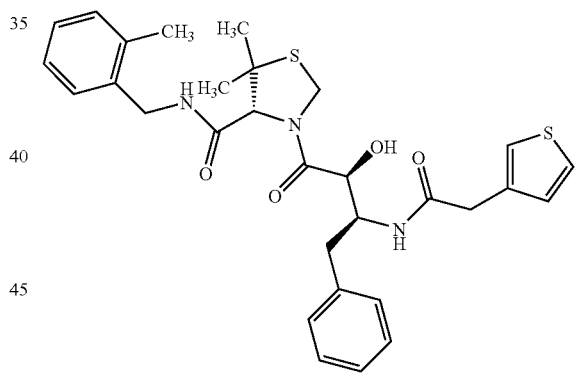
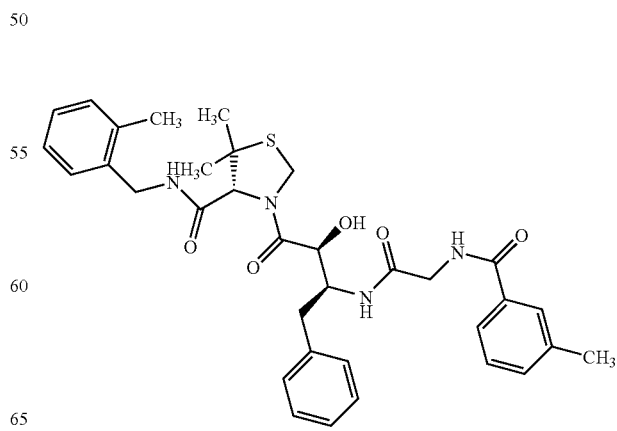

| 189 | 190 |
|---|---|
| TABLE 3-continued | TABLE 3-continued |
| 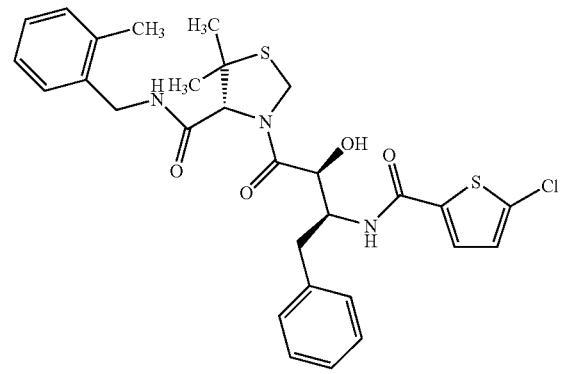 | 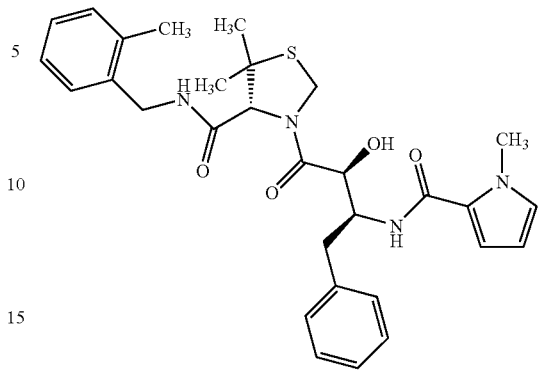 |
| 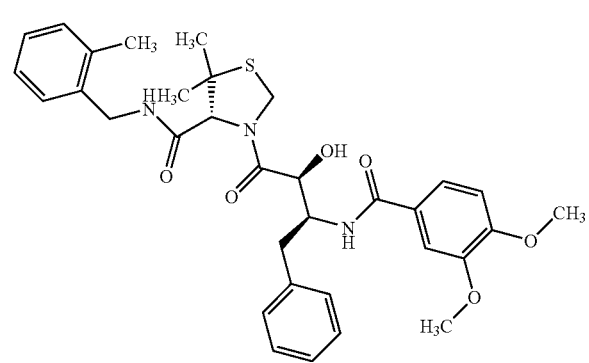 | 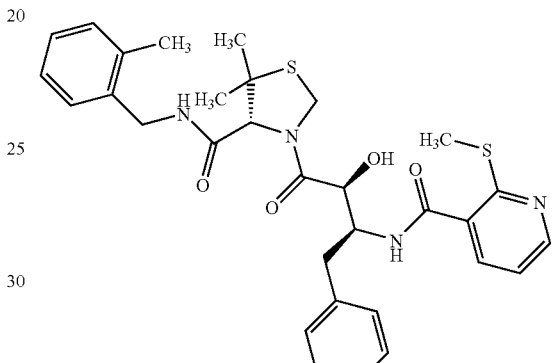 |
| 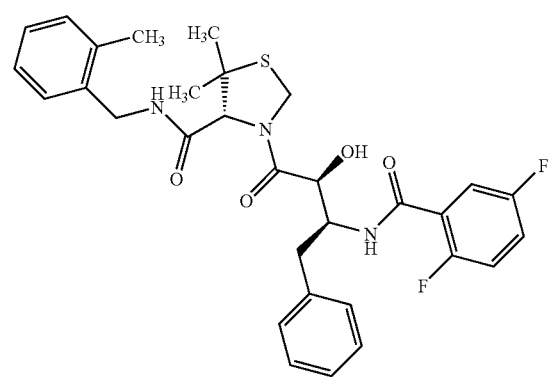 | 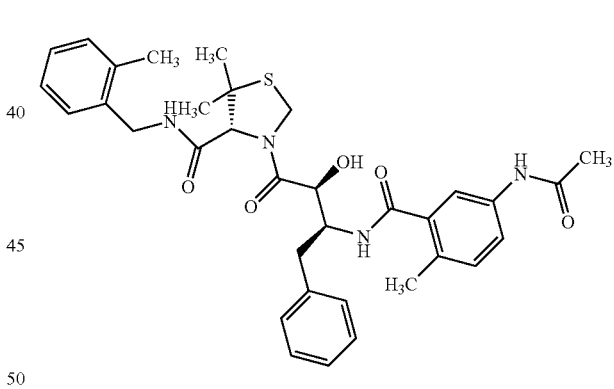 |
| 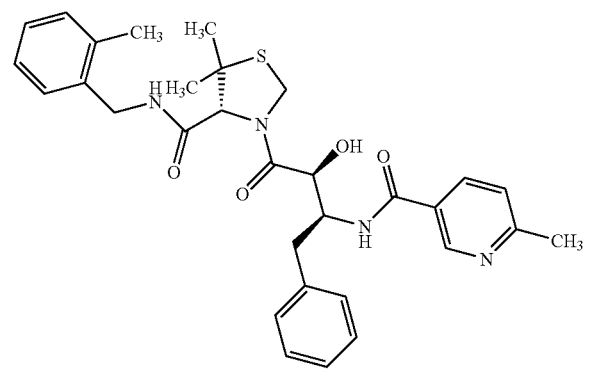 | 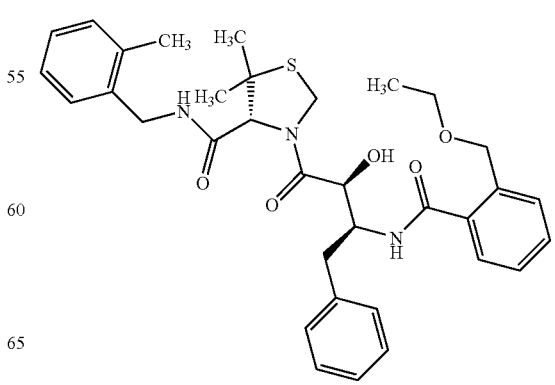 |

TABLE 3-continued

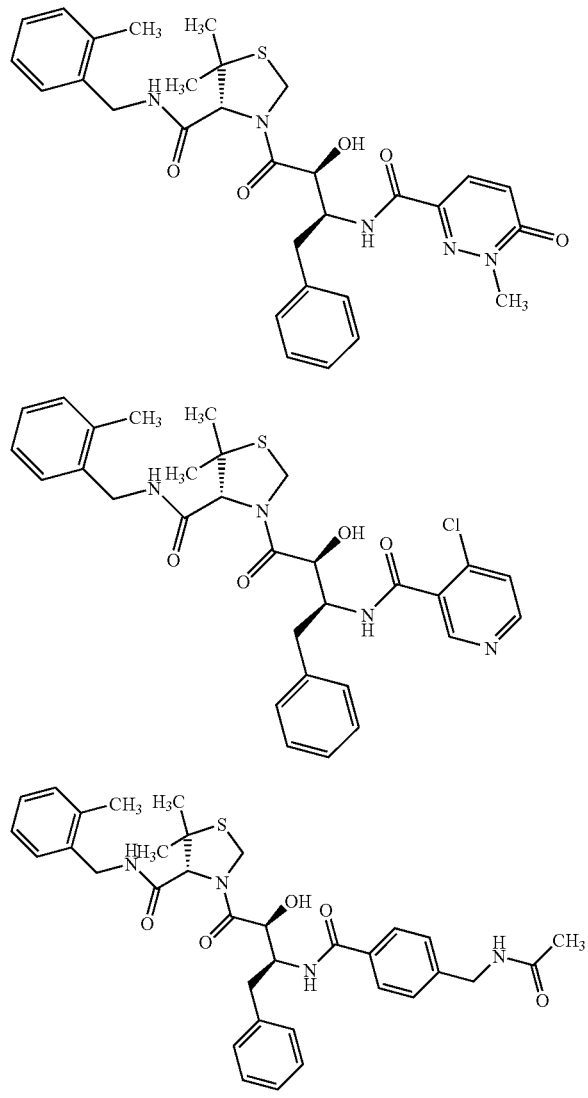

EXAMPLE F1

Preparation of (4R)-4-allylcarbamoyl-5,5-dimethyl-thiazolidine-3-carboxylic acid tert-butyl ester

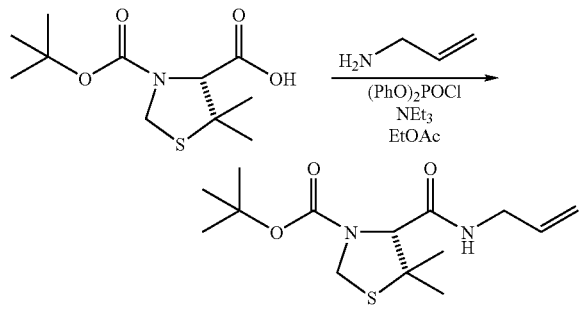

(4R)-5,5-Dimethyl-thiazolidine-3,4-dicarboxylic acid 3-tert-butyl ester (which can be prepared according to the methods of Ikunaka, M. et al., *Tetrahedron Asymm.* 2002, 13, 1201; Mimoto, T. et al., *J. Med. Chem.* 1999, 42, 1789; and Mimoto, T. et al., European Patent Application 0574135A1 (1993), 250 g; 0.957 mol) was added to an argon-purged 5-L flask and was dissolved in EtOAc (1.25 L). The solution was cooled to 2° C. and (PhO)$_2$POCl (208 mL; 1.00 mol) was then added in one portion. NEt$_3$ (280 mL; 2.01 mol) was added dropwise via addition funnel and the resulting suspension was then stirred at 0° C. Seven minutes later, allylamine (75.4 mL; 1.00 mol) was added dropwise. The ice bath was removed and the suspension was allowed to warm to room temperature. One-half hour later, 1 N HCl (750 mL; 0.750 mol) was added. The mixture was transferred to a 4-L separatory funnel using EtOAc (50 mL) for rinsing. The layers were separated. The organic fraction was washed with 7.2% aqueous Na$_2$CO$_3$ (2×1.25 L), and was then transferred to a 3-L distillation flask and was diluted with EtOAc (400 mL). The solution was dried azeotropically and concentrated to a volume of 800 mL by distillation of EtOAc at one atmosphere. After cooling to 25° C., the resulting clear yellowish EtOAc solution of (4R)-4-allylcarbamoyl-5,5-dimethyl-thiazolidine-3-carboxylic acid tert-butyl ester was carried on directly into the next step. An aliquot was removed and concentrated to give (4R)-4-allylcarbamoyl-5,5-dimethyl-thiazolidine-3-carboxylic acid tert-butyl ester as a white crystalline solid: mp=94–98° C., $^1$H NMR (300 MHz, CDCl$_3$) δ 6.12 (br s, 1H), 5.88 (app ddt, J=10.2, 17.1, 5.6 Hz, 1H), 5.28 (app dq, J=17.1, 1.5 Hz, 1H), 5.18 (app dd, J=1.2, 10.2 Hz, 1H), 4.68 (s, 2H), 4.14 (br s, 1H), 3.95 (br t, J=5.4 Hz, 2H), 1.62 (s, 3H), 1.49 (s, 9H), 1.46 (s, 3H); $^{13}$C NMR (75 MHz, CDCl$_3$) δ 170.0, 154.0, 134.4, 116.9, 82.0, 73.3, 54.0, 48.7, 42.0, 30.6, 28.6, 24.6; MS (CI) m/z 301.1599 (301.1586 calcd for C$_{14}$H$_{25}$N$_2$O$_3$S, M+H$^+$); elemental analysis calcd for C$_{14}$H$_{24}$N$_2$O$_3$S: C, 55.97; H, 8.05; N, 9.32; found: C, 56.11; H, 8.01; N, 9.11.

EXAMPLE F2

Preparation of (4R)-5,5-dimethyl-thiazolidine-4-carboxylic acid allylamide

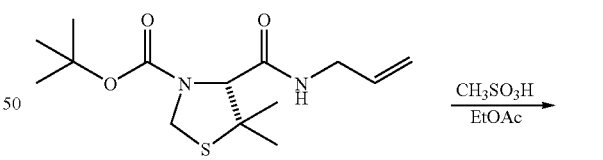

Methanesulfonic acid (155 mL; 2.39 mol) was added dropwise to the EtOAc solution of (4R)-4-allylcarbamoyl-5,5-dimethyl-thiazolidine-3-carboxylic acid tert-butyl ester in a 3-L flask. After stirring at room temperature overnight, the solution was cooled to 7° C. and H$_2$O (400 mL) was poured in. The mixture was transferred to a 4-L separatory funnel [using H$_2$O (30 mL) for rinsing] and the layers were separated. The organic fraction was extracted with H$_2$O (190 mL). The combined H₂O extracts were transferred to a 5-L flask and were cooled to 8° C. The pH was adjusted from 0.4 to 9.3 using 3 N NaOH (~1.05 L). 2-Methyltetrahydrofuran (1.55 L) was poured in, followed by the addition of NaCl (150 g). The ice bath was removed and the mixture was allowed to warm to room temperature. The pH was readjusted to 9.0 using 3 N NaOH (~1 mL). The mixture was transferred to a 4-L separatory funnel, using 2-methyltetrahydrofuran (50 mL) for rinsing, and the layers were separated. The aqueous phase was extracted with 2-methyltetrahydrofuran (950 mL). The organic extracts were vacuum-filtered through Celite directly into a 5-L distillation flask, using 2-methyltetrahydrofuran (200 mL) for rinsing. The solution was dried azeotropically and concentrated to a volume of 1.2 L by distillation of 2-methyltetrahydrofuran at one atmosphere. A measured aliquot was concentrated and weighed, which showed that 161 g of (4R)-5,5-Dimethyl-thiazolidine-4-carboxylic acid allylamide was present in solution [84% from (4R)-5,5-dimethyl-thiazolidine-3,4-dicarboxylic acid 3-tert-butyl ester]. This solution was then carried on directly into the next step. The concentrated aliquot from above yielded (4R)-5,5-Dimethyl-thiazolidine-4-carboxylic acid allylamide as a crystalline solid: mp=45–47° C., ¹H NMR (300 MHz, CDCl₃) δ 6.73 (br s, 1H), 5.87 (app ddt, J=10.2, 17.1, 5.7 Hz, 1H), 5.17–5.27 (m, 2H), 4.27 (AB q, $J_{AB}$=9.7 Hz, Δν=22.5 Hz, 2H), 2.94 (app tt, J=1.5, 5.8 Hz, 2H), 3.51 (s, 1H), 1.74 (s, 3H), 1.38 (s, 3H); ¹³C NMR (75 MHz, DCl₃) δ 169.7, 134.4, 116.9, 74.8, 57.2, 51.6, 41.9, 29.1, 27.3; MS (CI) m/z 201.1063 (201.1062 calcd for C₉H₁₇N₂OS, M+H⁺); elemental analysis calcd for C₉H₁₆N₂OS: C, 53.97; H, 8.05; N, 13.99; found: C, 53.93; H, 8.09; N, 14.07.

EXAMPLE F3

Preparation of (2S,3S)-3-(3-acetoxy-2-methyl-benzoylamino)-2-hydroxy-4-phenyl-butyric acid

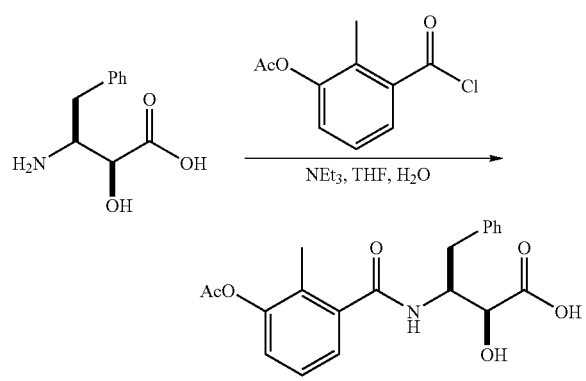

(2S,3S)-3-Amino-2-hydroxy-4-phenyl-butyric acid (which can be prepared according to the method of Pedrosa et al., *Tetrahedron Asymm.* 2001, 12, 347; M. Shibasaki et al., *Tetrahedron Lett.* 1994, 35, 6123; and Ikunaka, M. et al. *Tetrahedron Asymm.* 2002, 13, 1201; 185 g; 948 mmol) was added to a 5-L flask and was suspended in THF (695 mL). H₂O (695 mL) was poured in, followed by NEt₃ (277 mL; 1990 mmol). After stirring for 45 min, the solution was cooled to 6° C. A solution of acetic acid 3-chlorocarbonyl-2-methyl-phenyl ester (201 g; 948 mmol) in THF (350 mL) was then added dropwise. One-half hour later, the pH was adjusted from 8.7 to 2.5 with 6 N HCl (~170 mL). Solid NaCl (46 g) was added, the ice bath was then removed and the mixture was stirred vigorously while warming to room temperature. The mixture was transferred to 4-L separatory funnel, using 1:1 THF/H₂O (50 mL) for the transfer, and the lower aqueous phase was then removed. The organic fraction was transferred to a 5-L distillation flask, and was then diluted with fresh THF (2.5 L). The solution was azeotropically dried and concentrated to a volume of 1.3 L by distillation of THF at one atmosphere. To complete the azeotropic drying, fresh THF (2.0 L) was added and the solution was concentrated to 1.85 L by distillation at one atmosphere and was then held at 55° C. n-Heptane (230 mL) was added dropwise via addition funnel and the solution was then immediately seeded. After crystallization had initiated, additional n-heptane (95 mL) was added dropwise. The resulting crystal slurry was stirred vigorously for 7 min. Additional n-heptane (1.52 L) was then added as a slow stream. The crystal slurry was then allowed to cool to room temperature slowly and stir overnight. The suspension was vacuum-filtered and the filter cake was then washed with 1:1 THF/n-heptane (700 mL). After drying in a vacuum oven at 45–50° C., 324 g (92%) of (2S,3S)-3-(3-acetoxy-2-methyl-benzoylamino)-2-hydroxy-4-phenyl-butyric acid was obtained as a crystalline solid contaminated with ~7 mol % Et₃N.HCl: mp=189–191° C., ¹H NMR (300 MHz, DMSO-d₆) δ 12.65 (br s, 1H), 3.80 (d, J=9.7 Hz, 1H), 7.16–7.30 (m, 6H), 7.07 (dd, J=1.1, 8.0 Hz, 1H), 7.00 (dd, J=1.1, 7.5 Hz), 4.40–4.52 (m, 1H), 4.09 (d, J=6.0 Hz, 1H), 2.92 (app dd, J=2.9, 13.9 Hz, 1H), 2.76 (app dd, J=11.4, 13.9 Hz, 1H), 2.29 (s, 3H), 1.80 (s, 3H); ¹³C NMR (75 MHz, DMSO-d₆) δ 174.4, 169.3, 168.1, 149.5, 139.7, 139.4, 129.5, 128.3, 127.9, 126.5, 126.3, 124.8, 123.3, 73.2, 53.5, 35.4, 20.8, 12.6; MS (CI) m/z 372.1464 (372.1447 calcd for C₂₀H₂₂NO₆, M+H⁺); elemental analysis calcd for C₂₀H₂₁NO₆.0.07 Et₃N.HCl: C, 64.34; H, 5.86; N, 3.95; Cl, 0.70; found: C, 64.27; H, 5.79; N, 3.96; Cl; 0.86.

EXAMPLE F4

Preparation of acetic acid 3-{(1S,2S)-3-[(4R)-4-allylcarbamoyl-5,5-dimethyl-thiazolidin-3-yl]-1-benzyl-2-hydroxy-3-oxo-propylcarbamoyl}-2-methyl-phenyl ester

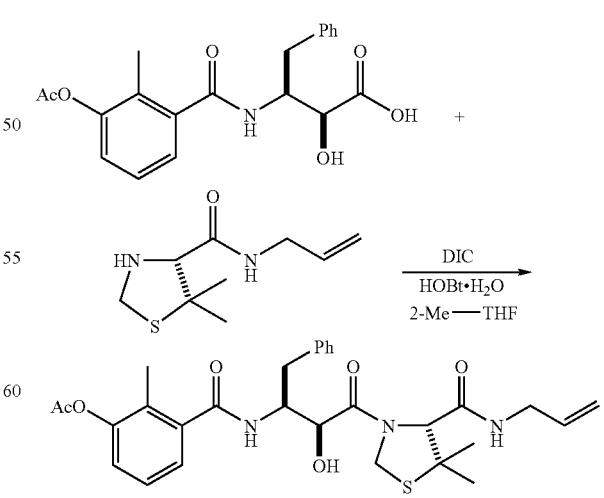

(2S,3S)-3-(3-Acetoxy-2-methyl-benzoylamino)-2-hydroxy-4-phenyl-butyric acid (271 g; 731 mmol) was added to a 5-L flask containing a solution of (4R)-5,5-Dimethyl-thiazolidine-4-carboxylic acid allylamide (161 g; 804 mmol) in 2-methyltetrahydrofuran (1.20 L total solution), while using 2-methyltetrahydrofuran (500 mL) for rinsing. HOBt.H₂O (32.6 g; 241 mmol) was added, using 2-methyltetrahydrofuran (50 mL) for rinsing. The white suspension was allowed to stir at room temperature for 10 min. Diisopropylcarbodiimide (119 mL; 760 mmol) was added in three portions (40 mL+40 mL+39 mL) at 30 min intervals. One hour after the final DIC addition, Celite (100 g) was added and the suspension was allowed to stir at room temperature for 3 h. The mixture was vacuum-filtered, while 2-methyltetrahydrofuran (400 mL) was used to rinse over the solids and wash the resulting filter cake. The filtrate was transferred to 4-L separatory funnel, using 2-methyltetrahydrofuran (50 mL) for rinsing. The solution was washed with 1 N HCl (1.25 L), and then with an aqueous solution of NaHCO₃ (27 g), NaCl (134 g) and H₂O (1.25 L). The resulting organic phase was transferred to a 3-L distillation flask and the solution was then reduced to a volume of 1.12 L by distillation of 2-methyltetrahydrofuran at one atmosphere. The solution was then diluted with 2-methyltetrahydrofuran (230 mL) to bring the total volume to 1.35 L. After cooling the solution to 23° C., the solution of crude acetic acid 3-{(1 S,2S)-3-[(4R)-4-allylcarbamoyl-5,5-dimethyl-thiazolidin-3-yl]-1-benzyl-2-hydroxy-3-oxo-propylcarbamoyl}-2-methyl-phenyl ester on directly into the next step.

EXAMPLE F5

Preparation of (4R)-3-[(2S,3S)-2-hydroxy-3-(3-hydroxy-2-methyl-benzoylamino)-4-phenyl-butyryl]-5,5-dimethyl-thiazolidine-4-carboxylic acid allylamide NaCl (83.0 g) in H₂O (1.60 L). The organic fraction was washed with 0.5 N HCl (1.66 L) and then with a saturated aqueous NaCl solution (400 mL). The resulting organic fraction was transferred to a 4-L Erlenmeyer flask and MgSO₄ (120 g) was added. After stirring for 10 min, the mixture was vacuum-filtered directly into a 5-L distillation flask, using 2:1 i-PrOAc/2-methyltetrahydrofuran (600 mL) for rinsing the separatory funnel and Erlenmeyer flask and washing the MgSO₄. The 2-methyltetrahydrofuran was displaced by distillation at one atmosphere with the simultaneous addition of i-PrOAc in five portions (a total of 3.60 L was used), while maintaining a minimum pot volume of ~2.50 L. The resulting crystallizing mixture was cooled to 75° C. and was held at this temperature for 30 min. The suspension was then allowed to slowly cool to room temperature overnight. The suspension was vacuum-filtered, using i-PrOAc (600 mL) for transferring and washing the crystals. After drying in a vacuum oven at 40° C., 204 g (54% from (2S,3S)-3-(3-Acetoxy-2-methyl-benzoylamino)-2-hydroxy-4-phenyl-butyric acid) of crystalline (4R)-3-[(2S,3S)-2-Hydroxy-3-(3-hydroxy-2-methyl-benzoylamino)-4-phenyl-butyryl]-5,5-dimethyl-thiazolidine-4-carboxylic acid allylamide was obtained. This material was recrystallized as described below.

EXAMPLE F6

Recrystallization of (4R)-3-[(2S,3S)-2-hydroxy-3-(3-hydroxy-2-methyl-benzoylamino)-4-phenyl-butyryl]-5,5-dimethyl-thiazolidine-4-carboxylic acid allylamide

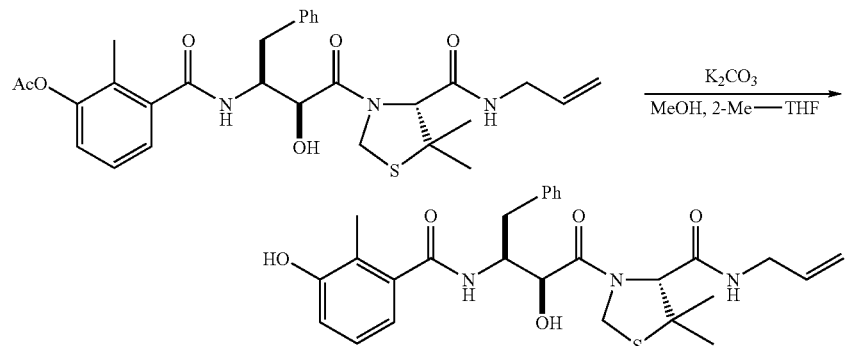

MeOH (330 mL) and K₂CO₃ (66.9 g; 484 mmol) were sequentially added to a 2-methyltetrahydrofuran solution of crude acetic acid 3-{(1S,2S)-3-[(4R)-4-allylcarbamoyl-5,5-dimethyl-thiazolidin-3-yl]-1-benzyl-2-hydroxy-3-oxo-propylcarbamoyl}-2-methyl-phenyl ester (theoretical amount: 405 g; 731 mmol) in a 3-L flask at room temperature. Two and a half hours later, additional K₂CO₃ (20 g; 144 mmol) was added. Three hours later the reaction mixture was vacuum-filtered on a pad of Celite, using 4:1 2-methyltetrahydrofuran/MeOH (330 mL) for rinsing over the solids and washing the filter cake. The filtrate was transferred to a 6-L separatory funnel, using 4:1 2-methyltetrahydrofuran/MeOH (80 mL) for rinsing. The solution was diluted with i-PrOAc (1.66 L) and was then washed with a solution of

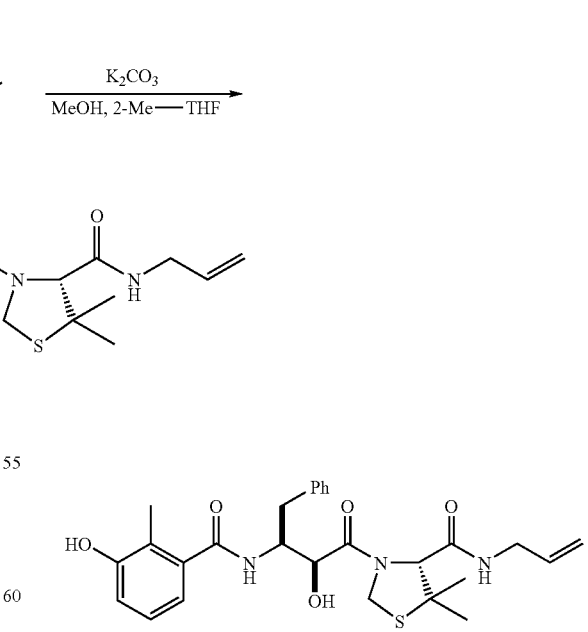

(4R)-3-[(2S,3S)-2-Hydroxy-3-(3-hydroxy-2-methyl-benzoylamino)-4-phenyl-butyryl]-5,5-dimethyl-thiazolidine-4-carboxylic acid allylamide (193 g, 378 mmol) was added to a 5-L flask and was then suspended in EtOAc (1.28 L). After heating the suspension to 76° C., MeOH (68 mL) was added and the internal temperature was then reduced to 70° C. n-Heptane (810 mL) was added dropwise to the solution, while maintaining the internal temperature at 70° C. After the n-heptane addition was complete, the resulting crystal suspension was held at 70° C. for 30 min, and was then allowed to slowly cool to room temperature overnight. The suspension was vacuum-filtered, using 1.6:1 EtOAc/n-heptane (500 mL) to transfer and wash the crystals. The crystals were then dried in a vacuum oven at 45° C. to give 162 g (84% recovery) of purified (4R)-3-[(2S,3S)-2-Hydroxy-3-(3-hydroxy-2-methyl-benzoylamino)-4-phenyl-butyryl]-5,5-dimethyl-thiazolidine-4-carboxylic acid allylamide as a white crystalline solid: mp=173–175° C., $^1$H NMR (300 MHz, DMSO-$d_6$) displayed a ~10:1 mixture of rotamers, major rotamer resonances δ 9.35 (s, 1H), 8.04–8.15 (m, 2H), 7.13–7.38 (m, 5H), 6.96 (t, J=7.7 Hz, 1H), 6.79 (d, J=7.2 Hz, 1H), 6.55 (d, J=7.5 Hz, 1H), 5.71–5.87 (m, 1H), 5.45 (br d, J=6.2 Hz, 1H), 4.98–5.27 (m, 4H), 4.38–4.52 (m, 3H), 3.58–3.86 (m, 2H), 2.68–2.90 (m, 2H), 1.84 (s, 3H), 1.52 (s, 3H), 1.37 (s, 3H) [characteristic minor rotamer resonances δ 9.36 (s), 8.21 (d, J=10.5 Hz), 7.82 (5, J=5.8 Hz), 4.89 (s), 4.78 (AB q, $J_{AB}$=9.8 Hz, Δv=27.1 Hz), 4.17–4.24 (m), 2.93–3.01 (m), 1.87 (s), 1.41 (s)]; $^{13}$C NMR (75 MHz, DMSO-$d_6$) displayed a ~10:1 mixture of rotamers, major rotamer resonances δ 170.4, 169.5, 168.2, 155.7, 139.6, 139.4, 135.5, 135.4, 129.9, 128.2, 126.2, 126.1, 121.9, 117.8, 115.6, 72.4, 72.1, 53.1, 51.4, 48.2, 41.3, 34.2, 30.5, 25.0, 12.6 [characteristic minor rotamer resonances δ 171.4, 169.7, 168.6, 139.0, 129.5, 128.4, 70.6, 54.2, 49.1, 41.5, 31.4, 24.8]; MS (CI) m/z 512.2224 (512.2219 calcd for $C_{27}H_{34}N_3O_5S$, M+H$^+$), elemental analysis calcd for $C_{27}H_{33}N_3O_5S$: C, 63.38; H, 6.50; N, 8.22; found: C, 63.19; H, 6.52; N, 8.10.

EXAMPLE F7

Preparation of (R)-5,5-dimethyl-thiazolidine-4-carboxylic acid allylamide; hydrochloride

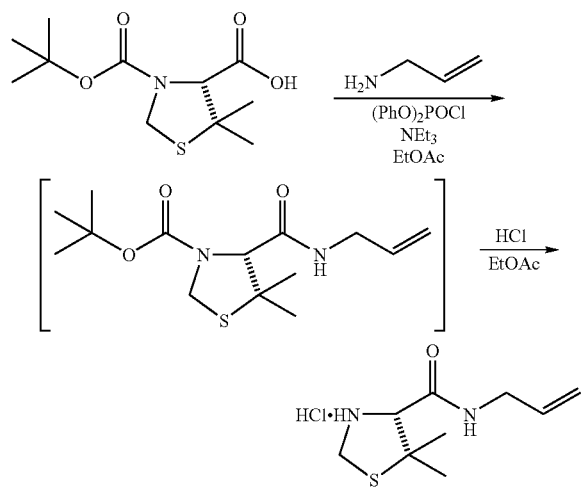

A solution of (R)-5,5-Dimethyl-thiazolidine-3,4-dicarboxylic acid 3-tert-butyl ester (105 kg, 402 mol) and ethyl acetate (690 L) was treated with diphenylchlorophosphate (113 kg, 422 mol) and was then cooled to 0° C. NEt$_3$ (85.5 kg, 844 mol) was added while maintaining the temperature at 5° C., and the mixture was then held at this temperature for 2 h. The mixture was cooled to 0° C., and allylamine (24.1 kg, 422 mol) was then added while maintaining the temperature at 5° C. The mixture was warmed to 20° C. and was then quenched with 10 wt. % aqueous HCl (310 L). After separation of the layers, the organic fraction was washed with 8.6 wt. % aqueous Na$_2$CO$_3$ (710 L). After separation of the layers, the aqueous fraction was extracted with ethyl acetate (315 L). The combined ethyl acetate extracts containing AG-074278 were dried by azeotropic distillation at one atmosphere, while maintaining a minimum pot volume of approximately 315 L. The resulting suspension of (R)-4-Allylcarbamoyl-5,5-dimethyl-thiazolidine-3-carboxylic acid tert-butyl ester was cooled to 5° C. A 13 wt. % solution of anhydrous HCl (36.8 kg, 1008 mol) in ethyl acetate (263 L) was cooled to 5° C. and was then added to the (R)-4-Allylcarbamoyl-5,5-dimethyl-thiazolidine-3-carboxylic acid tert-butyl ester suspension while maintaining the temperature at 15° C. The resulting suspension was held at 20° C. for 19 h, and was then cooled and held at 5° C. for 2 h. The suspension was then filtered, using cold ethyl acetate for rinsing. The wet cake was dried under vacuum at 45° C. to give 90.5 kg (95.2%) of (R)-5,5-Dimethyl-thiazolidine-4-carboxylic acid allylamide hydrochloride as a white solid: $^1$H NMR (300 MHz, DMSO-$d_6$) δ 8.94 (app t, J=5.5 Hz, 1H), 5.82 (ddt, J=10.4, 17.2, 5.2 Hz, 1H), 5.19–5.25 (m, 1H), 5.10–5.14(m, 1H),4.38(ABq, $J_{AB}$=9.8Hz, Δv=14.5Hz, 2H),4.08(s, 1H), 3.72–3.91 (m, 2H), 1.58 (s, 3H), 1.32 (s, 3H); $^{13}$C NMR (75 MHz, DMSO-$d_6$) δ 161.7, 132.2, 114.0, 67.9, 51.4, 43.5, 39.3, 25.3, 24.3; MS (CI) m/z 201.1070 (201.1062 calcd for $C_9H_{17}N_2OS$, M+H$^+$); elemental analysis calcd for $C_9H_{17}ClN_2OS$: C, 45.65; H, 7.24; N, 11.83; Cl, 14.97; found: C, 45.41; H, 7.33; N, 11.69; Cl, 15.22.

EXAMPLE F8

Preparation of (2S,3S)-2-acetoxy-3-(3-acetoxy-2-methyl-benzoylamino)-4-phenyl-butyric acid

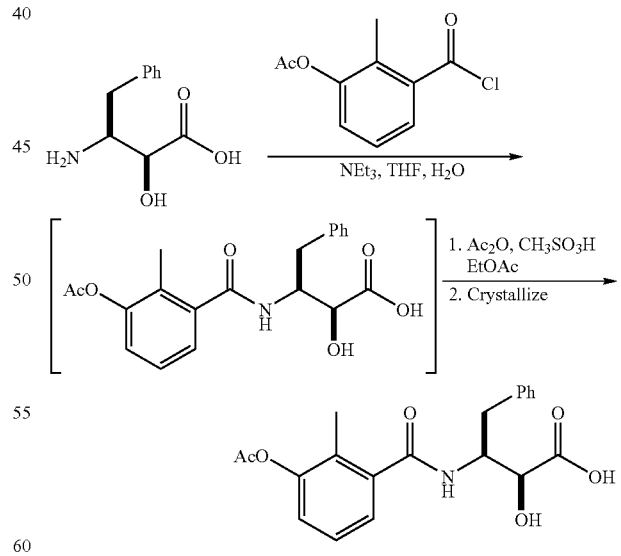

A mixture of (2S,3S)-3-Amino-2-hydroxy-4-phenyl-butyric acid (110 kg, 563 mol), NaCl (195 kg), and THF (413 L) was charged with NEt$_3$ (120 kg, 1183 mol) and H$_2$O (414 L) at ambient temperature. The resulting mixture was cooled to 0° C. Acetic acid 3-chlorocarbonyl-2-methyl-phenyl ester (120 kg, 563 mol) was added to a separate reactor and was then dissolved in THF (185 L). The resulting solution of acetic acid 3-chlorocarbonyl-2-methyl-phenyl ester was cooled to 10° C., and was then added to the (2S,3S)-3-amino-2-hydroxy-4-phenyl-butyric acid mixture while maintaining the temperature <10° C. during addition. The resulting biphasic mixture was agitated at 5° C. for 1 h, and was then adjusted to pH 2.5–3.0 with concentrated HCl (62 kg). The mixture was then warmed to 25° C., and the layers were separated. The resulting THF fraction, containing (2S,3S)-3-(3-acetoxy-2-methyl-benzoylamino)-2-hydroxy-4-phenyl-butyric acid, was partially concentrated by distillation at one atmosphere. THF was then replaced with ethyl acetate by distillation at one atmosphere, while maintaining a minimum pot volume of 1500 L. The resulting solution was cooled to 25° C., and was then charged with acetic anhydride (74.8 kg, 733 mol) and methanesulfonic acid (10.8 kg, 112 mol). The mixture was heated at 70° C. for approximately 3 h. The mixture was cooled to 25° C., and was then quenched with H$_2$O (1320 L) while maintaining the temperature at 20° C. After removal of the aqueous layer, the organic fraction was charged with ethyl acetate (658 L) and H$_2$O (563 L). After agitation, the aqueous phase was removed. The organic fraction was washed twice with 13 wt. % aqueous NaCl (2×650 L). The organic fraction was partially concentrated and dried by vacuum distillation (70–140 mm Hg) to a volume of approximately 1500 L. The resulting solution was heated to 40° C., and was then charged with n-heptane (1042 L) while maintaining the temperature at 40° C. The solution was seeded with (2S, 3S)-2-acetoxy-3-(3-acetoxy-2-methyl-benzoylamino)-4-phenyl-butyric acid (0.1 kg), and additional n-heptane (437 L) was then added slowly. The crystallizing mixture was maintained at 40° C. for 1 h. Additional n-heptane (175 L) was added while maintaining the temperature at 40° C. The crystalline suspension was cooled and held at 25° C. for 1 h, then at 0° C. for 2 h. The suspension was filtered, using n-heptane for rinsing. The wet cake was dried under vacuum at 55° C. to give 174 kg (74.5%) of (2S,3S)-2-acetoxy-3-(3-acetoxy-2-methyl-benzoylamino)-4-phenyl-butyric acid as a white solid: m.p.=152–154° C.; $^1$H NMR (300 MHz, CDCl$_3$) δ 7.21–7.35 (m, 5H), 7.13 (app t, J=7.9 Hz, 1H), 7.01 (app d, J=8.1 Hz, 1H), 6.94 (app d, J=7.2 Hz, 1H), 5.99 (d, J=9.0 Hz, 1H), 5.33 (d, J=4.1 Hz, 1H), 4.96–5.07 (m, 1H), 3.07 (dd, J=5.5, 14.6 Hz, 1H), 2.90 (dd, J=10.0, 14.5 Hz, 1H), 2.30 (s, 3H), 2.18 (s, 3H), 1.96 (s, 3H); $^{13}$C NMR (125 MHz, CDCl$_3$) δ 170.4, 170.2, 169.6, 169.5, 149.5, 137.81, 136.5, 129.2, 128.6, 128.4, 127.0, 126.6, 124.5, 123.7, 73.1, 50.9, 35.9, 20.6, 20.5, 12.4; elemental analysis calcd for C$_{22}$H$_{23}$NO$_7$: C, 63.92; H, 5.61; N, 3.39; found: C, 64.22; H, 5.68; N, 3.33; MS (CI) m/z 414.1572 (414.1553 calcd for C$_{22}$H$_{24}$NO$_7$, M+H$^+$).

EXAMPLE F9

Preparation of (4R)-3-[(2S,3S)-2-hydroxy-3-(3-hydroxy-2-methyl-benzoylamino)-4-phenyl-butyryl]-5,5-dimethyl-thiazolidine-4-carboxylic acid allylamide

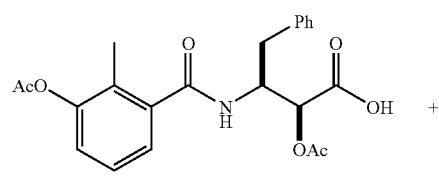

+

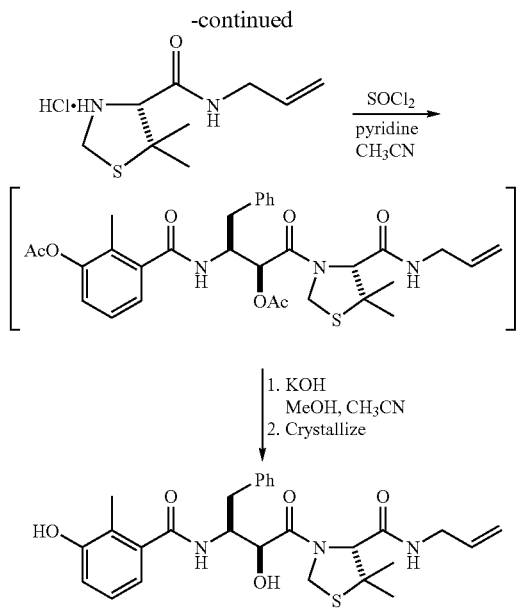

A solution of (2S,3S)-2-acetoxy-3-(3-acetoxy-2-methyl-benzoylamino)-4-phenyl-butyric acid (140 kg, 339 mol), CH$_3$CN (560 L), and pyridine (64.3 kg, 813 mol) was cooled to 15° C. SOCl$_2$ (44.3 kg, 373 mol) was charged while maintaining the temperature at 15° C. The mixture was held at 15° C. for 1 h. A separate reactor was charged with (R)-5,5-dimethyl-thiazolidine-4-carboxylic acid allylamide hydrochloride (96.6 kg, 408 mol), CH$_3$CN (254 L), and pyridine (29.5 kg, 373 mol), and was then cooled to 15° C. The (2S,3S)-2-acetoxy-3-(3-acetoxy-2-methyl-benzoylamino)-4-phenyl-butyric acid chloride solution was added to the (R)-5,5-dimethyl-thiazolidine-4-carboxylic acid allylamide solution, while maintaining the temperature at 15° C. The mixture was held at 15° C. for 6 h. A separate reactor was charged with KOH (167 kg, 2709 mol) and methanol (280 L) using a 0° C. cooling jacket. The resulting KOH/methanol solution was cooled to 5° C. The crude acetic acid 3-{(1S,2S)-2-acetoxy-3-[(R)-4-allylcarbamoyl-5,5-dimethyl-thiazolidin-3-yl]-1-benzyl-3-oxo-propylcarbamoyl}-2-methyl-phenyl ester mixture was added to the KOH/methanol solution while maintaining the temperature at 10° C. After addition was complete, the mixture was held at 25° C. for 3 h. The mixture was charged with H$_2$O (840 L) and ethyl acetate (840 L), and was then followed by acidification to pH 5–6.5 with concentrated HCl (85 kg) while maintaining the temperature at 20° C. The resulting layers were separated. The organic fraction was sequentially washed with 6.8 wt. % aqueous NaHCO$_3$ (770 L), an aqueous HCl/NaCl solution (H$_2$O: 875 L; conc. HCl: 207 kg; NaCl: 56 kg), 8.5 wt. % aqueous NaHCO$_3$ (322 L), and then with 3.8 wt. % aqueous NaCl (728 L). The resulting organic fraction was partially concentrated by distillation at one atmosphere. The solvent was exchanged with ethyl acetate by continuing distillation and maintaining the pot temperature at ≧70° C. Ethyl acetate was added such that the pot volume remained at approximately 840 L. The solution was then cooled to 20° C. and held at this temperature until crystallization was observed. n-Heptane (280 L) was added and the suspension was agitated at 15° C. for 4 h. The crystals were, using cold 2.4:1 (v/v) ethyl acetate/n-heptane for rinsing. The wet cake was dried under vacuum at 45° C.

to provide crude (R)-3-[(2S,3S)-2-hydroxy-3-(3-hydroxy-2-methyl-benzoylamino)-4-phenyl-butyryl]-5,5-dimethyl-thiazolidine-4-carboxylic acid allylamide. Decolorization and recrystallization was conducted as follows: A mixture of crude (R)-3-[(2S,3S)-2-hydroxy-3-(3-hydroxy-2-methyl-benzoylamino)-4-phenyl-butyryl]-5,5-dimethyl-thiazolidine-4-carboxylic acid allylamide, ADP carbon (21 kg), Supercel (3 kg), and ethyl acetate (780 L) was heated to 70° C. $CH_3OH$ (40 L) was added to the mixture. The mixture was filtered, and the resulting clear filtrate was heated to reflux at one atmosphere to begin distillation. $CH_3OH$ was displaced as follows: ethyl acetate (388 L) was charged while maintaining the pot volume at approximately 840 L and at 70° C. The solution was slowly charged with n-heptane (316 L), while maintaining a temperature of 70° C. The mixture was then cooled to 20° C. and was held at this temperature for 4 h. The crystals were filtered, using cold 2.1:1 (v/v) ethyl acetate/n-heptane for rinsing. The wet cake was dried under vacuum at 45° C. to give 103 kg (59.6%) of (4R)-3-[(2S,3S)-2-hydroxy-3-(3-hydroxy-2-methyl-benzoylamino)-4-phenyl-butyryl]-5,5-dimethyl-thiazolidine-4-carboxylic acid allylamide as a white crystalline solid: mp=173–175° C., $^1H$ NMR (300 MHz, DMSO-$d_6$) displayed a ~10:1 mixture of rotamers, major rotamer resonances δ 9.35 (s, 1H), 8.04–8.15 (m, 2H), 7.13–7.38 (m, 5H), 6.96 (t, J=7.7 Hz, 1H), 6.79 (d, J=7.2 Hz, 1H), 6.55 (d, J=7.5 Hz, 1H), 5.71–5.87 (m, 1H), 5.45 (br d, J=6.2 Hz, 1H), 4.98–5.27 (m, 4H), 4.38–4.52 (m, 3H), 3.58–3.86 (m, 2H), 2.68–2.90 (m, 2H), 1.84 (s, 3H), 1.52 (s, 3H), 1.37 (s, 3H) [characteristic minor rotamer resonances δ 9.36 (s), 8.21 (d, J=10.5 Hz), 7.82 (5, J=5.8 Hz), 4.89 (s), 4.78 (AB q, $J_{AB}$=9.8 Hz, Δv=27.1 Hz), 4.17–4.24 (m), 2.93–3.01 (m), 1.87 (s), 1.41 (s)]; $^{13}C$ NMR (75 MHz, DMSO-$d_6$) displayed a ~10:1 mixture of rotamers, major rotamer resonances δ 170.4, 169.5, 168.2, 155.7, 139.6, 139.4, 135.5, 135.4, 129.9, 128.2, 126.2, 126.1, 121.9, 117.8, 115.6, 72.4, 72.1, 53.1, 51.4, 48.2, 41.3, 34.2, 30.5, 25.0, 12.6 [characteristic minor rotamer resonances δ 171.4, 169.7, 168.6, 139.0, 129.5, 128.4, 70.6, 54.2, 49.1, 41.5, 31.4, 24.8]; MS (CI) m/z 512.2224 (512.2219 calcd for $C_{27}H_{34}N_3O_5S$, M+H$^+$), elemental analysis calcd for $C_{27}H_{33}N_3O_5S$: C, 63.38; H, 6.50; N, 8.22; found: C, 63.19; H, 6.52; N, 8.10.

BIOLOGICAL EVALUATION

Cells and Virus

T-cell lines, CEM-SS, and MT-2, and viruses HIV-1 RF and HIV-1 NL4–3 (pNL4–3) were obtained from the National Institutes of Health (AIDS Research and Reference Reagent Program, Bethesda, Md.). HIV-1 NL4–3(184V/L90M) was derived from a clinical isolate that exhibited the protease inhibitor-resistance associated substitutions 184V and L90M, by cloning of an reverse transcriptase-polymerase chain reaction amplified fragment into the unique Age I and Spe I restriction sites of pNL4–3.

Cytopathic Effect (CPE) Inhibition Assays

The ability of compounds to protect cells against HIV infection was measured by the MTT dye reduction method, essentially as described (See Pauwels, R. Balzarini, J. Baba, M. Snoeck, R. Schols, D. Herdewijn, P. Desmyter, J. and De Clercq, E. 1988, "Rapid and automated tetrazolium-based colorimetric assay for the detection of anti-HIV compounds,". *J Virol Methods.*, 20: 309–321 and Weislow, O. S. Kiser, R. Fine, D. L. Bader, J. Shoemaker, R. H. and Boyd, M. R. 1989. "New soluble-formazan assay for HIV-1 cytopathic effects: application to high-flux screening of synthetic and natural products for AIDS-antiviral activity". *J. Natl. Cancer Inst.* 81:577–586). Subject cells were infected with test virus at an moi of 0.025 to 0.819 or mock infected with medium only and added at 2×10$^4$ cells per well into 96 well plates containing half-log dilutions of test compounds. Six days later, 50 μl of XTT (1 mg/ml XTT tetrazolium, 0.02 nM phenazine methosulfate) was added to the wells and the plate was reincubated for four hours. Viability, as determined by the amount of XTT formazan produced, was quantified spectrophotometrically by absorbance at 450 nm. Data from CPE assays were expressed as the percent of formazan produced in compound-treated cells compared to formazan produced in wells of uninfected, compound-free cells. The fifty percent effective concentration ($EC_{50}$) was calculated as the concentration of compound that effected an increase in the percentage of formazan production in infected, compound-treated cells to 50% of that produced by uninfected, compound-free cells. The 50% cytotoxicity concentration ($CC_{50}$) was calculated as the concentration of compound that decreased the percentage of formazan produced in uninfected, compound-treated cells to 50% of that produced in uninfected, compound-free cells. The therapeutic index was calculated by dividing the cytotoxicity ($CC_{50}$) by the antiviral activity ($EC_{50}$).

Susceptibility Assays

Compounds were tested in phenotypic susceptibility assays at Virologic, Inc., (See Petropoulos C. J., Parkin N. T., Limoli K. L., Lie Y. S., Wrin T., Huang W., Tian H., Smith D., Winslow G. A., Capon D J, Whitcomb J M. 2000, "A novel phenotypic drug susceptibility assay for human immunodeficiency virus type 1," *Antimicrob Agents Chemother* 44(4):920–928) or using the assay described here. MT-2 cells were infected with either HIV-1 NL4–3 or HIV-1 NL4–3(184V/L90M) and incubated in the presence of serial 0.5 log dilutions of test compounds. Three days later, culture supernatants were collected and virus production, as determined by p24 ELISA, was assayed. Percent inhibition was calculated as p24 concentration in compound-treated samples as compared to infected, compound-free controls. Inhibition of viral replication is determined by measuring reduction in HIV p24 present in the culture supernatant, using a Beckman-Coulter p24 HIV-1 Ag EIA kit and following the supplied protocol. Absorbance is read on a MRX microplate reader (Dynex Technologies). The $EC_{50}$ was calculated as the concentration of compound that effected a decrease in the p24 production by infected, compound-treated cells to 50% of that produced by infected, compound-free cells.

HIV-1 Protease RET Assay

Ki's for the inhibitors of HIV-1 protease were determined using a resonance energy transfer (RET) assay. A mutant form of this enzyme (Q7S) is used for this assay because it is more stable against auto-proteolysis than the wild-type protein. This enzyme is first partially purified as inclusion bodies from cell lysate. It is then solublized in 8M urea and passed through a Q-Sepharose column (Pharmacia) for further purification. To refold this protein, samples containing Q7S is dialyzed into 50 mM sodium phosphate pH 7.0, 50 mM NaCl, 10 mM DTT, and 10% glycerol.

The commercially available peptide substrate (Molecular Probes Cat. # H-2930) RE(EDANS)SQNYPIVQK(DAB-CYL)R is used to assess activity and Ki's. This peptide is cleaved quantitatively by HIV-1 Pr at the Tyr-Pro bond. The EDANS fluorophore absorbs at 340 nm and emits at 490 nm. The reaction is carried out in a 96 well plate in a total volume of 100 μL and is run for 12 minutes at 37 C under steady-state conditions with 5 μM substrate and 2 nM active dimer enzyme concentration. The literature value Km for this substrate and enzyme is 103+/−8 μM (See Matayoshi, et al., "Novel Fluorogenic Substrates for Assaying Retroviral Proteases by Resonance Energy Transfer," *Science* 247, 954 (1990)). The buffer for this reaction is 0.1M sodium acetate pH 4.8, 1M NaCl, 1 mM EDTA, 5 mM dithiothreitol, 10% dimethyl sulfoxide and 1 mg/ml bovine serum albumin. Inhibition curves are fit using the Morrison tight binding equation.

| Example No. | Ave. $K_i$ (nM) | Ave CPE $EC_{50}$ (mM) | $EC_{50}$ or $IC_{50}$ (mM) |
|---|---|---|---|
| A3 | 1.7 | 0.37 | |
| A4 | 4.1 | 0.591 | |
| A5 | 2 | 0.433 | |
| A6 | 0.22 | 0.036 | |
| A7 | 0.49 | 0.104 | 0.832 |
| A8 | 0.23 | 0.036 | |
| A9 | 4 | 0.565 | |
| A10 | 51 | >1 | |
| A11 | 19 | 0.93 | |
| A12 | 1.7 | 1.09 | |
| A13 | 44.1 | >1 | |
| A14 | 0.44 | 0.052 | 0.071* |
| A15 | 10.9 | 0.13 | |
| A16 | 0.63 | 0.134 | |
| A17 | <0.1 | 0.045 | 0.102* |
| A18 | 0.38 | 0.193 | |
| A19 | 10 | 0.442 | |
| A20 | 0.13 | 0.037 | 0.147* |
| A21 | 1.9 | 0.717 | |
| A22 | 0.32 | 0.061 | 0.226* |
| A23 | 0.65 | 0.072 | |
| A24 | 0.18 | 0.104 | 0.831 |
| A25 | 5.8 | 0.248 | |
| A26 | 0.38 | 0.119 | 0.321* |
| A27 | 0.62 | 0.072 | |
| A28 | <0.1 | 0.041 | |
| A29 | <0.1 | 0.117 | |
| A30 | 1.1 | 0.507 | 0.829* |
| A31 | <0.1 | 0.041 | |
| A32 | <0.1 | 0.045 | 0.486 |
| A33 | <0.1 | 0.577 | |
| A34 | <0.1 | 0.036 | |
| A35 | <0.1 | 0.017 | 0.063 |
| A36 | 0.59 | 0.519 | |
| A37 | 0.13 | 0.161 | |
| A38 | 0.17 | 0.078 | 0.401 |
| A39 | 0.27 | 0.367 | |
| A40 | 1.2 | 0.275 | |
| A41 | 1.6 | 0.527 | |
| A42 | 0.23 | 0.126 | 0.307 |
| A43 | 0.35 | 0.561 | |
| A44 | 0.14 | 0.022 | 0.472 |
| A45 | 0.51 | 0.165 | |
| A46 | 0.31 | 0.091 | 0.79 |
| A47 | 2.3 | 1.813 | |
| A48 | 0.19 | 0.417 | |
| A49 | 1.2 | 0.13 | |
| A50 | 0.26 | 0.224 | |
| A51 | 1.3 | 0.667 | |
| A52 | 37 | | |
| B1 | 2.5 | 0.905 | |
| B2 | 0.78 | 0.369 | |
| B3 | 4 | 0.409 | |
| B8 | 0.31 | 0.095 | 0.405* |
| B4 | 1.7 | 0.551 | |
| B5 | 1.6 | 0.508 | |
| B6 | 1.6 | 0.589 | |
| B7 | 1.9 | 0.68 | |
| B8 | 1.5 | 0.552 | |
| B10 | <0.1 | 1.1 | |
| B11 | 1.2 | 1.175 | 1.716* |
| B12 | 0.45 | 1.398 | |
| B13 | 19% @64 nM | | |
| B14 | 3.7 | 3.054 | |
| B15 | 2 | 1.086 | |
| B16 | <0.1 | 0.298 | 1.754 |
| B17 | 0.42 | 0.534 | 1.579 |
| B18 | 0.29 | 0.457 | |
| B19 | <0.1 | 0.124 | 1.369 |
| B20 | 2.1 | 0.427 | |
| B21 | 4.6 | 0.598 | |
| B22 | 1.8 | 1.613 | |
| B23 | 0.42 | 1.42 | |
| B24 | 5.5 | 2.316 | |
| B25 | 2.7 | 1.794 | |
| B26 | 2.9 | 1.712 | |
| B27 | 3.5 | | |
| B28 | 153 | | |
| B29 | 0.12 | 1.256 | |
| B30 | 1.1 | 1.227 | |
| B31 | 1.5 | 1.316 | |
| B32 | 4.9 | | |
| B33 | 1.2 | 1.286 | |
| B34 | | | |
| B35 | | | |
| B36 | <0.1 | 0.615 | |
| B37 | 0.11 | 0.736 | |
| B38 | | | |
| B39 | 0.16 | | |
| B40 | 2.8 | 1.396 | |
| B41 | 0.15 | | |
| B42 | 0.73 | | |
| B43 | 0.2 | | |
| B44 | 0.76 | 0.629 | |
| B45 | 19.7 | | |
| B46 | 12.5 | | |
| B47 | 6.9 | | |
| B48 | 12 | >3.2 | |
| B49 | 17.2 | | |
| C1 | 0.38 | 0.627 | 0.427 |
| C3 | 1.3 | 0.5 | |
| C4 | 4.2 | | |
| C4 | 69 | | |
| C5 | 3.2 | | |
| C6 | <0.1 | 0.164 | 1.475 |
| C7 | 7.9 | | |
| C8 | 0.26 | 0.447 | |
| C9 | 0.34 | 0.233 | |
| C10 | 36 | | |
| C11 | 1.1 | 1.562 | |
| D1 | <0.01 | 0.052 | 0.601 |
| D3 | 0.5 | 0.162 | 1.954 |
| D4 | 0.7 | 0.016 | 1.954 |

*$IC_{50}$ (mM) Data was determined at Virologic Inc against the 46I, 84V, 90M virus The following compounds have been prepared according to the procedures described herein and have demonstrated the noted activity:

| MOLSTRUCTURE | $K_i$ | $EC_{50}$ |
|---|---|---|
| 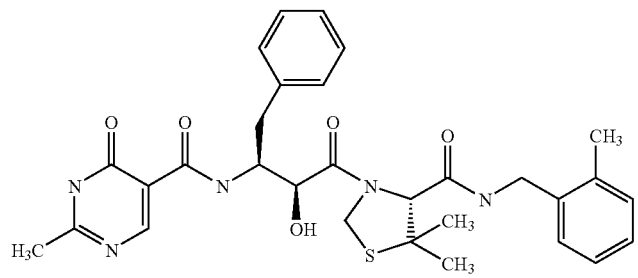 | 209 | 10 |
| 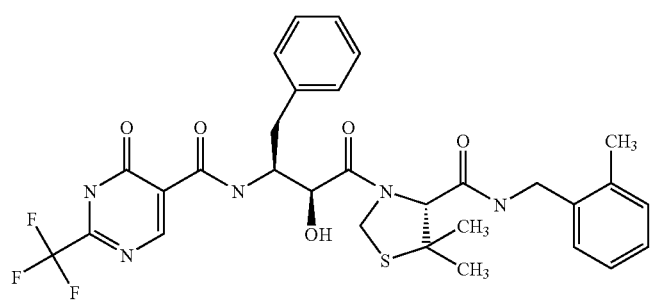 | 1700 | 10 |
| 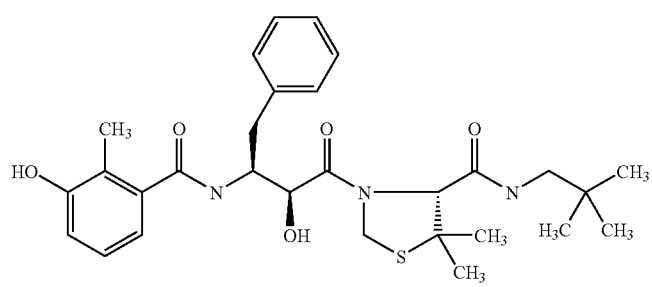 | 0.1 | 0.053 |
| 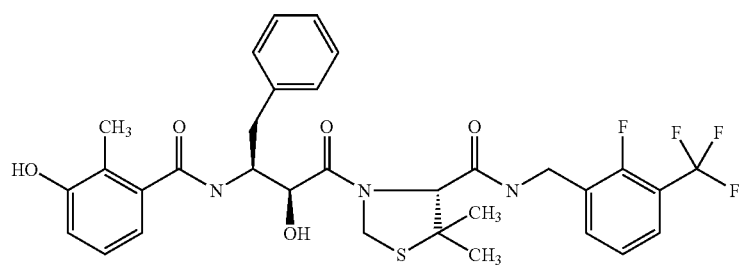 | 62 | |
| 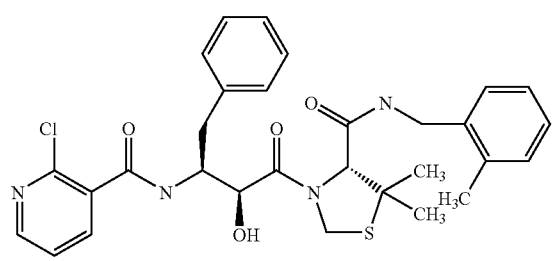 | 0.75 | |

-continued
| MOLSTRUCTURE | $K_i$ | $EC_{50}$ |
|---|---|---|
| 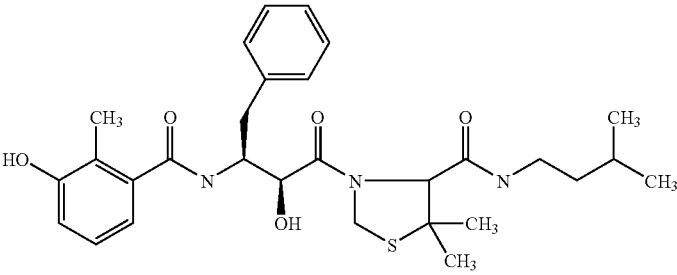 | 0.1 | 0.072 |
| 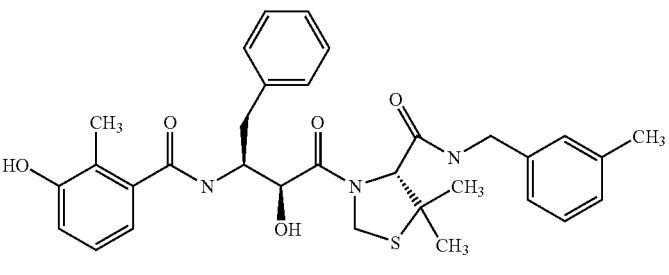 | 1.5 | 0.076 |
| 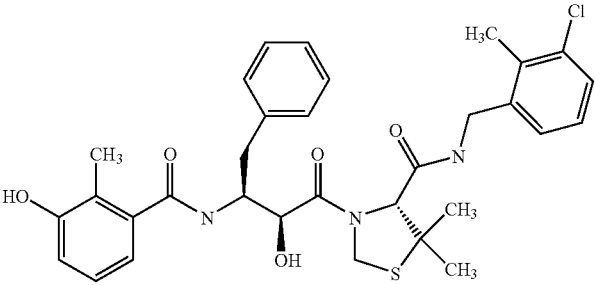 | 0.2 | 0.113 |
| 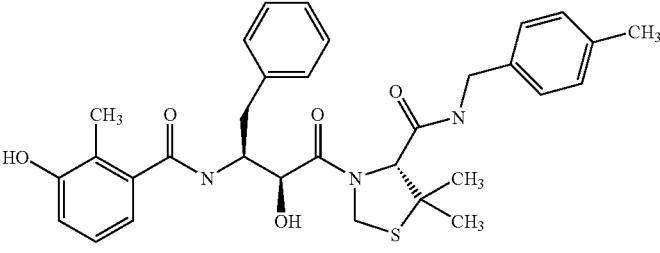 | 0.73 | 0.141 |
| 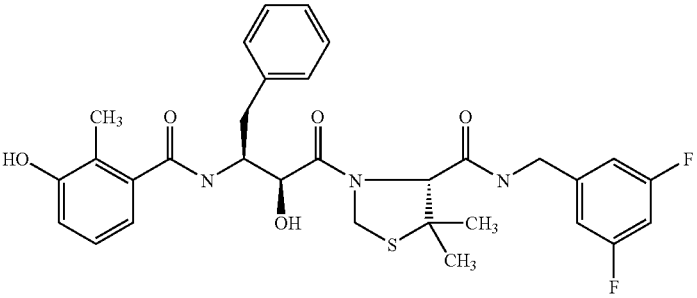 | 0.36 | 0.144 |

-continued

| MOLSTRUCTURE | $K_i$ | $EC_{50}$ |
|---|---|---|
| | 0.24 | 0.158 |
| | 0.26 | 0.207 |
| | 0.17 | 0.289 |
| | 0.11 | 0.334 |
| | 0.2 | 0.585 |

-continued
| MOLSTRUCTURE | $K_i$ | $EC_{50}$ |
|---|---|---|
| 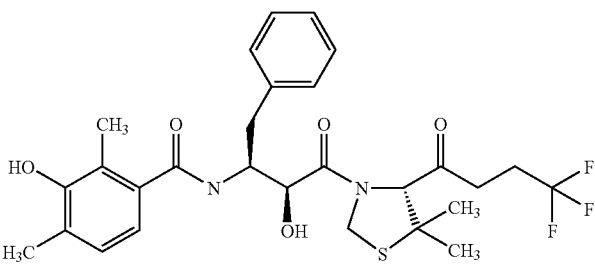 | 9.6 | 0.723 |
| 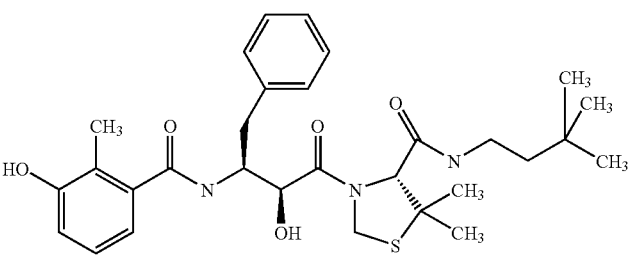 | 4.7 | 1.064 |
| 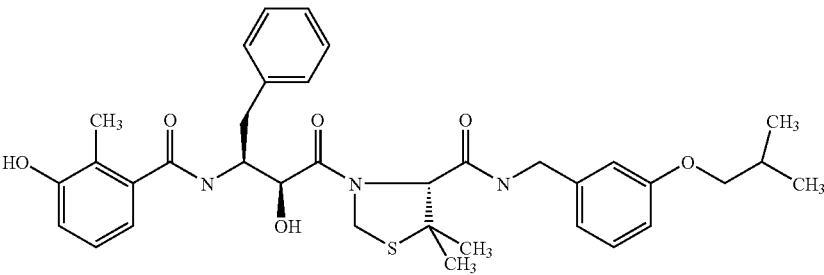 | 1.1 | 1.114 |
| 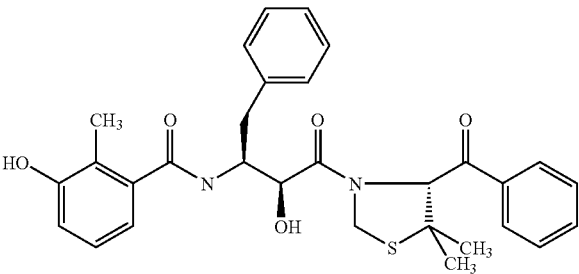 | 2.5 | 1.221 |
| 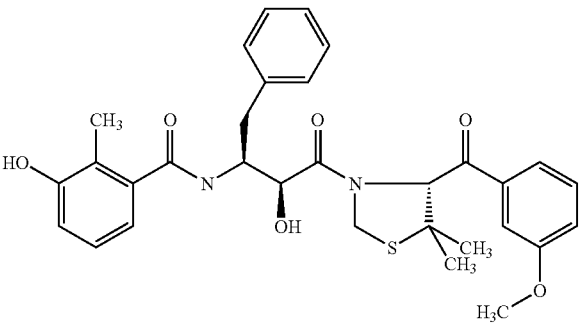 | 7.4 | |

-continued

| MOLSTRUCTURE | $K_i$ | $EC_{50}$ |
|---|---|---|
| | 2.6 | 1.3095 |
| | 2.6 | 1.3095 |
| | 3.4 | |
| | 3.7 | 1.332 |
| | 72 | |

| MOLSTRUCTURE | $K_i$ | $EC_{50}$ |
|---|---|---|
| 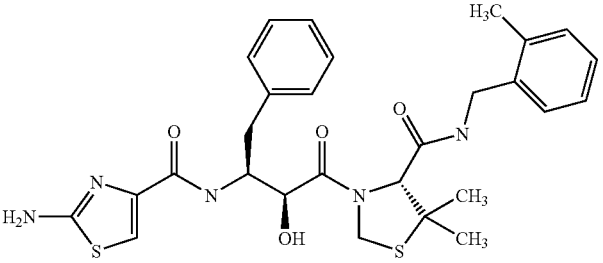 | 2.3 | 1.378 |
| 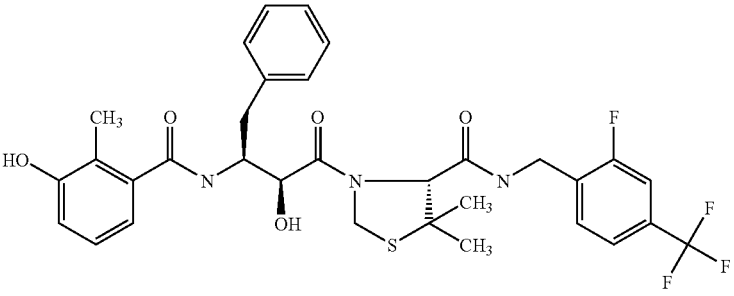 | 11.1 | 1.401 |
| 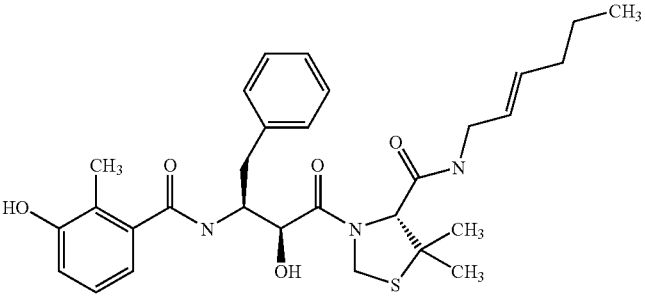 | 2.6 | 1.416 |
| 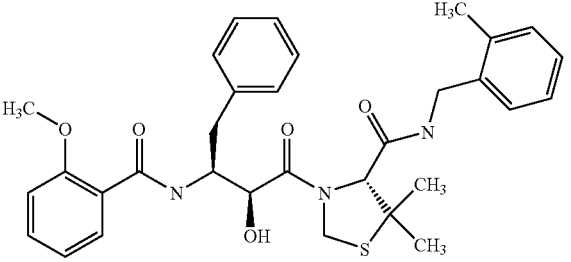 | 2.1 | 1.488 |
| 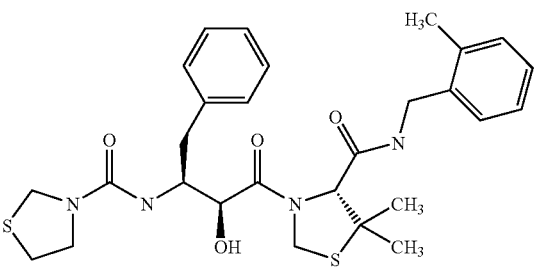 | 14 | 1.512 |

-continued

| MOLSTRUCTURE | $K_i$ | $EC_{50}$ |
|---|---|---|
| | 18.5 | |
| | 19.5 | 3 |
| | 12.1 | |
| | 10.5 | 3.2 |
| | 17.3 | 3.303 |

-continued
| MOLSTRUCTURE | $K_i$ | $EC_{50}$ |
|---|---|---|
| 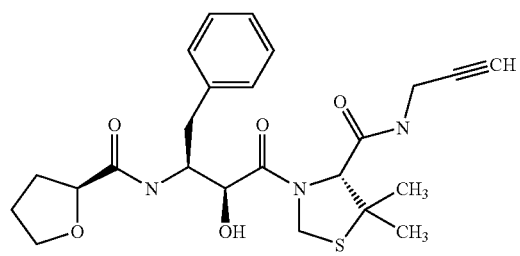 | 16.8 | 3.745 |
| 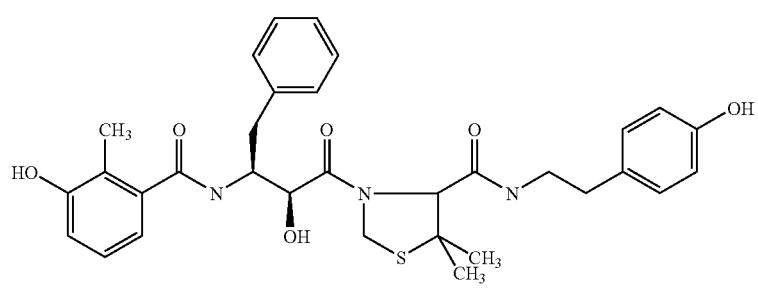 | 13.1 | |
| 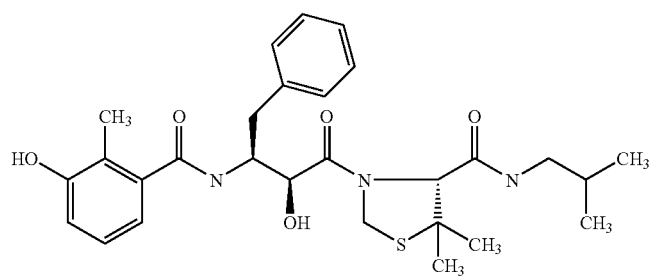 | 0.1 | |
| 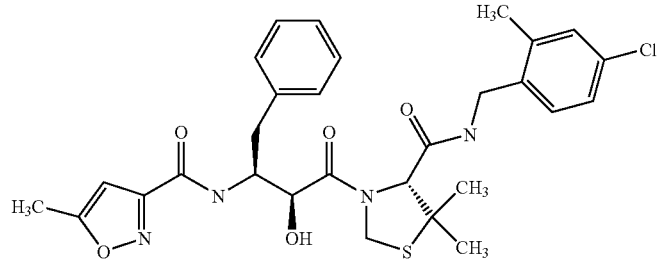 | 28 | 4.132 |
| 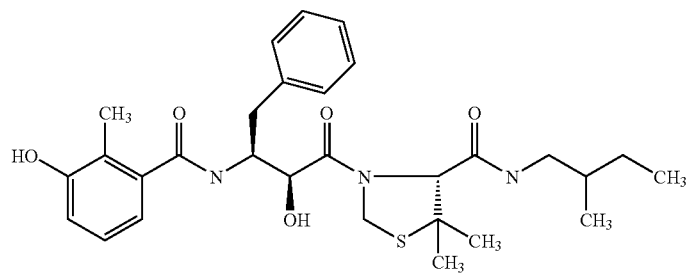 | 0.1 | |

-continued

| MOLSTRUCTURE | $K_i$ | $EC_{50}$ |
|---|---|---|
| 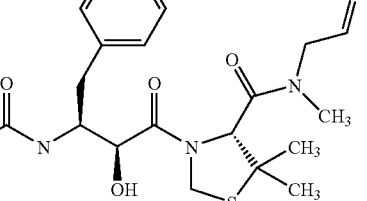 | 24.6 | 4.951 |
| 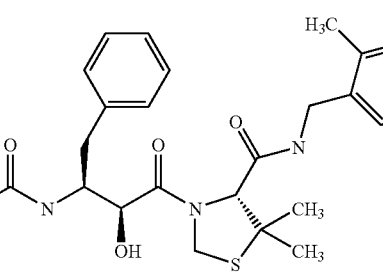 | 55.8 | 10 |
| 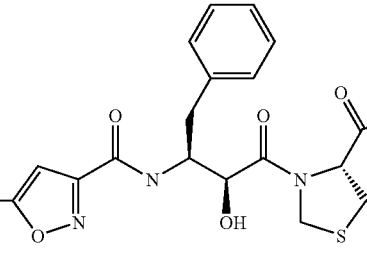 | 214 | 10 |

The following compounds have been prepared according to the procedures described herein and have demonstrated the noted activity:

While the invention has been described in terms of preferred embodiments and specific examples, those skilled in the art will recognize that various changes and modifications can be made through routine experimentation without departing from the spirit and scope of the invention. Thus, the invention should be understood as not being limited by the foregoing detailed description, but as being defined by the appended claims and their equivalents.

We claim:

1. A process for preparing a compound of formula (I-C), comprising:

(i) reacting a compound of formula (IV-A) with a compound of formula (V-A),

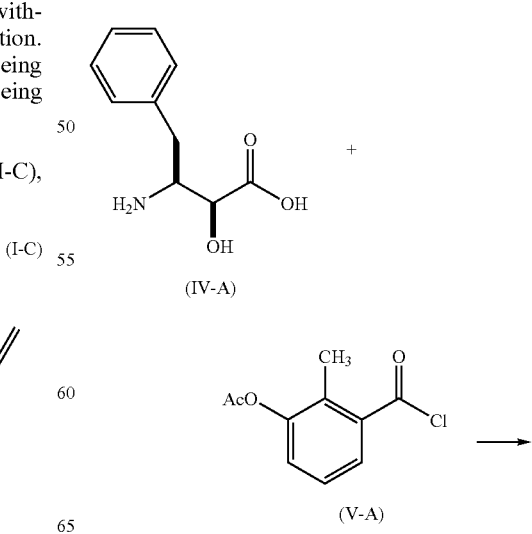

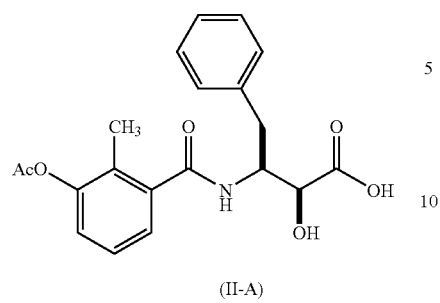
(II-A)
to afford a compound of formula (II-A);
(ii) reacting the compound of formula (II-A) with a compound of formula (III-A), or a salt or solvate thereof,
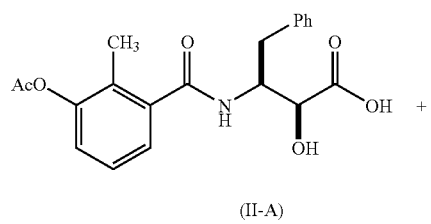 +
(II-A)
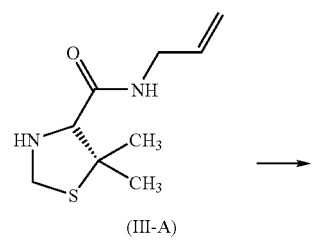 
(III-A)
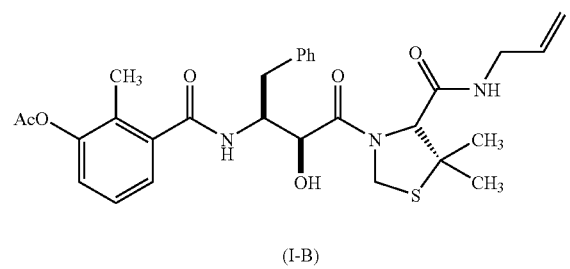
(I-B)
to afford a compound of formula (I-B); and
(iii) deprotecting the compound of formula (I-B).
* * * * *